(12) United States Patent
Sannomiya et al.

(10) Patent No.: US 9,985,219 B2
(45) Date of Patent: May 29, 2018

(54) ORGANIC ELECTROLUMINESCENT ELEMENT

(71) Applicant: NIPPON STEEL & SUMIKIN CHEMICAL CO., LTD., Tokyo (JP)

(72) Inventors: Rumi Sannomiya, Kitakyushu (JP); Takahiro Kai, Kitakyushu (JP); Masaki Komori, Kitakyushu (JP); Toshihiro Yamamoto, Tokyo (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 200 days.

(21) Appl. No.: 14/384,158

(22) PCT Filed: Feb. 28, 2013

(86) PCT No.: PCT/JP2013/055368
§ 371 (c)(1),
(2) Date: Sep. 9, 2014

(87) PCT Pub. No.: WO2013/137001
PCT Pub. Date: Sep. 19, 2013

(65) Prior Publication Data
US 2015/0041785 A1 Feb. 12, 2015

(30) Foreign Application Priority Data
Mar. 12, 2012 (JP) ................. 2012-055107

(51) Int. Cl.
| | | |
|---|---|---|
| H01L 51/54 | (2006.01) | |
| C09K 11/06 | (2006.01) | |
| H01L 51/00 | (2006.01) | |
| C07D 487/04 | (2006.01) | |
| H01L 51/50 | (2006.01) | |

(52) U.S. Cl.
CPC ........ *H01L 51/0067* (2013.01); *C07D 487/04* (2013.01); *C09K 11/06* (2013.01); *H01L 51/0072* (2013.01); *H01L 51/0073* (2013.01); *H01L 51/0074* (2013.01); *H01L 51/5012* (2013.01); *H01L 51/5064* (2013.01); *H01L 51/5096* (2013.01); *C09K 2211/1029* (2013.01); *C09K 2211/1044* (2013.01); *C09K 2211/1059* (2013.01); *C09K 2211/1088* (2013.01);
(Continued)

(58) Field of Classification Search
CPC ................ C09K 11/06; C09K 2211/00; C09K 2211/1018; C09K 2211/1028; C09K 2211/1044; C09K 2211/1059; C09K 2211/1088; C09K 2211/1092; C09K 2211/1096; C07D 209/82; C07D 209/86; C07D 209/88; C07D 307/91; C07D 333/76; C07D 487/00; C07D 487/02; C07D 487/04; H01L 51/0032; H01L 51/005; H01L 51/0062; H01L 51/0067; H01L 51/0071; H01L 51/0072; H01L 51/0073; H01L 51/0074; H01L 51/50; H01L 51/5012; H01L 51/5016; H01L 51/5064; H01L 51/5096
USPC ....... 428/690, 691, 411.4, 336, 917; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 5,942,340 A | 8/1999 | Hu et al. | |
| 5,952,115 A | 9/1999 | Hu et al. | |

(Continued)

FOREIGN PATENT DOCUMENTS

| | | | |
|---|---|---|---|
| KR | 20100131939 A | * | 12/2010 |
| KR | 10-2011-0111692 A | | 10/2011 |

(Continued)

OTHER PUBLICATIONS

Machine translation of KR20100131939. Date of Dec. 16, 2010.*

(Continued)

*Primary Examiner* — Andrew K Bohaty
(74) *Attorney, Agent, or Firm* — Cheng Law Group, PLLC

(57) ABSTRACT

Provided is an organic electroluminescent device (EL device) using an indolocarbazole compound. The organic EL device is obtained by laminating an anode, a plurality of organic layers including a phosphorescent light-emitting layer, and a cathode on a substrate, and the phosphorescent light-emitting layer, a hole-transporting layer, an electron-transporting layer, a hole-blocking layer, or an electron-blocking layer contains an indolocarbazole compound represented by the general formula (1). In the general formula (1), a ring I and a ring II represent rings represented by the formula (1a) and the formula (1b) to be fused to adjacent rings, As each represent C—R or N and at least one of As represents N, Ls each represent a substituted or unsubstituted aromatic hydrocarbon group, or a substituted or unsubstituted aromatic heterocyclic group, and at least one of Ls represents a two- to four-ring fused heterocyclic group, Rs each represent an aliphatic hydrocarbon group, an aromatic hydrocarbon group, or an aromatic heterocyclic group, ps each represent an integer of from 0 to 4, q represents an integer of from 0 to 2, r represents an integer of from 1 to 4, $X_1$ to $X_4$ each represent an aromatic hydrocarbon group or an aromatic heterocyclic group, and l, m, and n each represent an integer of from 0 to 5.

9 Claims, 2 Drawing Sheets

(52) U.S. Cl.
CPC ............... *C09K 2211/1092* (2013.01); *C09K 2211/1096* (2013.01); *H01L 51/5016* (2013.01)

(56) References Cited

U.S. PATENT DOCUMENTS

| | | | |
|---|---|---|---|
| 8,389,131 B2 * | 3/2013 | Kai | ............... C07D 487/04 257/40 |
| 2010/0148161 A1 | 6/2010 | Kai et al. | |
| 2010/0187977 A1 | 7/2010 | Kai et al. | |
| 2011/0315975 A1 | 12/2011 | Kai et al. | |
| 2012/0001165 A1 | 1/2012 | Komori et al. | |
| 2012/0007070 A1 | 1/2012 | Kai et al. | |

FOREIGN PATENT DOCUMENTS

| | | |
|---|---|---|
| KR | 10-2012-0072785 A | 7/2012 |
| WO | WO-2011/136755 A1 | 11/2011 |
| WO | WO-2013/012297 A1 | 1/2013 |

OTHER PUBLICATIONS

International Search Report for Application No. PCT/JP2013/055368 dated May 14, 2013.
Written Opinion of the International Searching Authority (PCT/ISA/237) for the Application No. PCT/JP2013/055368 dated May 14, 2013.

* cited by examiner

ORGANIC ELECTROLUMINESCENT ELEMENT

TECHNICAL FIELD

The present invention relates to an organic electroluminescent device containing an indolocarbazole compound, and more specifically, to a thin-film-type device that emits light when an electric field is applied to a light-emitting layer formed of an organic compound.

BACKGROUND ART

In general, an organic electroluminescent device (hereinafter referred to as organic EL device) is constructed of a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex (hereinafter referred to as Alq3) are formed between electrodes as thin films, resulting in a significant improvement in luminous efficiency, compared with conventional devices in which a single crystal of anthracene or the like is used. Thus, the development of the above-mentioned organic EL device has been promoted in order to accomplish its practical application to a high-performance flat panel having features such as self-luminescence and rapid response.

Further, studies have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of Alq3 are formed emit light by using fluorescent light emission. However, by using phosphorescent light emission, that is, by using light emission from a triplet excited state, luminous efficiency is expected to be improved by about three times to four times, compared with the case of using conventional devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet state, but highly efficient light emission has not been accomplished. In recent years, many studies on a phosphorescent light-emitting dopant material centered on an organic metal complex such as an iridium complex have been made, as described in Patent Literature 1, for the purpose of attaining high luminous efficiency and a long lifetime.

CITATION LIST

Patent Literature

[PTL 1] WO 01/041512 A1
[PTL 2] JP 2001-313178 A
[PTL 3] JP 11-162650 A
[PTL 4] JP 11-176578 A
[PTL 5] WO 2008/056746 A1
[PTL 6] WO 2008/146839 A1
[PTL 7] WO 2010/113726 A1
[PTL 8] WO 2010/113755 A1

In order to obtain high luminous efficiency, host materials that are used with the dopant materials described above play an important role. A typical example of the host materials proposed is 4,4'-bis(9-carbazolyl)biphenyl (hereinafter referred to as CBP) as a carbazole compound disclosed in Patent Literature 2. When CBP is used as a host material for a green phosphorescent light-emitting material typified by a tris(2-phenylpyridine) iridium complex (hereinafter referred to as Ir(ppy)$_3$), the injection balance between charges is disturbed because CBP has the characteristic of facilitating the delivery of holes and not facilitating the delivery of electrons. Thus, excessively delivered holes flow out into an electron-transporting layer side, with the result that the luminous efficiency from Ir(ppy)$_3$ lowers.

In order to provide high luminous efficiency to an organic EL device as described above, it is necessary to use a host material that has high triplet excitation energy, and is striking a good balance in both charge (hole and electron)-injecting/transporting property. Further desired is a compound that has electrochemical stability, has high heat resistance, and has excellent amorphous stability, and hence further improvement has been demanded.

Patent Literature 3 discloses the indolocarbazole compound shown below as a hole-transporting material.

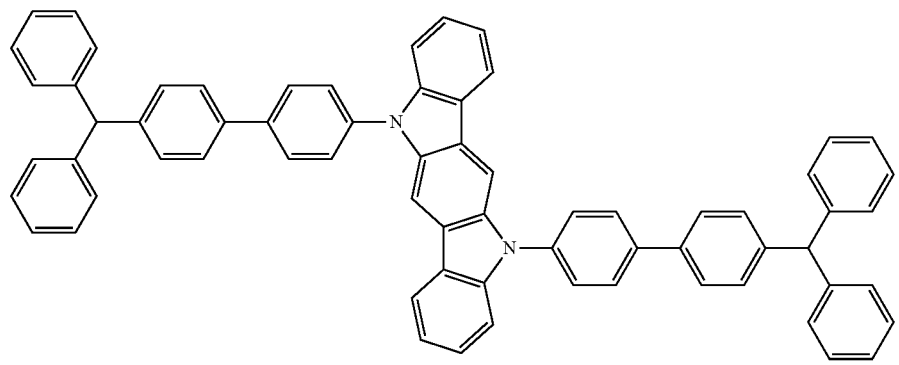 [SMILES: c1ccc(C(c2ccccc2)c2ccc(-c3ccc(-n4c5ccccc5c5cc6c(cc54)c4ccccc4n6-c4ccc(-c5ccc(C(c6ccccc6)c6ccccc6)cc5)cc4)cc3)cc2)cc1]

Patent Literature 4 discloses the indolocarbazole compound shown below as a hole-transporting material.

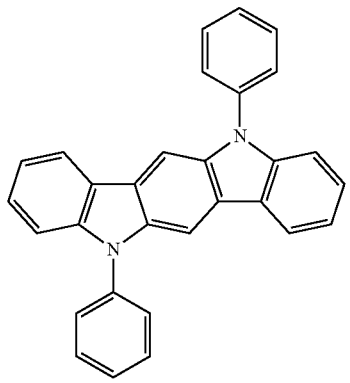 [SMILES: c1ccc(-n2c3ccccc3c3cc4c(cc32)c2ccccc2n4-c2ccccc2)cc1]

However, although the literatures recommend to use these compounds having an indolocarbazole skeleton as hole-transporting materials, the literatures do not disclose a compound substituted with a nitrogen-containing six-membered ring as a substituent on N of an indolocarbazole skeleton and its usefulness.

Patent Literature 5 and Patent Literature 6 disclose such indolocarbazole compounds as shown below as phosphorescent host materials, and disclose that organic EL devices using the compounds are improved in luminous efficiency and have high driving stability.

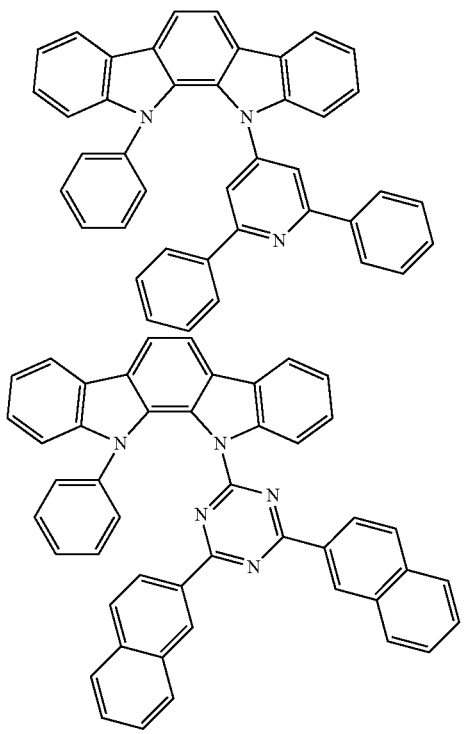

In addition, Patent Literature 7 and Patent Literature 8 each disclose a compound having a nitrogen-containing six-membered ring at the N-position of indolocarbazole and having a fused heterocycle as a substituent on the nitrogen-containing six-membered ring.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device that has high efficiency, has high driving stability, and is practically useful and a compound suitable for the organic EL device.

The inventors of the present invention have made intensive studies and have consequently found that, when a compound having an indolocarbazole skeleton with a specific structure is used in an organic EL device, the organic EL device exhibits excellent characteristics. As a result, the present invention has been completed.

The present invention relates to an organic electroluminescent device, including an anode, a plurality of organic layers including a phosphorescent light-emitting layer, and a cathode laminated on a substrate, in which at least one of the plurality of organic layers, which is selected from the group consisting of the phosphorescent light-emitting layer, a hole-transporting layer, an electron-transporting layer, a hole-blocking layer, and an electron-blocking layer, contains an indolocarbazole compound represented by the following general formula (1).

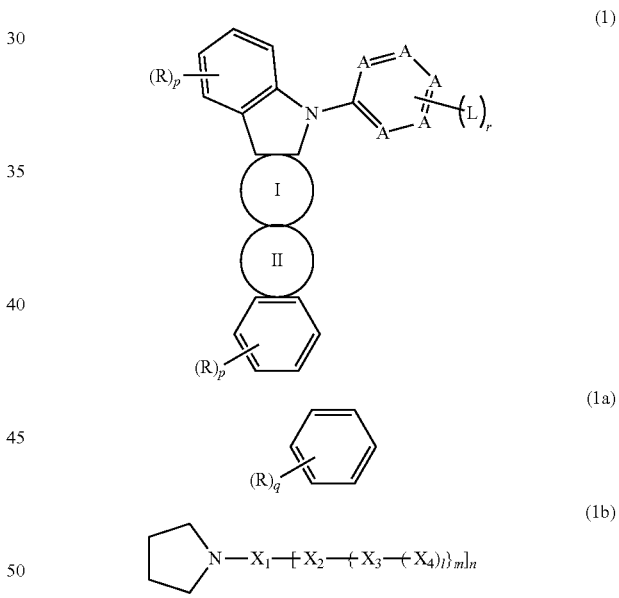

In the general formula (1), a ring I represents an aromatic hydrocarbon ring represented by the formula (1a) to be fused to adjacent rings at arbitrary positions, and a ring II represents a heterocycle represented by the formula (1b) to be fused to adjacent rings at arbitrary positions. As each represent C—R or N and at least one of As represents N. Ls each independently represent a substituted or unsubstituted aromatic hydrocarbon group having 6 to 18 carbon atoms, or a substituted or unsubstituted aromatic heterocyclic group having 3 to 17 carbon atoms, and r represents an integer of from 1 to 4; provided that at least one of Ls represents a fused heterocyclic group formed of two to four rings. In the general formula (1) and the formula (1a), Rs each independently represent an aliphatic hydrocarbon group having 1 to 10 carbon atoms, an aromatic hydrocarbon group having 6 to 18 carbon atoms, or an aromatic heterocyclic group having 3 to 17 carbon atoms, ps each independently represent an integer of from 0 to 4, and q represents an integer of from 0 to 2. In the formula (1b), $X_1$ to $X_4$ each independently represent an aromatic hydrocarbon group having 6 to 18 carbon atoms or an aromatic heterocyclic group having 3 to 17 carbon atoms, and l, m, and n each independently represent an integer of from 0 to 5. Here, when l, m, or n represents 2 or more, $X_2$s, $X_3$s, or $X_4$s may be identical to or different from each other.

In the general formula (1), at least one of Ls preferably represents a monovalent aromatic heterocyclic group represented by any one of the following formulae (2) and (3), and more preferably represents a monovalent aromatic heterocyclic group represented by a compound represented by the following formula (4).

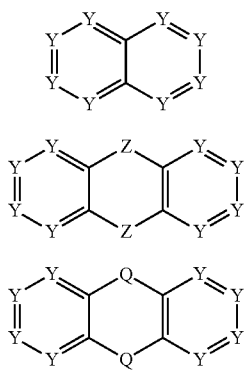

(In the formulae (2) to (4), Ys each independently represent methine, substituted methine, or nitrogen, and one of Ys represents a carbon atom providing a monovalent group, Zs each independently represent any one of a single bond, —S—, —O—, and N(Ar)—, and Qs each represent any one of a single bond, —S—, and O—. At least one of Ys in the formula (2), at least one of Ys and Zs in the formula (3), and at least one of Ys and Qs in the formula (4) each represent a heteroatom. Here, Ar represents an aromatic hydrocarbon group having 6 to 18 carbon atoms or an aromatic heterocyclic group having 6 to 17 carbon atoms.)

In addition, it is preferred that one of Zs in the formula (3), or one of Qs in the formula (4), represent a single bond, and the other represent —S— or —O.

At least one Lout of Ls in the general formula (1) more preferably represents a substituted or unsubstituted dibenzofuranyl or dibenzothiophenyl group.

The total number of $X_1$ to $X_4$ in the formula (1b) falls within the range of preferably from 2 to 10, more preferably from 4 to 7.

In addition, according to another embodiment of the present invention, in the above-mentioned organic electroluminescent device, the organic layer containing the indolocarbazole compound includes a light-emitting layer containing a phosphorescent light-emitting dopant.

DESCRIPTION OF EMBODIMENTS

Figure 1:
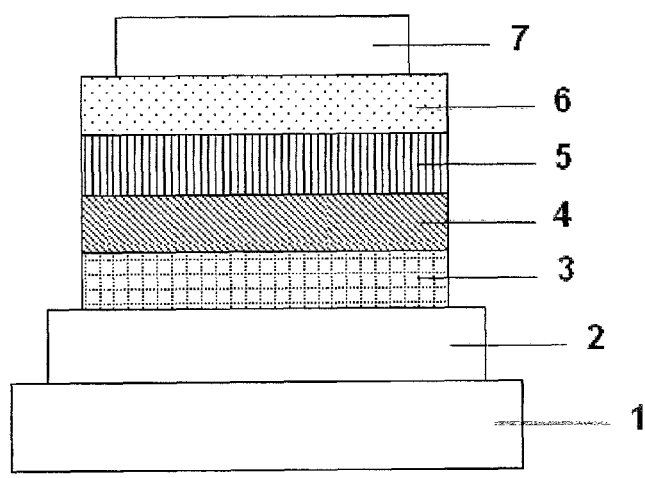
FIG. 1 is a sectional view illustrating a structure example of an organic EL device.

An organic electroluminescent device of the present invention contains an indolocarbazole compound represented by the general formula (1) (hereinafter sometimes referred to as "compound represented by the general formula (1)" or "indolocarbazole compound") in at least one organic layer.

In the general formula (1), a ring I represents an aromatic hydrocarbon ring represented by the formula (1a) to be fused to adjacent rings at arbitrary positions, and a ring II represents a heterocycle represented by the formula (1b) to be fused to adjacent rings at arbitrary positions.

In the indolocarbazole skeleton represented by the general formula (1), the aromatic hydrocarbon ring represented by the formula (1a) may be fused with two adjacent rings at arbitrary positions, but there is a position at which the aromatic hydrocarbon ring cannot be fused with the rings from the structural viewpoint. The aromatic hydrocarbon ring represented by the formula (1a) has six sides, and is not fused with the two adjacent rings through two adjacent sides. Further, the heterocycle represented by the formula (1b) may be fused with two adjacent rings at arbitrary positions, but there is a position at which the heterocycle cannot be fused with the rings from the structural viewpoint. That is, the heterocycle represented by the formula (1b) has five sides, and is not fused with the two adjacent rings through two adjacent sides and is not fused with an adjacent ring through a side including a nitrogen atom. Thus, there is a limitation on the kind of the indolocarbazole skeleton. Specifically, an indole skeleton can be fused at the 2,3-positions, 3,4-positions, or 4,5-positions of a carbazole skeleton, and hence five kinds of skeletal isomers exist.

In the general formula (1), the indolocarbazole skeleton is preferably represented by any one of the following forms. Preferred fusion positions of the aromatic hydrocarbon ring and the heterocycle in the indolocarbazole skeleton are understood from these examples.

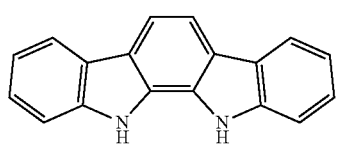

(IC-1)

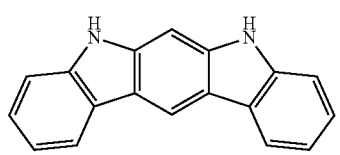

(IC-2)

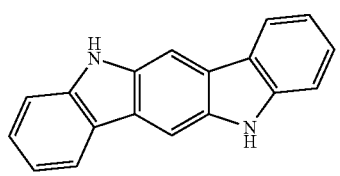

(IC-3)

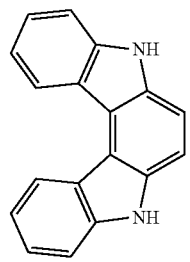
(IC-4)

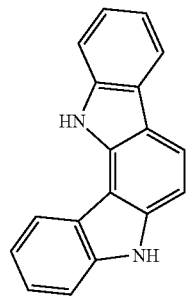
(IC-5)

In the general formula (1), As each represent C—R or N. Here, at least one of As represents N. One to three of As each preferably represent N.

In the general formula (1), Ls each independently represent a substituted or unsubstituted aromatic hydrocarbon group having 6 to 18 carbon atoms, or a substituted or unsubstituted aromatic heterocyclic group having 3 to 17 carbon atoms, and at least one of Ls represents a two- to four-ring fused heterocyclic group.

When L represents an unsubstituted aromatic hydrocarbon group having 6 to 18 carbon atoms or an unsubstituted aromatic heterocyclic group having 3 to 17 carbon atoms, a specific example thereof is a group produced by removing hydrogen from an aromatic ring such as benzene, pentalene, indene, naphthalene, anthracene, phenanthrene, pyrrole, imidazole, pyrazole, thiazole, thiophene, pyridine, pyrazine, pyrimidine, pyridazine, triazine, isoindole, indazole, purine, benzimidazole, indolizine, chromene, benzoxazole, isobenzofuran, quinolizine, isoquinoline, imidazole, naphthyridine, phthalazine, quinazoline, quinoxaline, cinnoline, quinoline, pteridine, perimidine, phenanthroline, phenanthridine, acridine, phenazine, phenothiazine, phenoxazine, phenazasiline, dibenzodioxin, carboline, indole, indoloindole, carbazole, furan, benzofuran, isobenzofuran, benzothiazole, oxanthrene, dibenzofuran, thiophene, thioxanthene, thianthrene, phenoxathiin, thionaphthene, isothianaphthene, thiophthene, thiophanthrene, or dibenzothiophene.

When L represents the fused heterocyclic group formed of two to four rings, specific examples thereof include groups produced by removing hydrogen atoms from fused heterocycles in the aromatic rings appearing in the description of L. The group is more preferably, for example, a monovalent aromatic heterocyclic group represented by any one of the formulae (2) to (4). In the formulae (2) to (4), Ys each independently represent methine, substituted methine, or nitrogen, and one of Ys represents a carbon atom (C), the carbon atom providing a radical enabling the group to become a monovalent group, Zs each represent any one of a single bond, —S—, —O—, and N(Ar)—, and Qs each represent any one of a single bond, —S—, and —O—. The formulae (2) to (4) each represent a fused heterocyclic group containing at least one heteroatom. Here, Ar represents an aromatic hydrocarbon group having 6 to 18 carbon atoms or an aromatic heterocyclic group having 6 to 17 carbon atoms. It should be noted that when L represents a substituted aromatic hydrocarbon group having 6 to 18 carbon atoms or a substituted aromatic heterocyclic group having 3 to 17 carbon atoms, a substituent in the case where Y represents substituted methine is preferably an alkyl group having 1 to 10 carbon atoms, a cycloalkyl group having 3 to 11 carbon atoms, an aromatic hydrocarbon group having 6 to 18 carbon atoms, or an aromatic heterocyclic group having 3 to 17 carbon atoms, more preferably an alkyl group having 1 to 4 carbon atoms, a cycloalkyl group having 3 to 7 carbon atoms, an aromatic hydrocarbon group having 6 to 12 carbon atoms, or an aromatic heterocyclic group having 3 to 12 carbon atoms. Preferred specific examples thereof include: an alkyl group having 1 to 6 carbon atoms such as a methyl group, an ethyl group, or a propyl group; a cycloalkyl group having 6 to 8 carbon atoms such as a cyclohexyl group or a methylcyclohexyl group; an aromatic hydrocarbon group having 6 to 12 carbon atoms such as a phenyl group or a naphthyl group; and an aromatic heterocyclic group having 3 to 12 carbon atoms such as a pyridyl group, a pyrimidyl group, a triazyl group, a carbazolyl group, a dibenzofuranyl group, or a dibenzothiophenyl group. Of those, a phenyl group, a pyridyl group, a pyrimidyl group, a triazyl group, a carbazolyl group, a dibenzofuranyl group, or a dibenzothiophenyl group is more preferred. In the general formula (1), r represents an integer of from 1 to 4, preferably an integer of from 1 to 3, more preferably an integer of from 1 to 2.

Of the monovalent aromatic heterocyclic groups represented by the general formulae (2) to (4), any one of a substituted or unsubstituted dibenzothiophenyl group, and a substituted or unsubstituted dibenzofuranyl group is particularly preferred. Here, a substituent in the case where the dibenzothiophenyl group or the dibenzofuranyl group has the substituent is the same as the substituent described for the case where Y represents substituted methine.

In the general formula (1) and the formula (1a), Rs each independently represent an alkyl group having 1 to 10 carbon atoms, a cycloalkyl group having 3 to 11 carbon atoms, an aromatic hydrocarbon group having 6 to 18 carbon atoms, or an aromatic heterocyclic group having 3 to 17 carbon atoms. Of those, an alkyl group having 1 to 4 carbon atoms, a cycloalkyl group having 3 to 7 carbon atoms, an aromatic hydrocarbon group having 6 to 12 carbon atoms, or an aromatic heterocyclic group having 3 to 12 carbon atoms is preferred, and preferred specific examples thereof include a methyl group, an ethyl group, a propyl group, a cyclohexyl group, a methylcyclohexyl group, a phenyl group, a naphthyl group, a pyridyl group, a pyrimidyl group, a triazyl group, and a carbazolyl group. Of those, a methyl group, an ethyl group, a phenyl group, or a pyridyl group is more preferred. When R represents an aromatic hydrocarbon group or an aromatic heterocyclic group, the group may have a substituent, and examples of the substituent include an alkyl group having 1 to 10 carbon atoms, a cycloalkyl group having 3 to 11 carbon atoms, an alkoxy group having 1 to 2 carbon atoms, an acetyl group, a secondary amino group having 6 to 18 carbon atoms, a secondary phosphanyl group having 6 to 18 carbon atoms, a silyl group having 3 to 18 carbon atoms, an aromatic hydrocarbon group having 6 to 18 carbon atoms, and an aromatic heterocyclic group having 3 to 17 carbon atoms. Of those, an alkyl group having 1 to 4 carbon atoms, a cycloalkyl group having 3 to 7 carbon atoms, an aromatic hydrocarbon group having 6 to 12 carbon atoms, or an aromatic heterocyclic group having 3 to 12 carbon atoms is preferred, and preferred specific examples thereof include a methyl group, an ethyl group, a propyl group, a cyclohexyl group, a methylcyclohexyl group, a phenyl group, a naphthyl group, a pyridyl group, a pyrimidyl group, a triazyl group, and a carbazolyl group. Of those, a methyl group, an ethyl group, a phenyl group, or a pyridyl group is more preferred.

In the general formula (1) and the formula (1a), ps each independently represent an integer of from 0 to 4 and q represents an integer of from 0 to 2. ps and q each preferably represent 0 or 1, and the total number of Rs preferably falls within the range of from 0 to 3.

In the formula (1b), $X_1$ to $X_4$ each represent an aromatic hydrocarbon group having 6 to 18 carbon atoms or an aromatic heterocyclic group having 3 to 17 carbon atoms. Such aromatic hydrocarbon group or aromatic heterocyclic group may be a single ring or a fused ring, but is not a group in which aromatic groups are linked in a chain manner.

Here, $X_2$ represents a group linked to $X_1$, $X_3$ represents a group linked to $X_2$, $X_4$ represents a group linked to $X_3$, and $X_4$ represents a monovalent group, and $X_1$ to $X_3$ represent groups that are monovalent or more determined by the numbers of n, m, and l. Specific examples of the aromatic hydrocarbon group having 6 to 18 carbon atoms or aromatic heterocyclic group having 3 to 17 carbon atoms represented by each of $X_1$ to $X_4$ include groups that are monovalent or more obtained by removing predetermined numbers of hydrogen atoms from aromatic rings given in the foregoing as the specific examples of the aromatic hydrocarbon group having 6 to 18 carbon atoms or aromatic heterocyclic group having 3 to 17 carbon atoms represented by L.

In the formula (1b), l, m, and n each represent an integer of from 0 to 5, preferably an integer of from 0 to 3.

In addition, in the formula (1b), the total number of $X_1$ to $X_4$ is desirably from 2 to 10, preferably from 4 to 7, more preferably from 5 to 7. When l, m, or n represents 2 or more, $X_2$s, X is, or $X_4$s may be identical to or different from each other. The total number of $X_1$ to $X_4$ is calculated from $1+n+mn+mnl=1+n(1+m+ml)$. Therefore, in order that the total number of $X_1$ to $X_4$ may be from 2 to 10, n represents an integer of 1 or more, and in order that the total number may be from 5 to 7, when n represents 1, (m+ml) represents from 3 to 5, and when n represents 2, (m+ml) represents from 1 to 2.

Examples of the formula —$X_1$—[$X_2$—{$X_3$—($X_4$)$_l$}$_m$]$_n$ in the case where the total number of $X_1$ to $X_4$ is 2 or more include the following formulae.

$$—X_1—X_2—X_3 \quad (5)$$

$$\begin{array}{c} X_3 \\ | \\ —X_1—X_2—X_3 \end{array} \quad (6)$$

$$\begin{array}{c} X_3 \\ | \\ —X_1—X_2—X_3 \\ | \\ X_3 \\ | \\ X_4 \end{array} \quad (7)$$

In the formulae (5) to (7), $X_1$ to $X_4$ each represent an aromatic hydrocarbon group or an aromatic heterocyclic group, and part or the entirety thereof may be a fused ring.

Specific examples of a group produced by linking a plurality of aromatic rings represented by the formula —$X_1$—[$X_2$—{$X_3$—($X_4$)$_l$}$_m$]$_n$ include such monovalent groups as shown below. In the monovalent groups shown below, R' represents an aromatic hydrocarbon group having 6 to 18 carbon atoms or an aromatic heterocyclic group having 3 to 17 carbon atoms. Specific examples of the aromatic hydrocarbon group having 6 to 18 carbon atoms or the aromatic heterocyclic group having 3 to 17 carbon atoms include the same examples as those described for A.

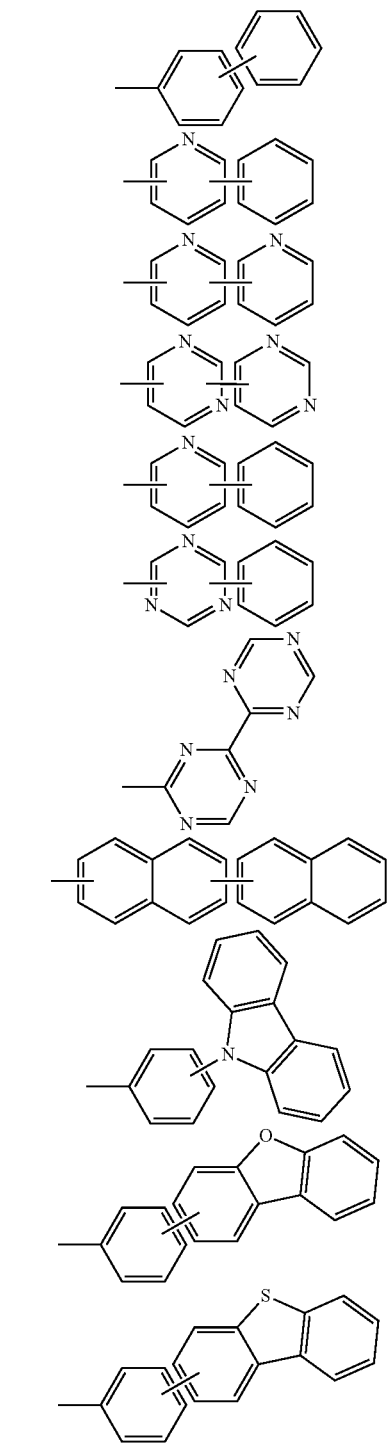

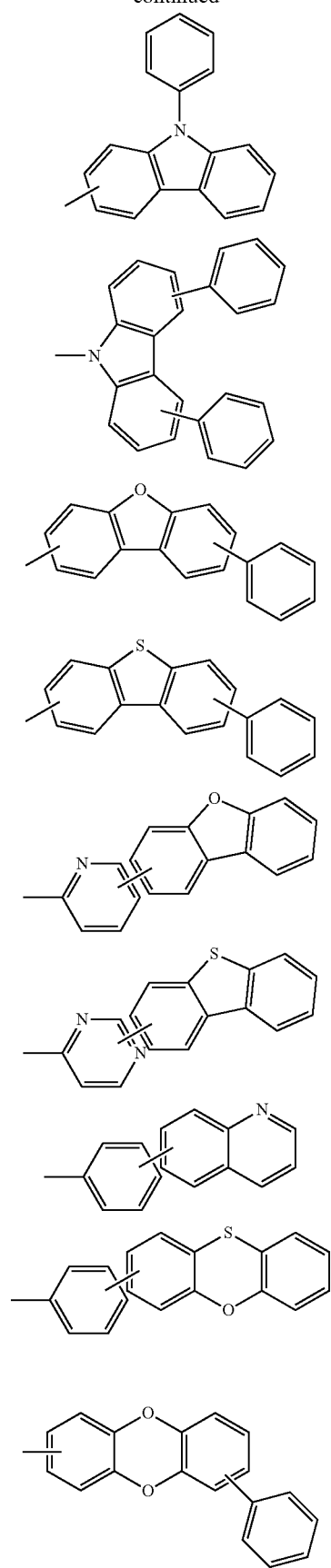
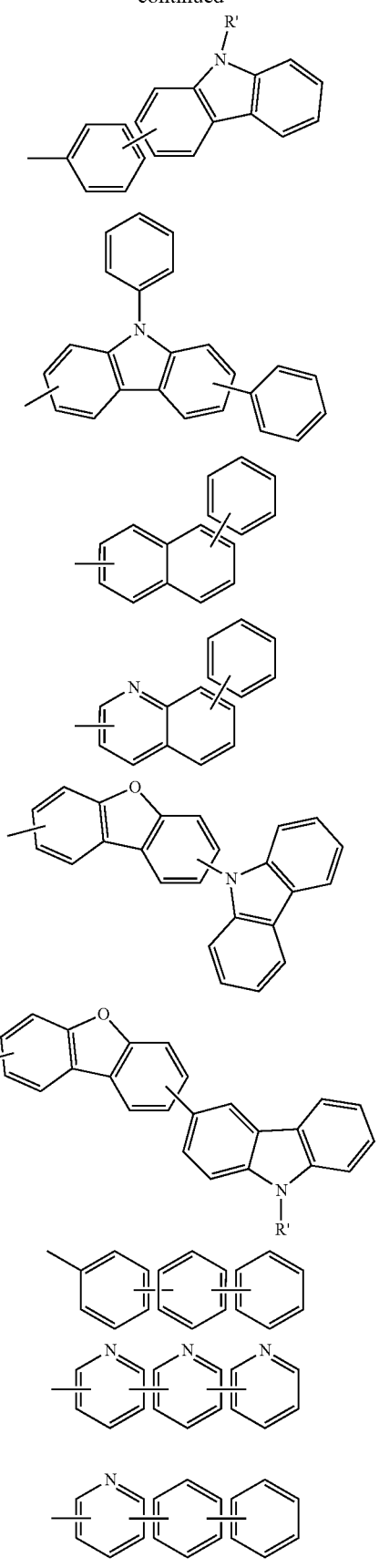

-continued
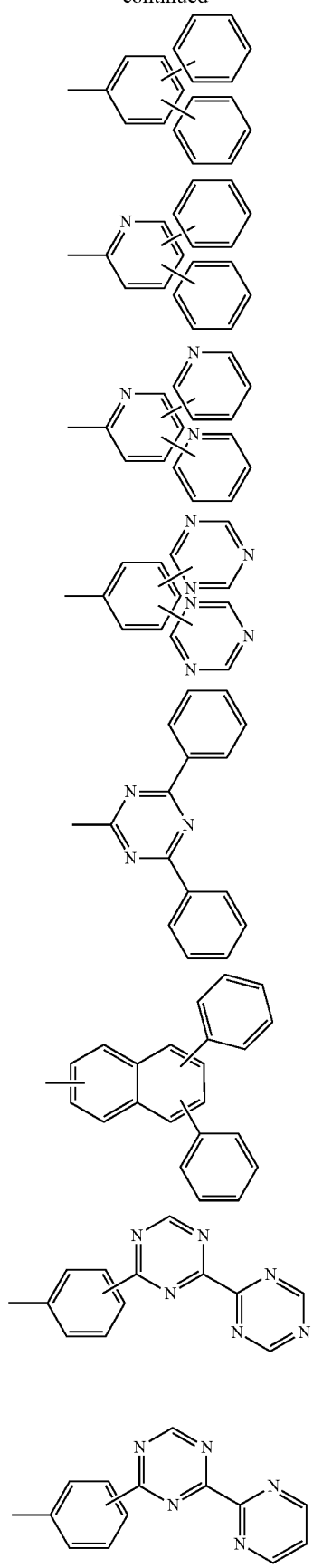
-continued
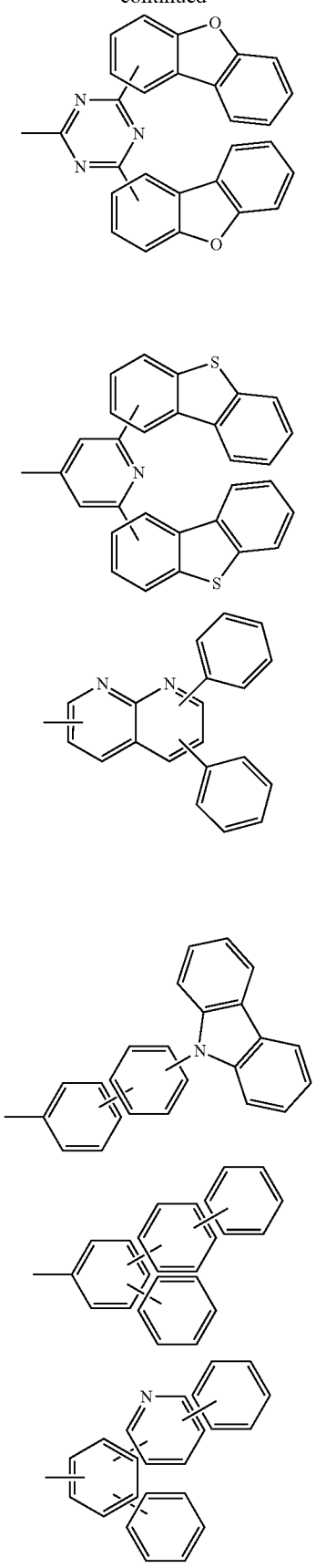

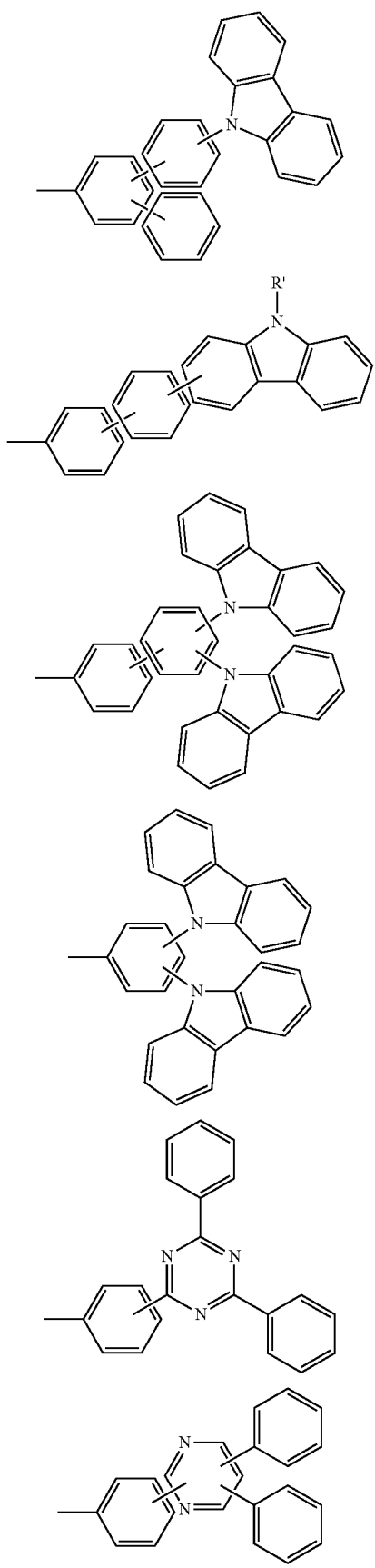
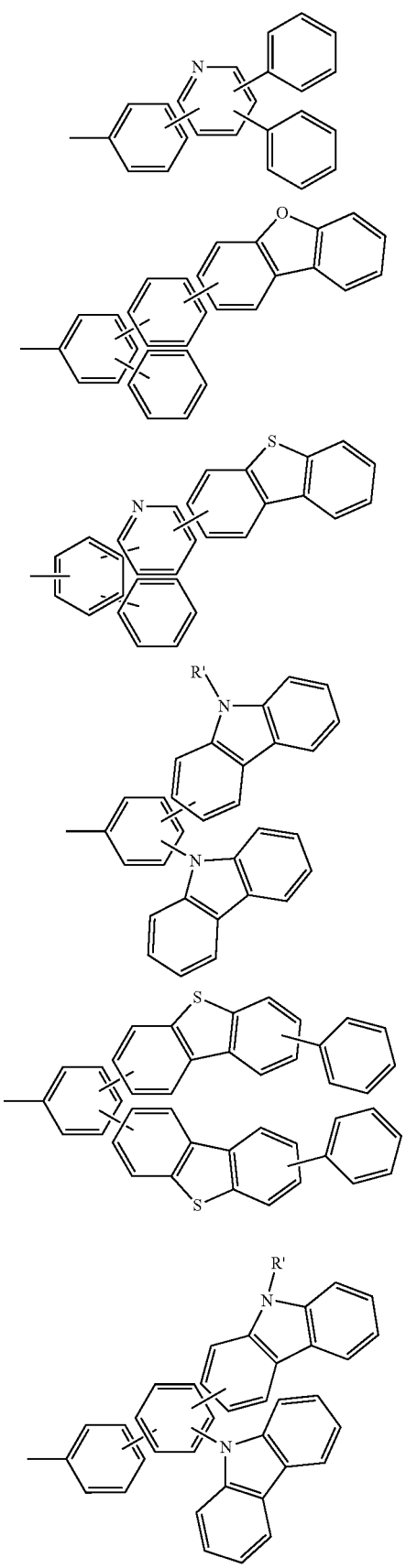

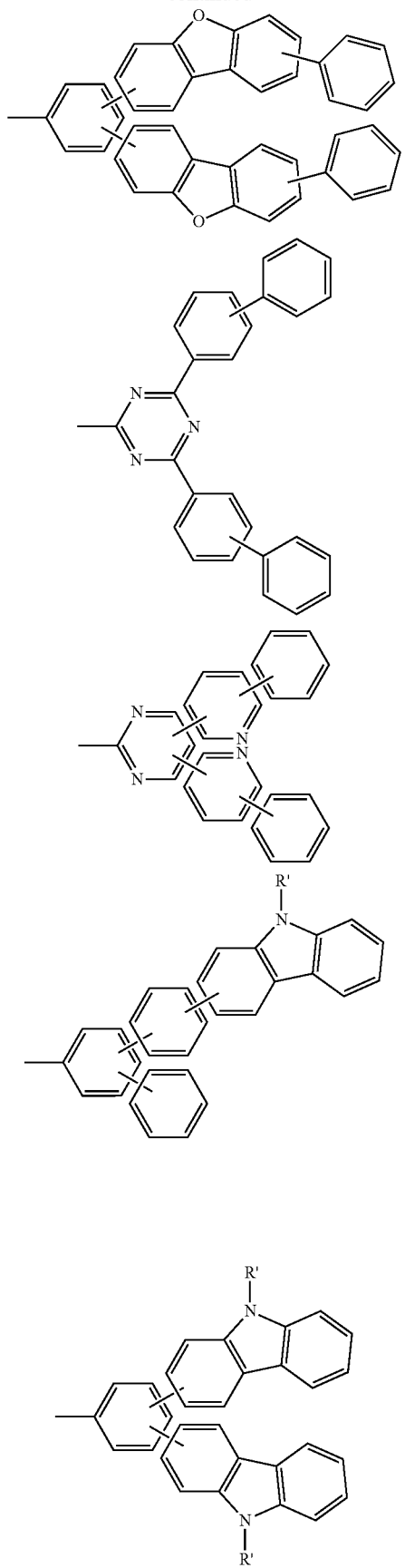

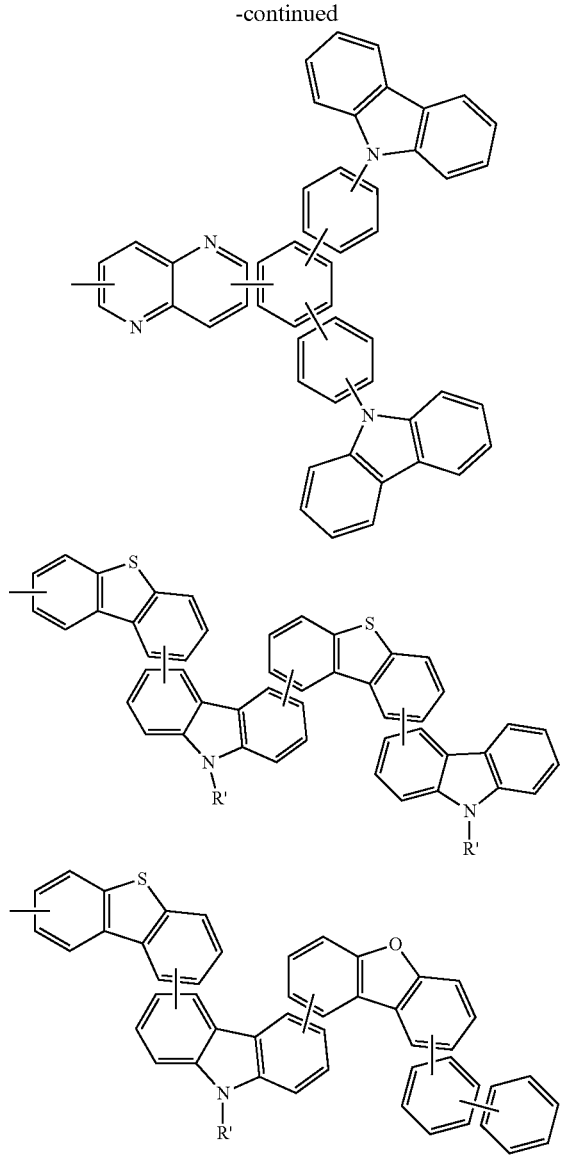
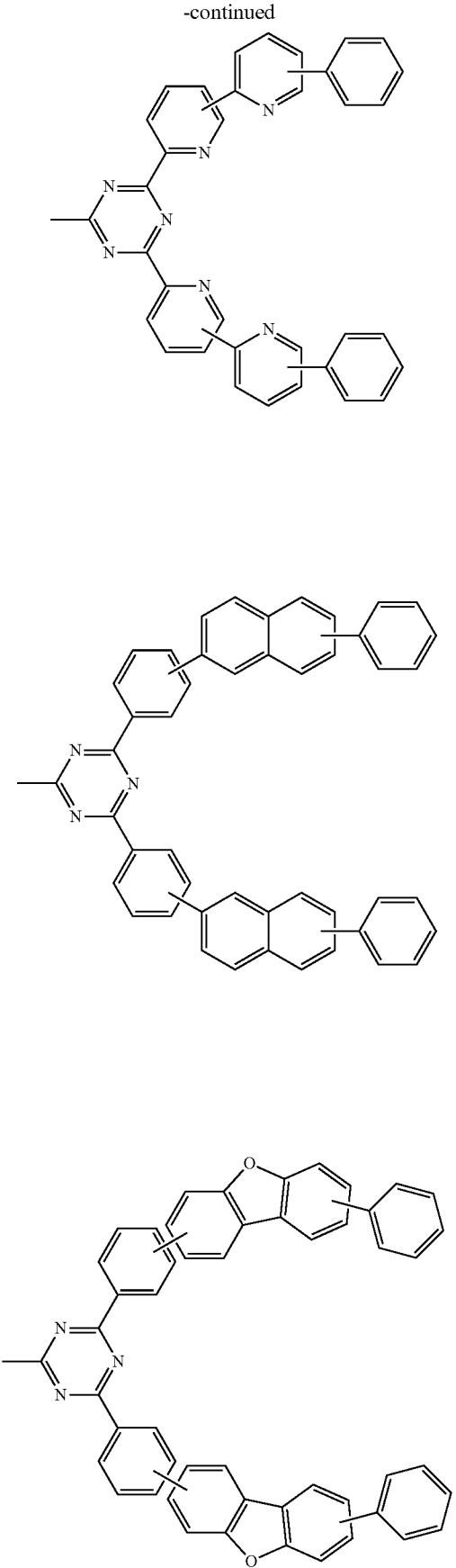

-continued

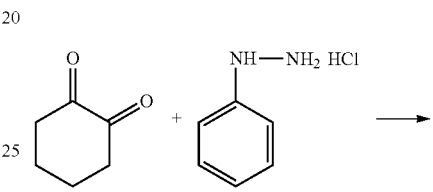

A skeleton represented by any one of the formulae (IC-1) to (IC-4) is available as a preferred skeleton of the indolocarbazole compound represented by the general formula (1). The general formula (1) is a concept comprehending the skeletons represented by the formulae (IC-1) to (IC-4), and these skeletons can be described by taking the compound represented by the general formula (1) as a typical example.

Such skeletons as represented in the forms of the formulae (IC-1) to (IC-4) are each conceivable as the skeleton of the indolocarbazole compound represented by the general formula (1), and these skeletons can each be synthesized by employing a known approach from a raw material selected in accordance with the structure of a target compound.

For example, the indolocarbazole skeleton represented by the formula (IC-1) can be synthesized by the following reaction formula with reference to a synthesis example described in Synlett, 2005, No. 1, p 42-48.

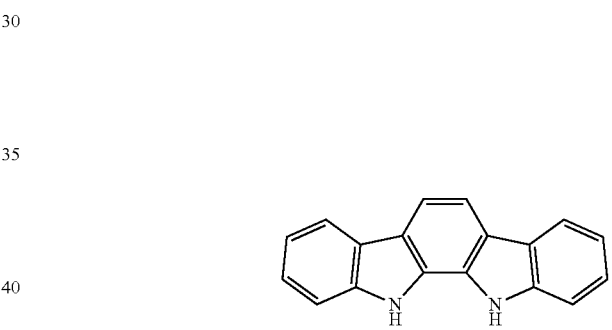

Further, the indolocarbazole skeleton represented by the formula (IC-3) can be synthesized by the following reaction formula with reference to a synthesis example described in Archiv der Pharmazie (Weinheim, Germany) 1987, 320(3), p 280-2.

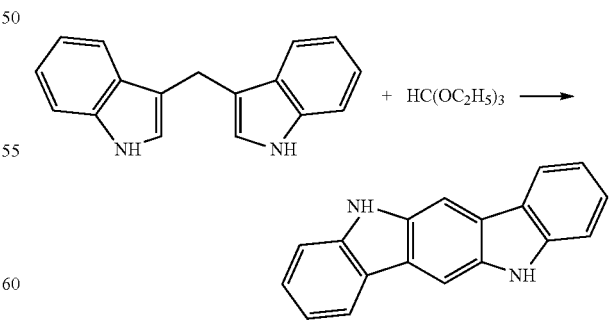

Specific examples of the indolocarbazole compound represented by the general formula (1) are shown below. However, the material for an organic electroluminescent device of the present invention is not limited thereto.

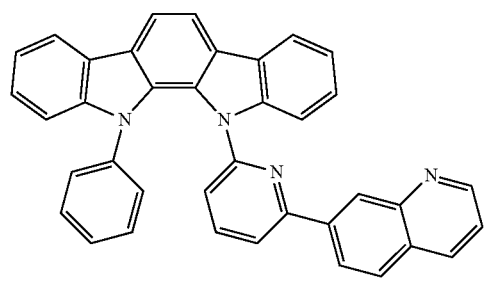
(A-1)
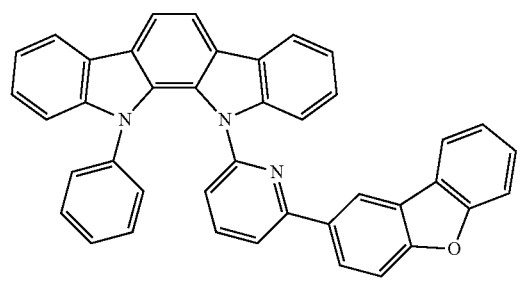
(A-2)
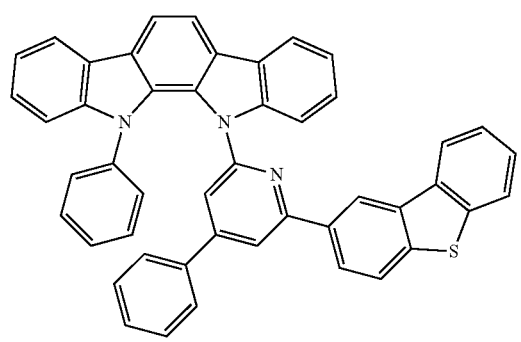
(A-3)
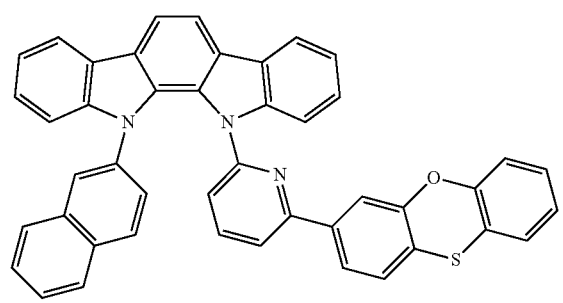
(A-4)
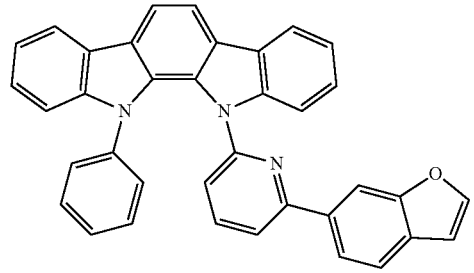
(A-5)
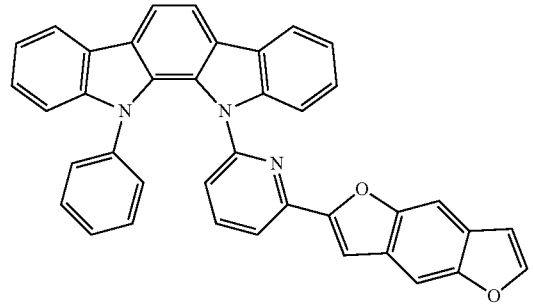
(A-6)
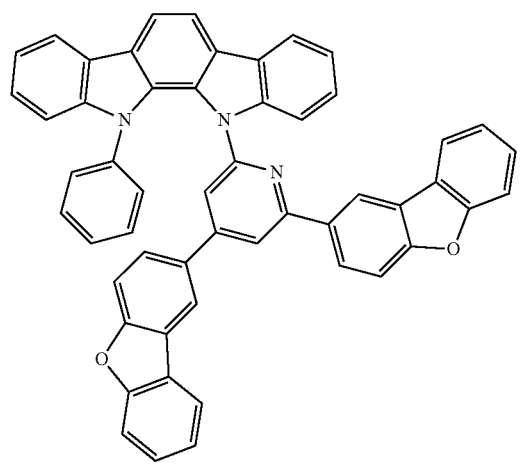
(A-7)
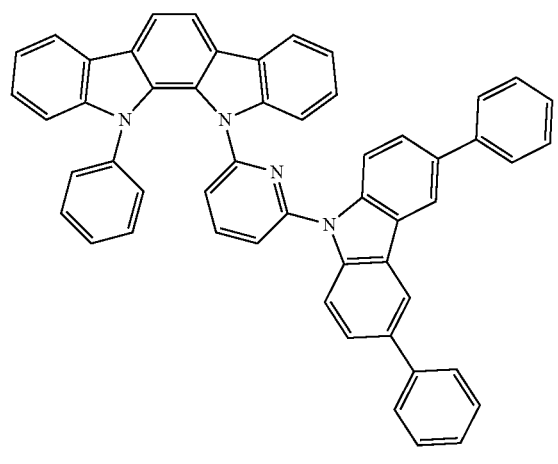
(A-8)

-continued
(A-9)
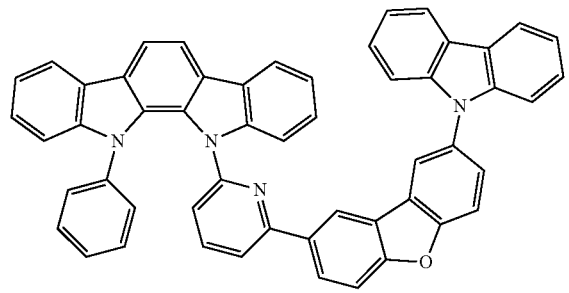
(A-10)
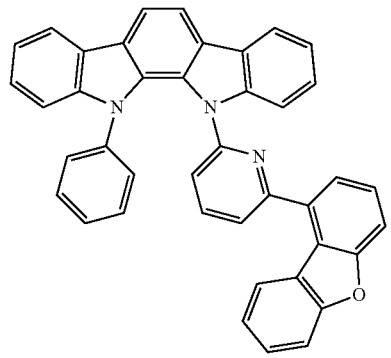
(A-11)
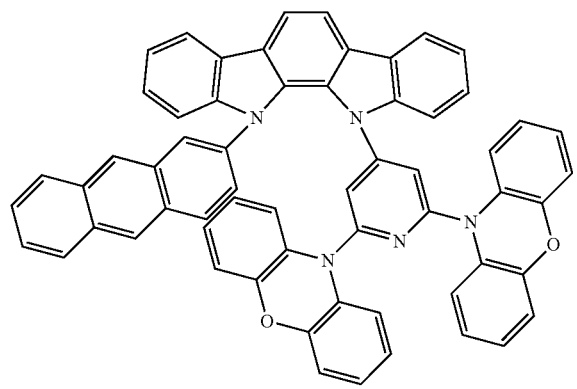
(A-12)
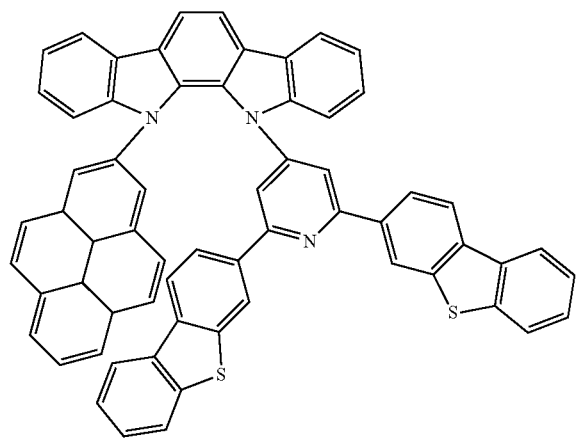
(A-13)
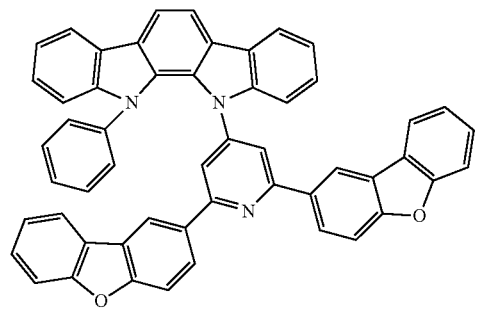
(A-14)
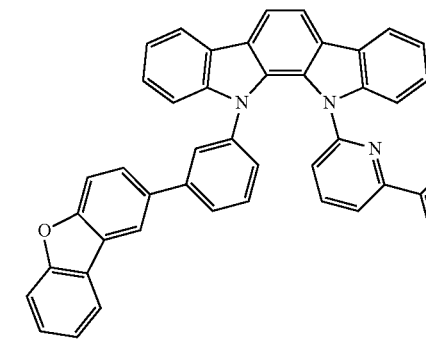
(A-15)
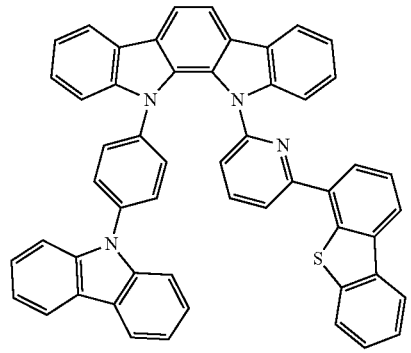
(A-16)
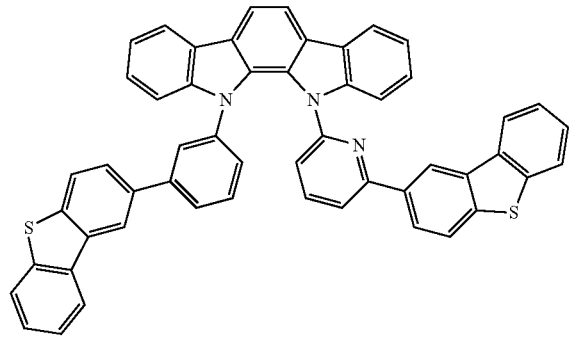

-continued
(A-17)
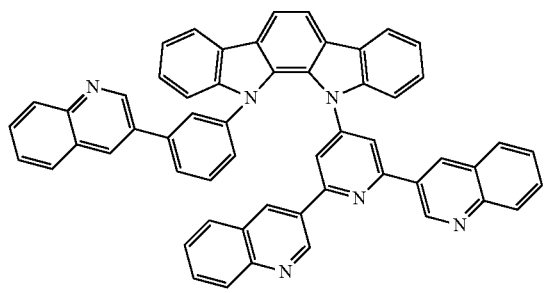
(A-18)
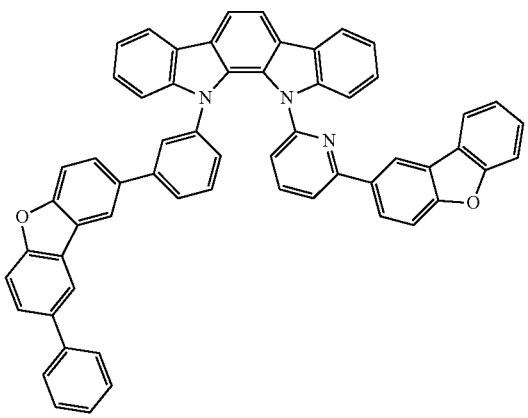
(A-19)
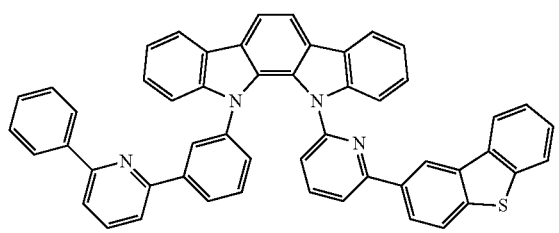
(A-20)
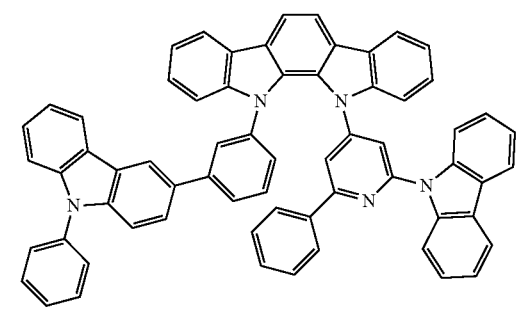
(A-21)
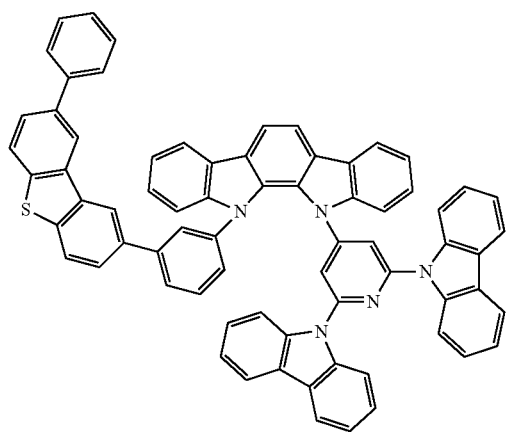
(A-22)
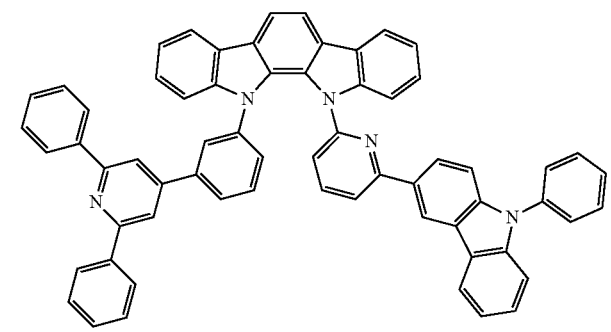
(A-23)
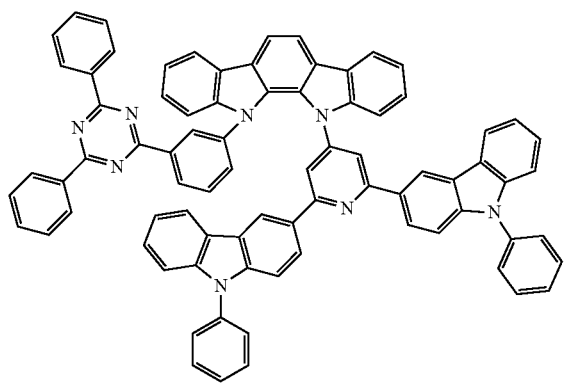
(A-24)
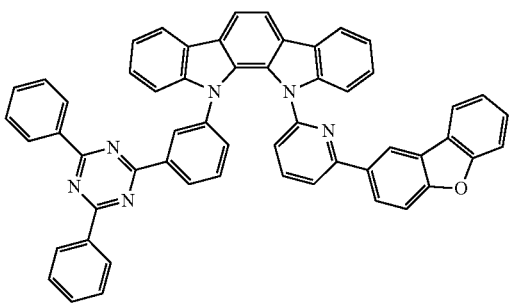

(A-25)
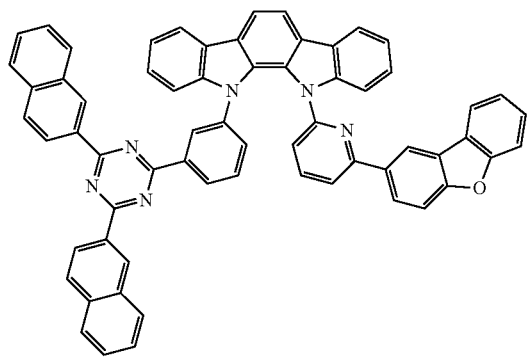
(A-26)
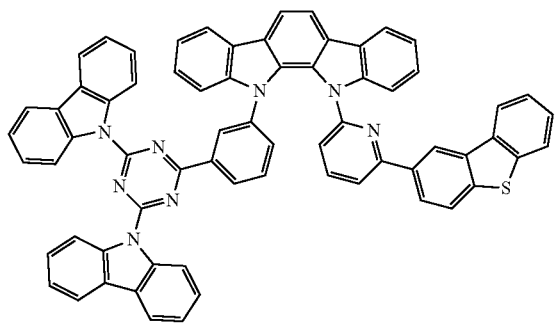
(A-27)
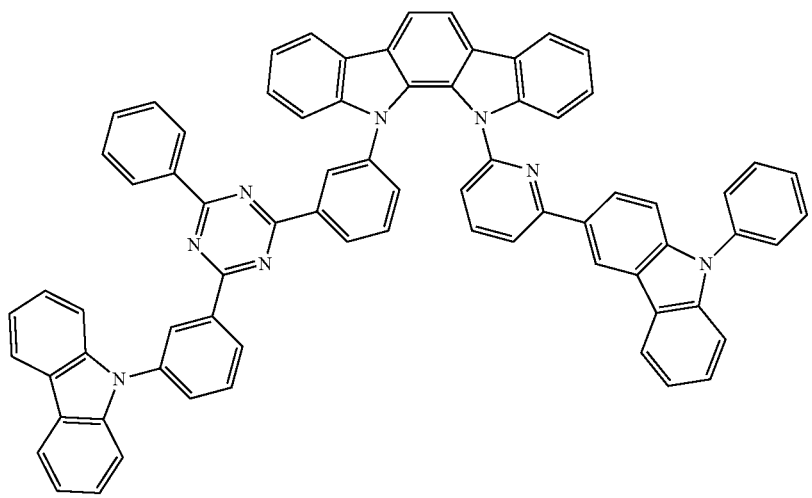
(A-28)
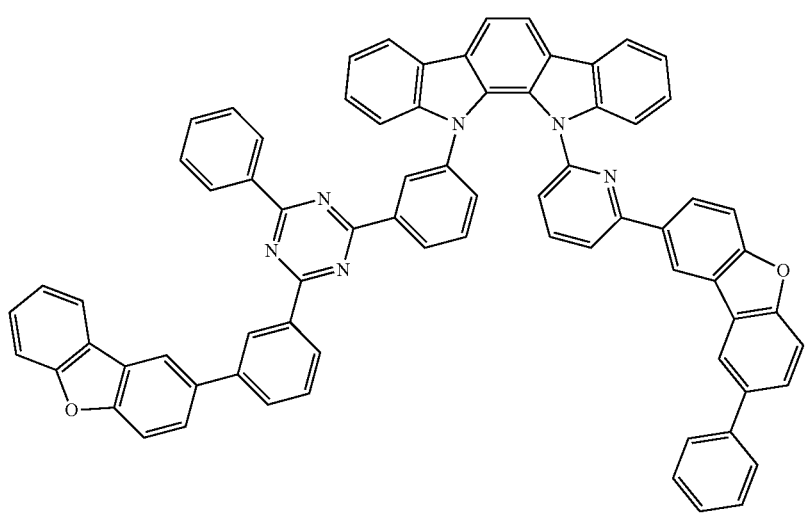

-continued
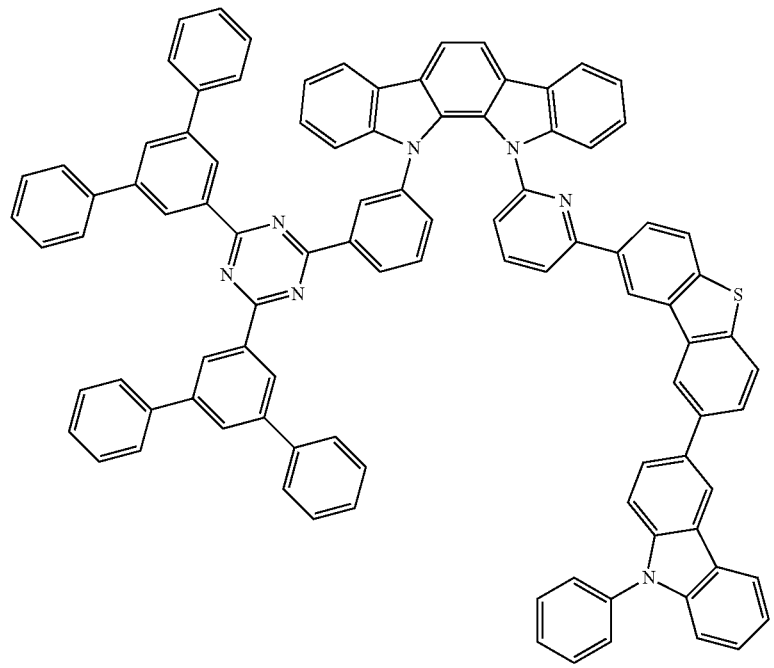
(A-29)
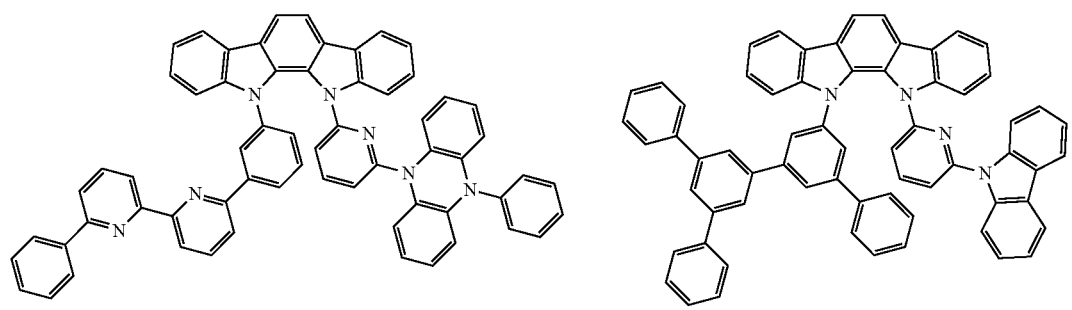
(A-30) (A-31)
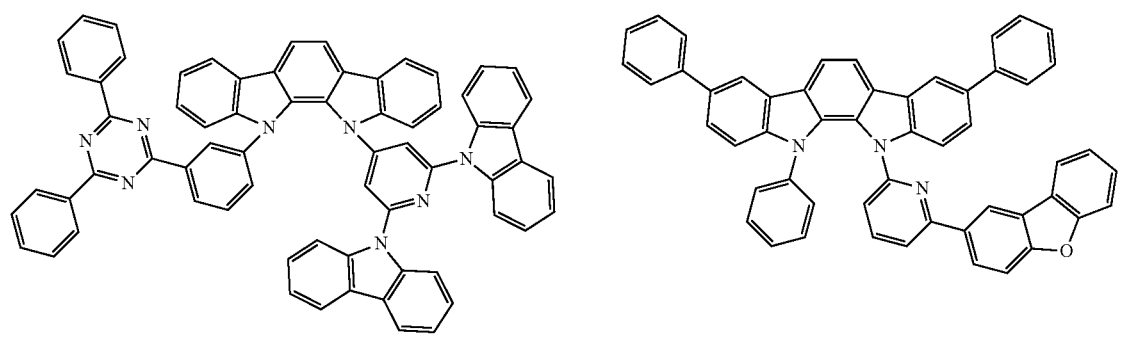
(A-32) (A-33)

-continued
(A-34)
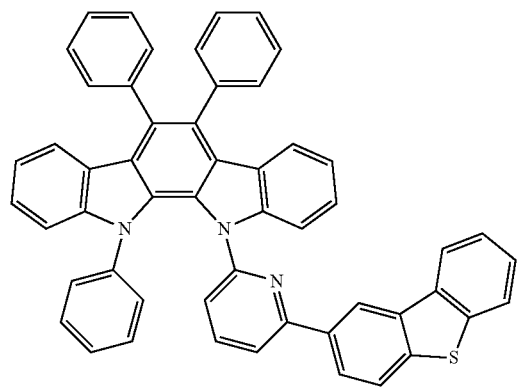
(A-35)
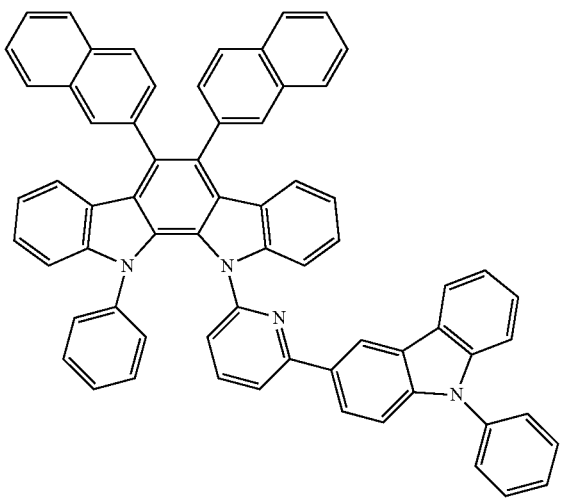
(A-36)
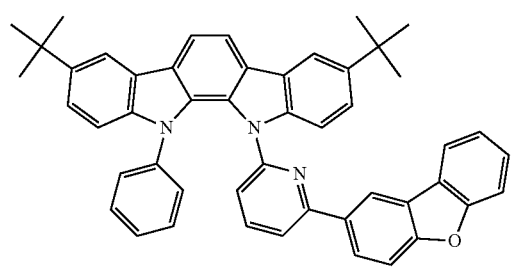
(A-37)
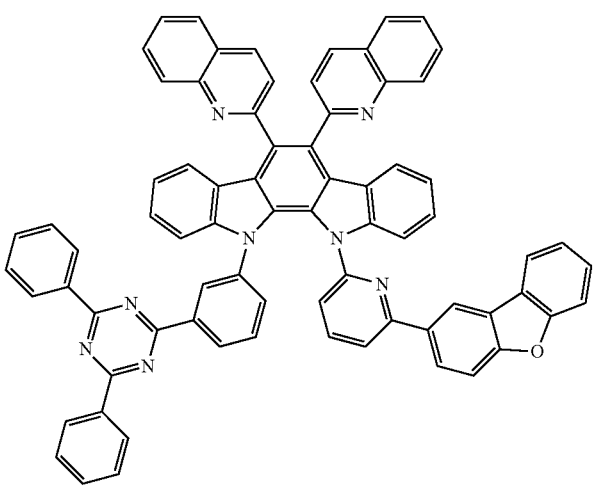
(A-38)
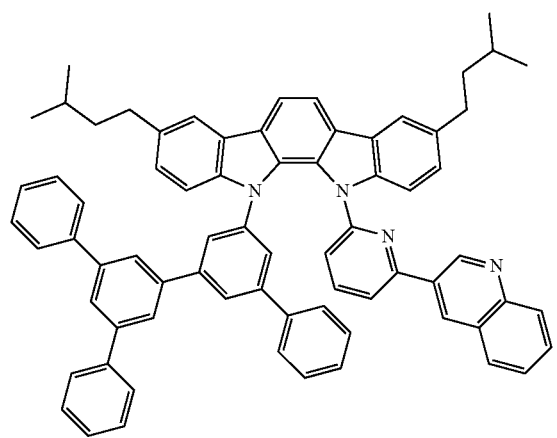
(A-39)
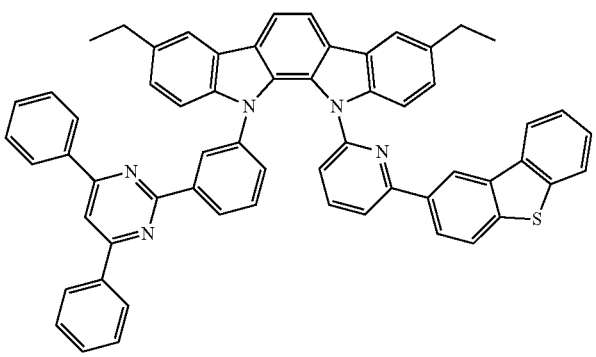

-continued
(A-40)
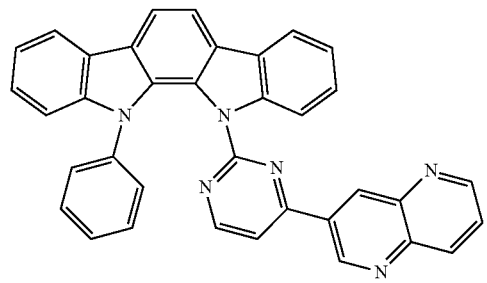
(A-41)
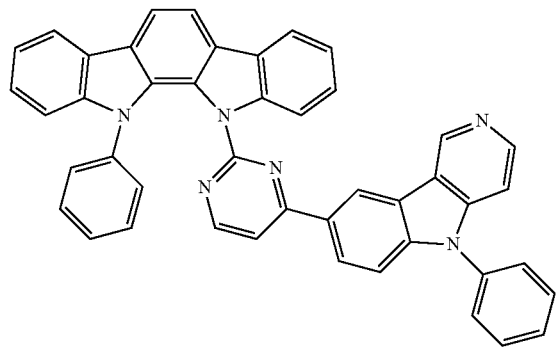
(A-42)
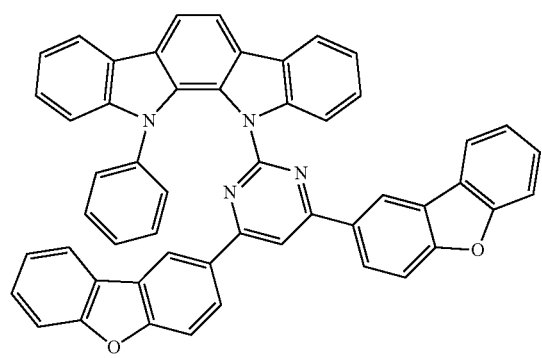
(A-43)
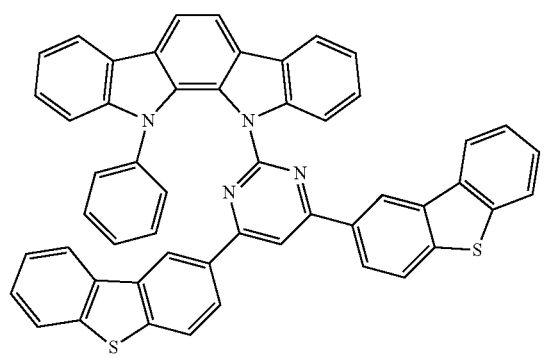
(A-44)
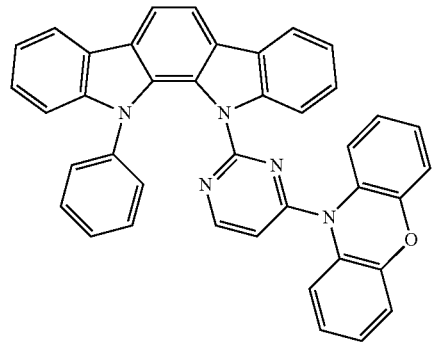
(A-45)
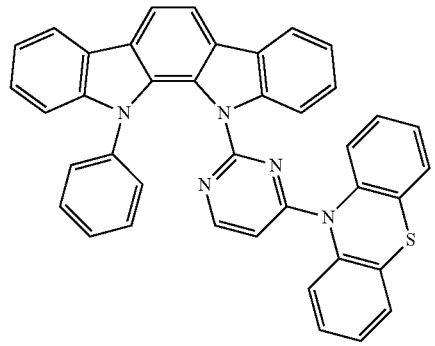
(A-46)
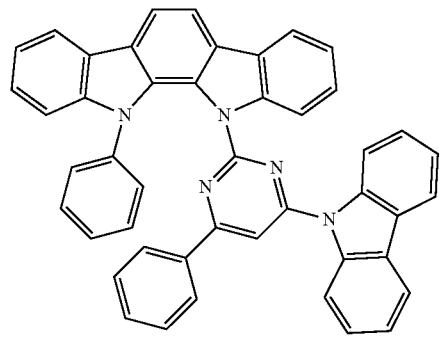
(A-47)
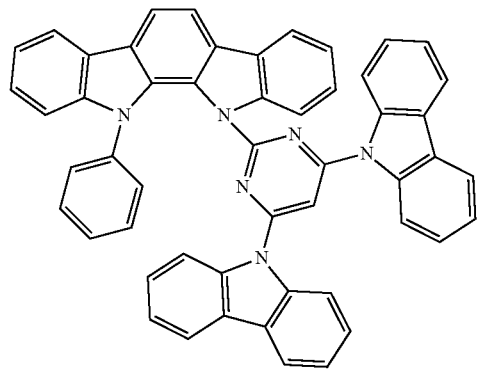

-continued
(A-48)
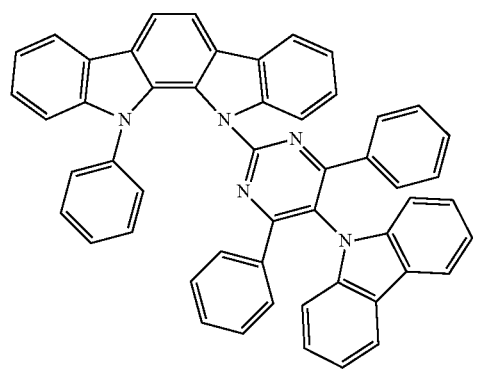
(A-49)
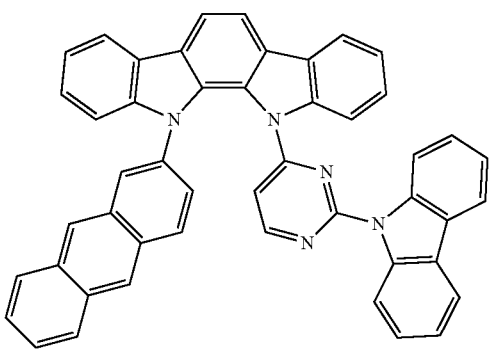
(A-50)
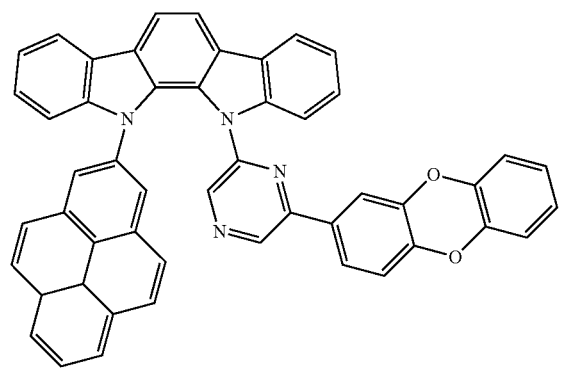
(A-51)
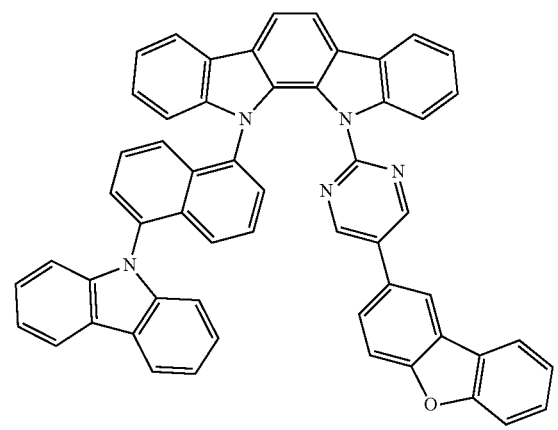
(A-52)
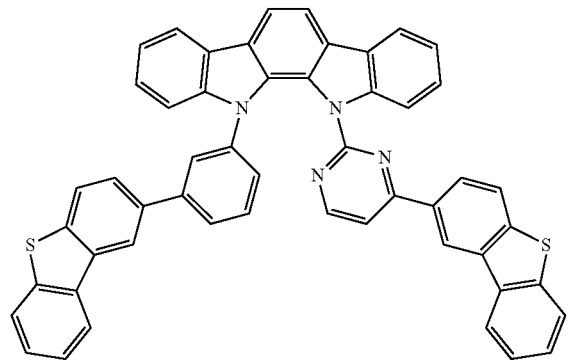
(A-53)
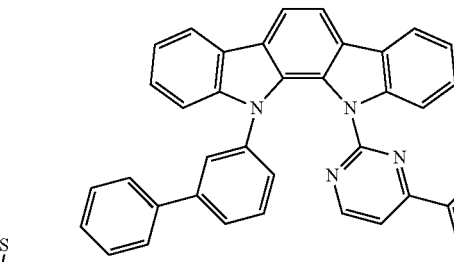
(A-54)
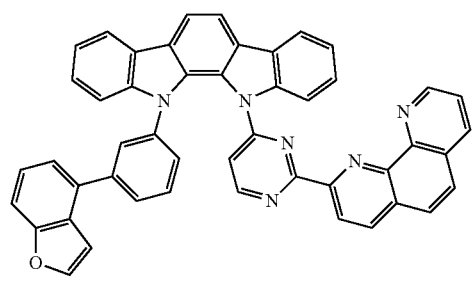
(A-55)
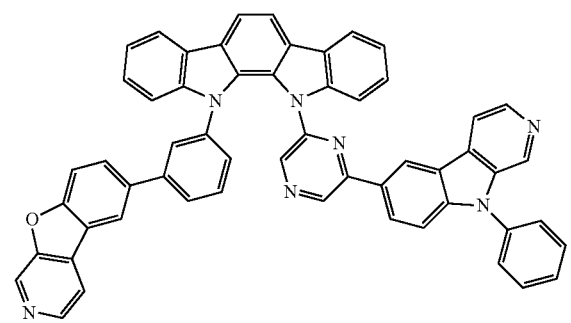

-continued
(A-56)
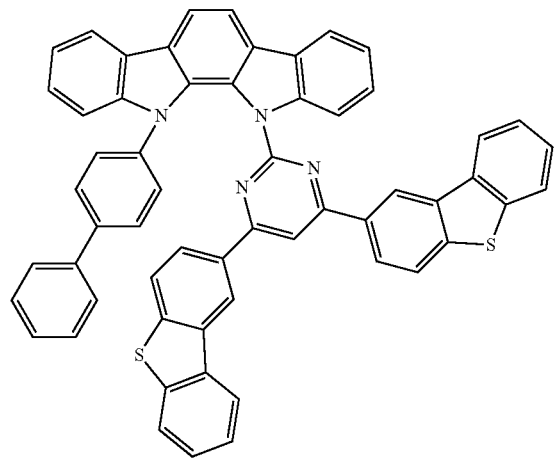
(A-57)
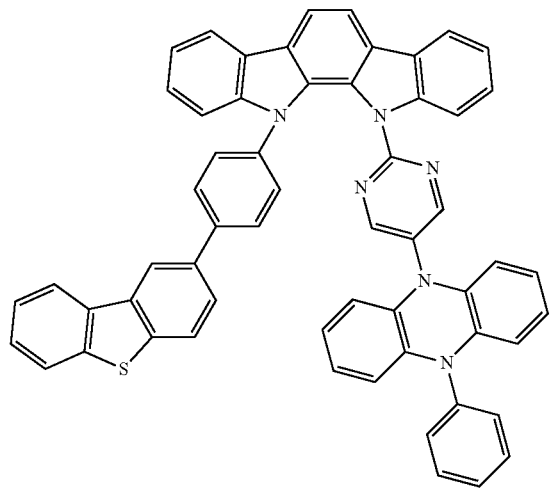
(A-58)
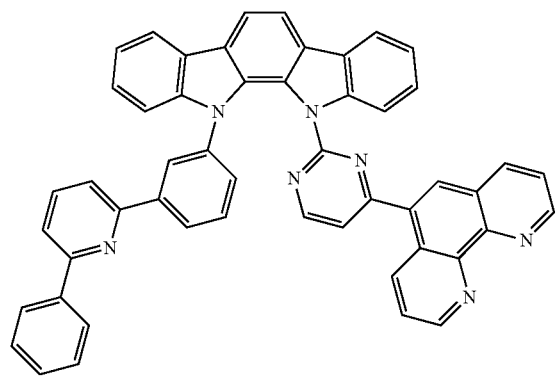
(A-59)
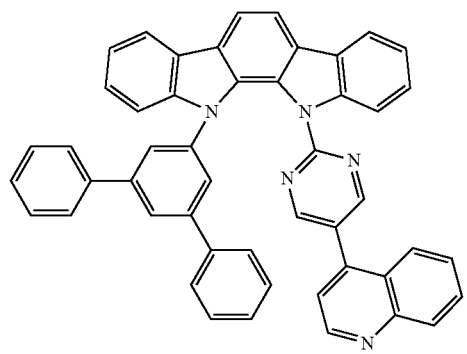
(A-59)
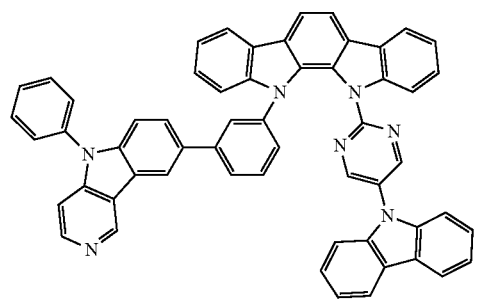
(A-60)
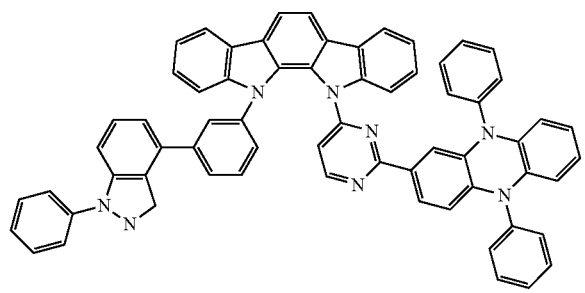
(A-62)
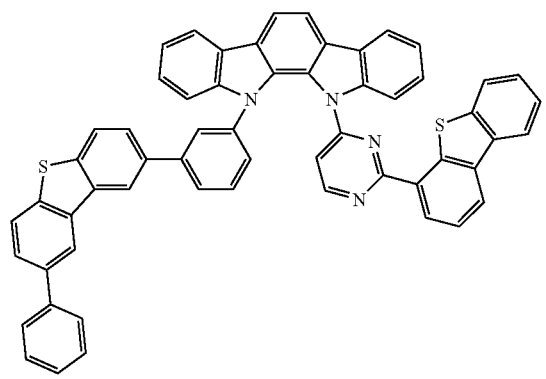
(A-63)
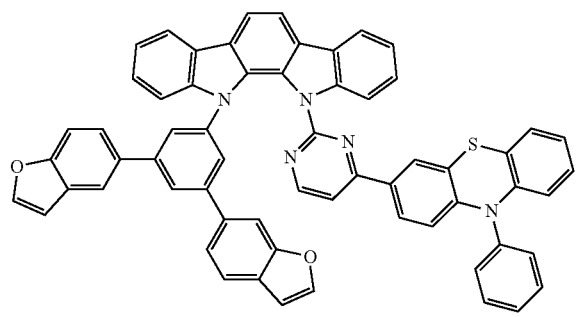

-continued
(A-64)
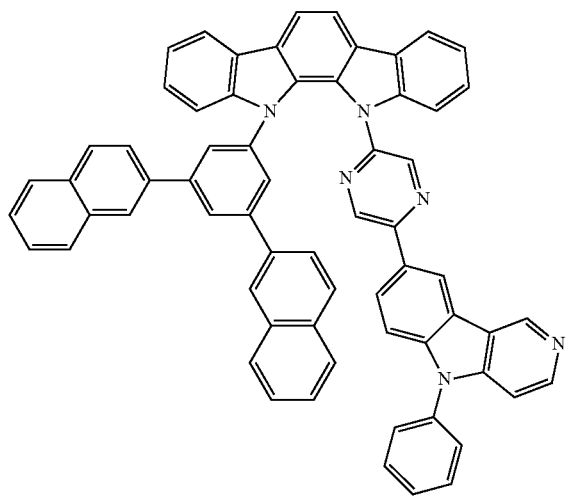
(A-65)
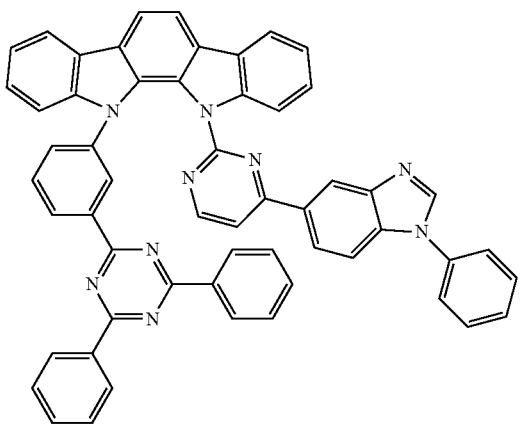
(A-66)
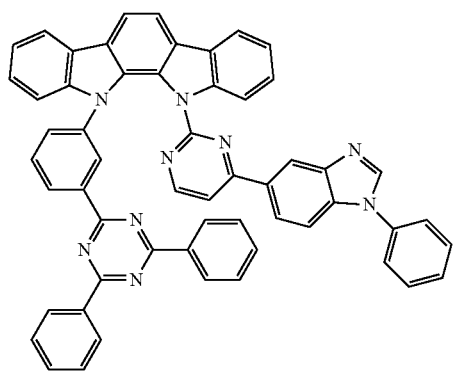
(A-67)
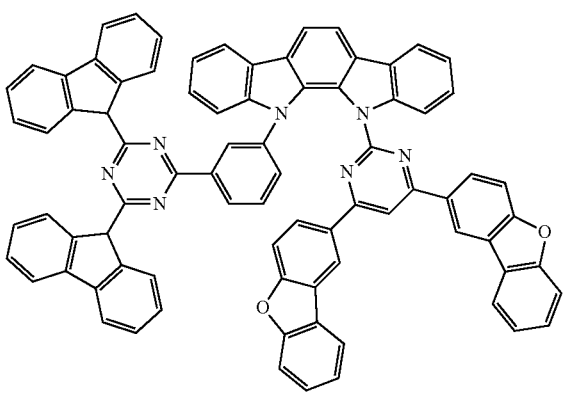
(A-68)
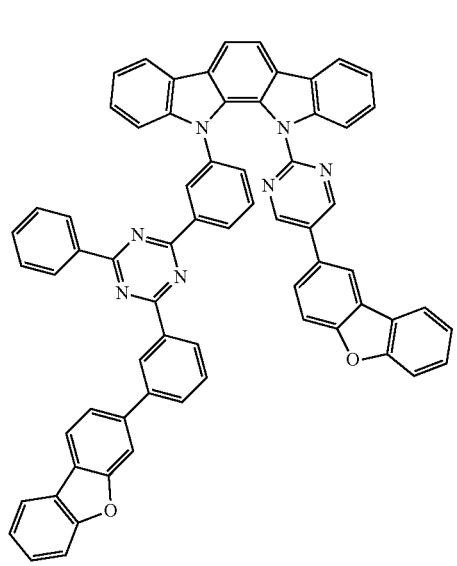
(A-69)
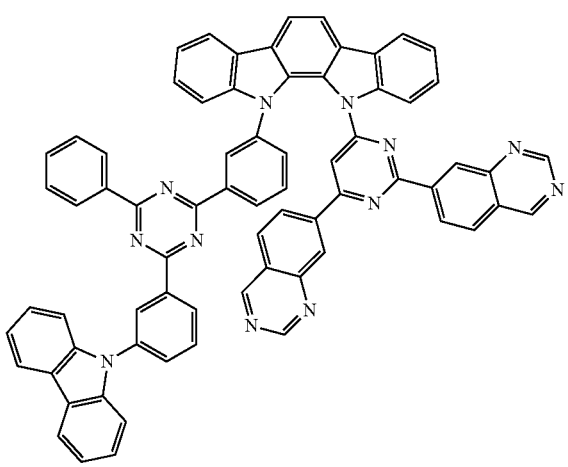

-continued
(A-70)
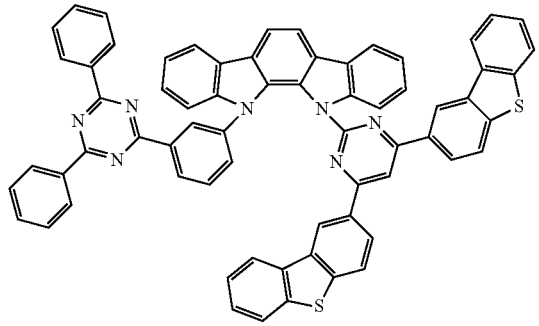
(A-71)
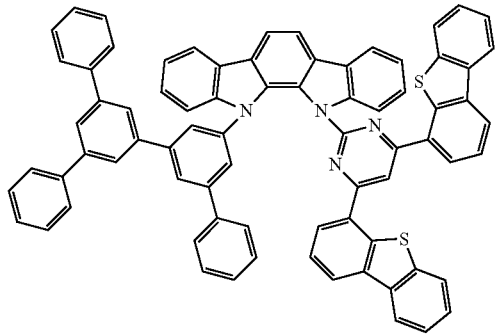
(A-72)
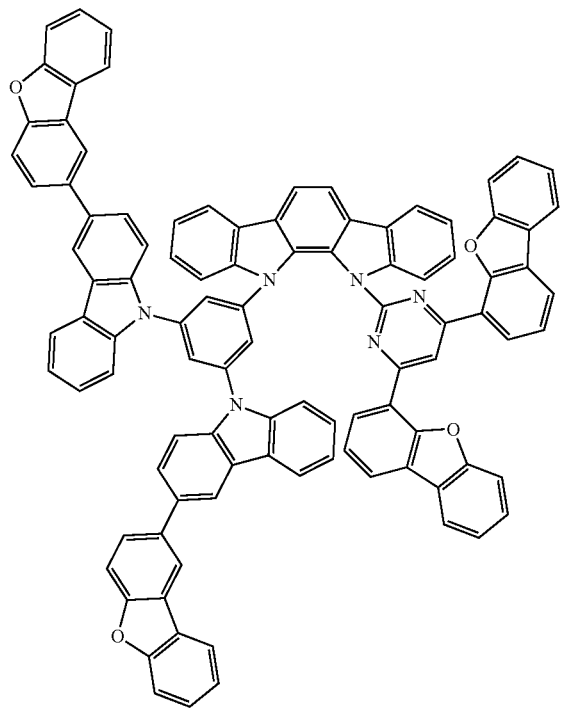
(A-73)
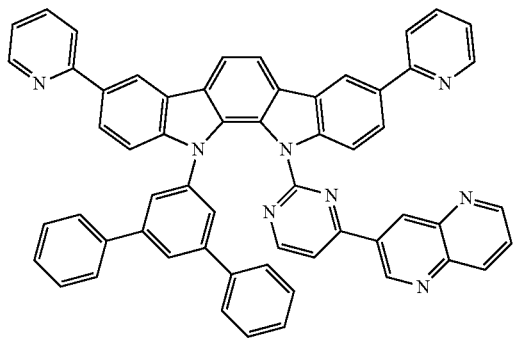
(A-74)
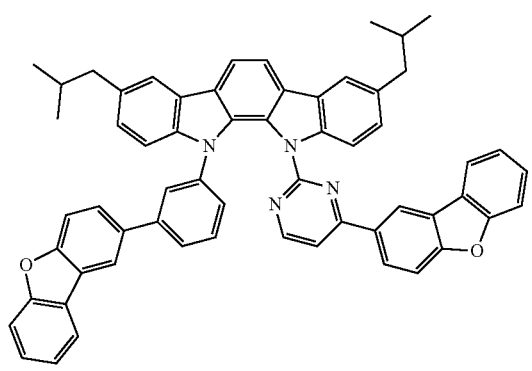
(A-75)
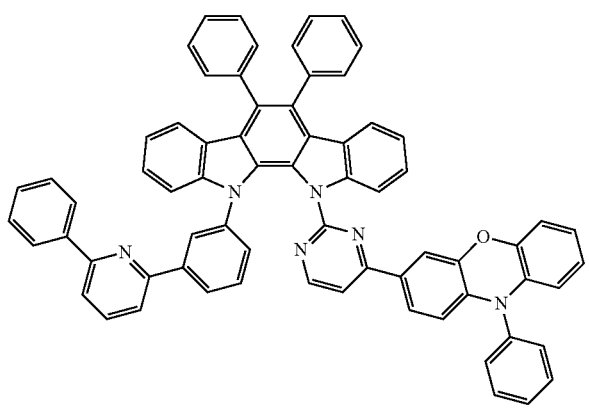

(A-76)
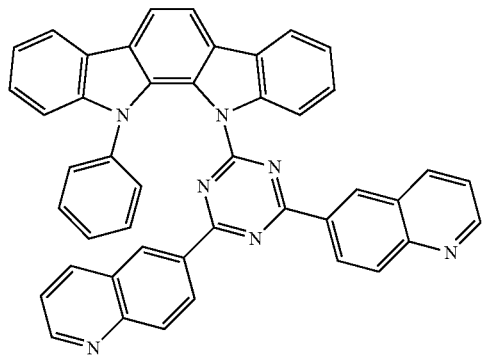
(A-77)
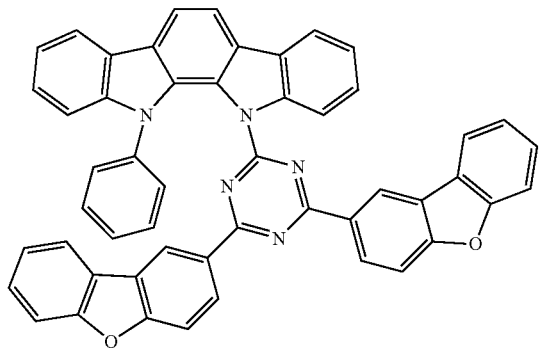
(A-78)
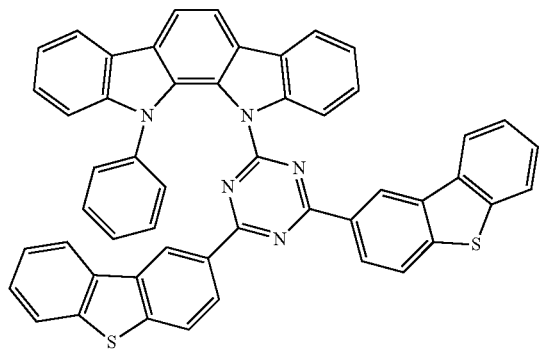
(A-79)
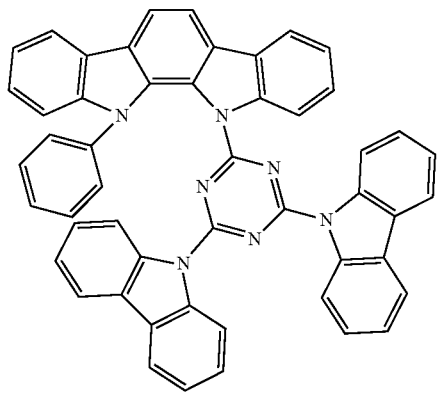
(A-80)
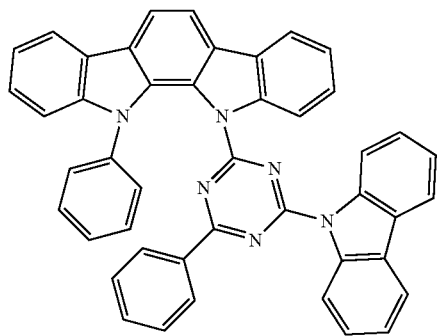
(A-81)
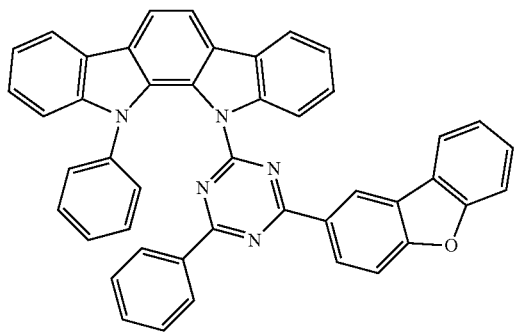
(A-82)
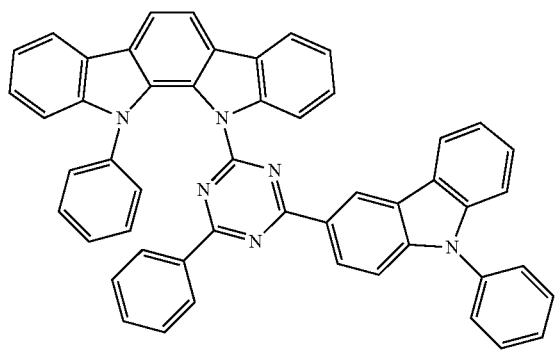
(A-83)
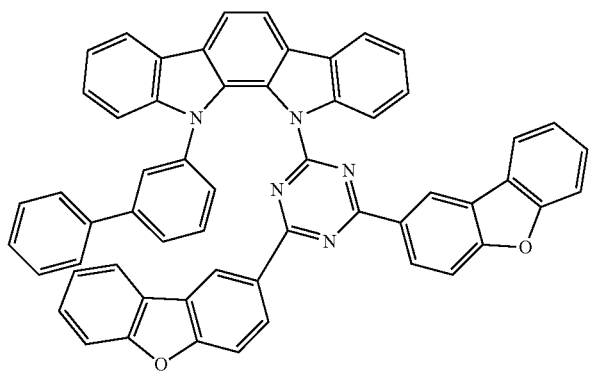

-continued
(A-84)
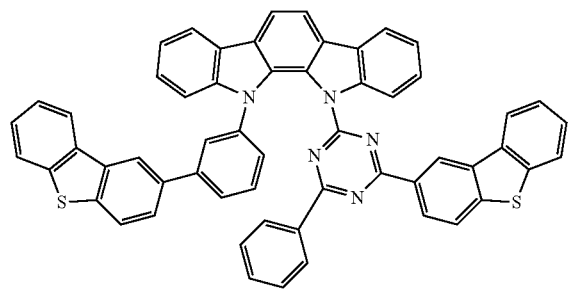
(A-85)
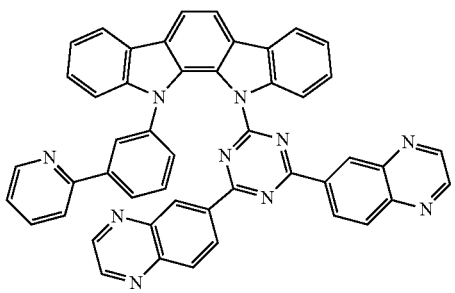
(A-86)
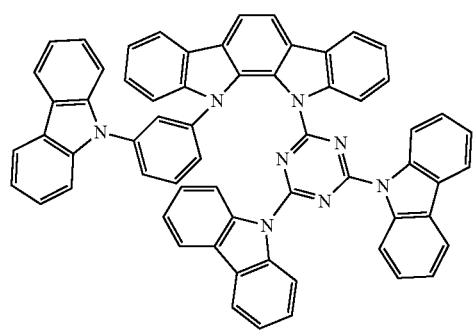
(A-87)
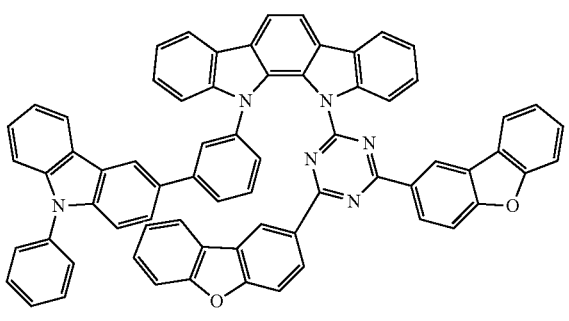
(A-88)
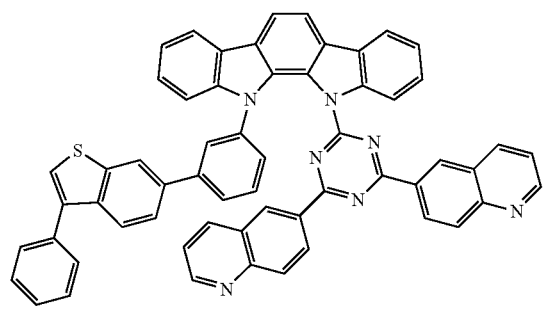
(A-89)
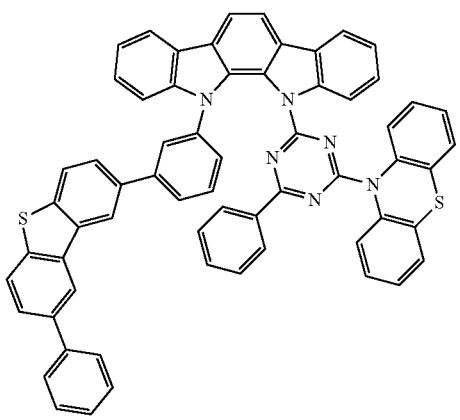
(A-90)
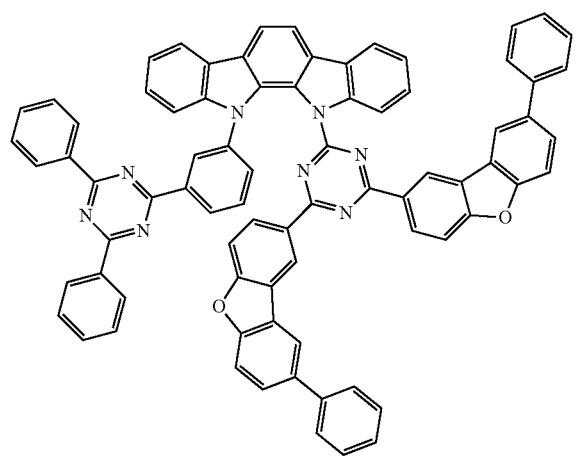
(A-91)
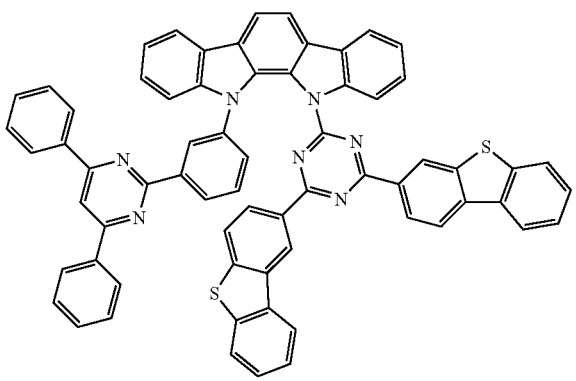

-continued
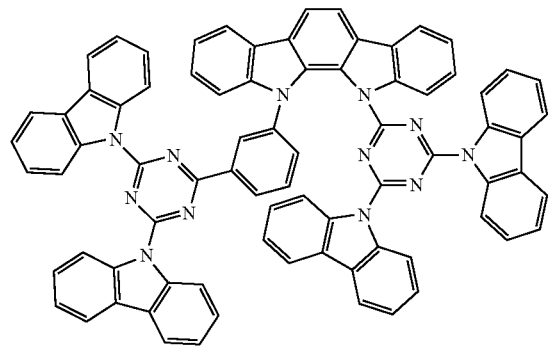
(A-92)
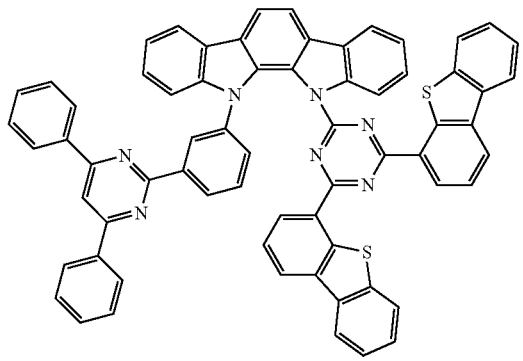
(A-93)
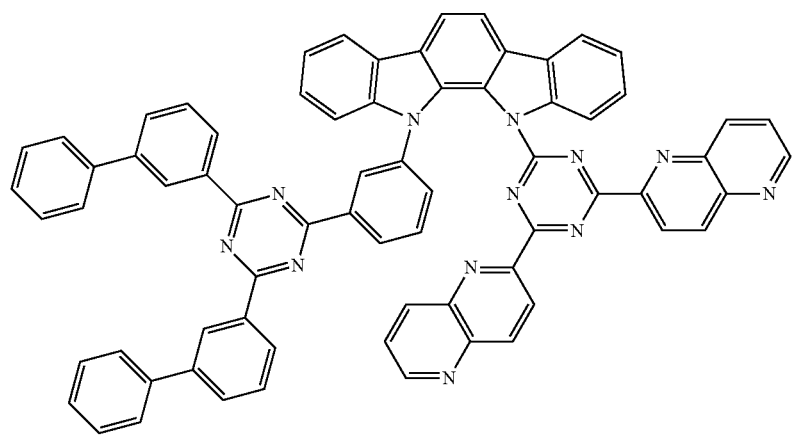
(A-94)
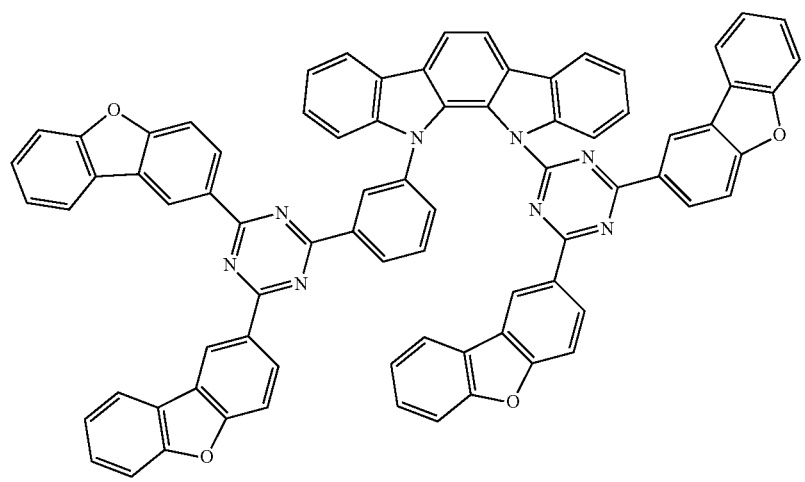
(A-95)

-continued
(A-96)
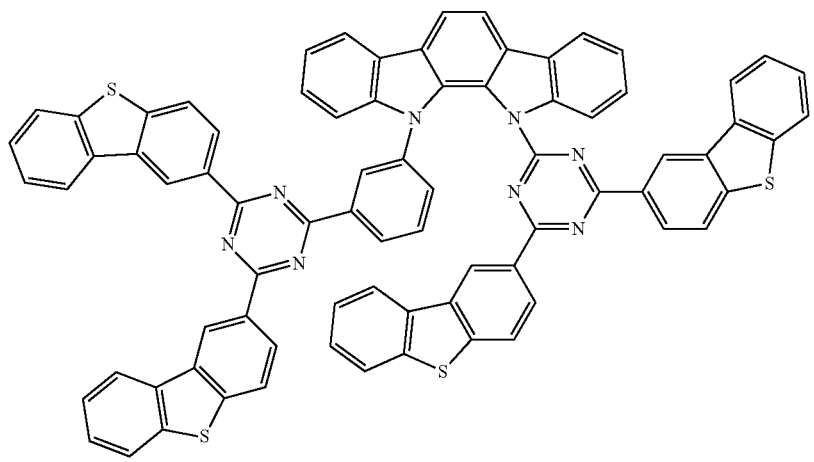
(A-97)
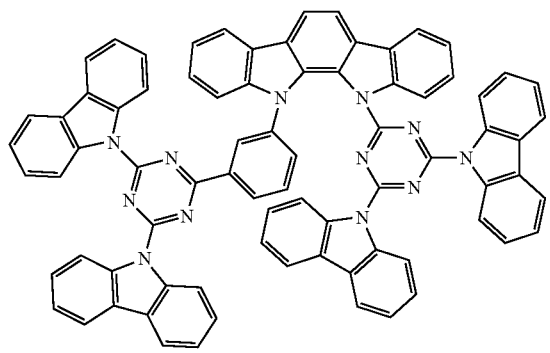
(A-98)
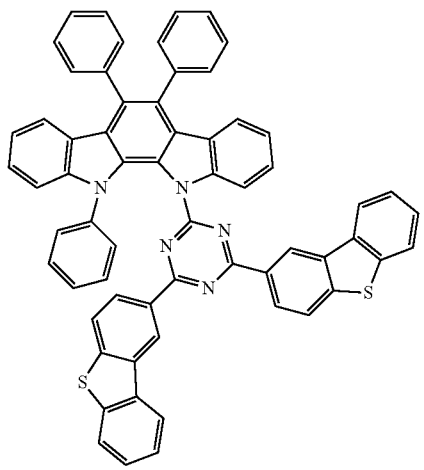
(A-99)
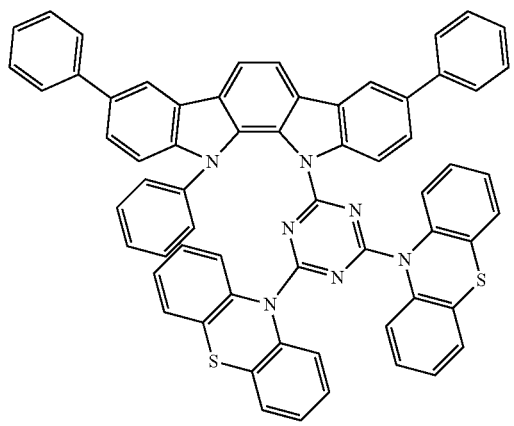
(A-100)
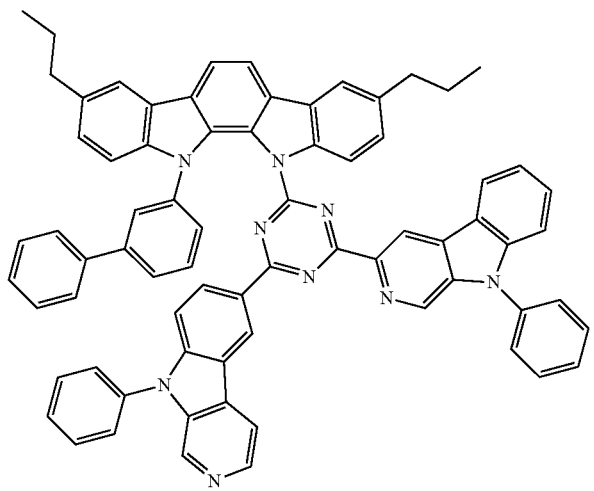

-continued
(A-101)
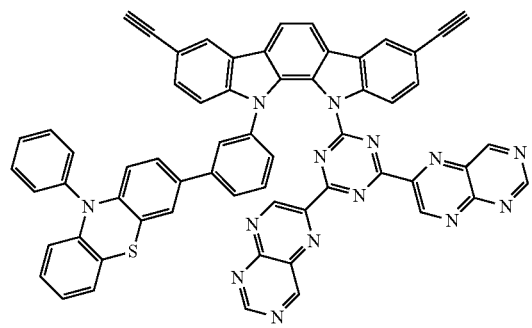
(A-102)
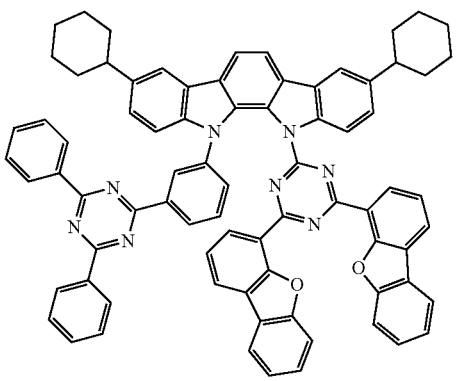
(B-1)
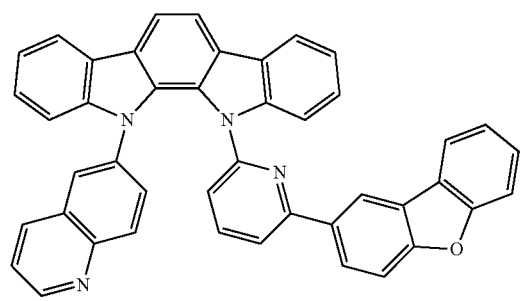
(B-2)
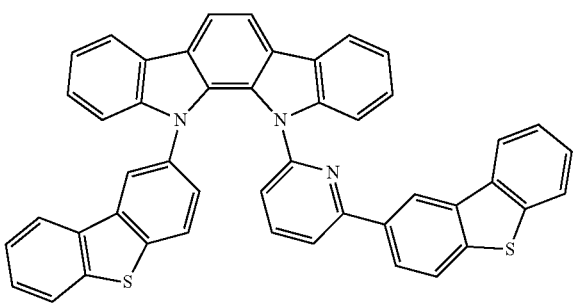
(B-3)
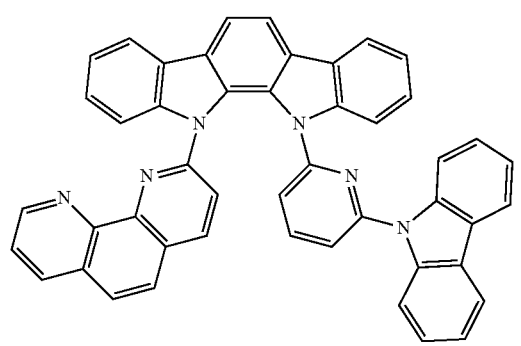
(B-4)
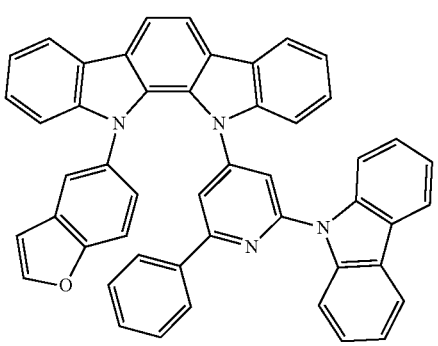
(B-5)
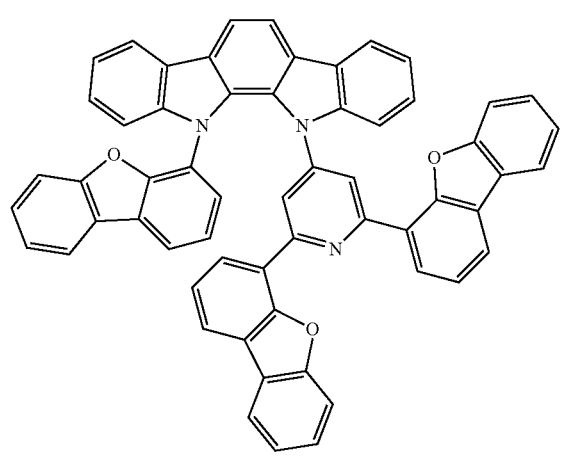
(B-6)
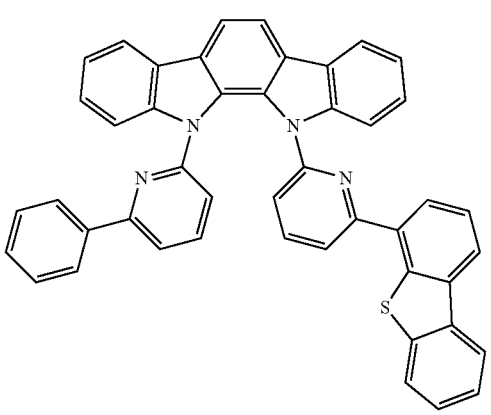

-continued
(B-7)
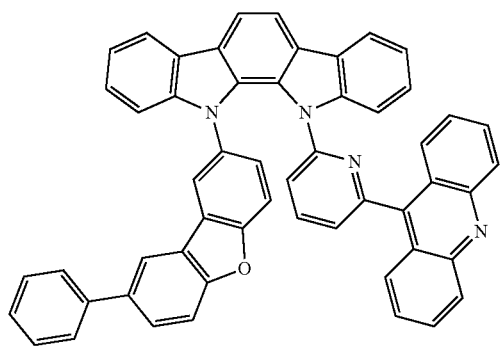
(B-8)
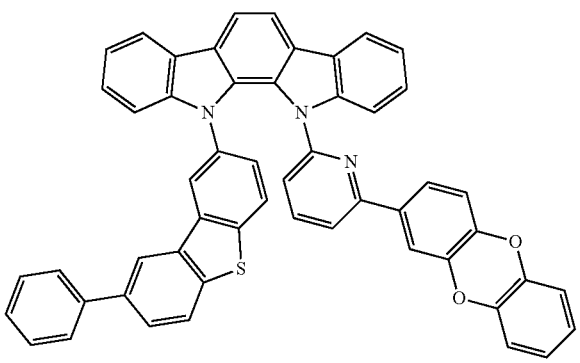
(B-9)
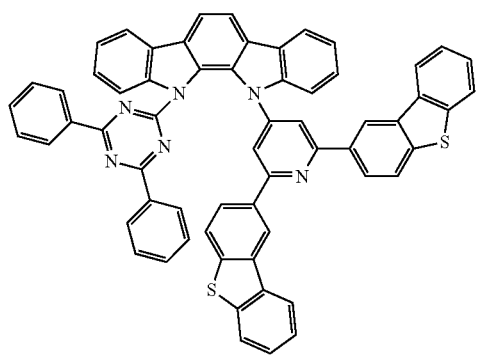
(B-10)
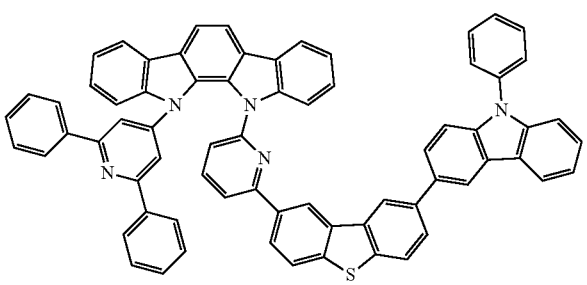
(B-11)
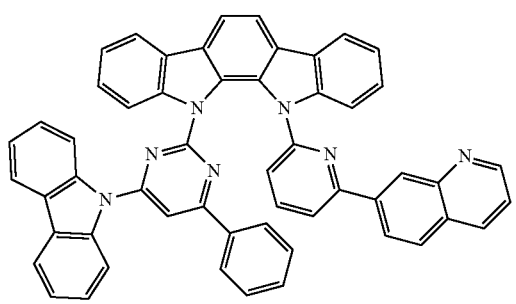
(B-12)
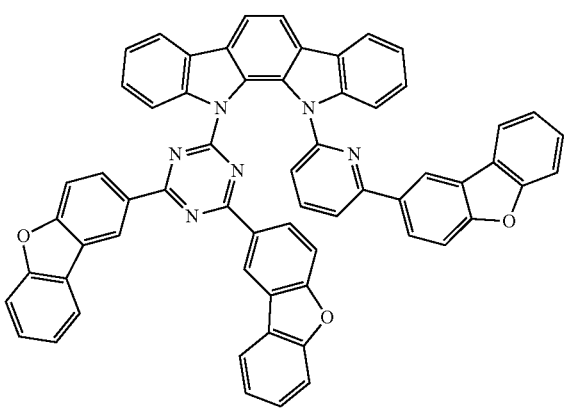
(B-13)
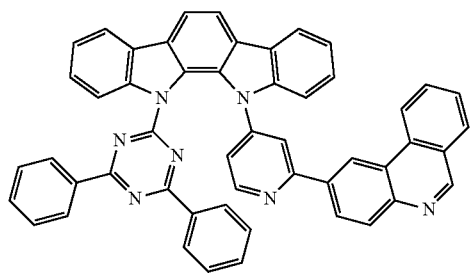
(B-14)
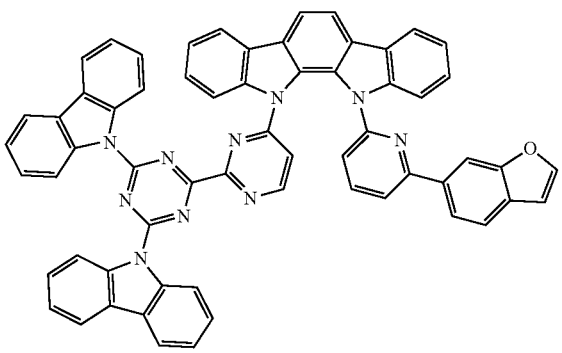

-continued
(B-15)
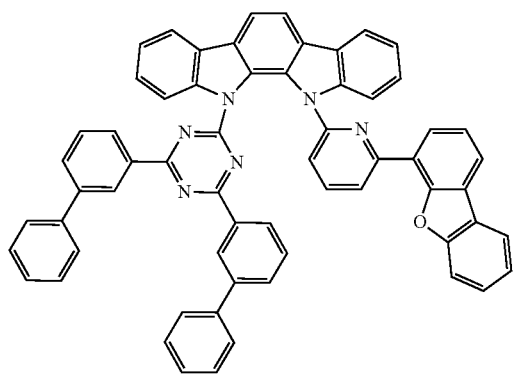
(B-16)
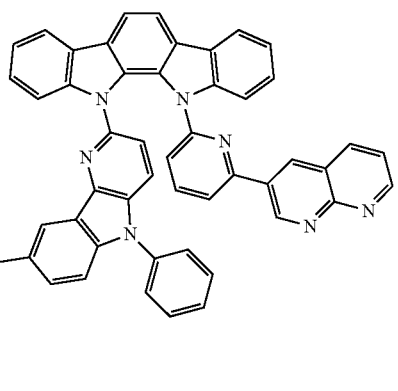
(B-17)
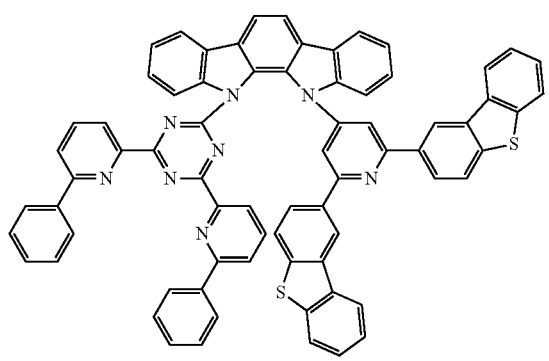
(B-18)
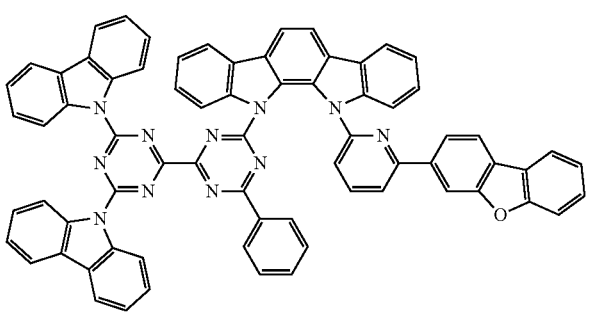
(B-19)
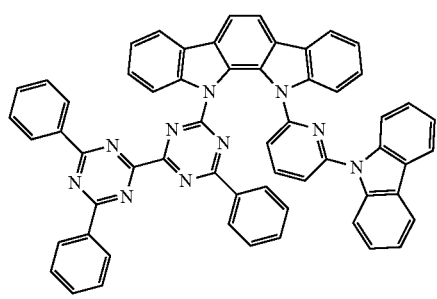
(B-20)
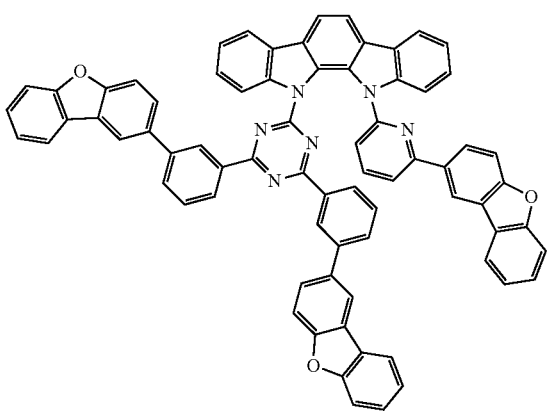

-continued
(B-21)
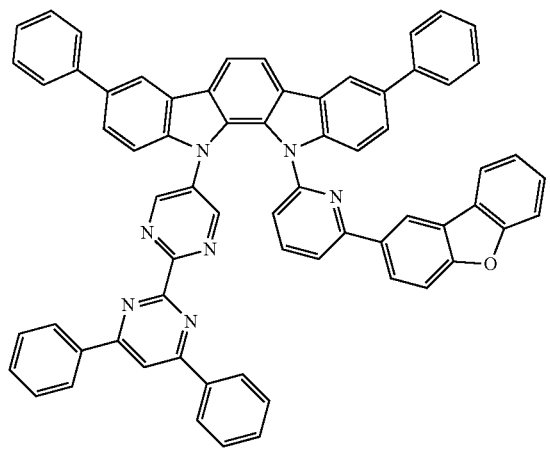
(B-22)
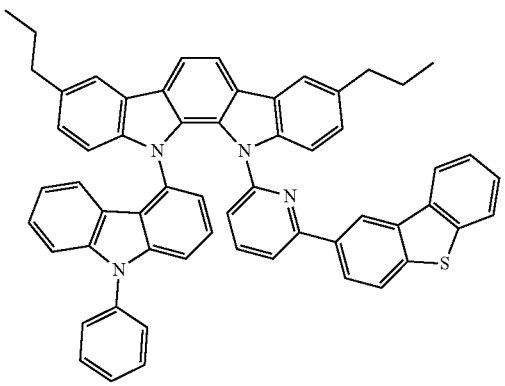
(B-23)
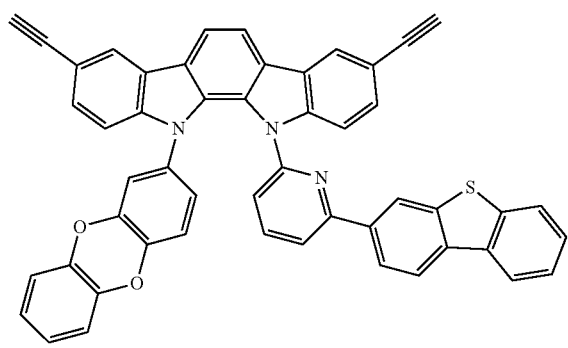
(B-24)
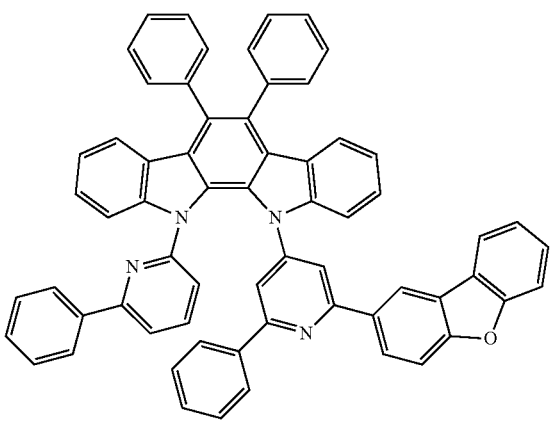
(B-25)
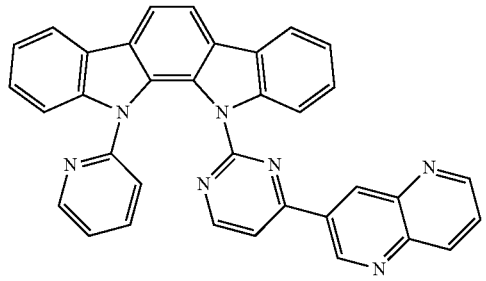
(B-26)
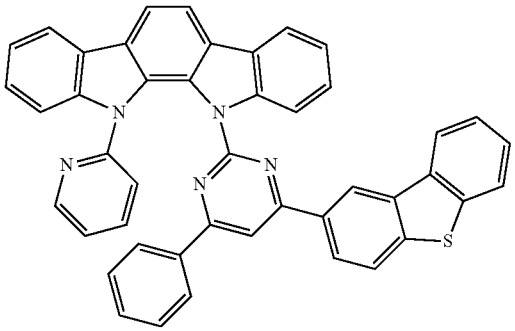
(B-27)
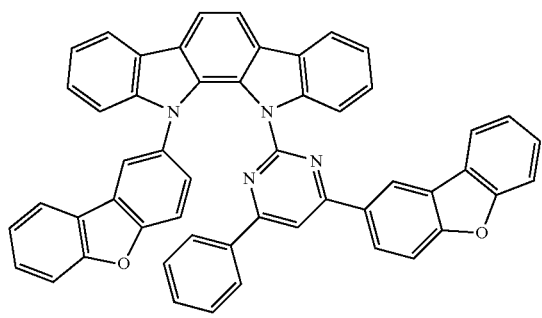
(B-28)
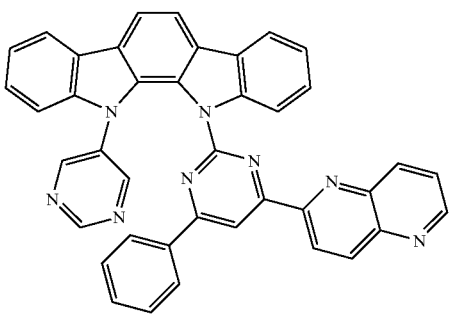

-continued
(B-29)
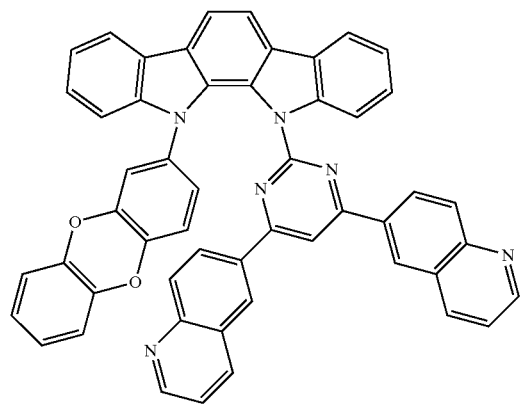
(B-30)
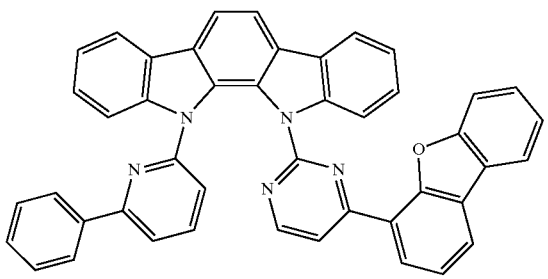
(B-31)
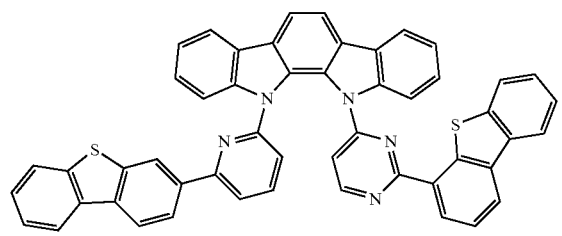
(B-32)
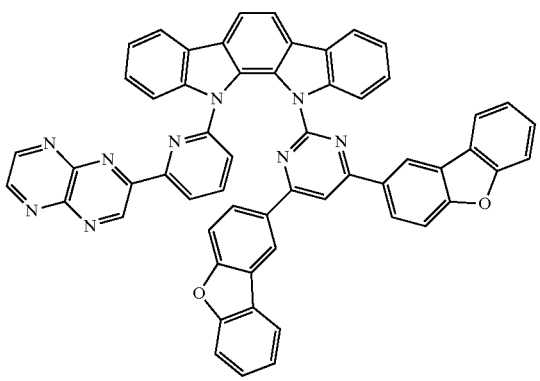
(B-33)
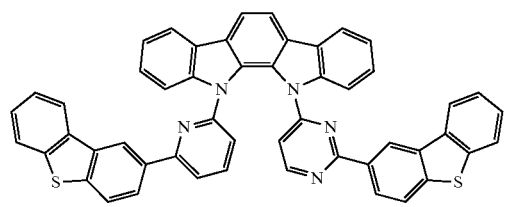
(B-34)
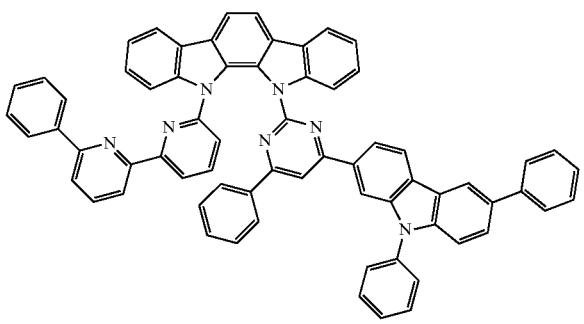
(B-35)
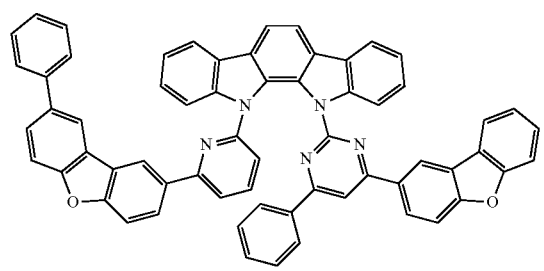
(B-36)
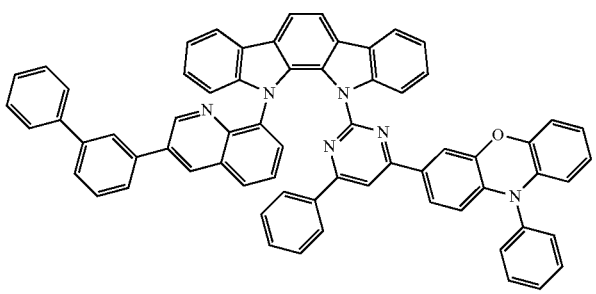

-continued
(B-37)
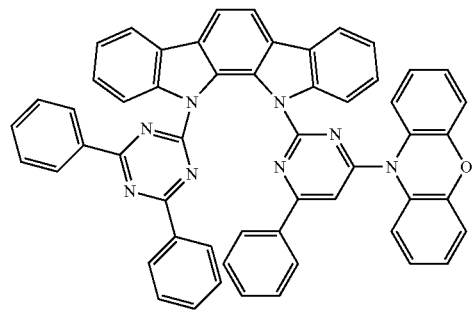
(B-38)
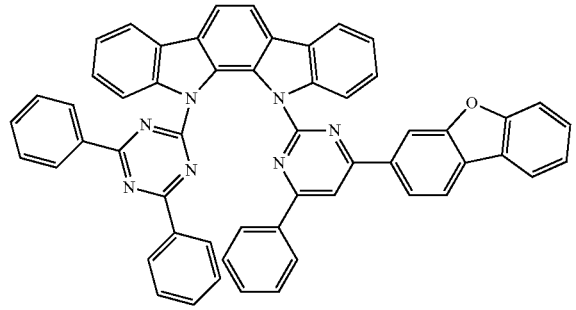
(B-39)
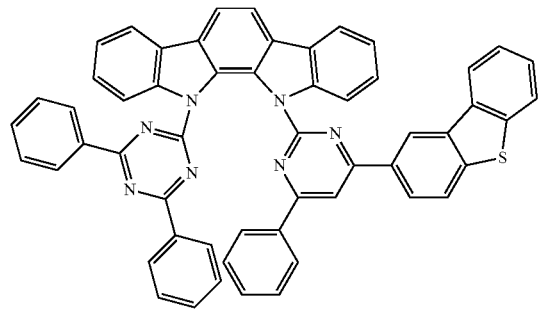
(B-40)
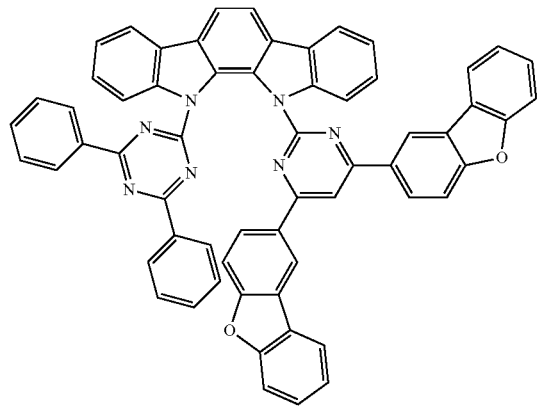
(B-41)
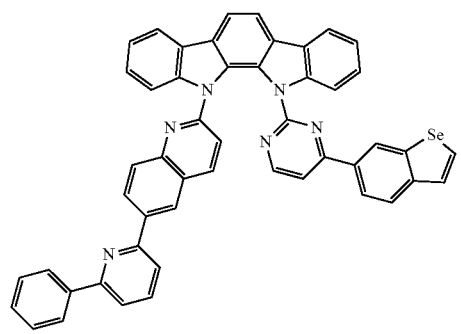
(B-42)
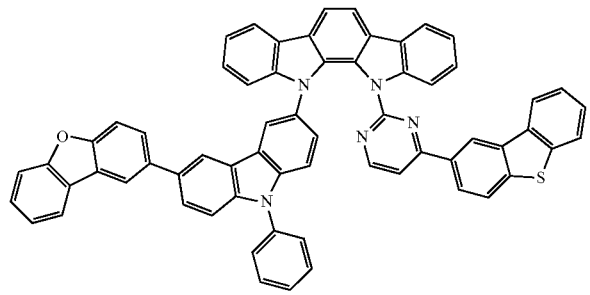
(B-43)
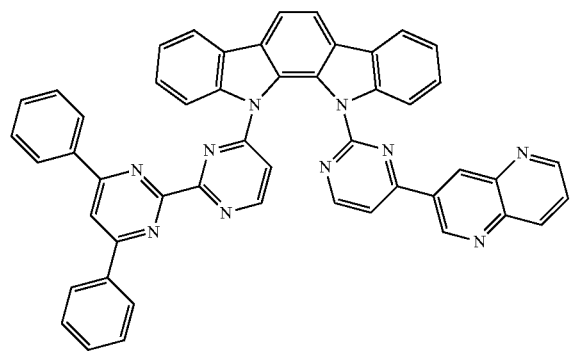
(B-44)
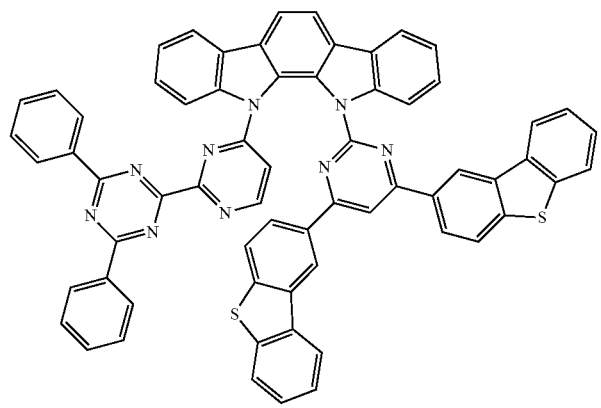

(B-45)
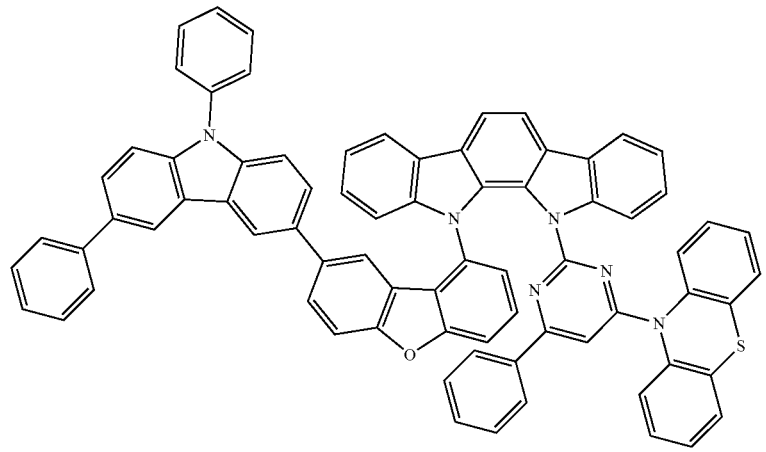
(B-46)
(B-47)
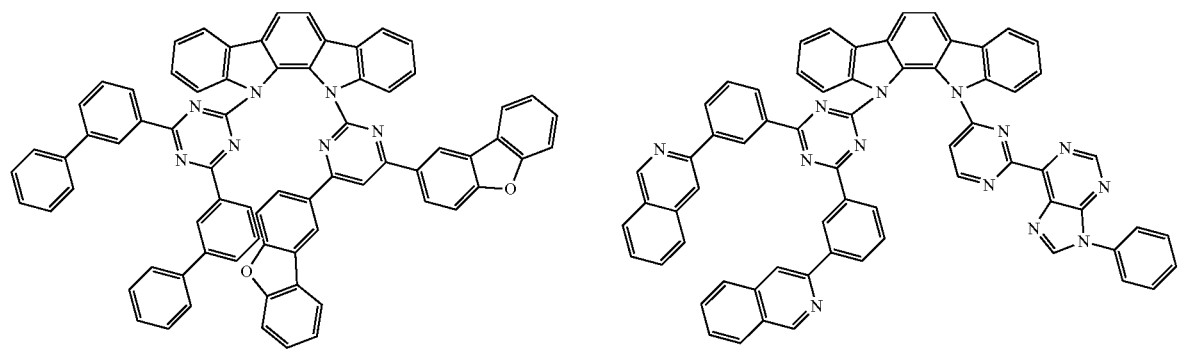
(B-48)
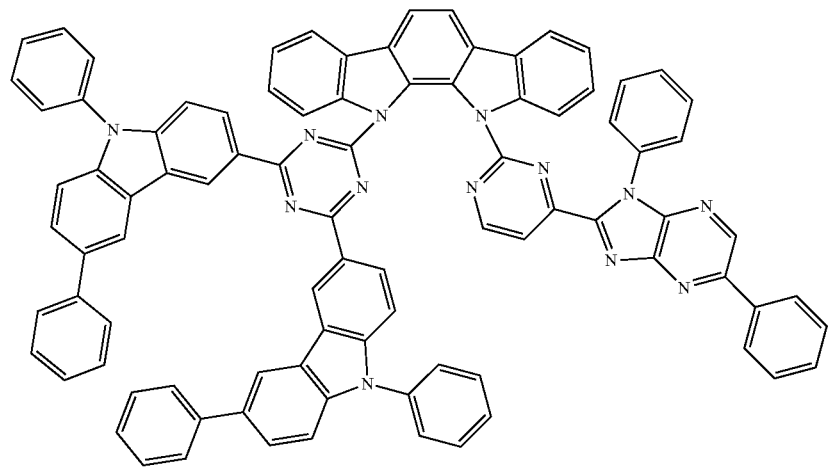

-continued
(B-49)
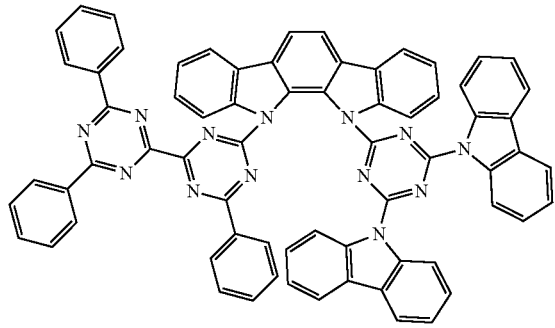
(B-50)
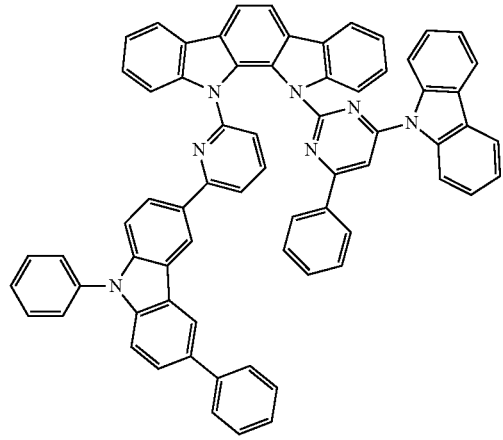
(B-51)
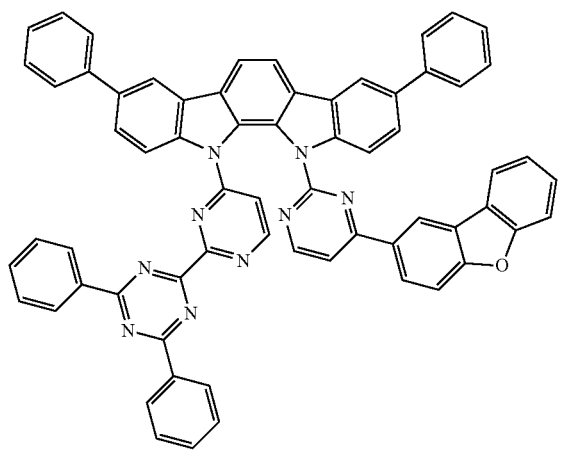
(B-52)
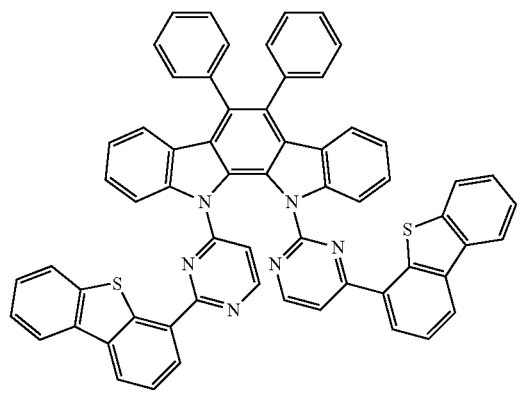
(B-53)
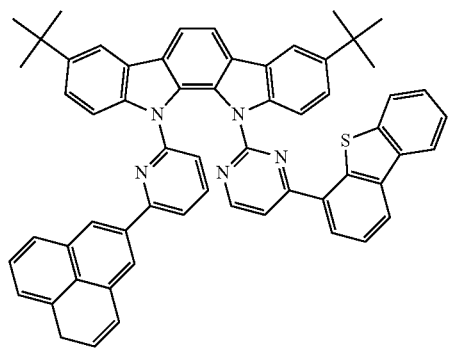
(B-54)
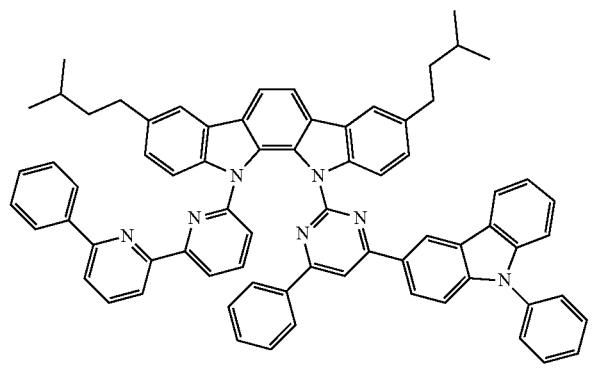

-continued
(B-55)
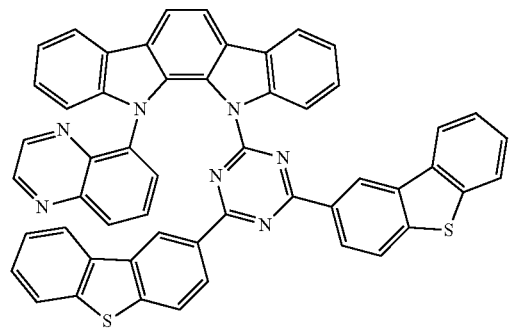
(B-56)
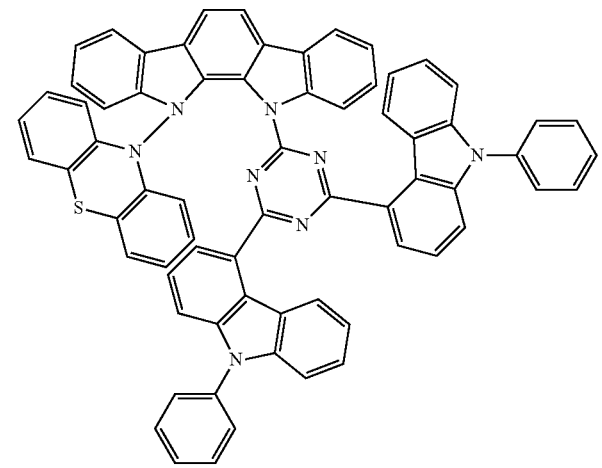
(B-57)
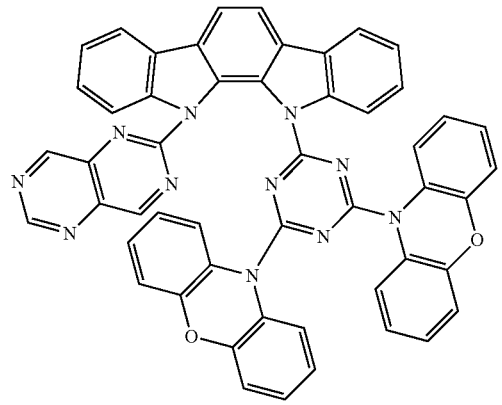
(B-58)
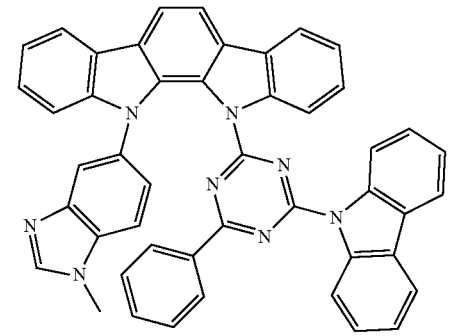
(B-59)
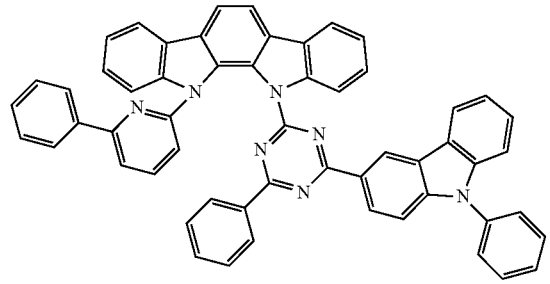
(B-60)
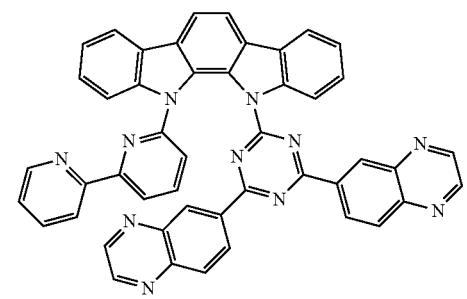
(B-61)
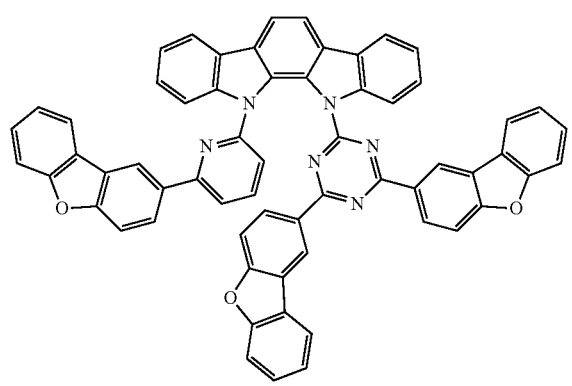
(B-62)
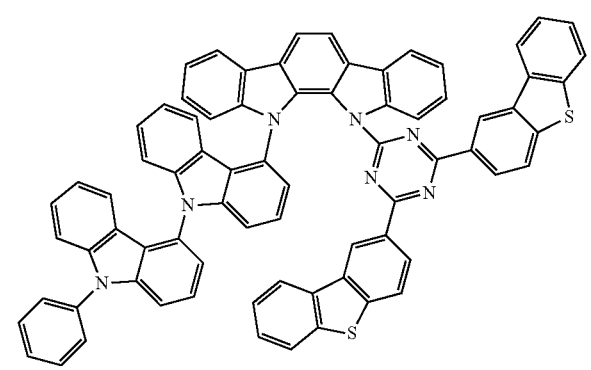

-continued
(B-63)
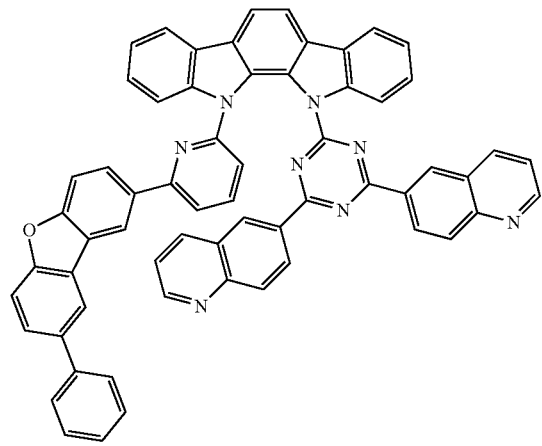
(B-64)
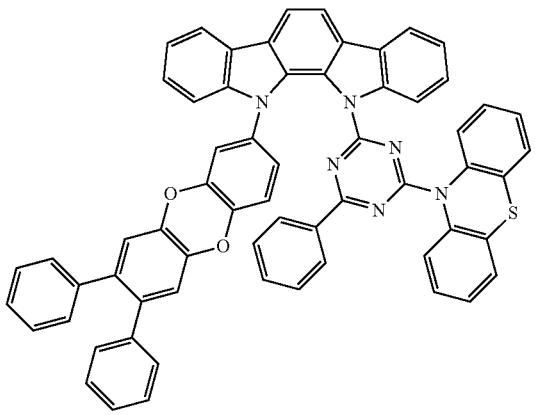
(B-65)
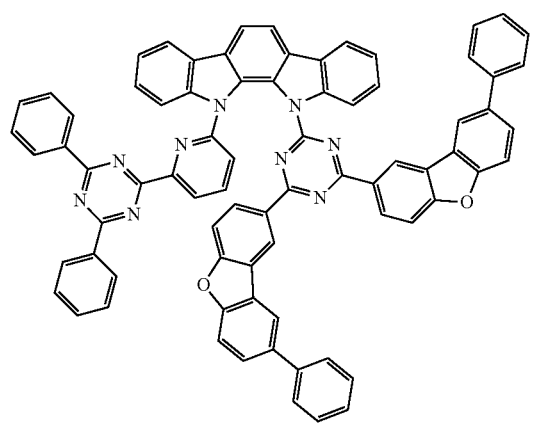
(B-66)
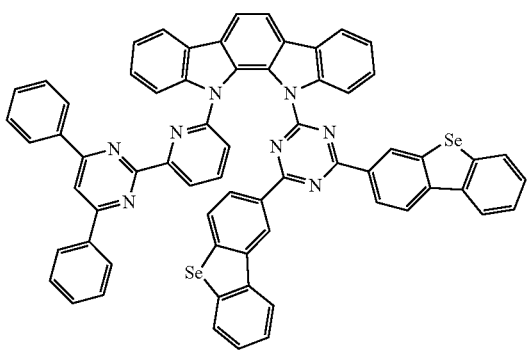
(B-67)
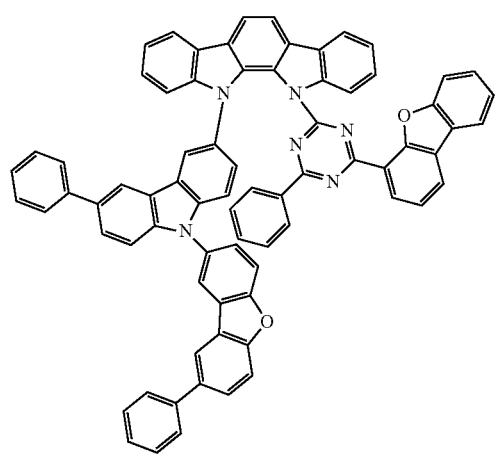
(B-68)
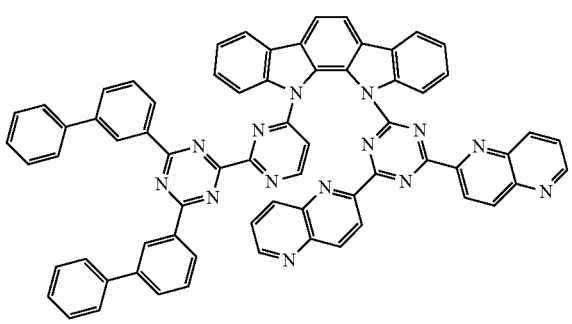

-continued
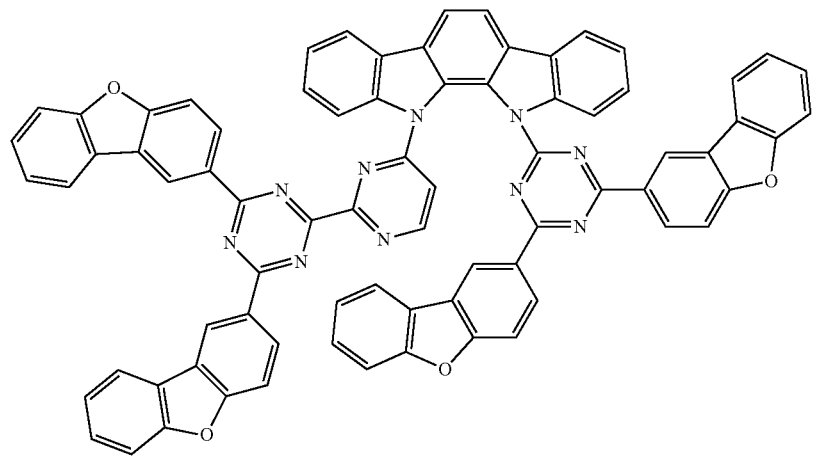
(B-69)
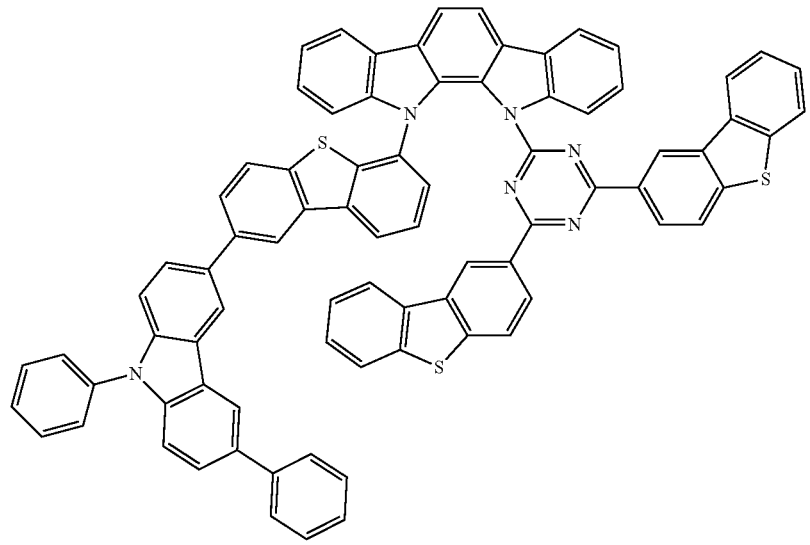
(B-70)
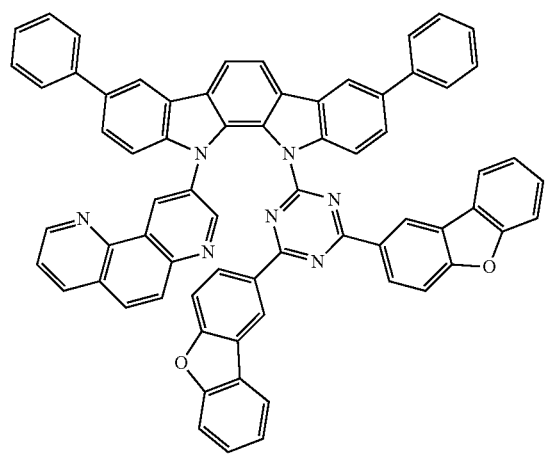
(B-71)
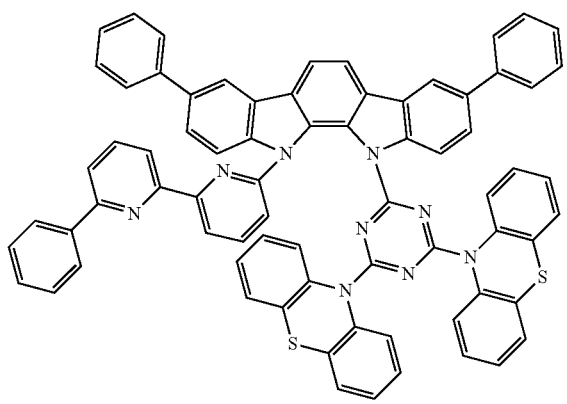
(B-72)

-continued
(B-73)
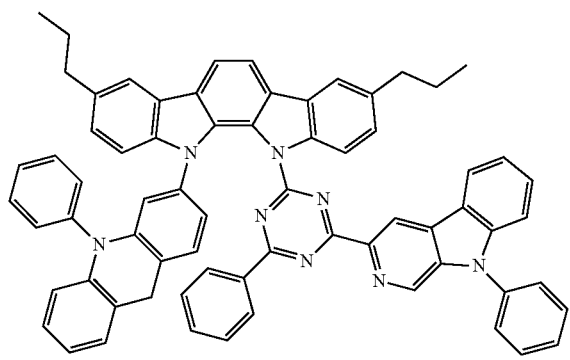
(B-74)
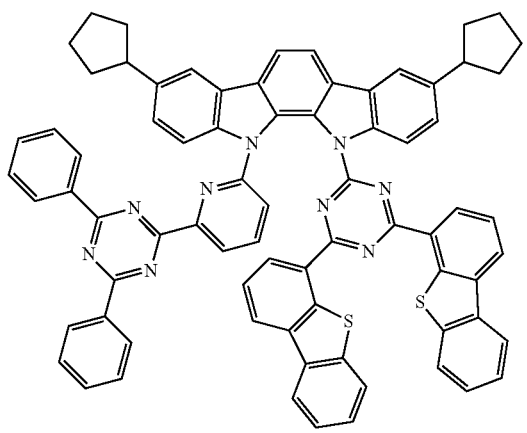
(C-1)
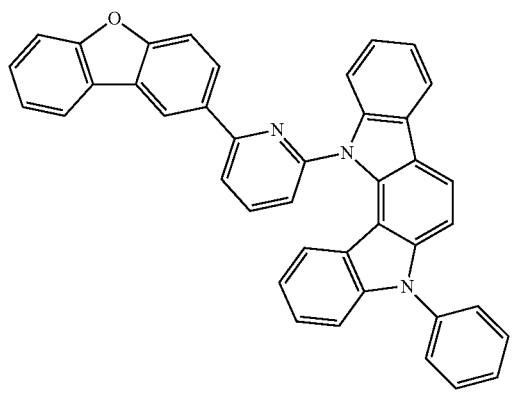
(C-2)
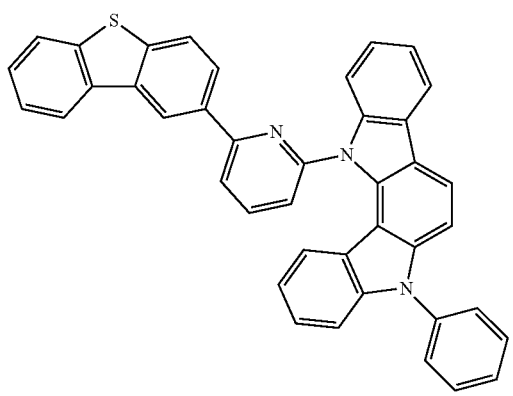
(C-3)
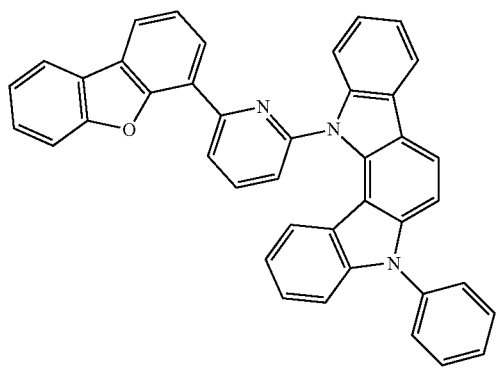
(C-4)
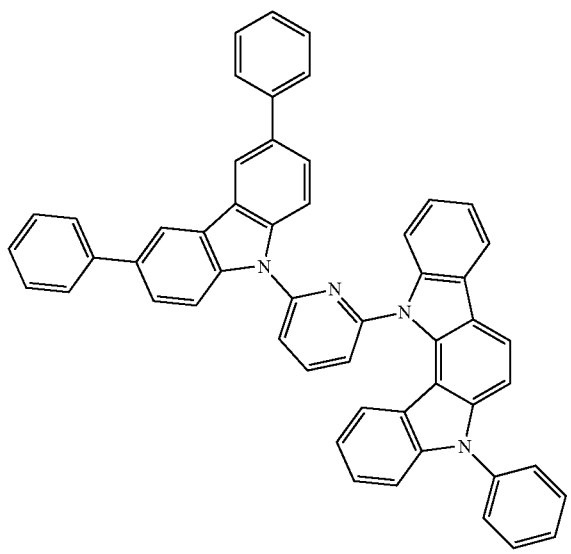

-continued
(C-5)
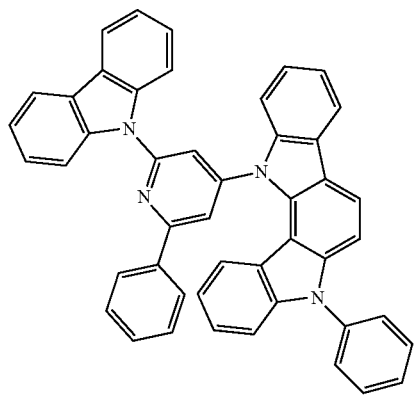
(C-6)
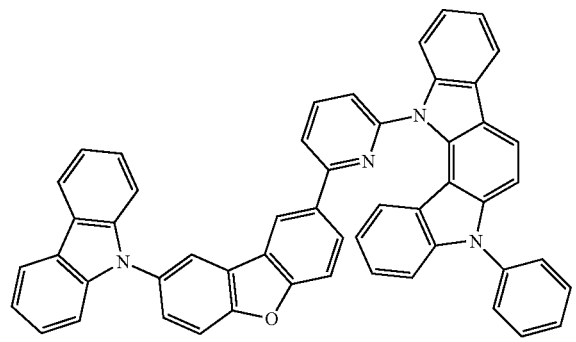
(C-7)
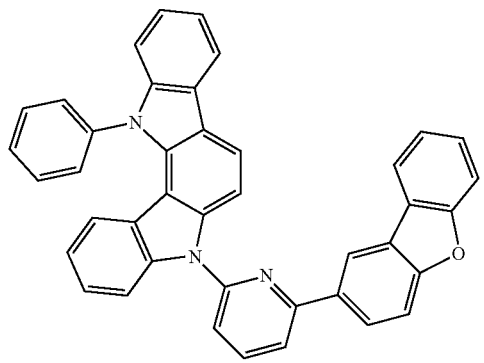
(C-8)
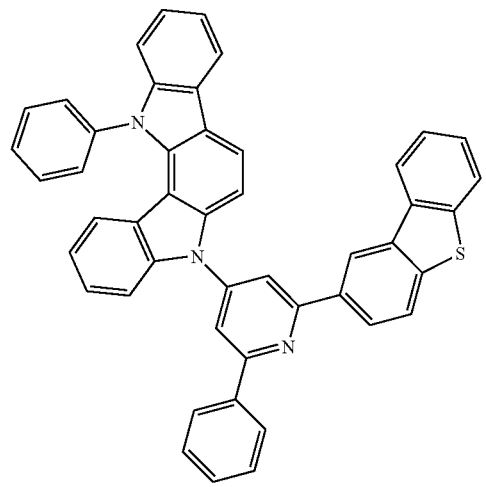
(C-9)
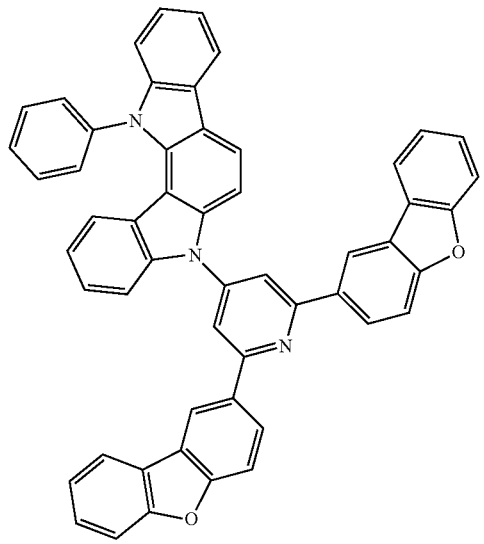
(C-10)
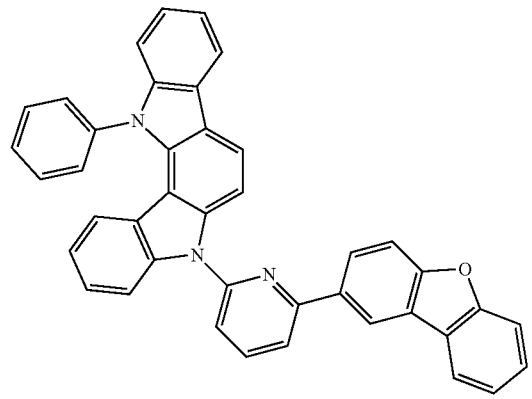

-continued
(C-11)
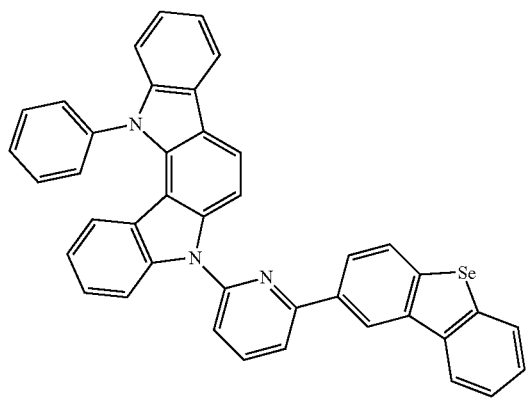
(C-12)
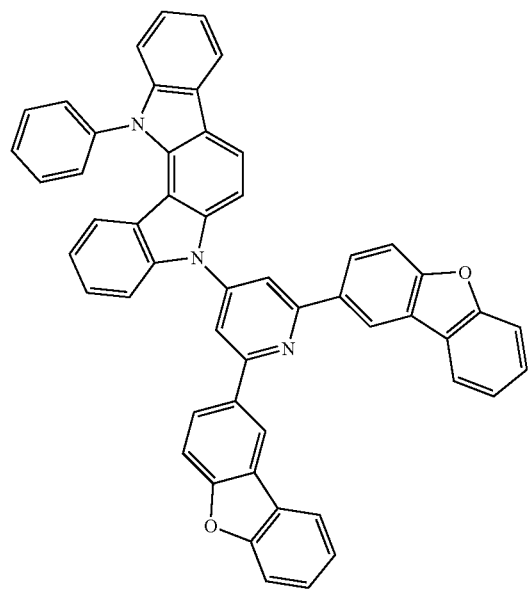
(C-13)
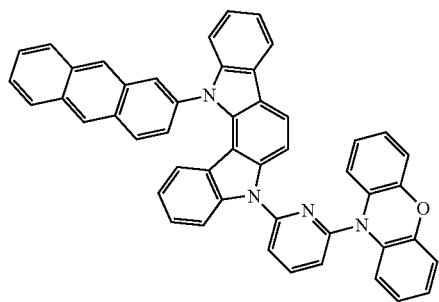
(C-14)
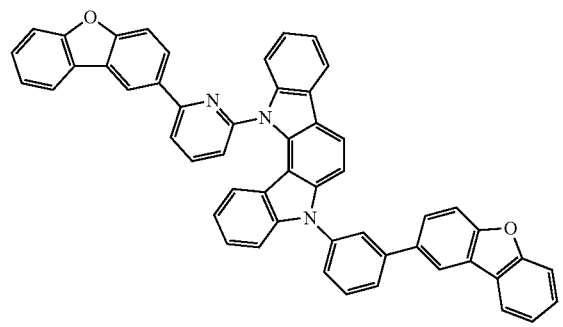
(C-15)
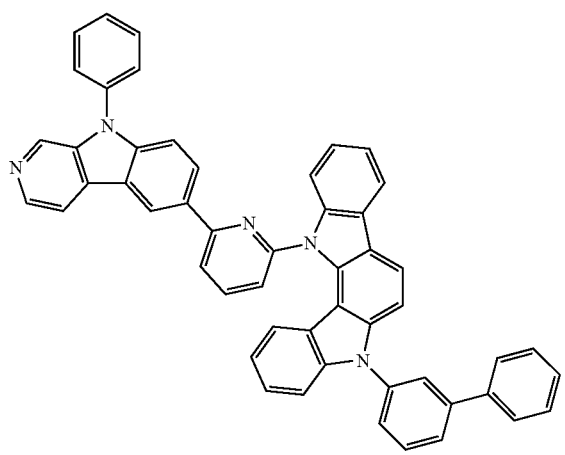
(C-16)
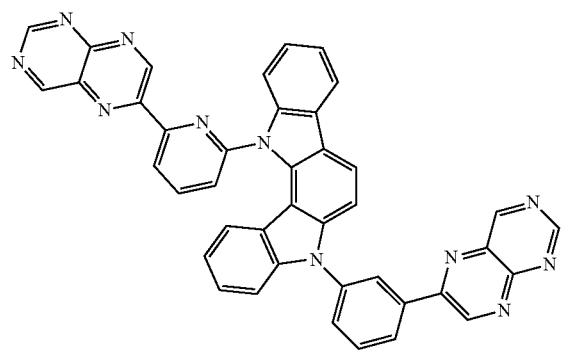

-continued
(C-17)
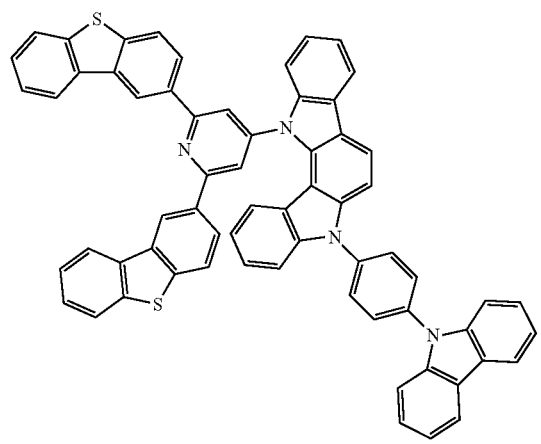
(C-18)
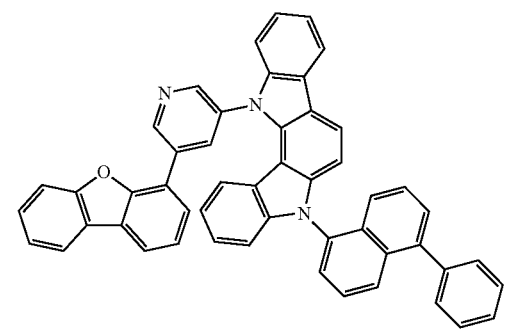
(C-19)
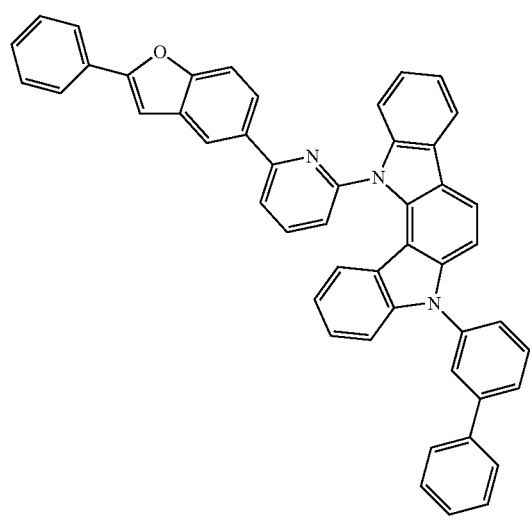
(C-20)
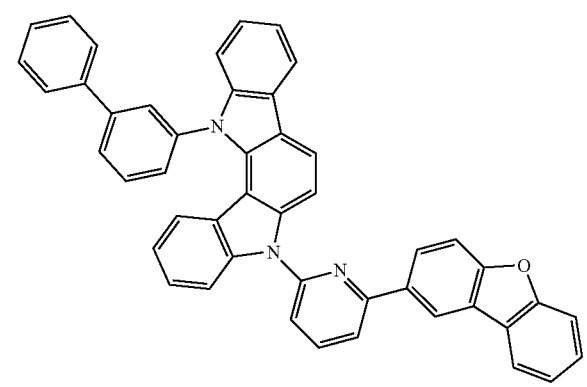
(C-21)
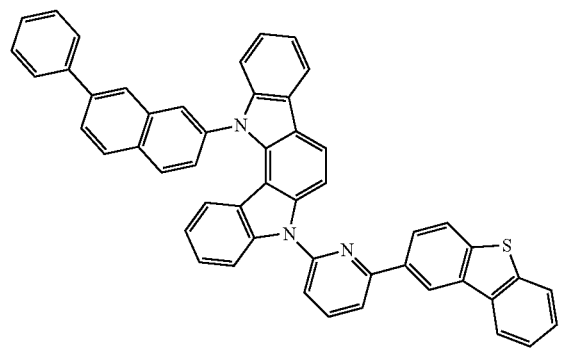
(C-22)
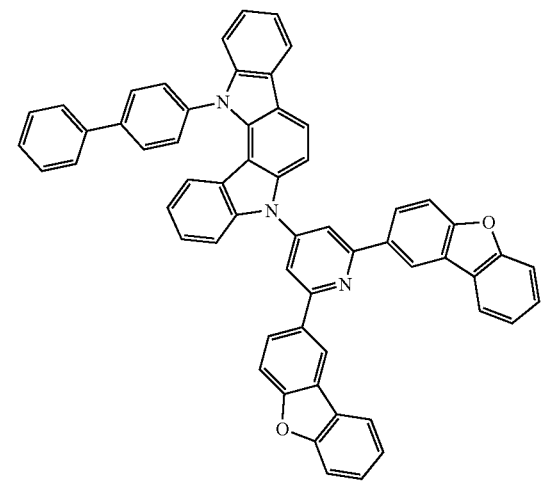

-continued
(C-23)
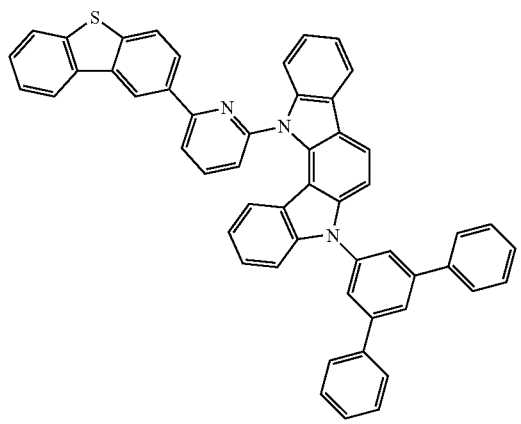
(C-24)
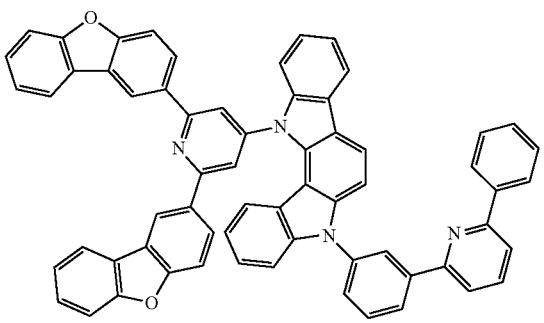
(C-25)
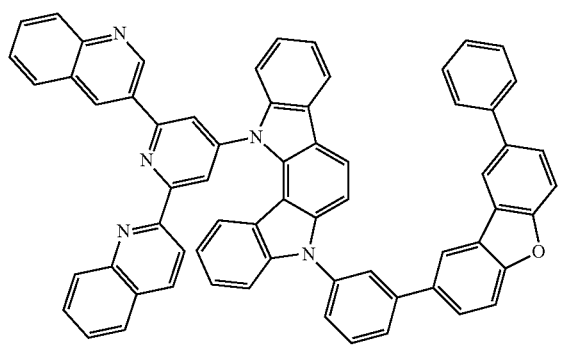
(C-26)
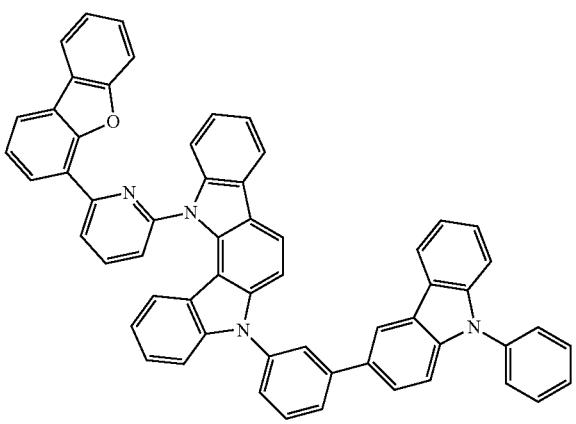
(C-27)
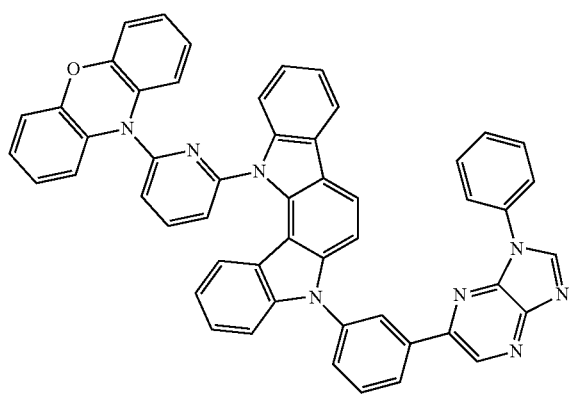
(C-28)
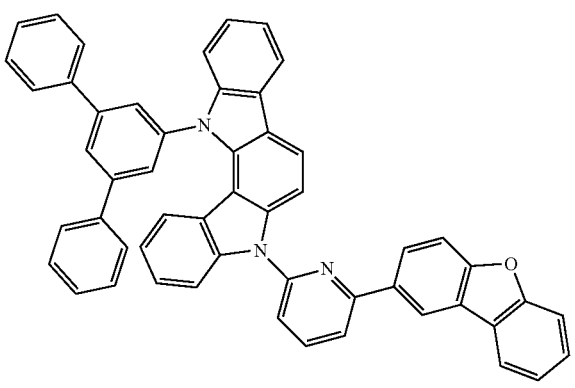

-continued
(C-29)
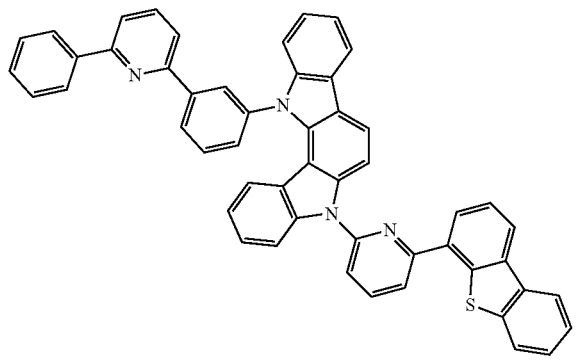
(C-30)
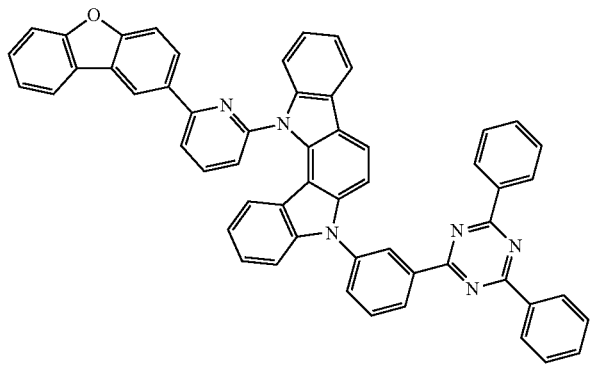
(C-31)
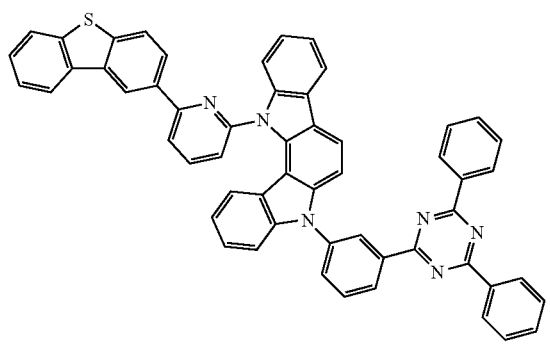
(C-32)
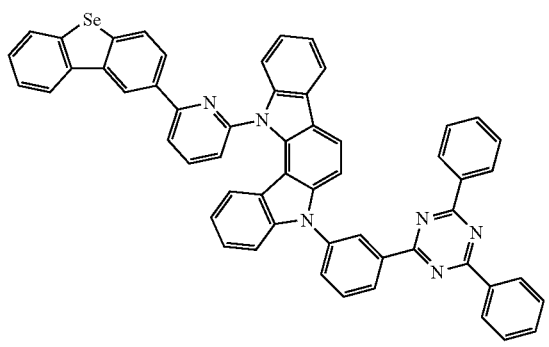
(C-33)
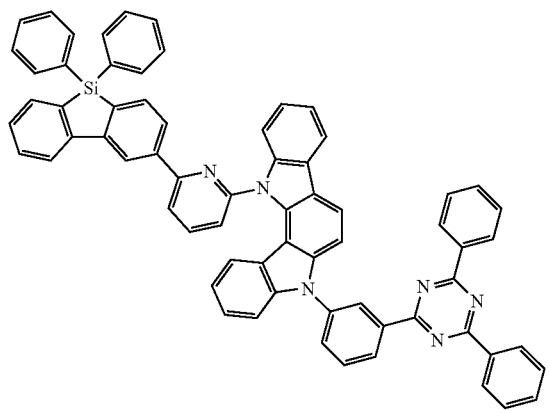
(C-34)
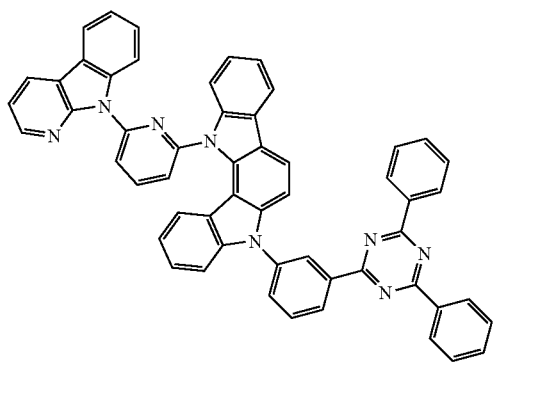
(C-35)
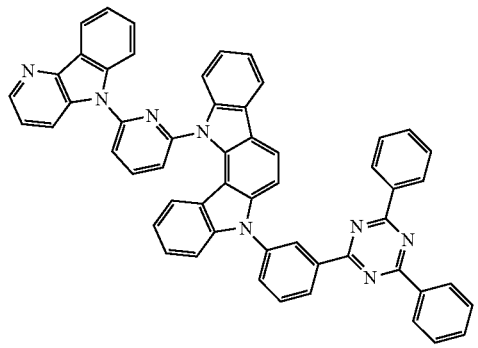
(C-36)
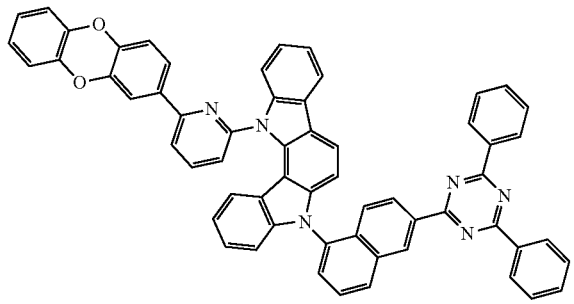

(C-37)
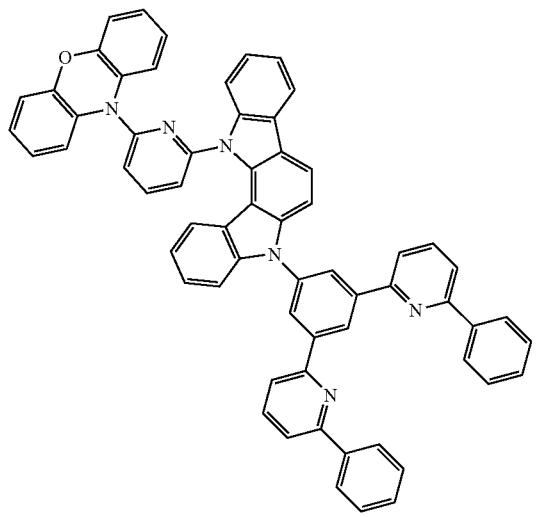
(C-38)
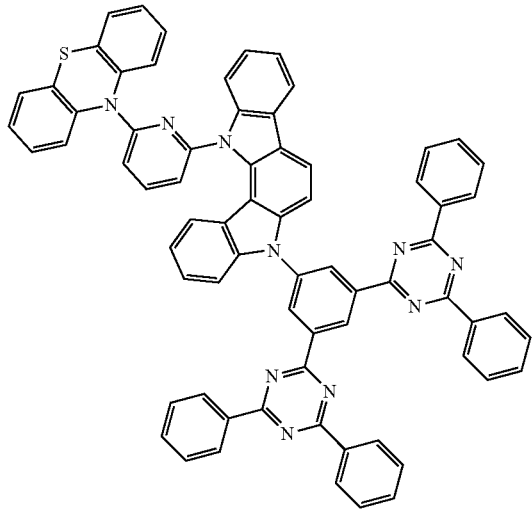
(C-39)
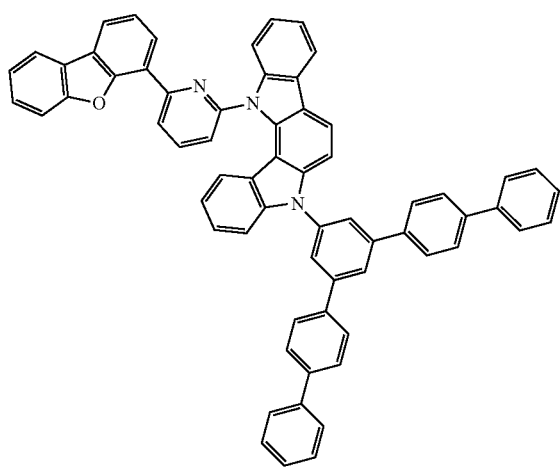

(C-40)
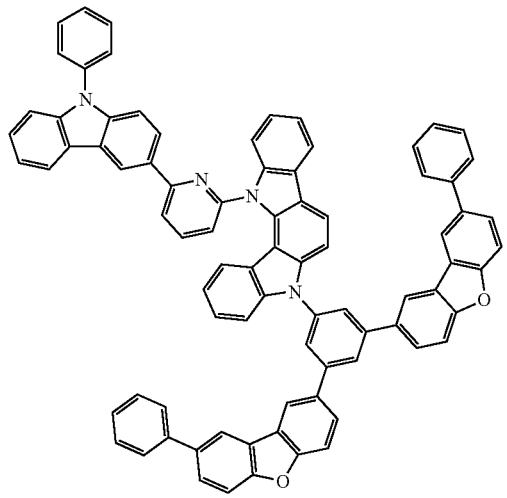
(C-41)
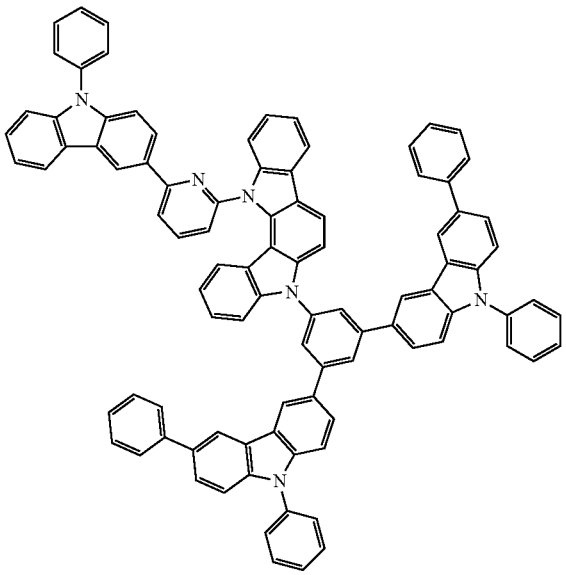
(C-42)
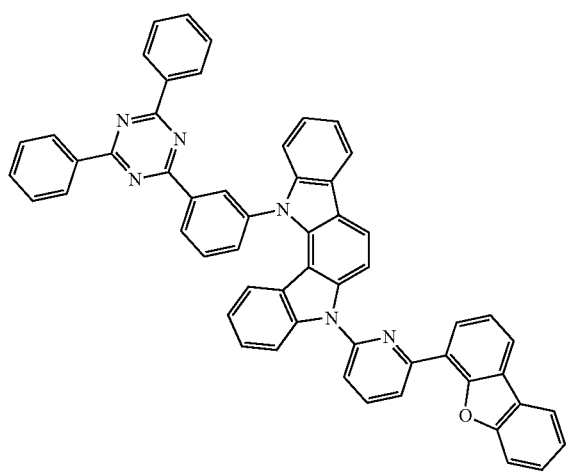
(C-43)
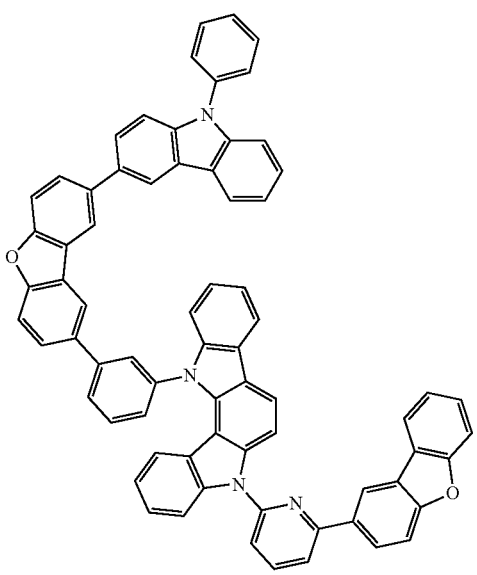
(C-44)
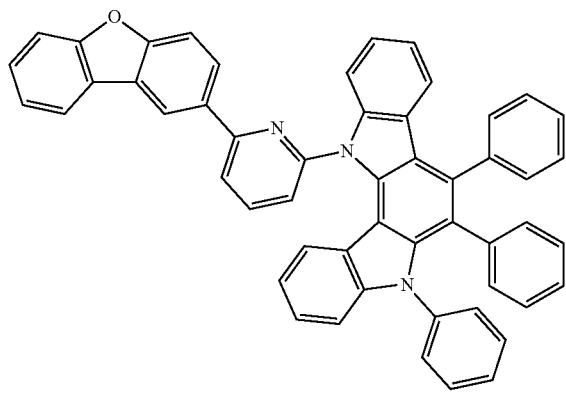
(C-45)
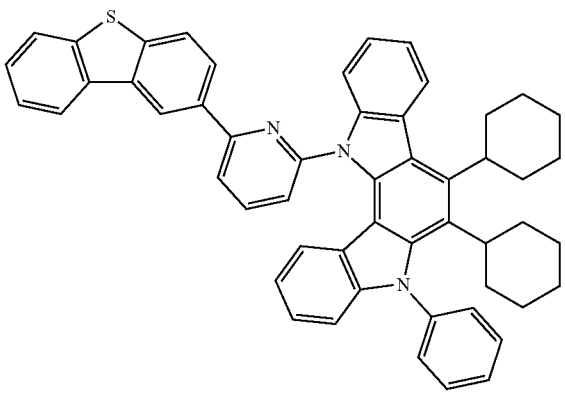

-continued
(C-46)
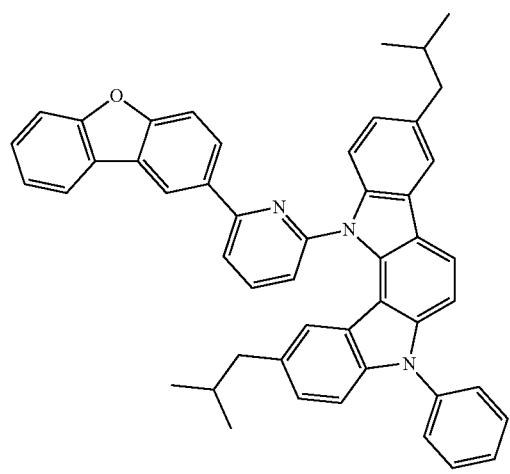
(C-47)
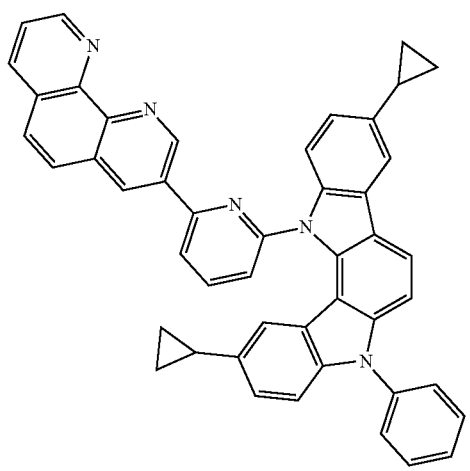
(C-48)
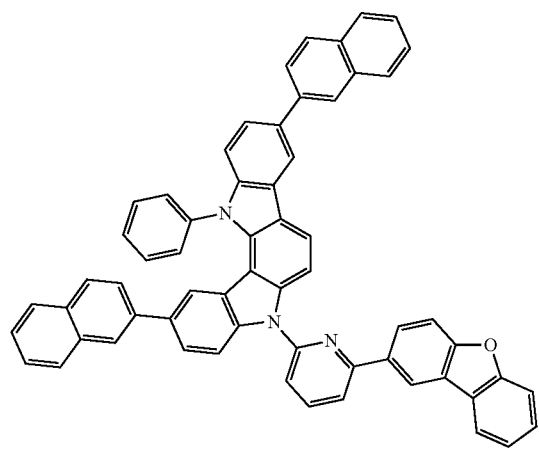
(C-49)
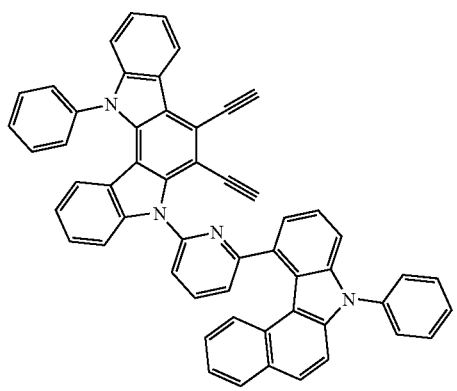
(C-50)
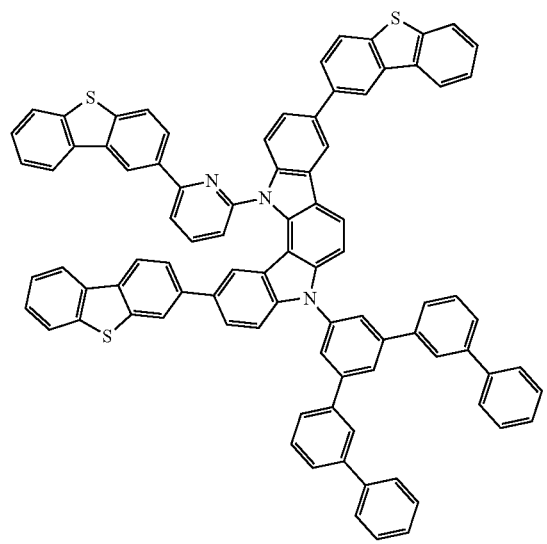
(C-51)
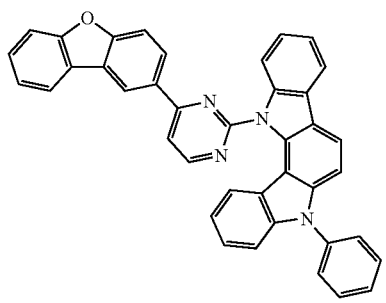

-continued
(C-52)
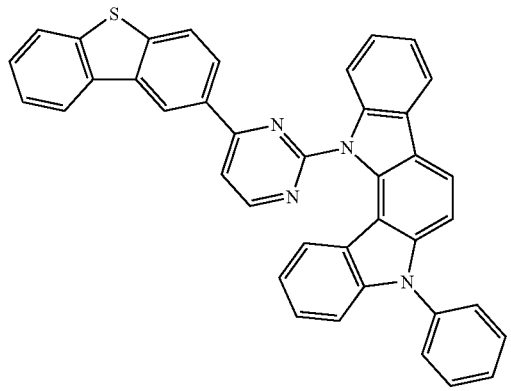
(C-53)
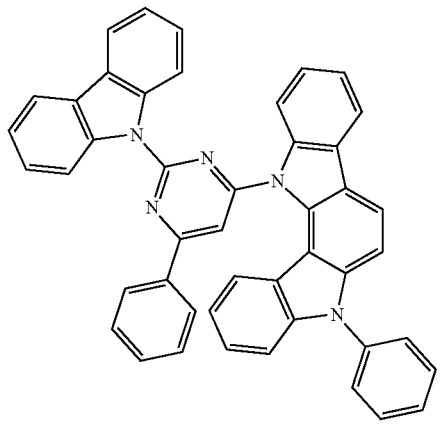
(C-54)
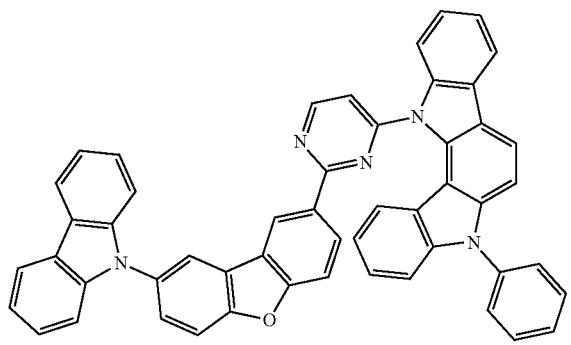
(C-55)
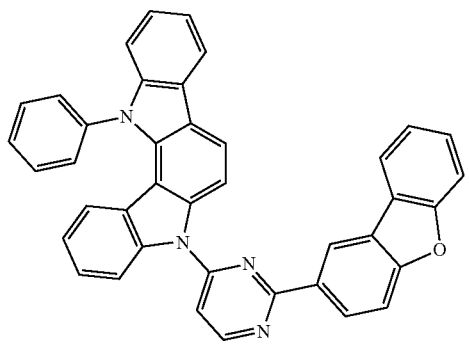
(C-56)
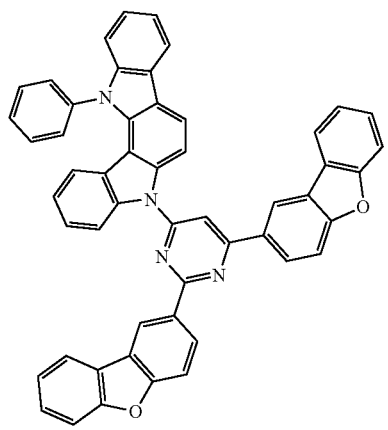
(C-57)
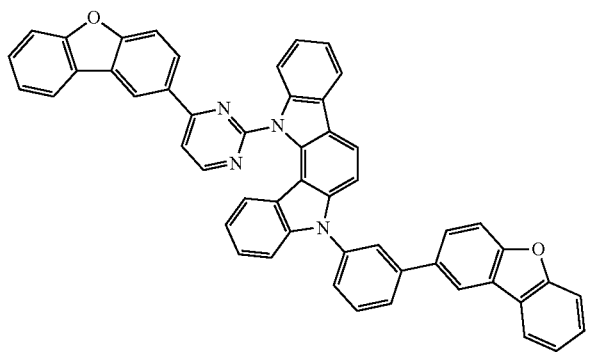
(C-58)
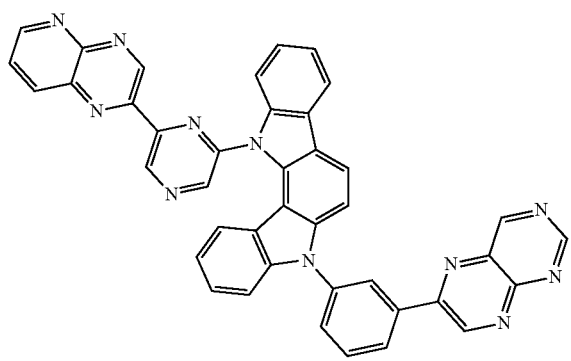
(C-59)
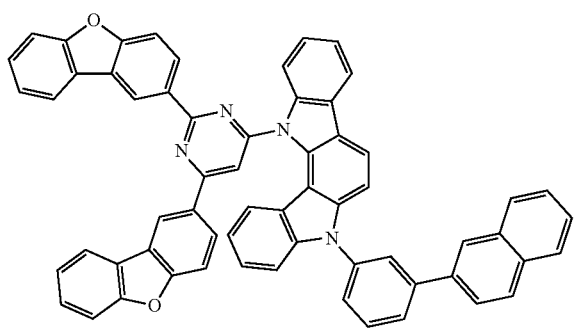

-continued
(C-60)
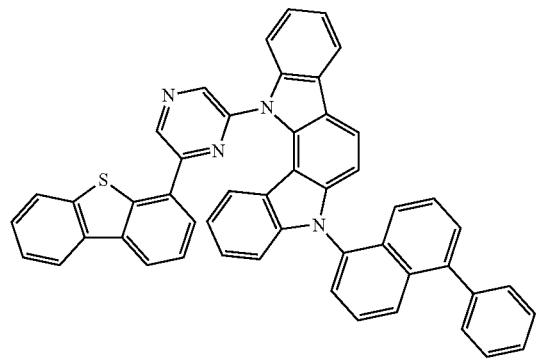
(C-61)
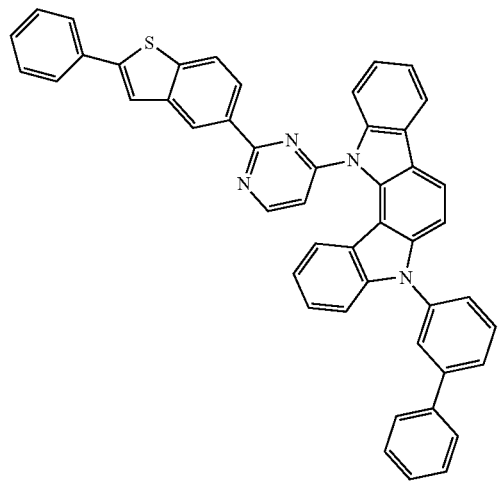
(C-62)
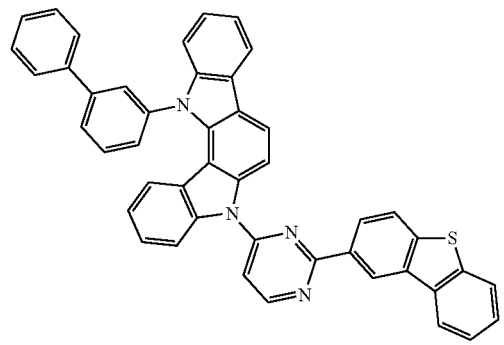
(C-63)
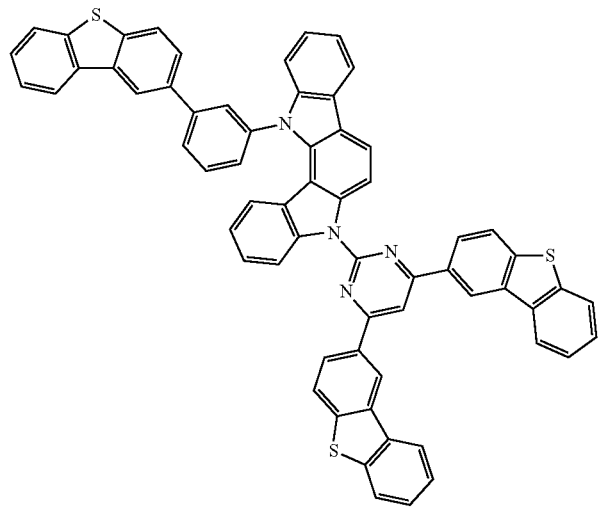
(C-64)
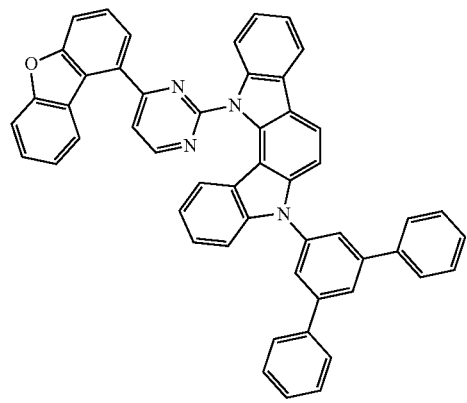
(C-65)
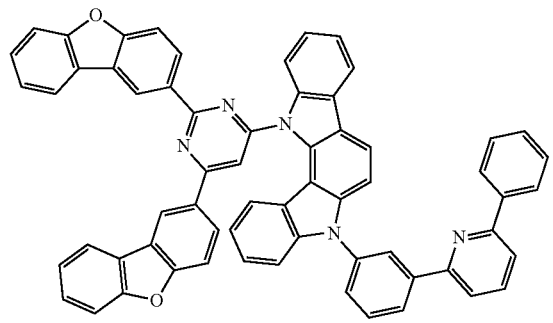

-continued
(C-66)
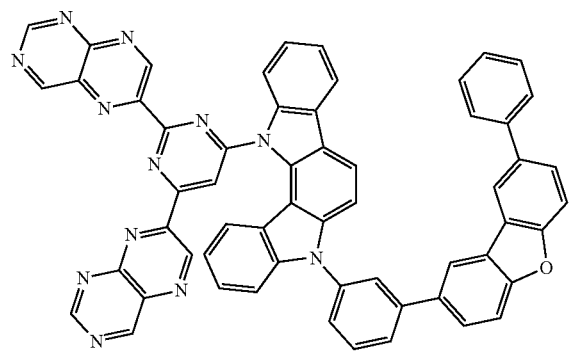
(C-67)
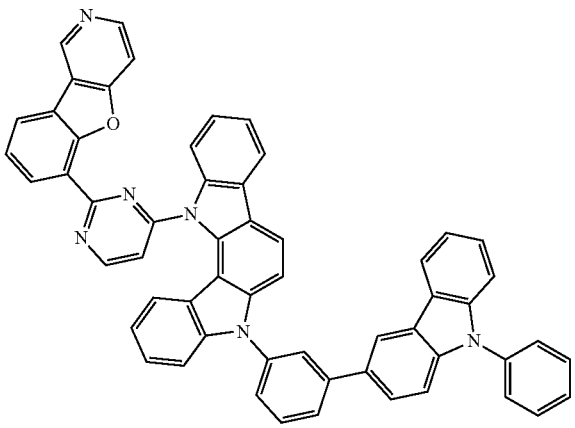
(C-68)
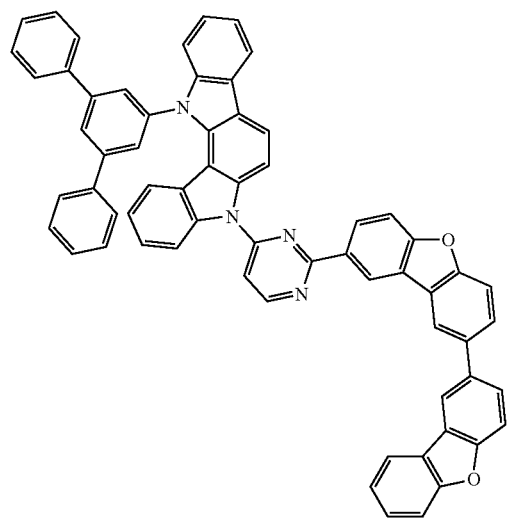
(C-69)
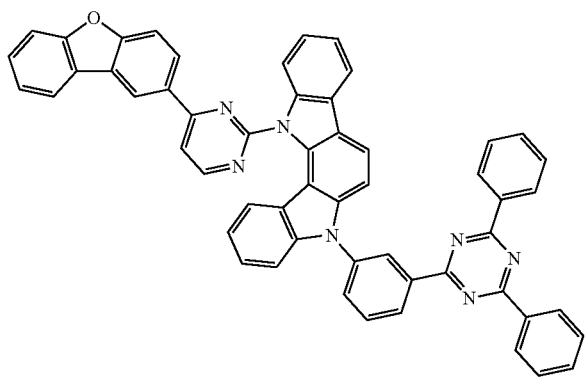
(C-70)
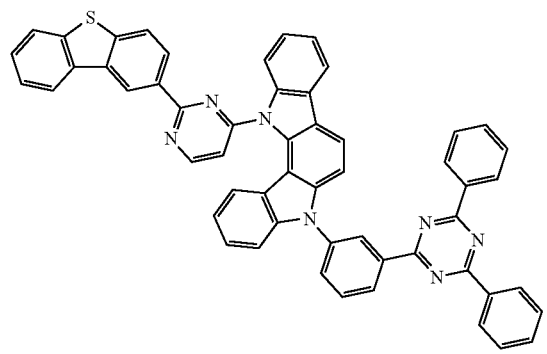
(C-71)
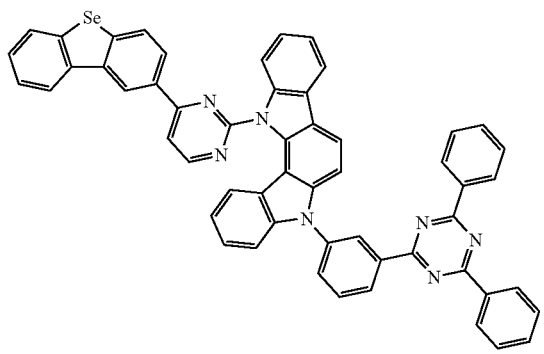

-continued
(C-72)
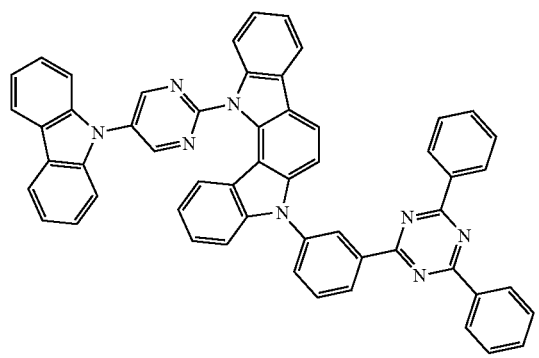
(C-73)
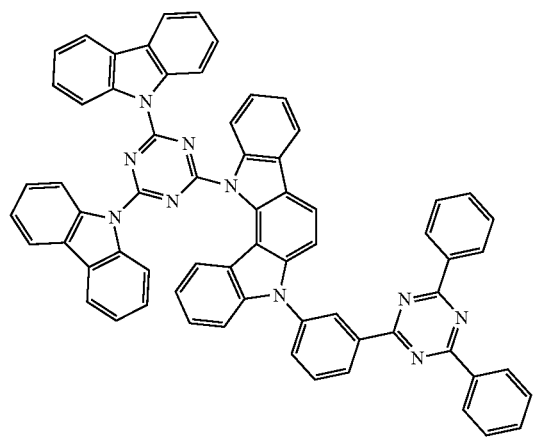
(C-74)
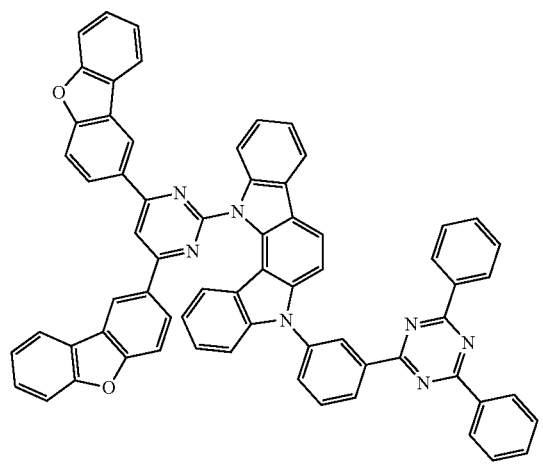
(C-75)
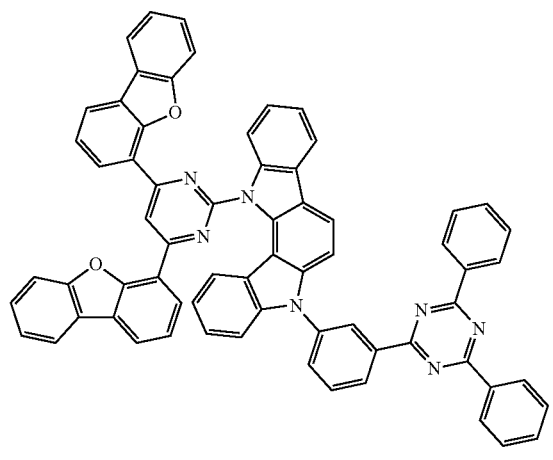
(C-76)
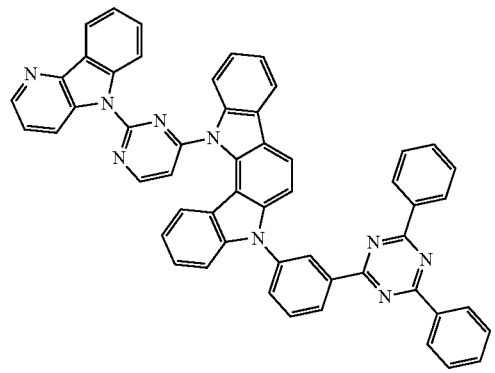
(C-77)
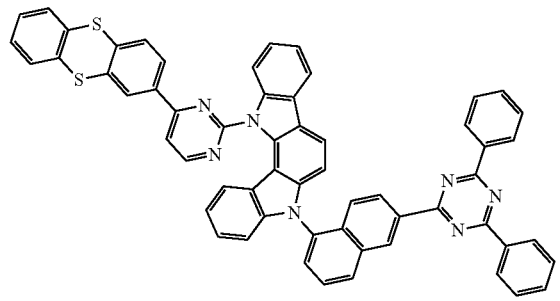

-continued
(C-78)
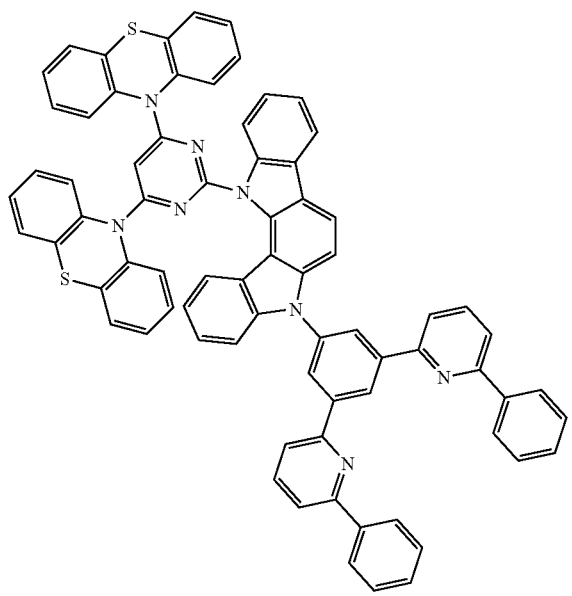
(C-79)
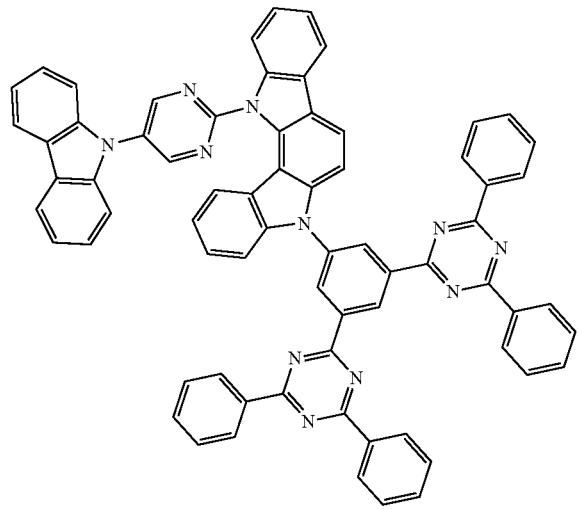
(C-80)
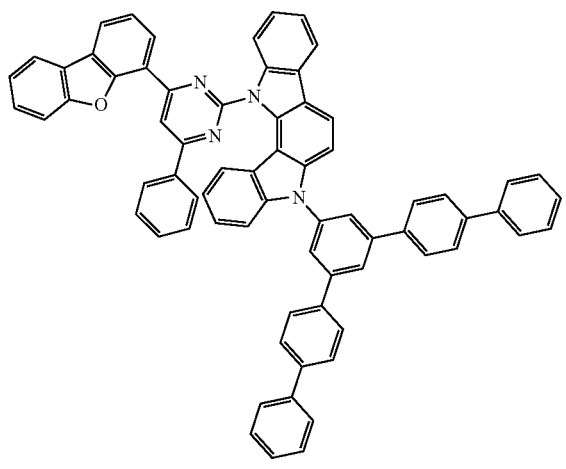
(C-81)
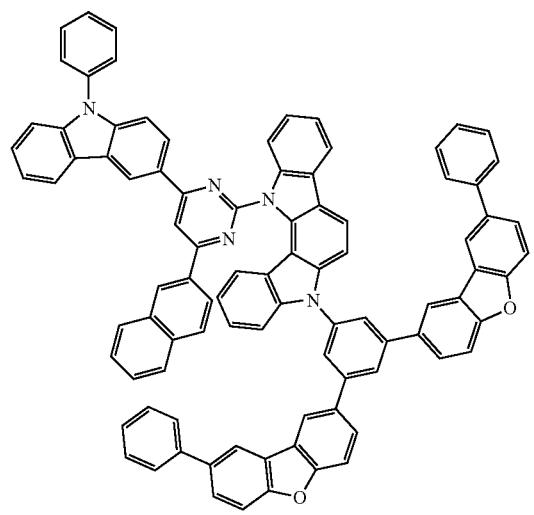

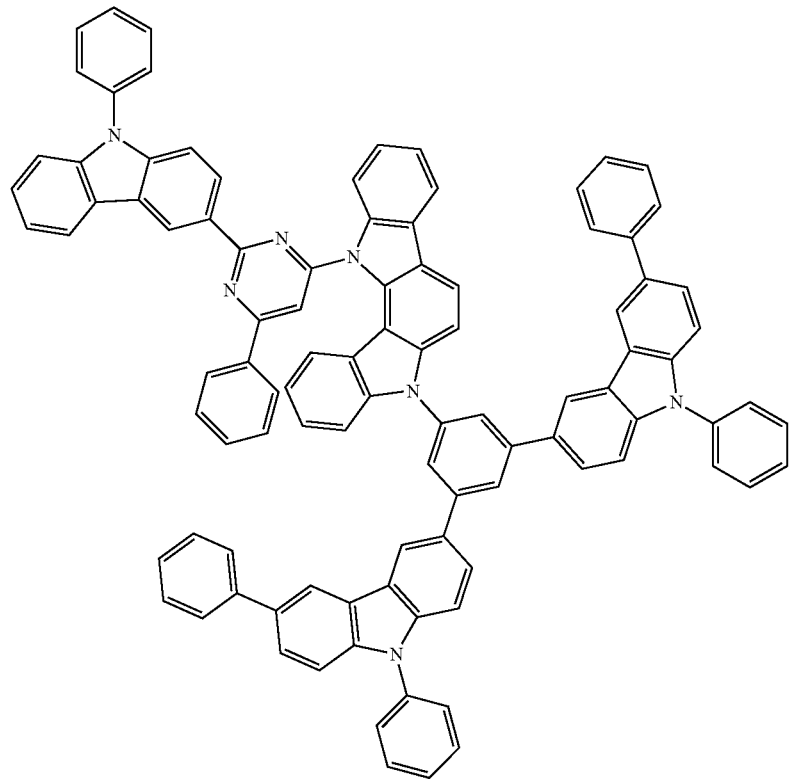
(C-82)
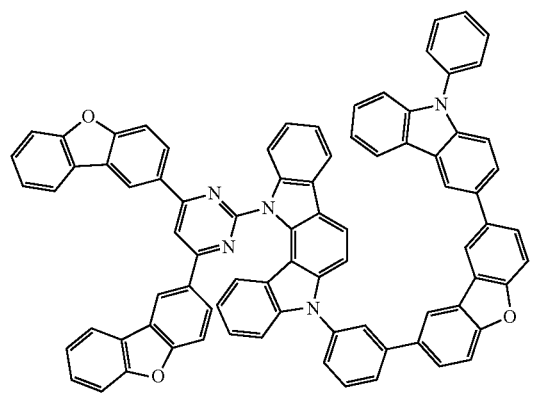
(C-83)
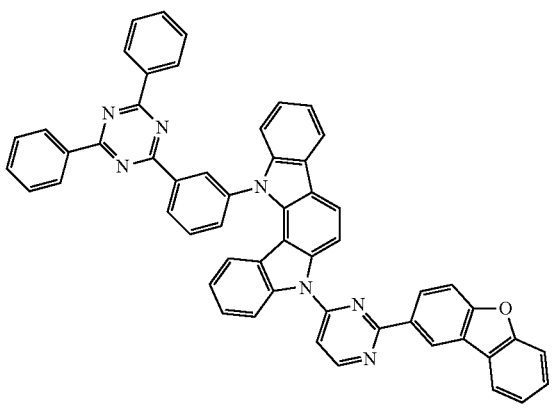
(C-84)

-continued
(C-85)
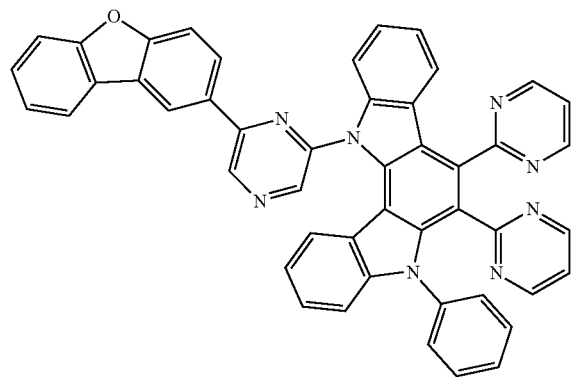
(C-86)
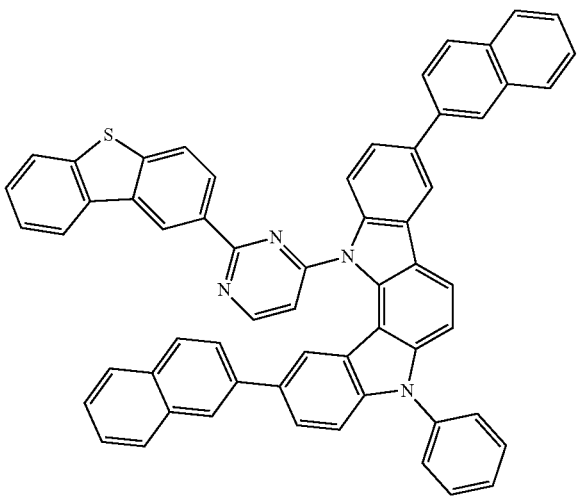
(C-87)
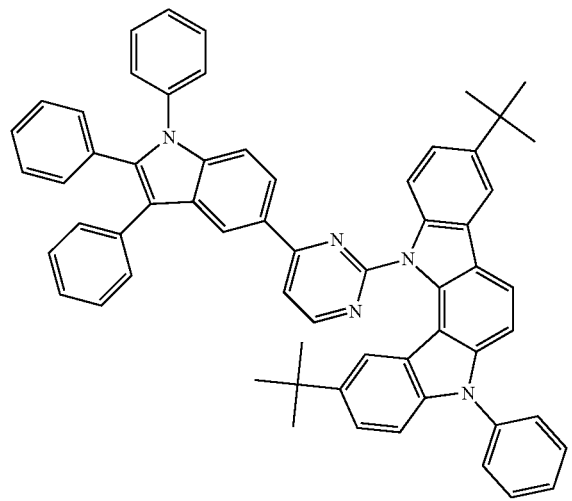
(C-88)
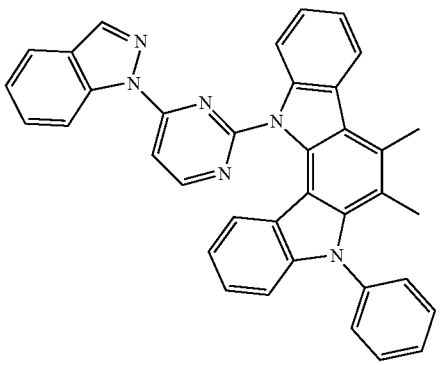

-continued
(C-89)
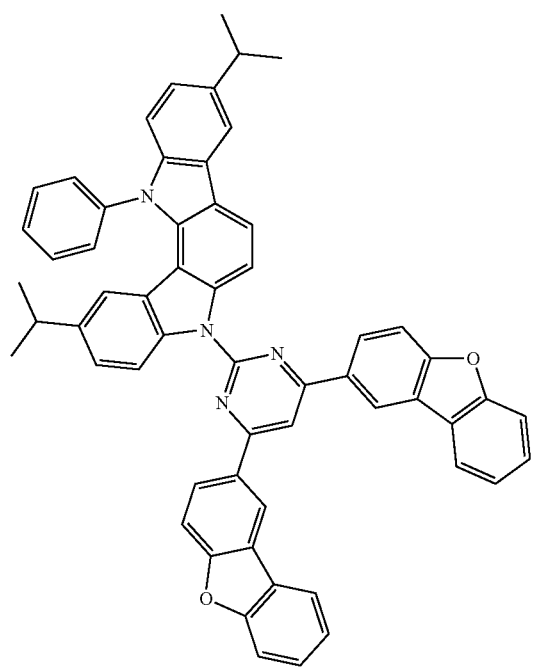
(C-90)
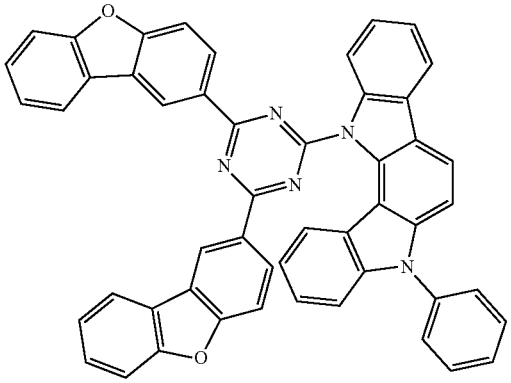
(C-91)
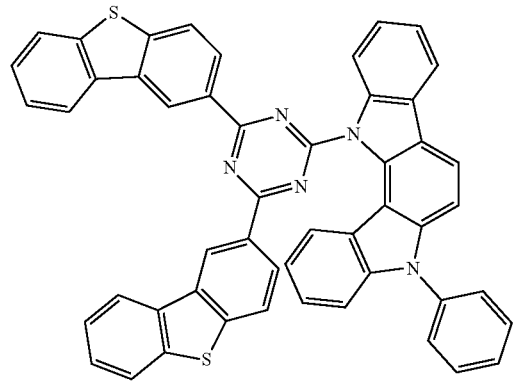
(C-92)
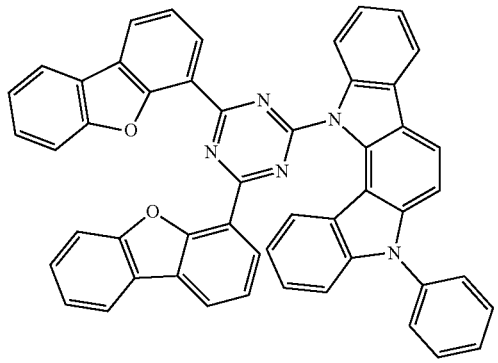
(C-93)
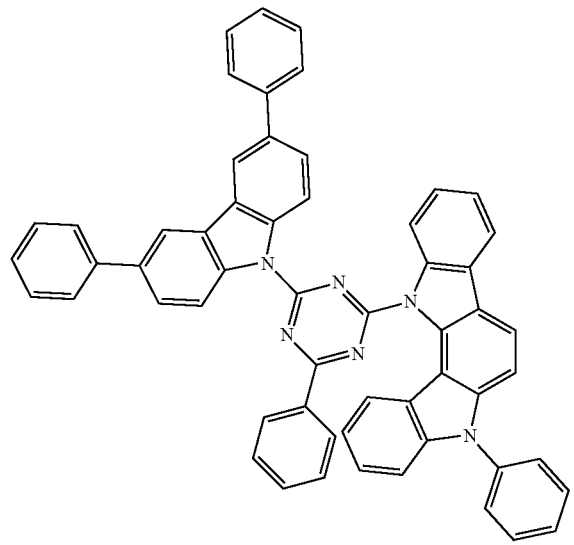
(C-94)
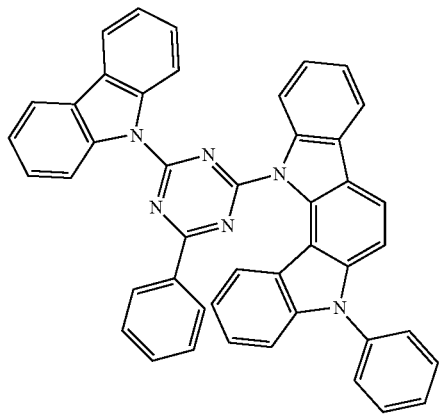

-continued
(C-95)
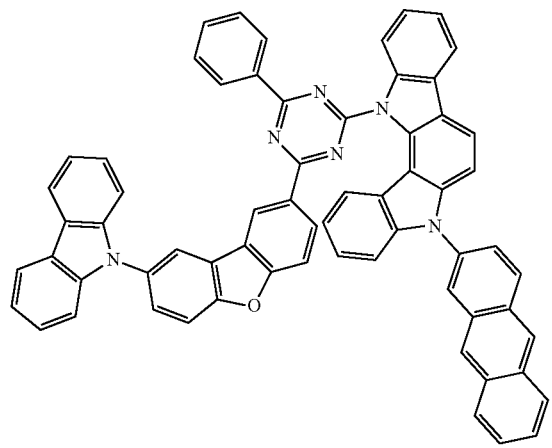
(C-96)
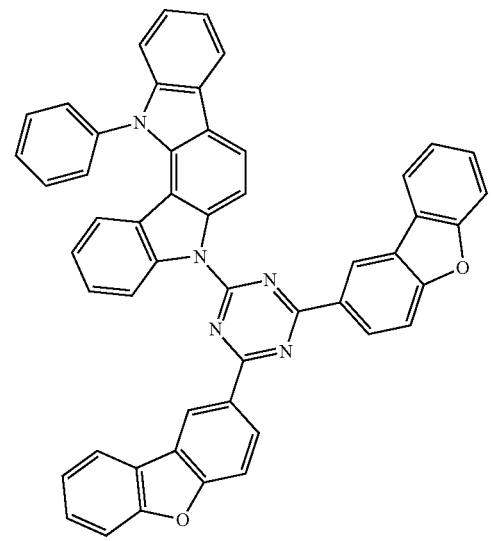
(C-97)
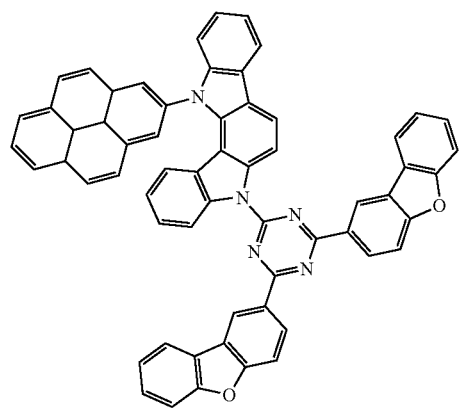
(C-98)
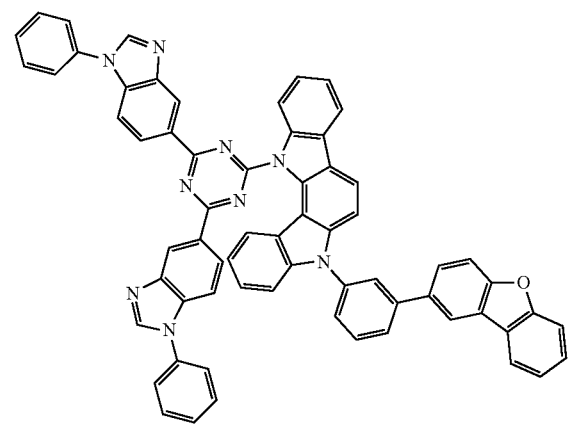
(C-99)
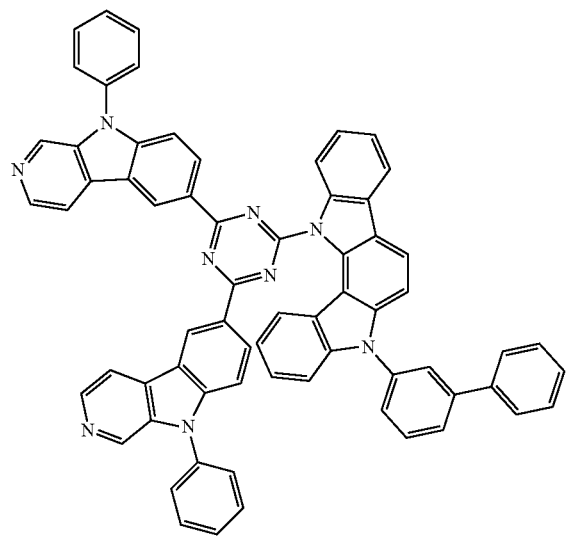
(C-100)
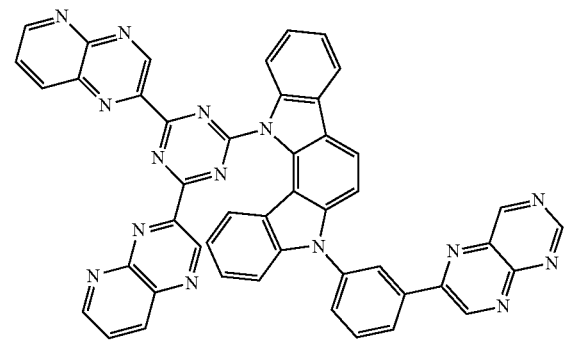

-continued
(C-101)
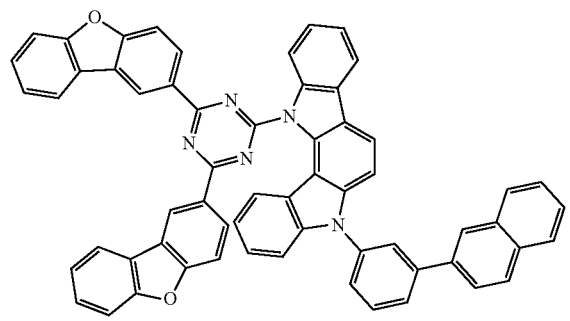
(C-102)
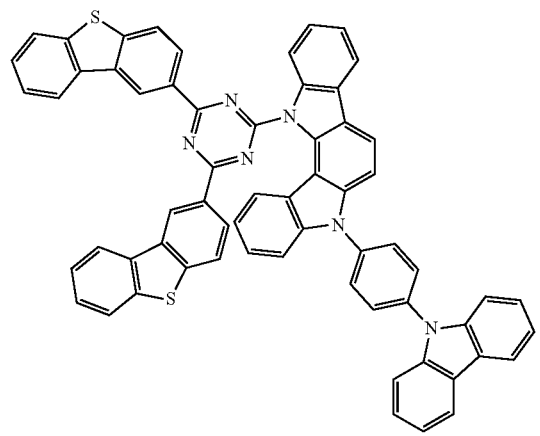
(C-103)
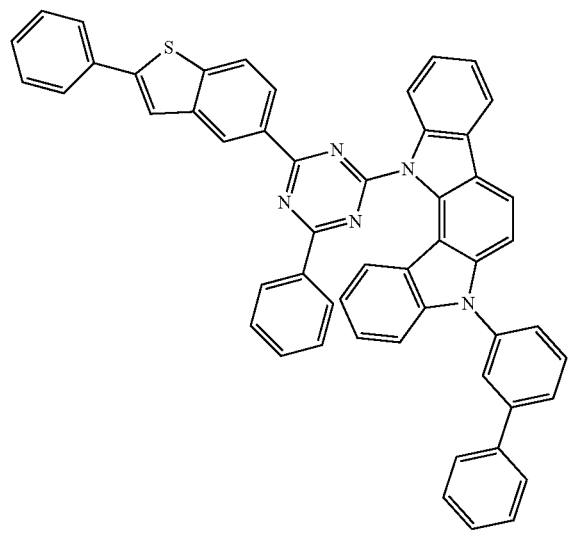
(C-104)
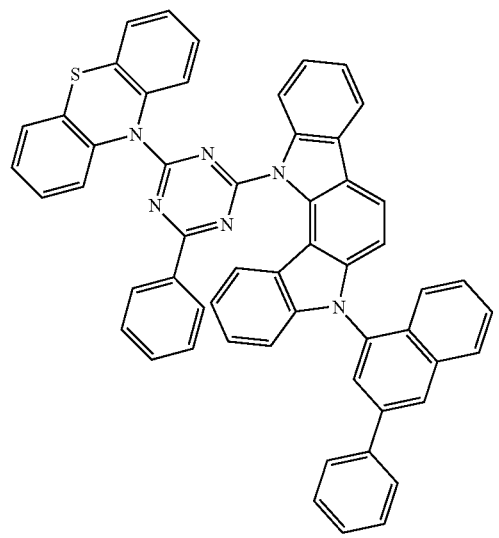
(C-105)
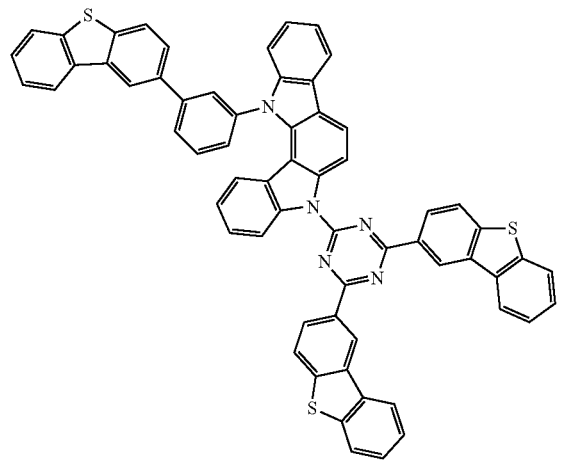
(C-106)
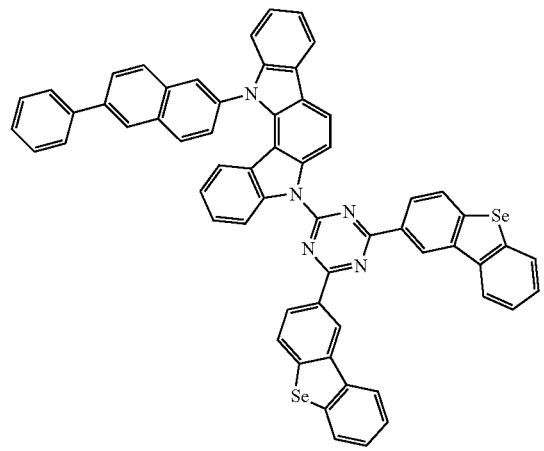

-continued
(C-107)
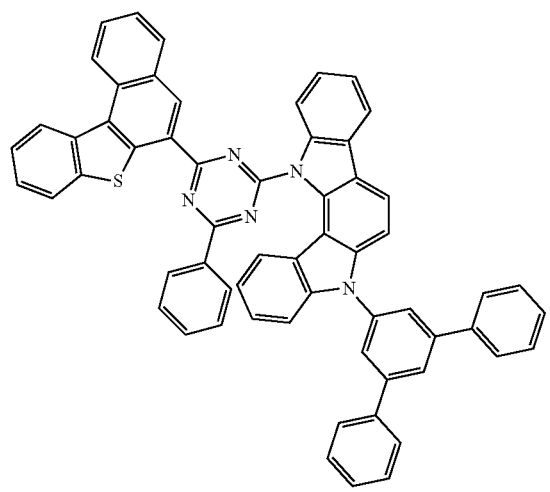
(C-108)
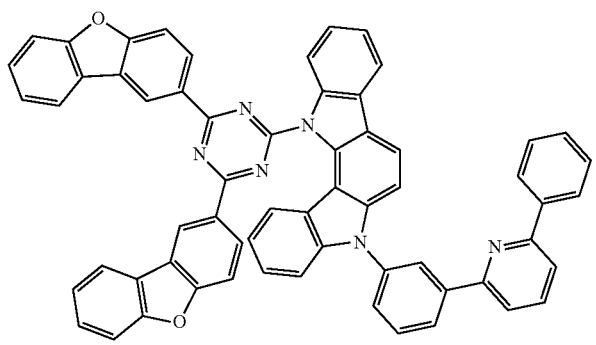
(C-109)
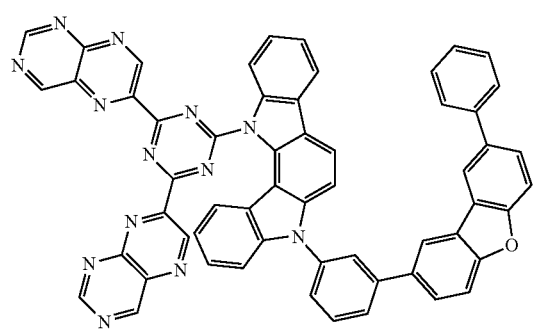
(C-110)
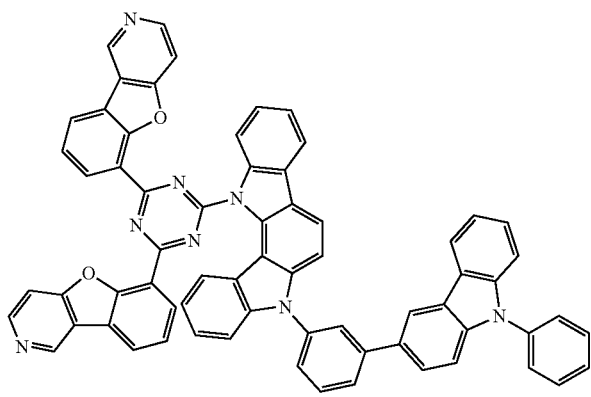
(C-111)
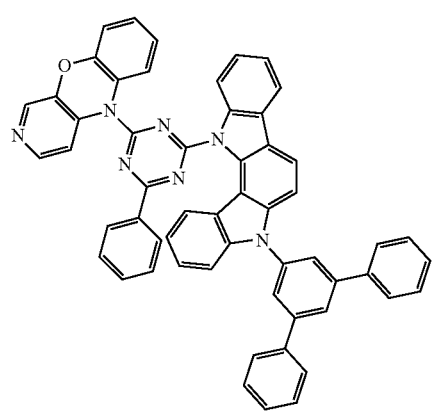
(C-112)
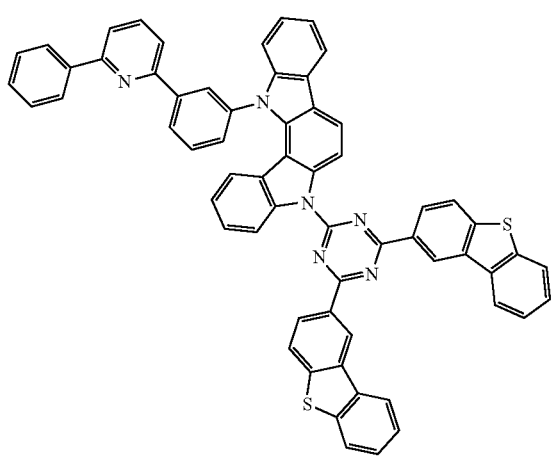

-continued
(C-113)
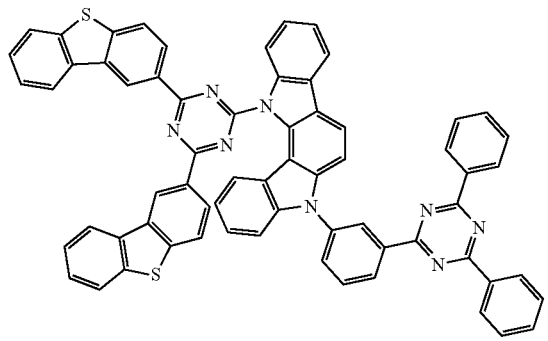
(C-114)
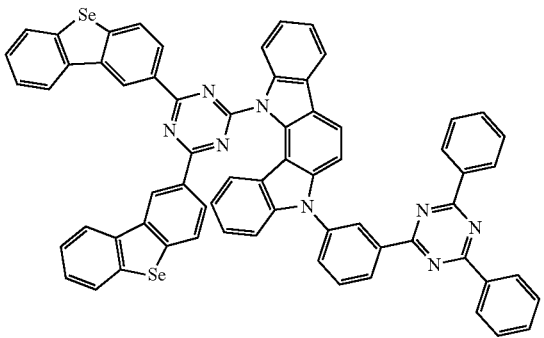
(C-115)
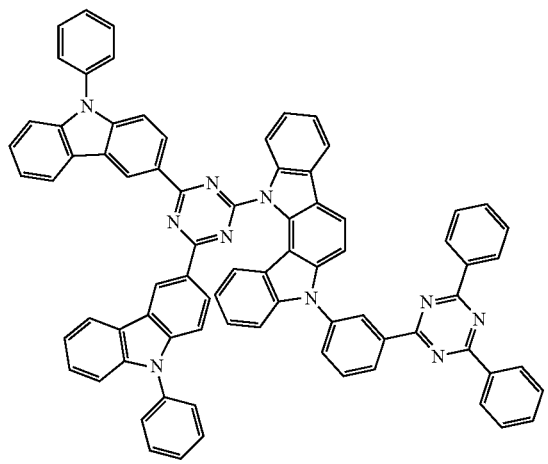
(C-116)
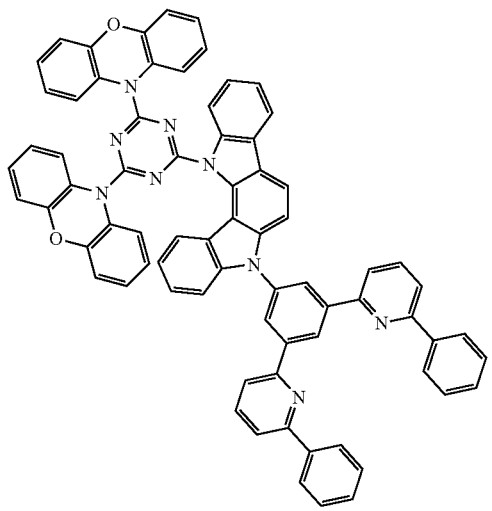
(C-117)
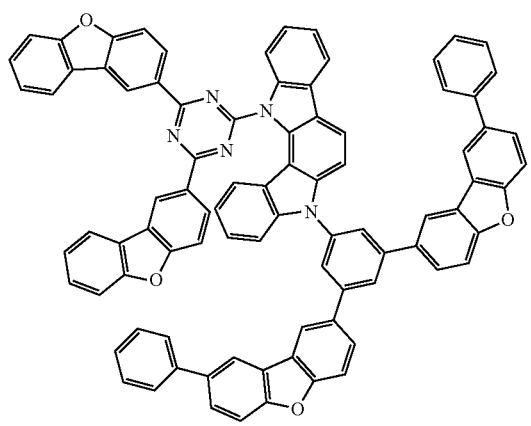
(C-118)
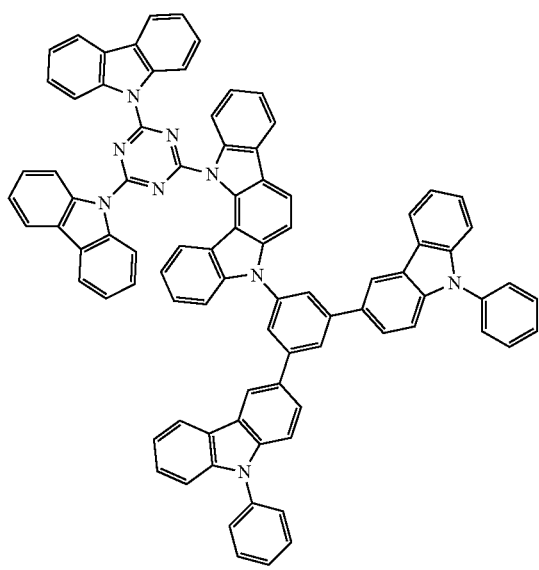

(C-119)
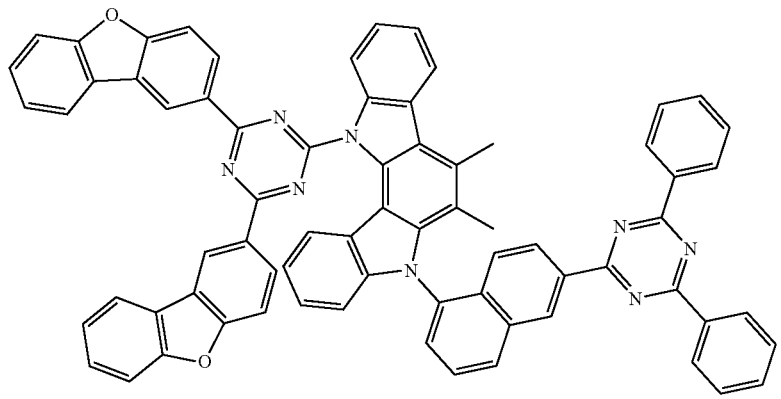
(C-120)
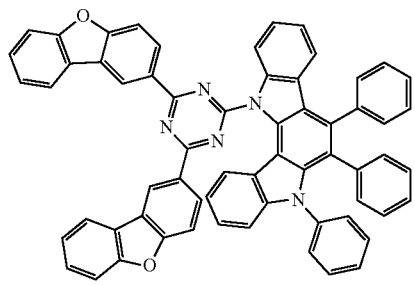
(C-121)
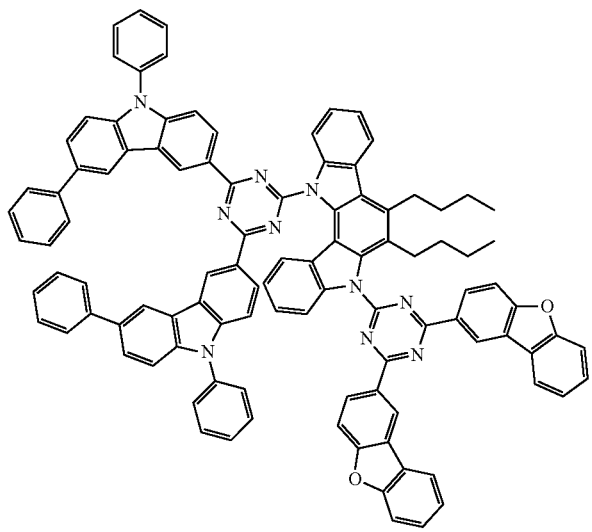
(C-122)
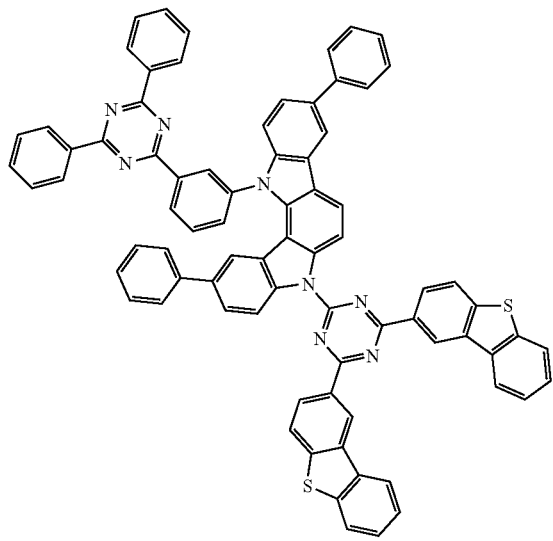
(D-1)
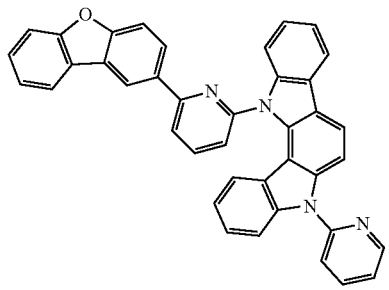

-continued
(D-2)
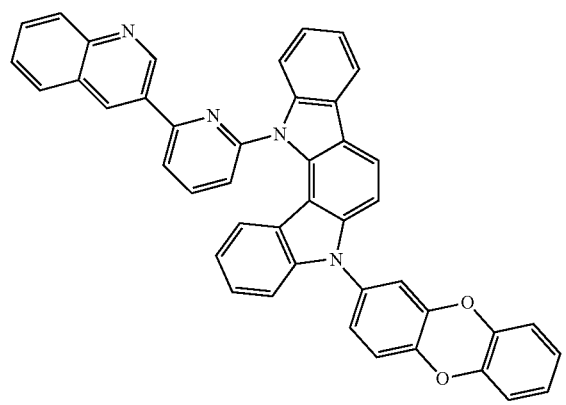
(D-3)
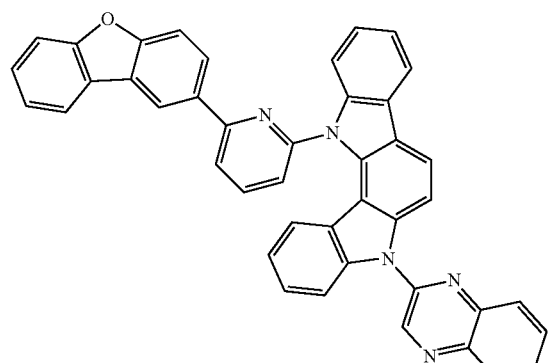
(D-4)
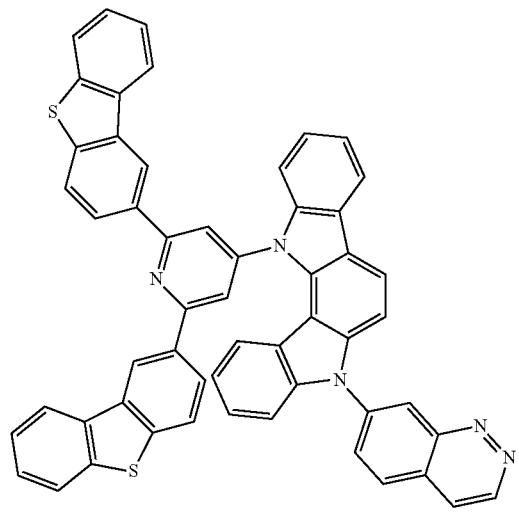
(D-5)
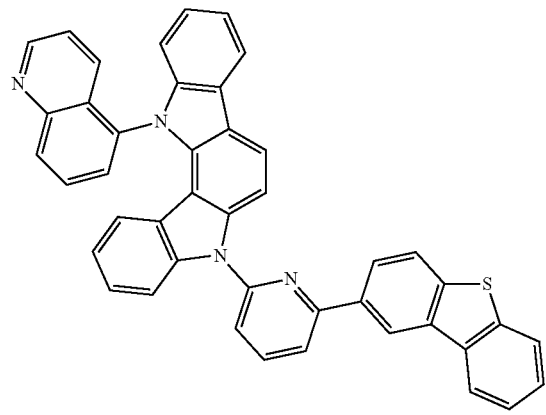
(D-6)
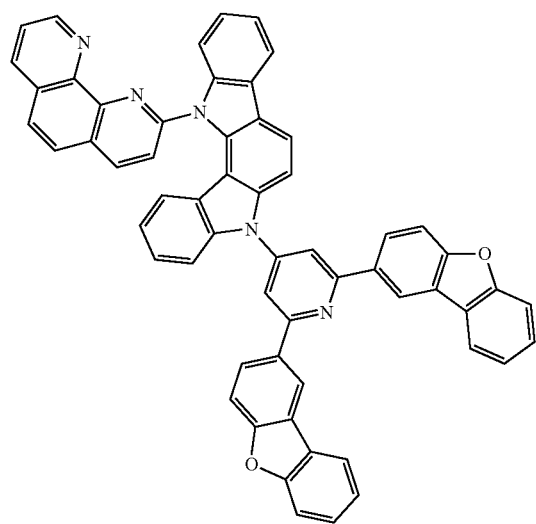
(D-7)
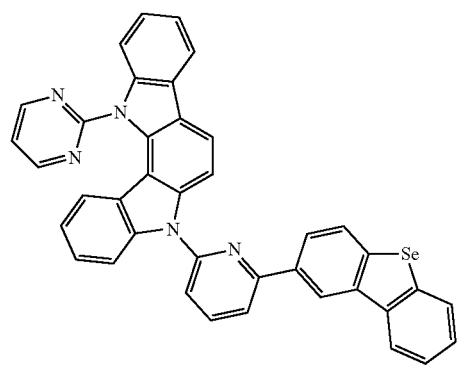

-continued
(D-8)
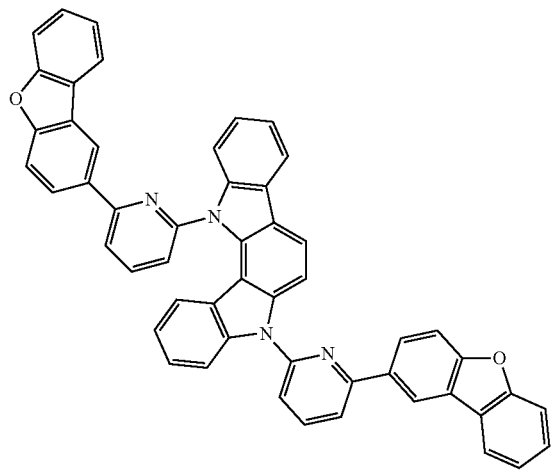
(D-9)
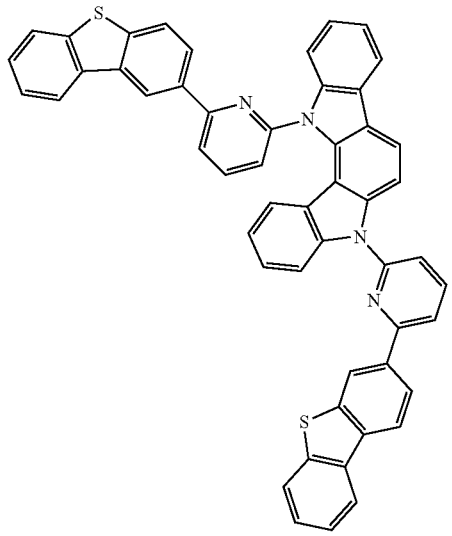
(D-10)
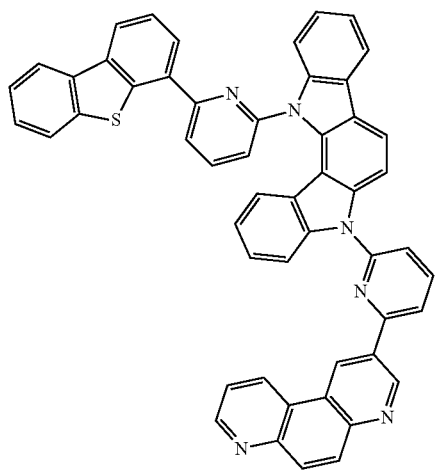
(D-11)
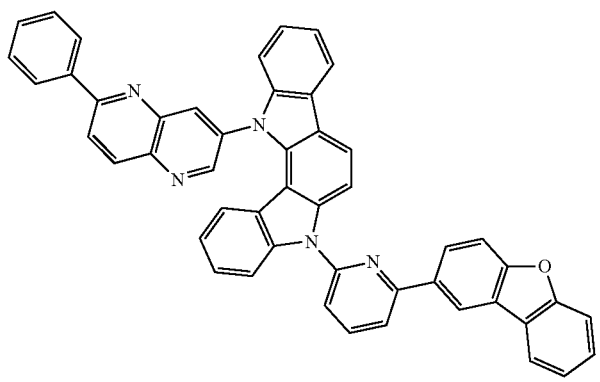
(D-12)
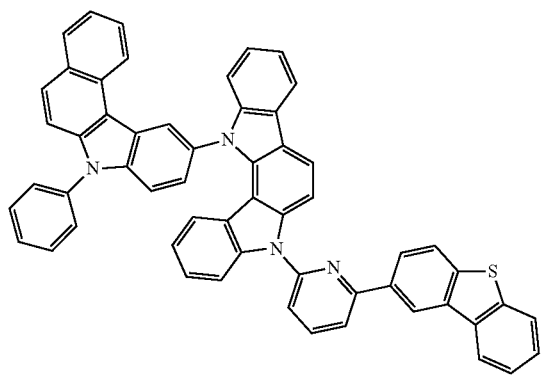
(D-13)
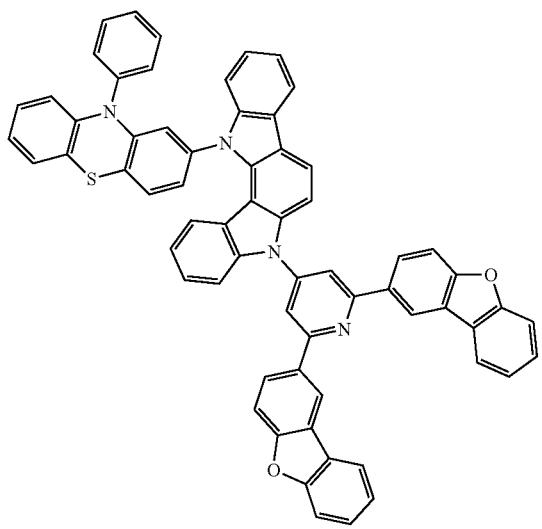

-continued
(D-14)
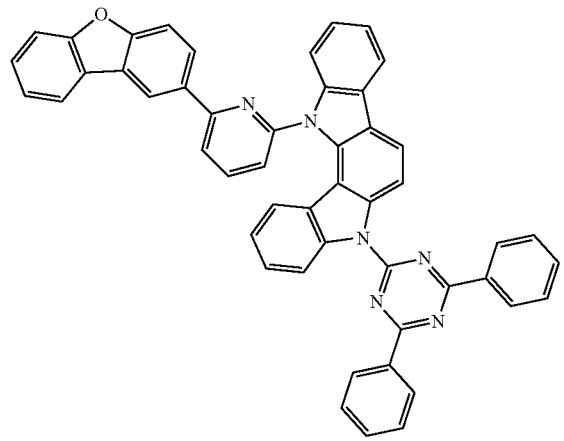
(D-15)
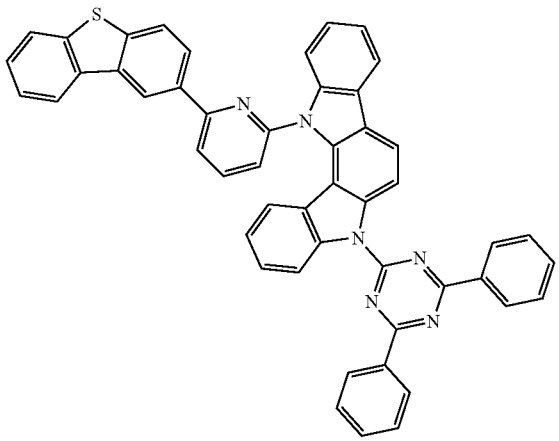
(D-16)
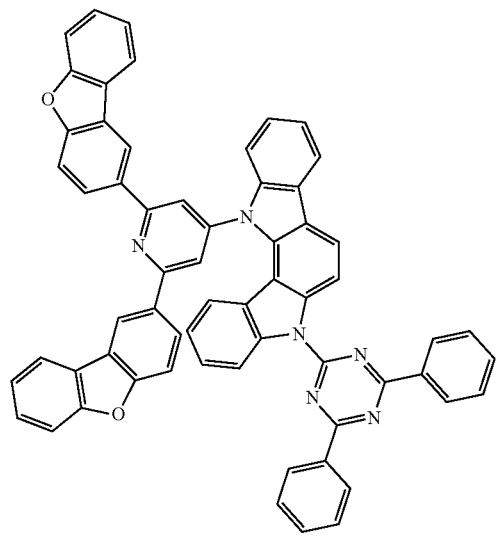
(D-17)
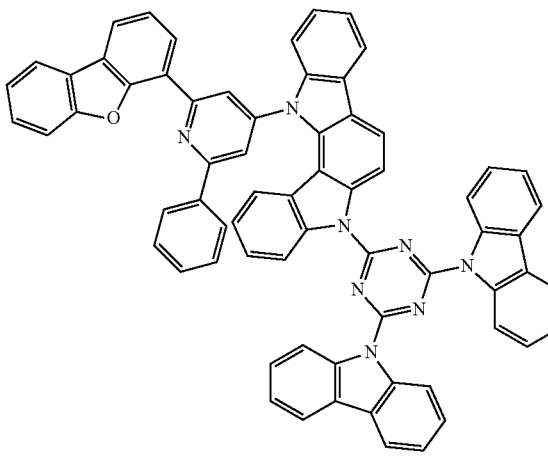
(D-18)
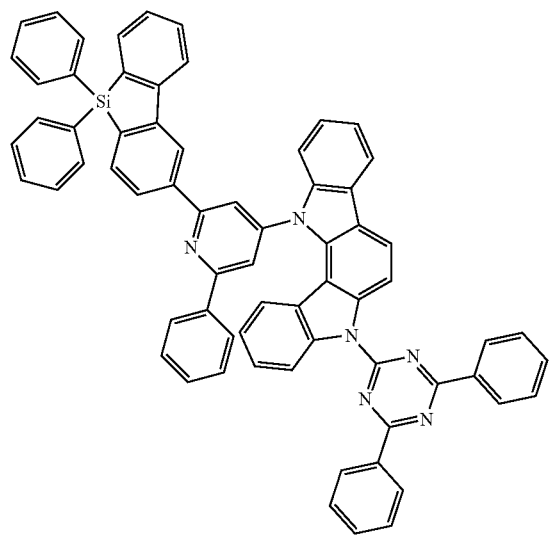
(D-19)
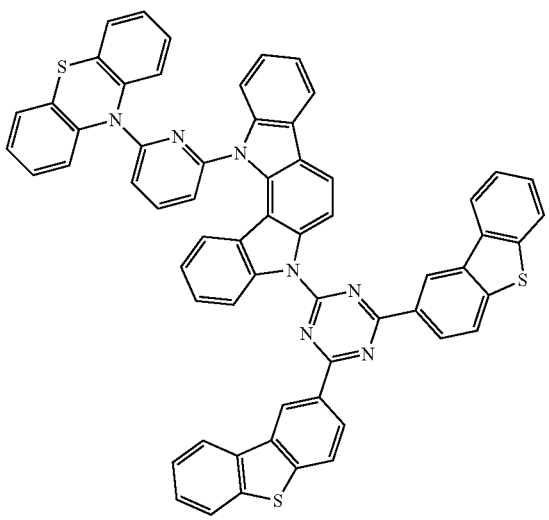

-continued
(D-20)
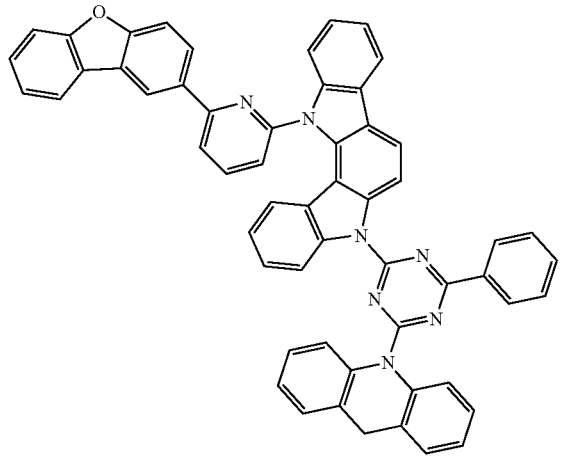
(D-21)
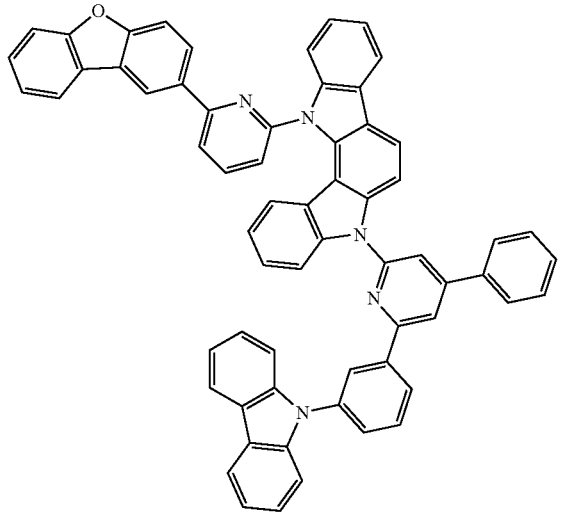
(D-22)
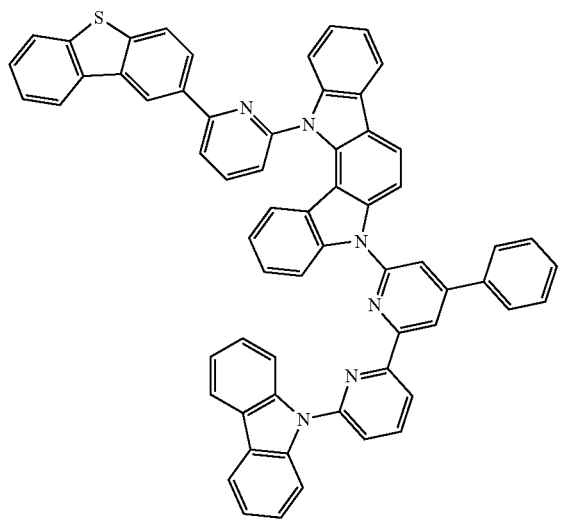
(D-23)
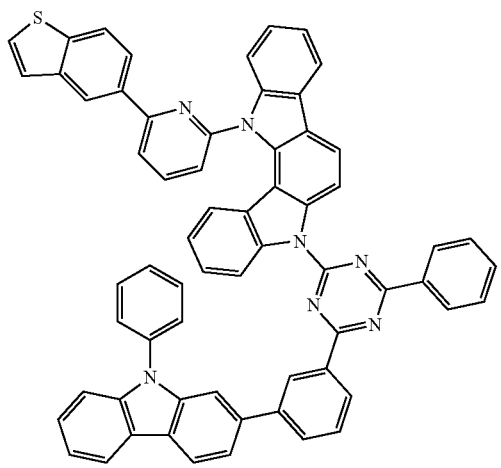
(D-24)
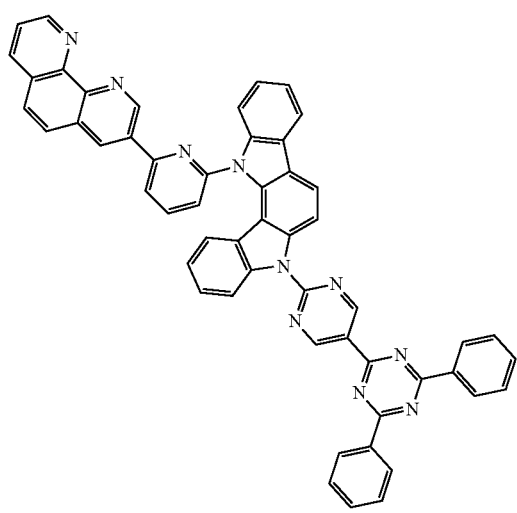
(D-25)
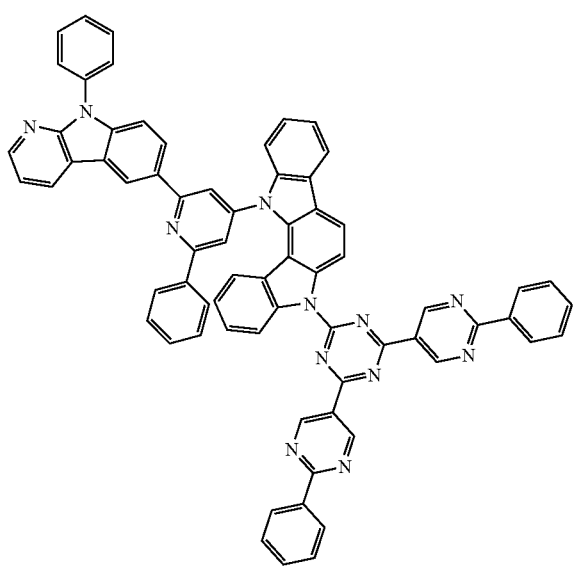

-continued
(D-26)
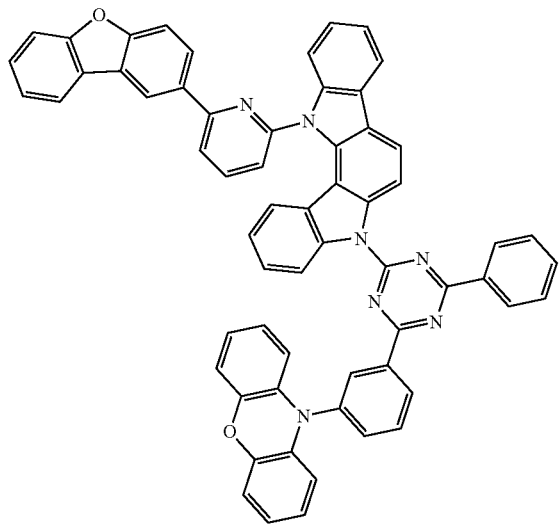
(D-27)
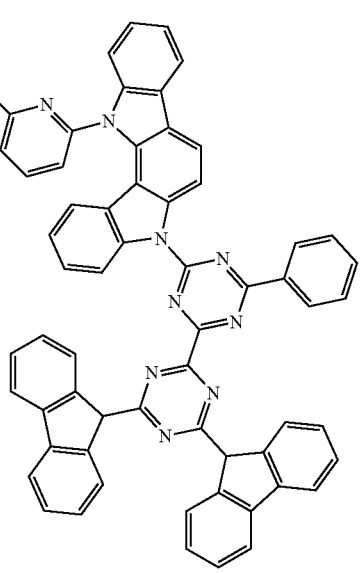
(D-28)
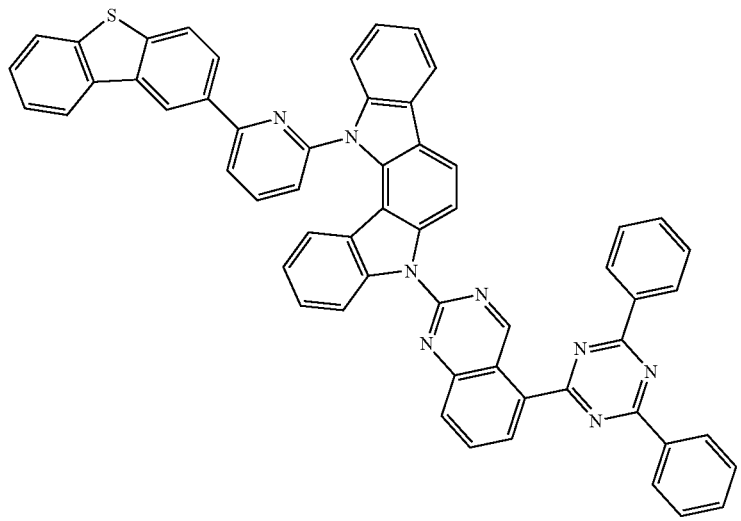
(D-29)
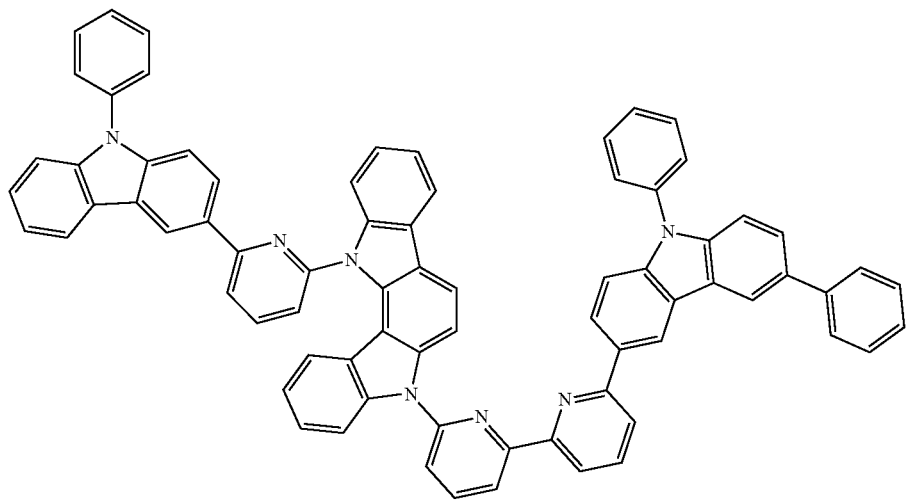

-continued
(D-30)
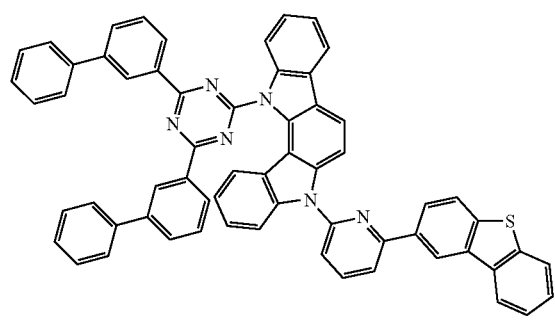
(D-31)
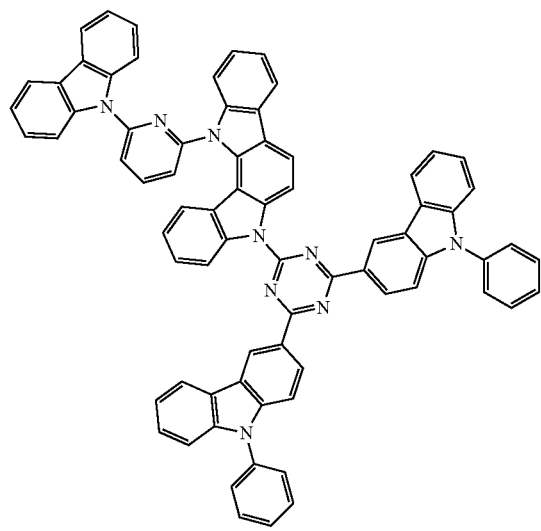
(D-32)
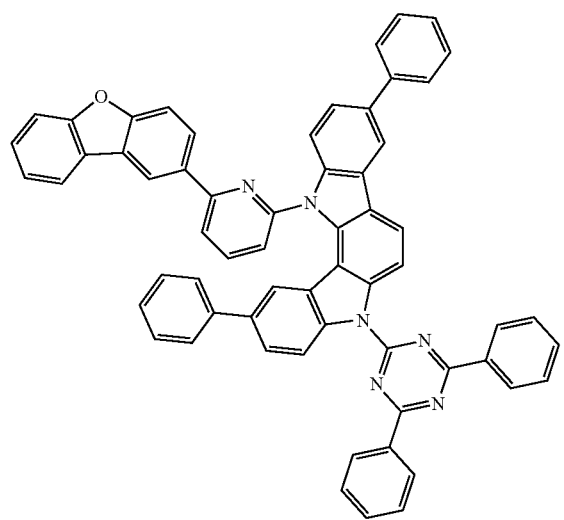
(D-33)
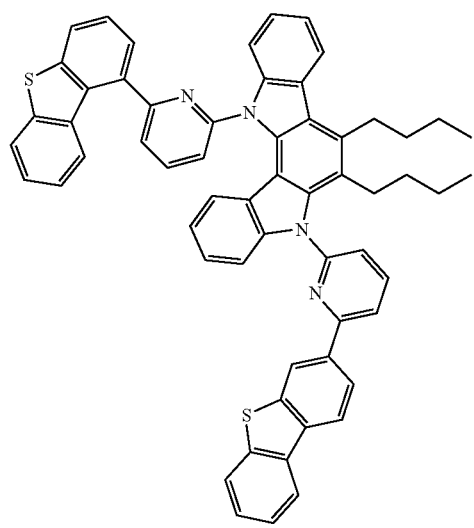
(D-34)
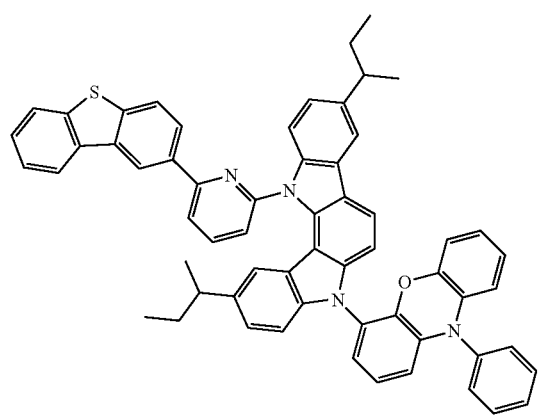
(D-35)
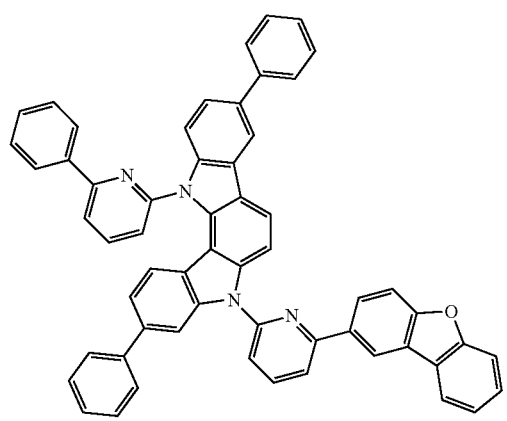

-continued
(D-36)
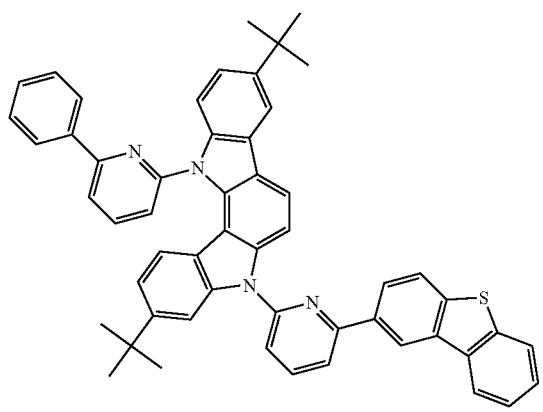
(D-37)
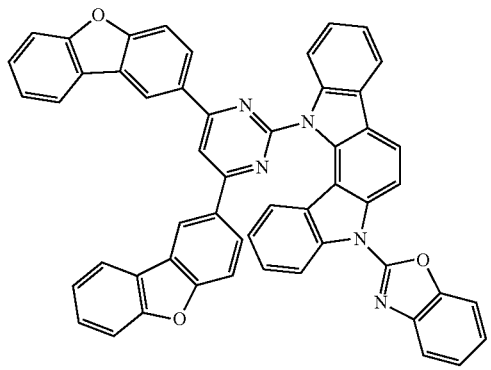
(D-38)
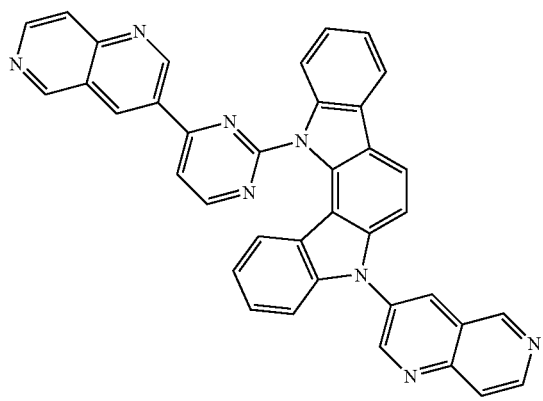
(D-39)
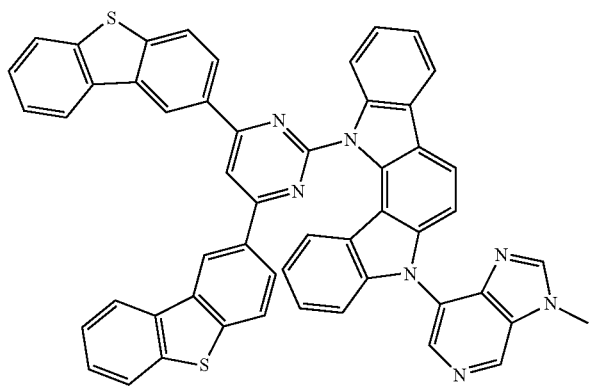
(D-40)
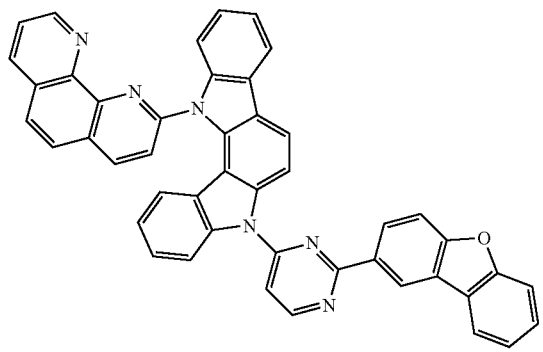
(D-41)
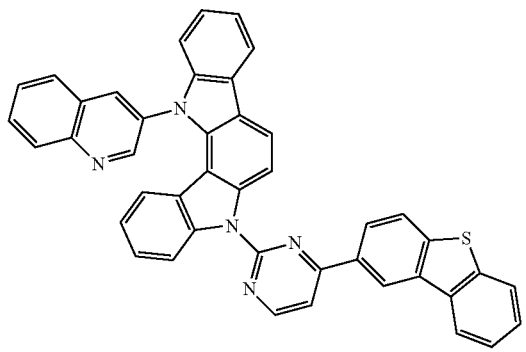

-continued
(D-42)
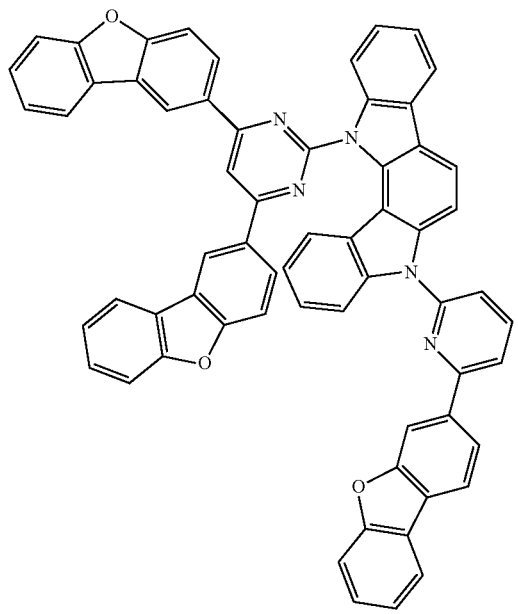
(D-43)
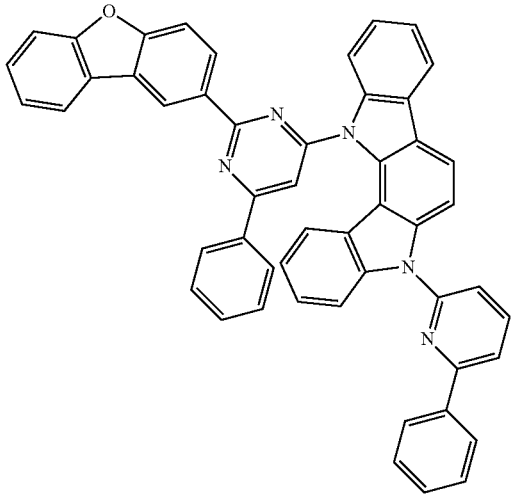
(D-44)
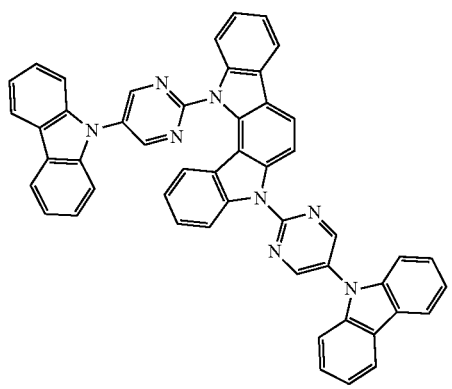
(D-45)
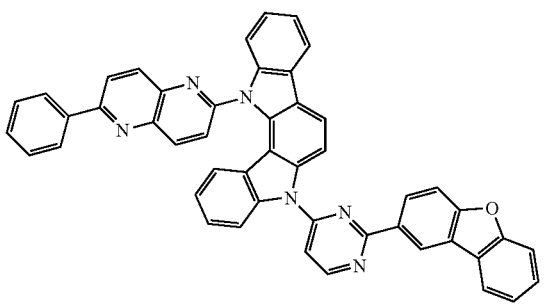
(D-46)
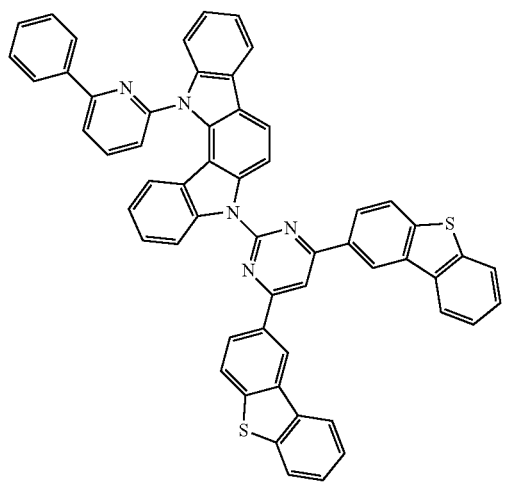
(D-47)
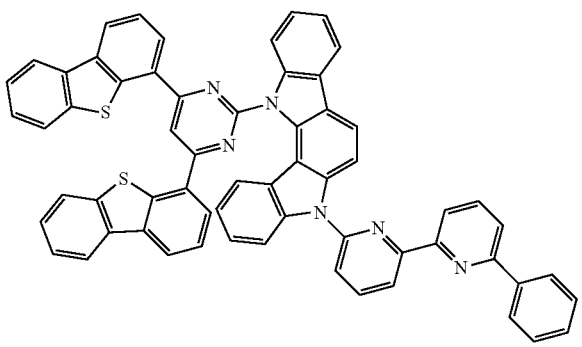

(D-48)
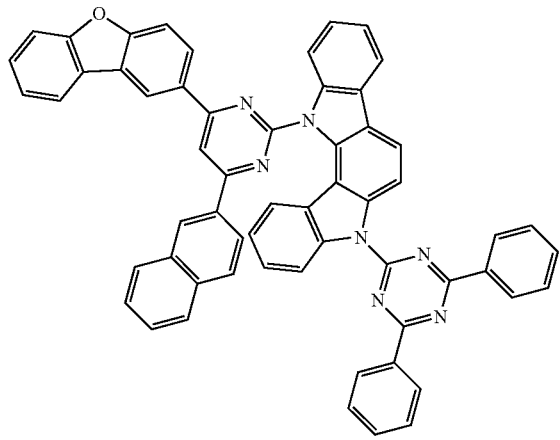
(D-49)
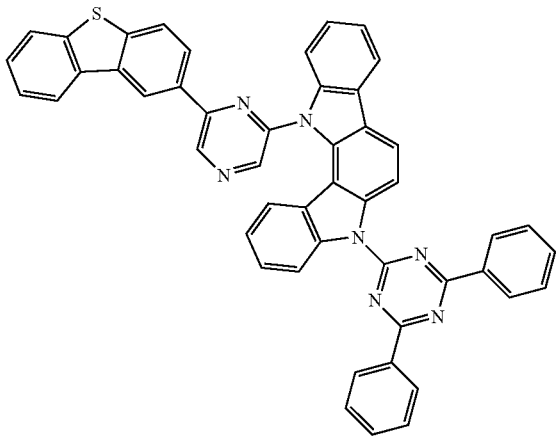
(D-50)
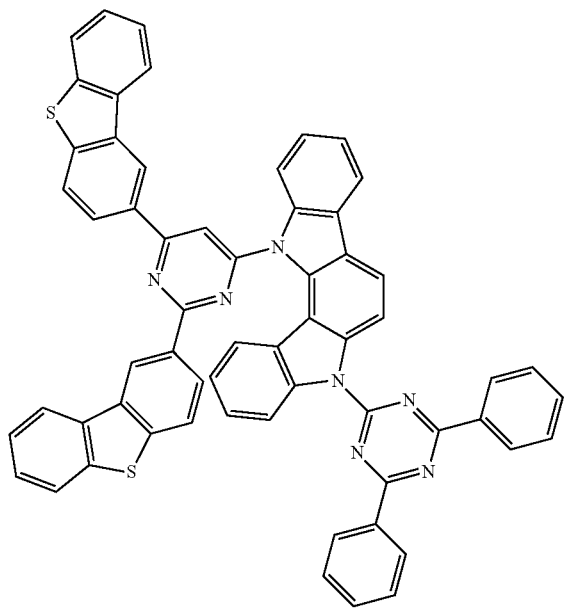
(D-51)
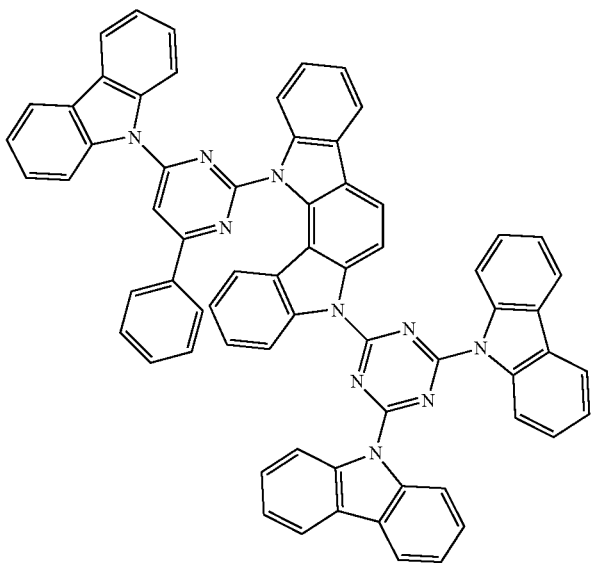
(D-52)
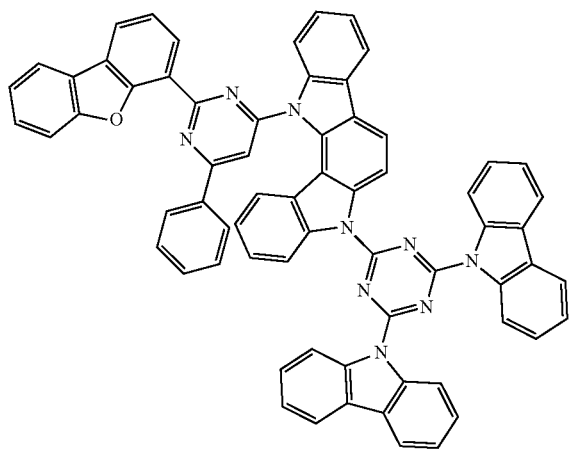
(D-53)
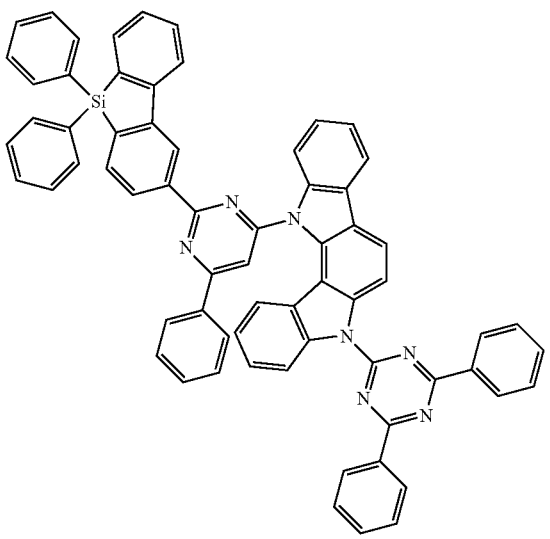

(D-54)
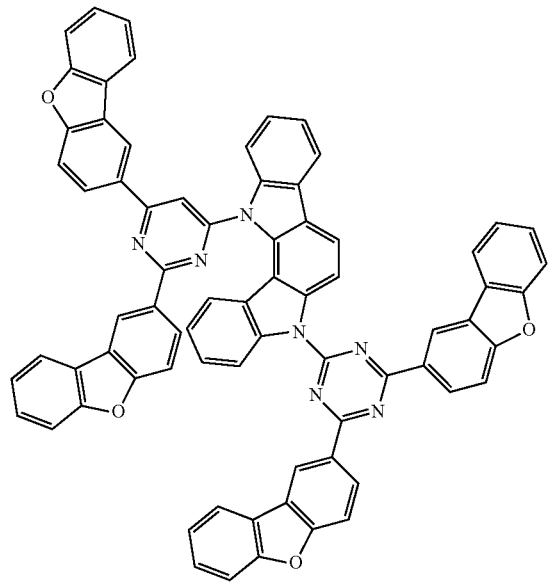
(D-55)
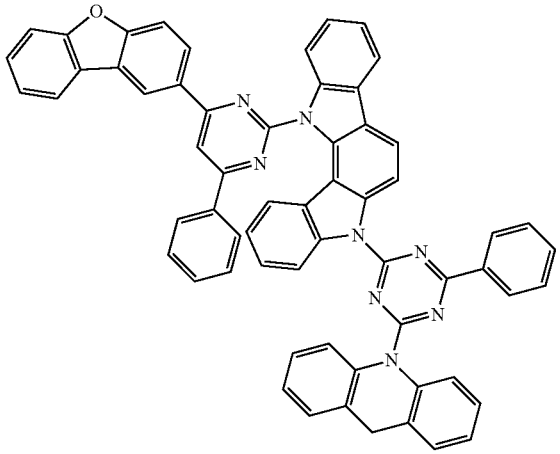
(D-56)
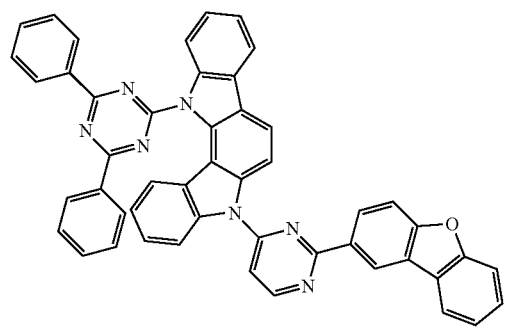
(D-57)
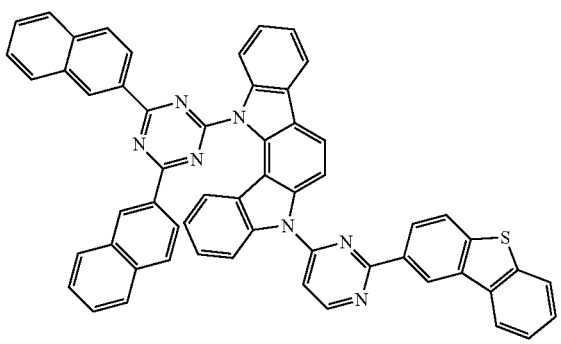
(D-58)
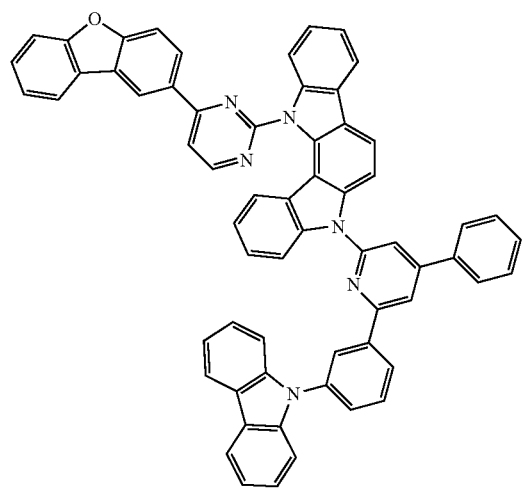
(D-59)
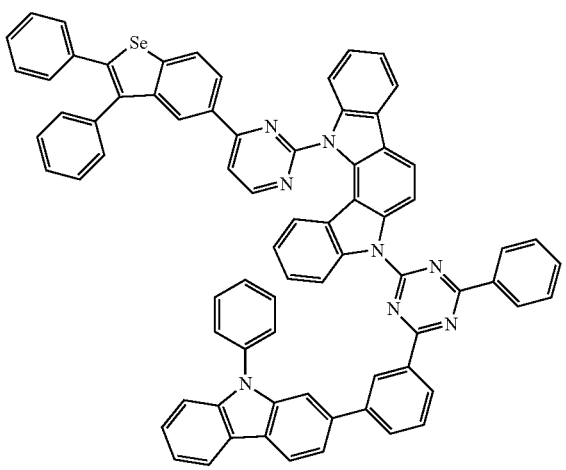

-continued
(D-60)
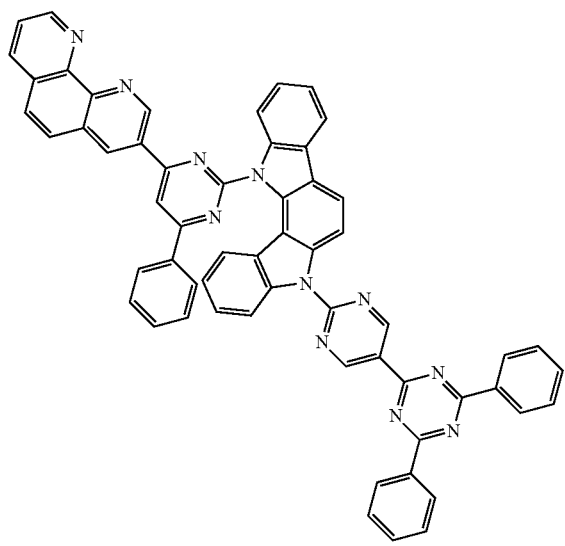
(D-61)
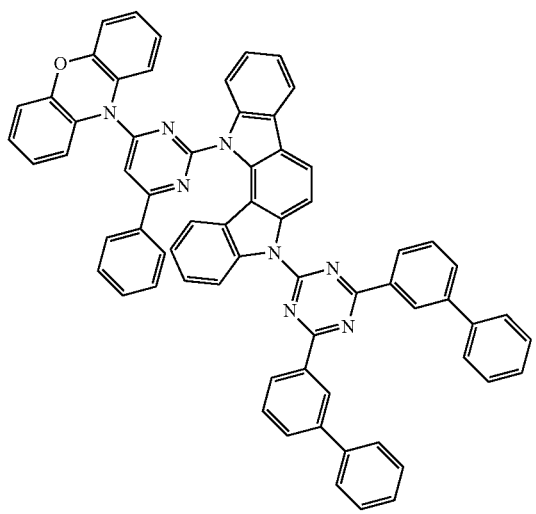
(D-62)
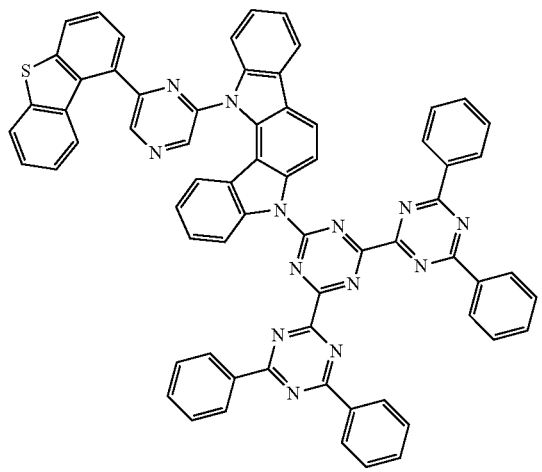
(D-63)
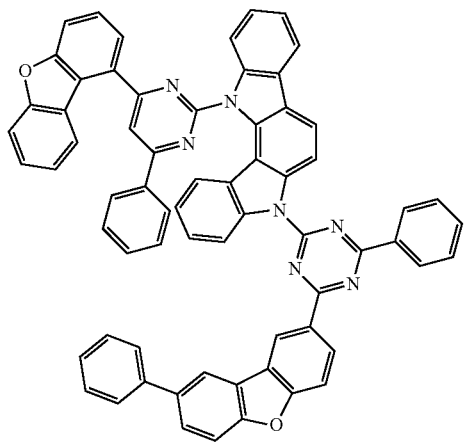

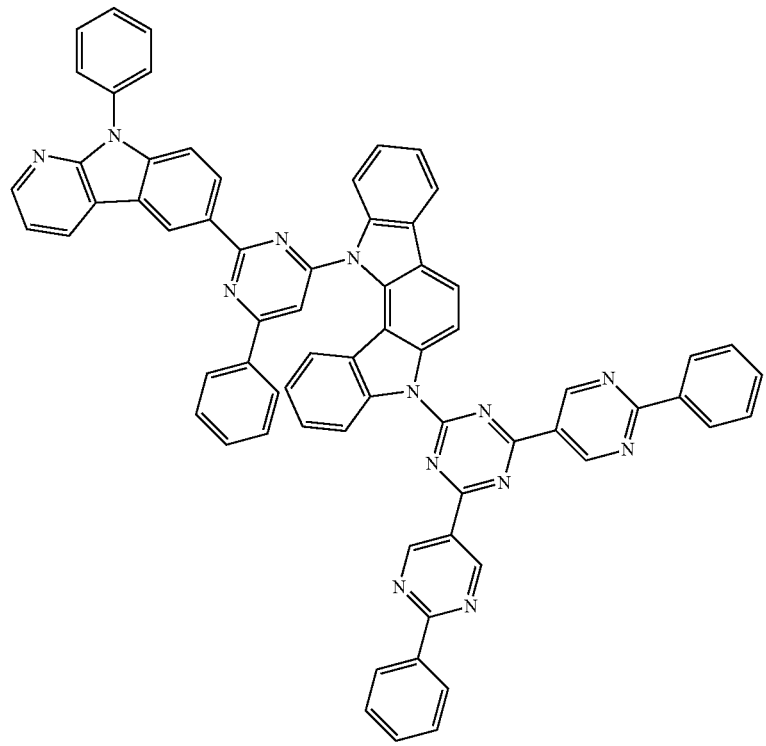
(D-64)
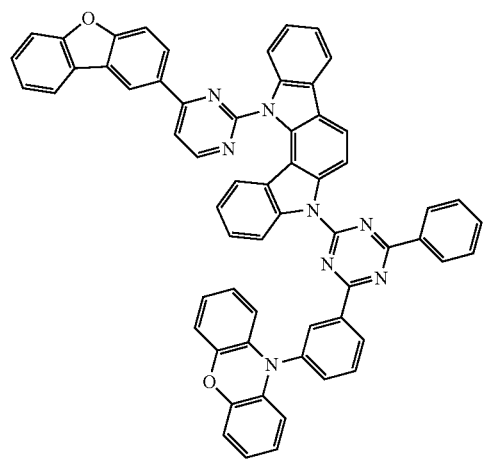
(D-65)
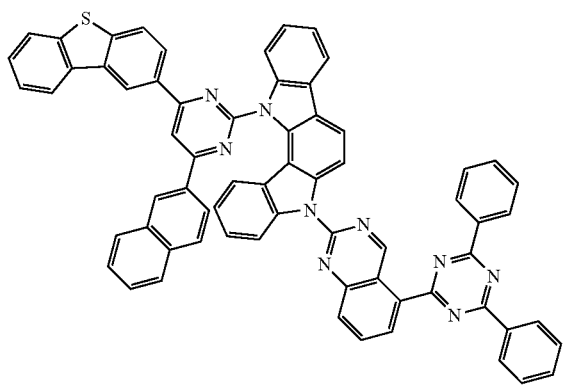
(D-66)

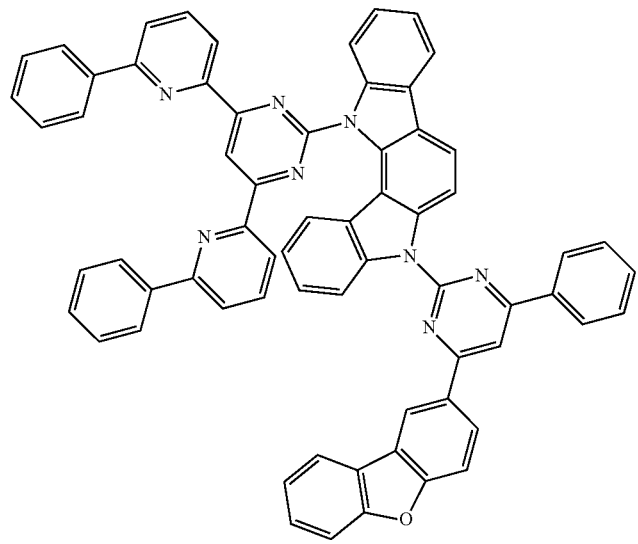
(D-67)
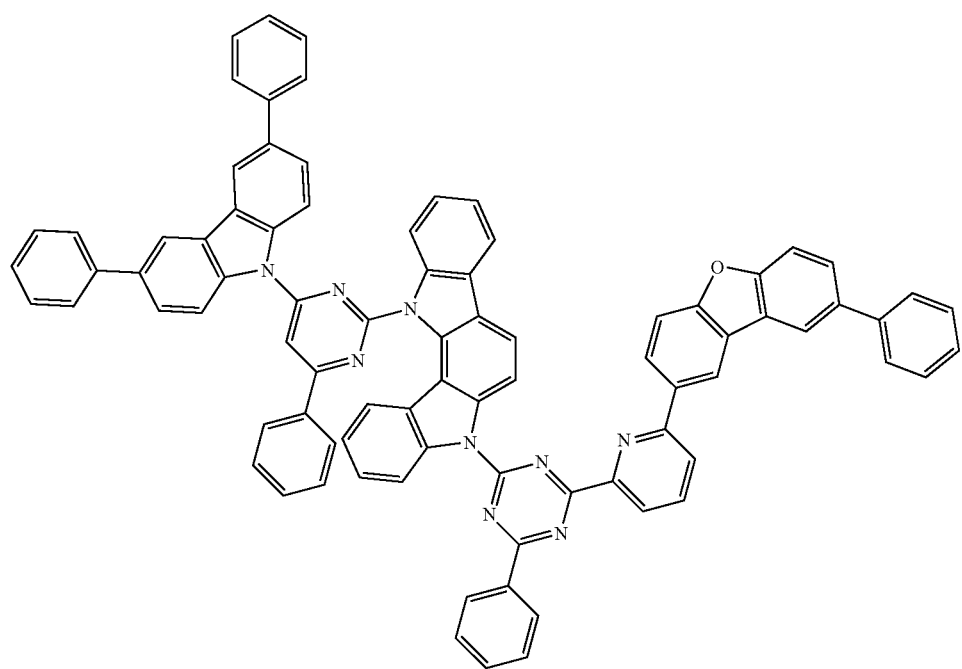
(D-68)

-continued
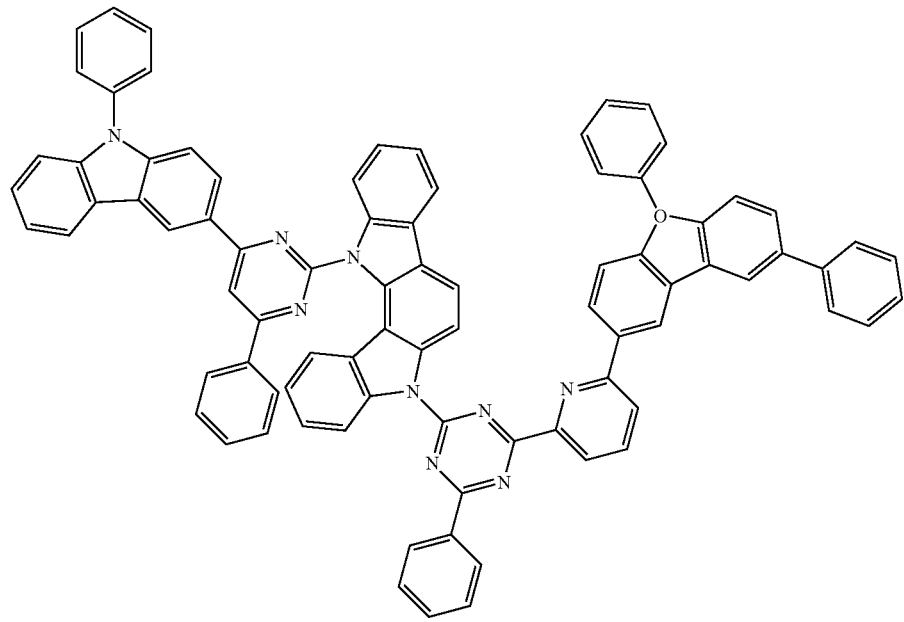
(D-69)
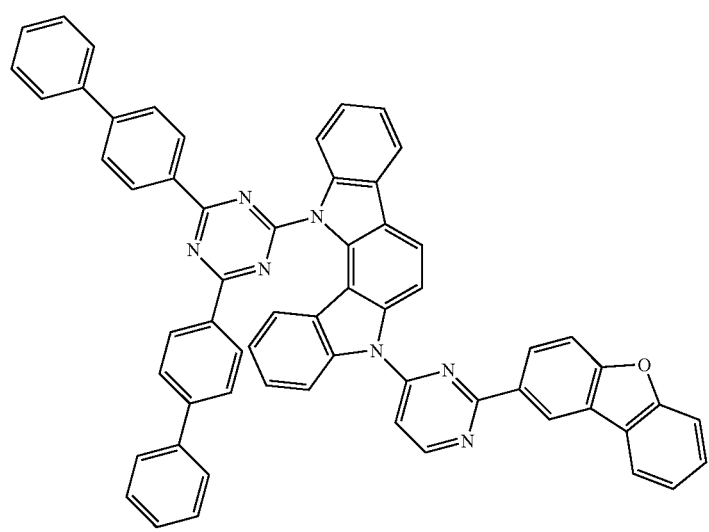
(D-70)

-continued
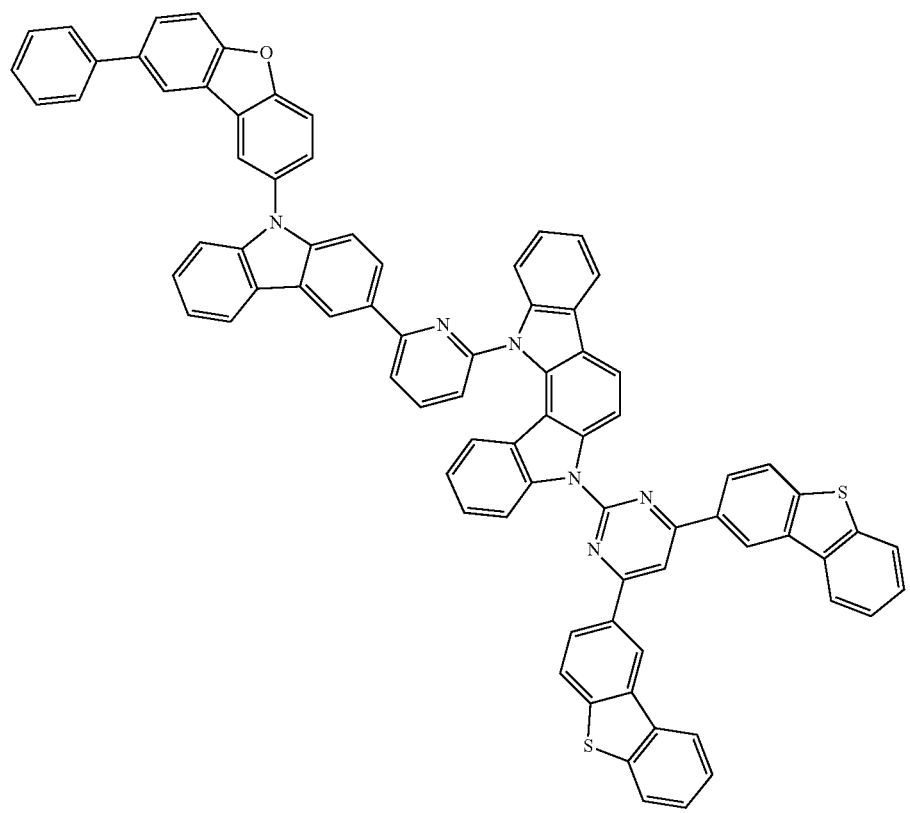
(D-71)
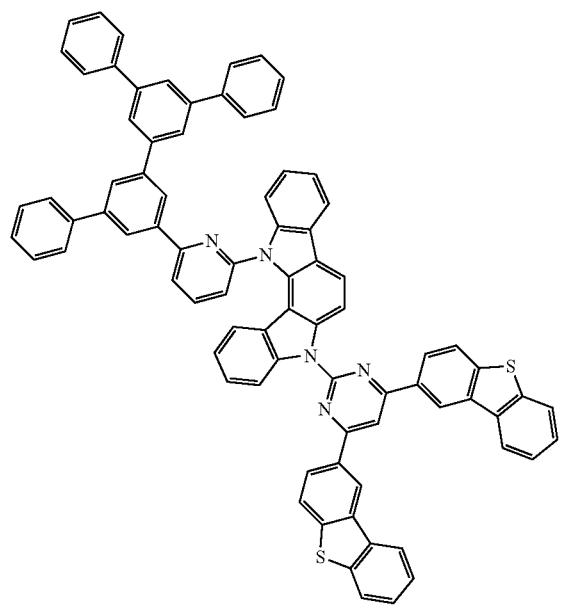
(D-72)
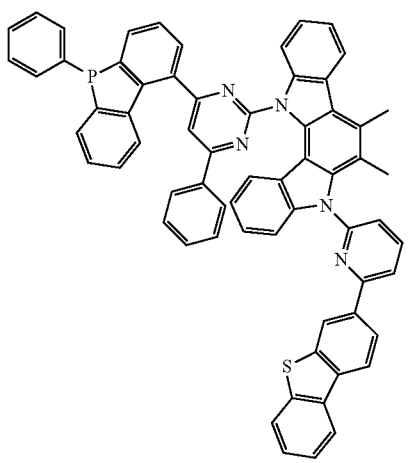
(D-73)

-continued
(D-74)
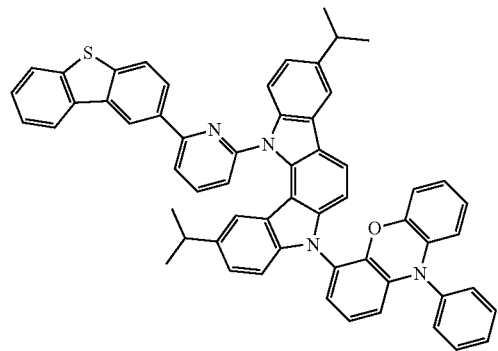
(D-75)
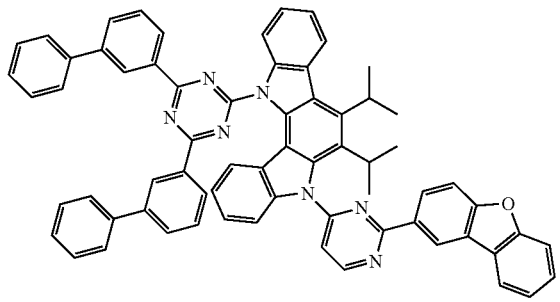
(D-76)
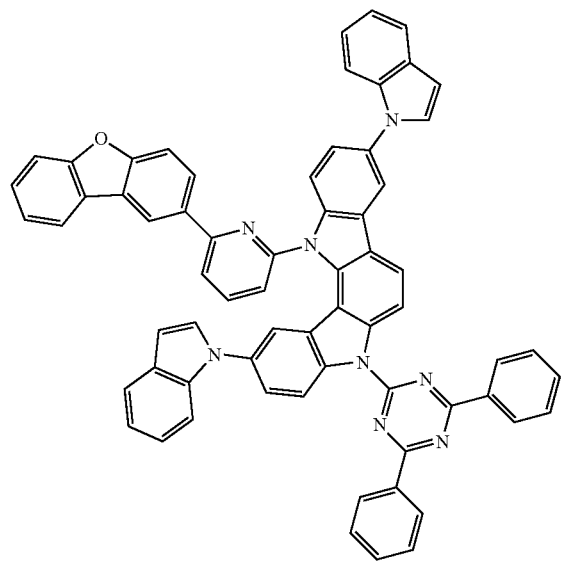
(D-77)
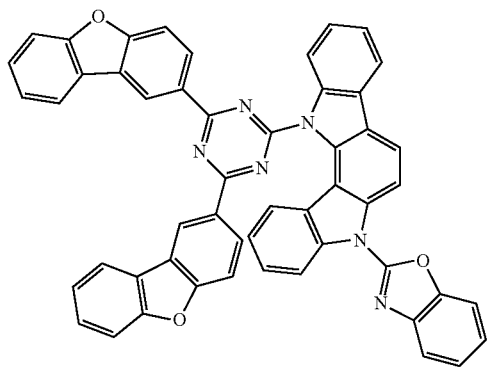
(D-78)
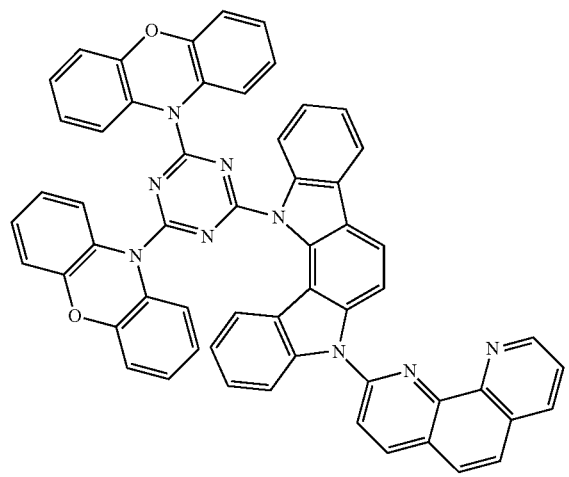
(D-79)
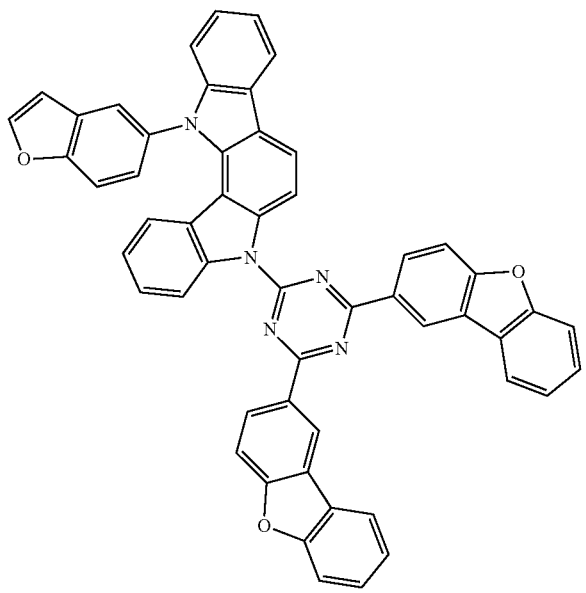

-continued
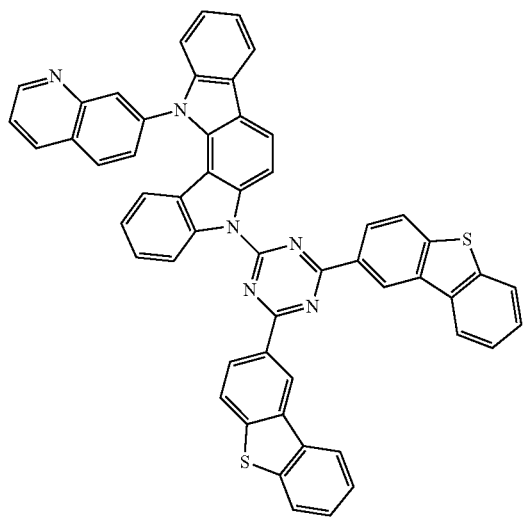
(D-80)
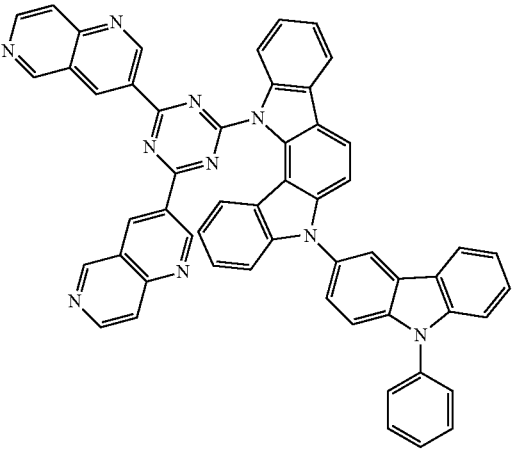
(D-81)
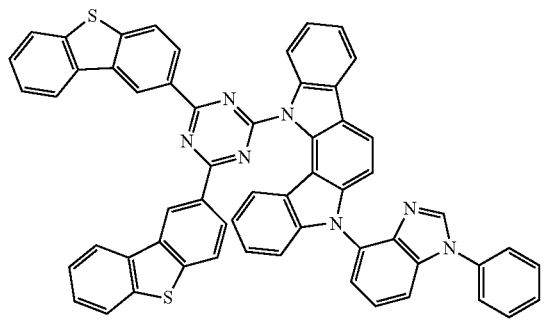
(D-82)
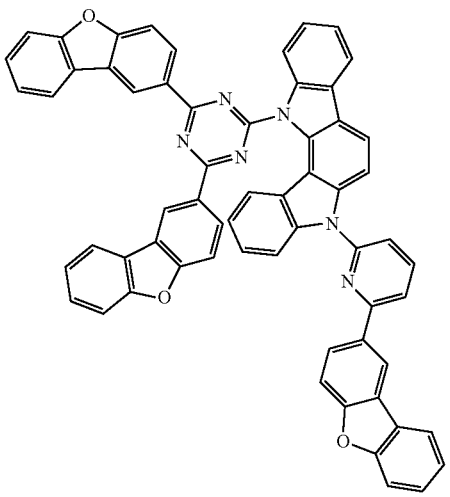
(D-83)
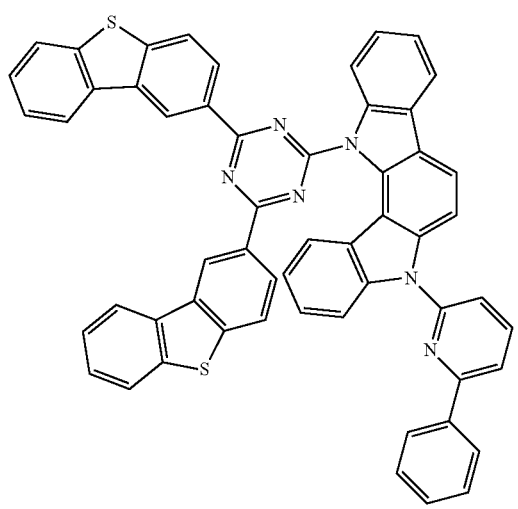
(D-84)

153 154
(D-85) (D-86)
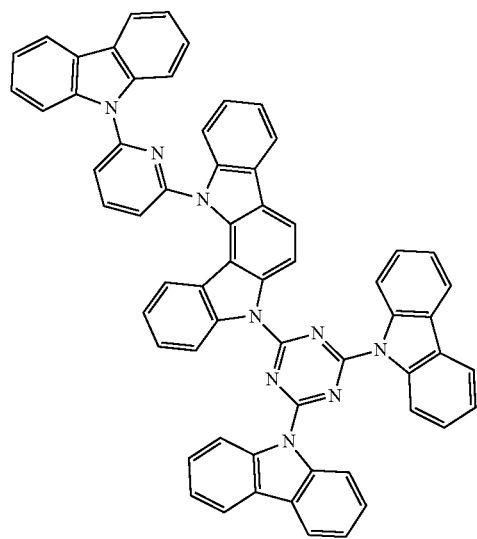 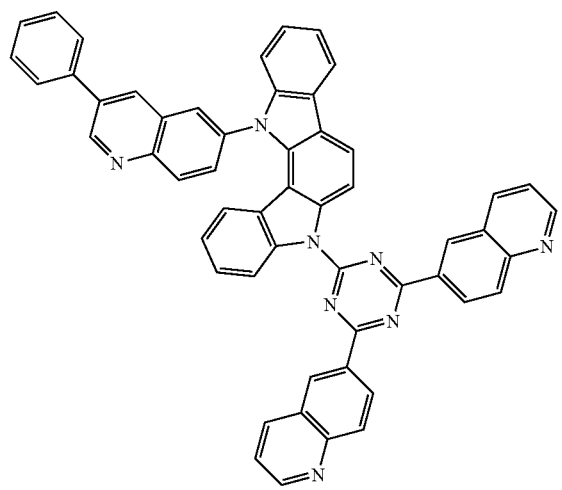
(D-87) (D-88)
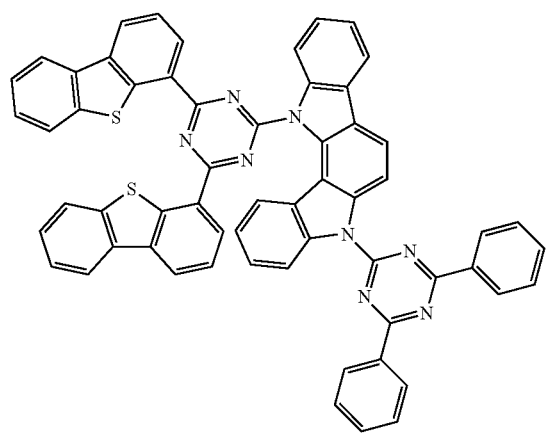 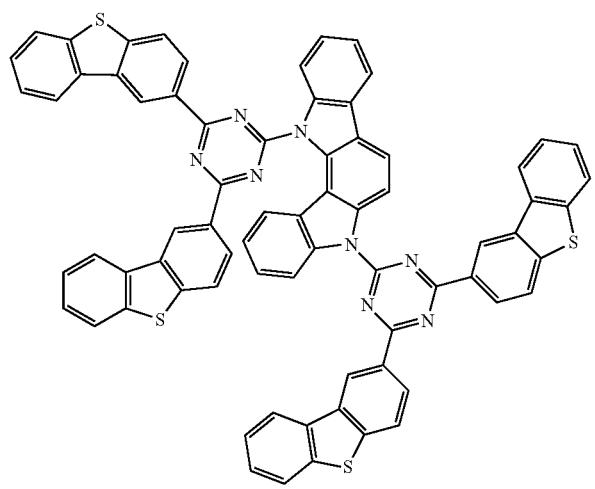

-continued
(D-89)
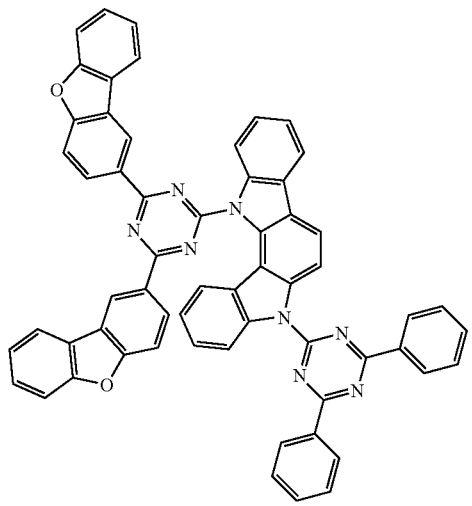
(D-90)
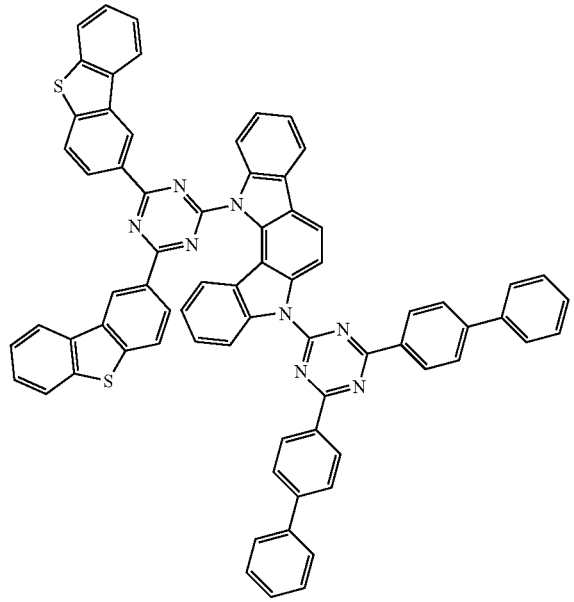
(D-91)
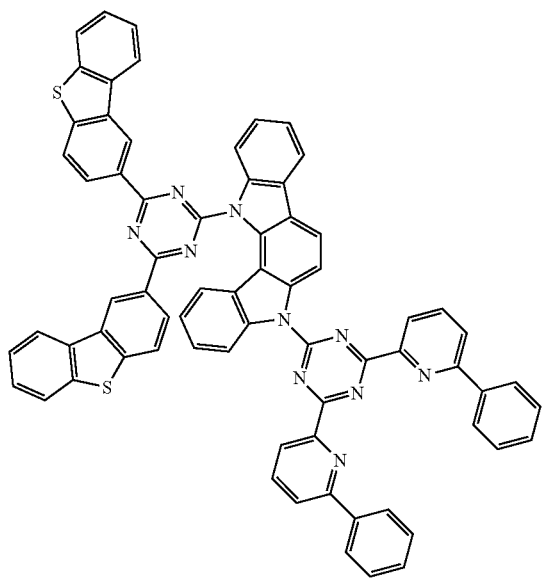
(D-92)
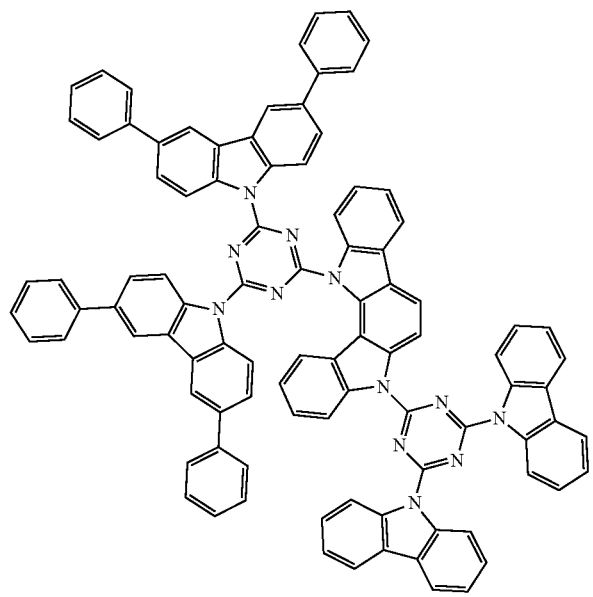

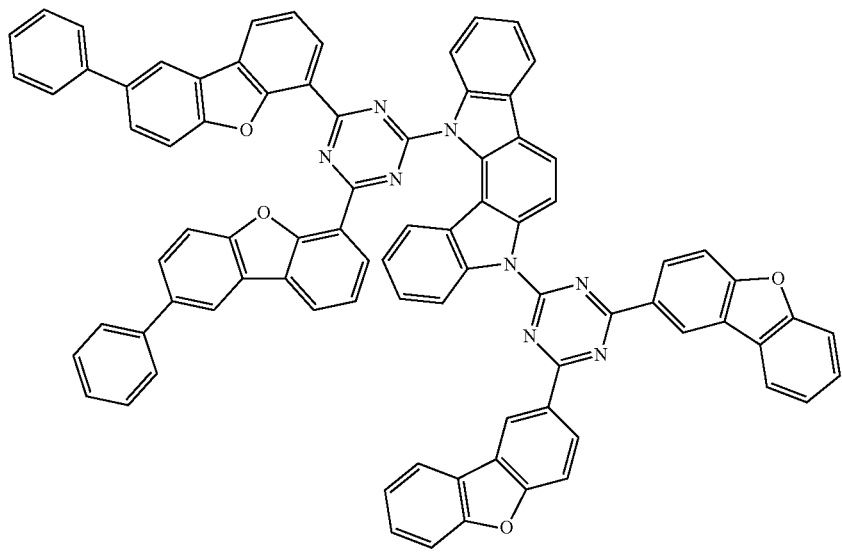
(D-93)
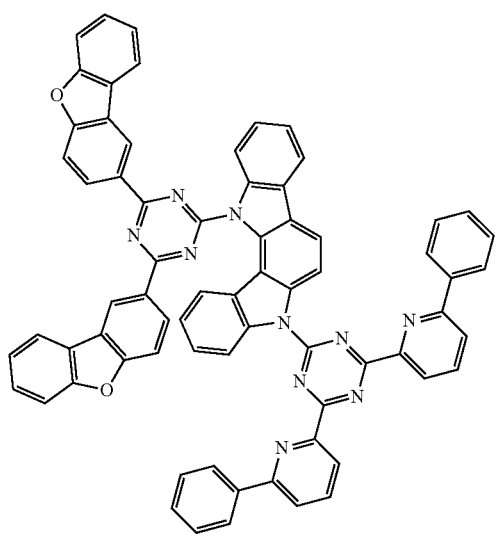
(D-94)
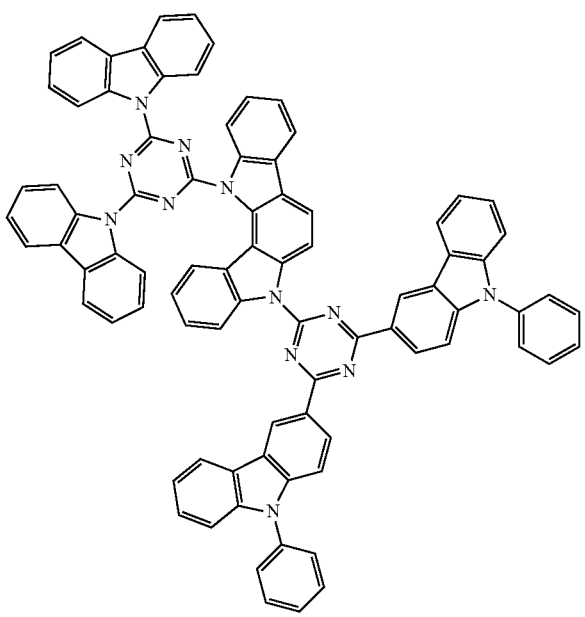
(D-95)

-continued
(D-96)
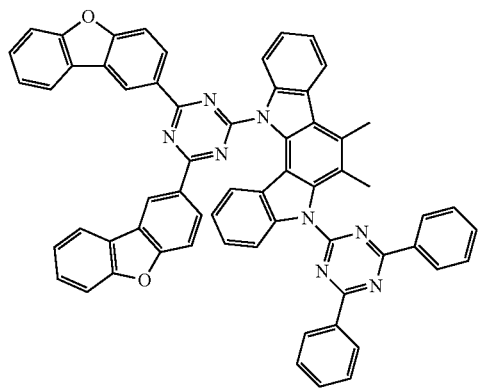
(D-97)
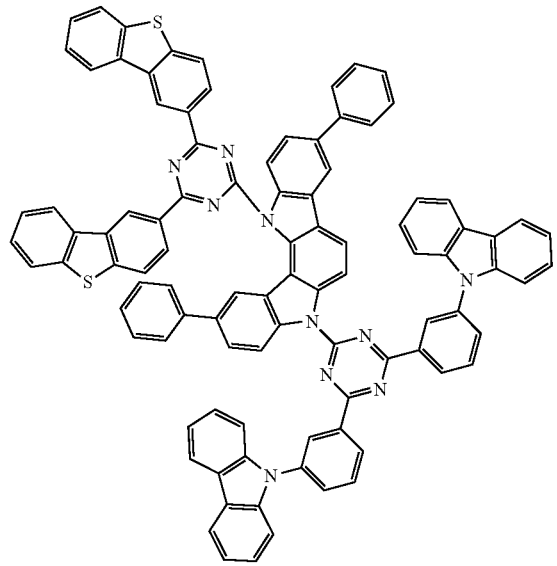
(E-1)
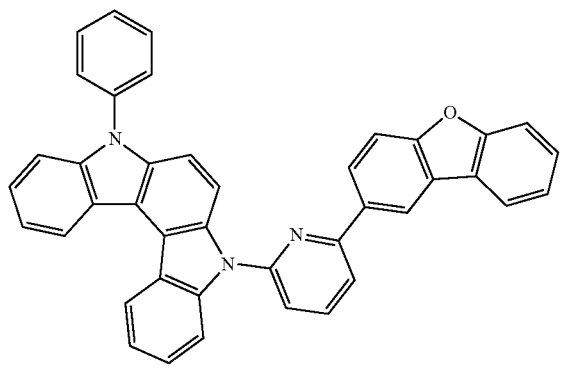
(E-2)
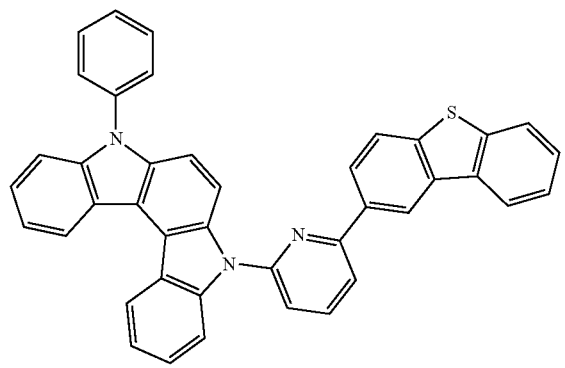
(E-3)
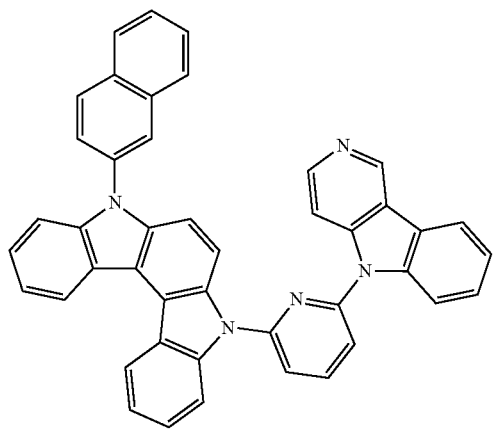
(E-4)
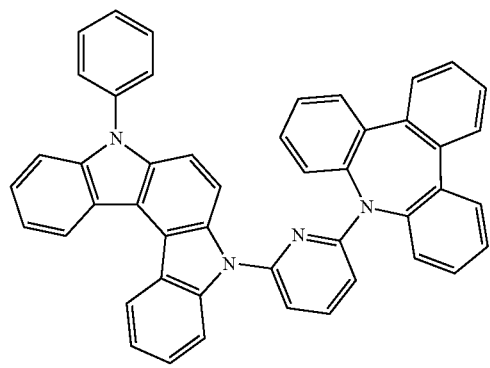

-continued
(E-5)
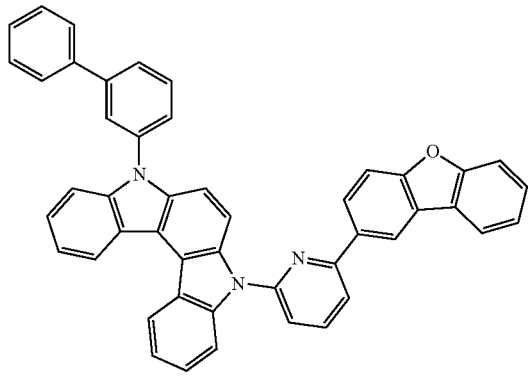
(E-6)
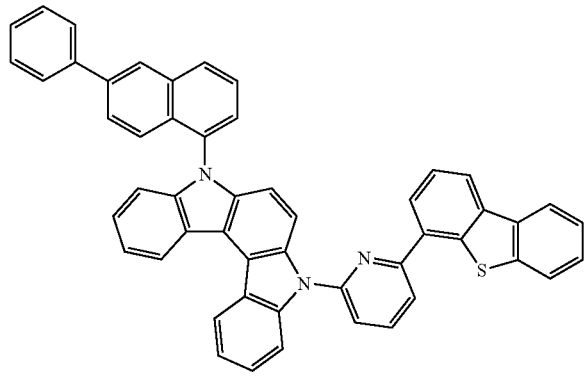
(E-7)
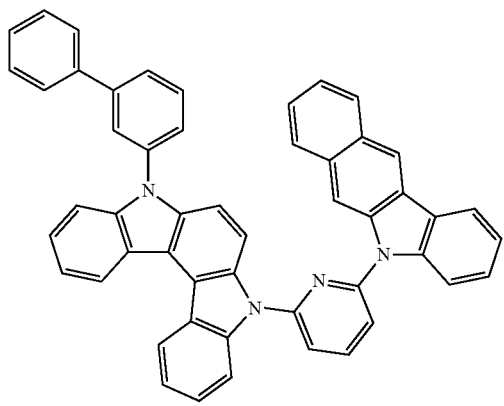
(E-8)
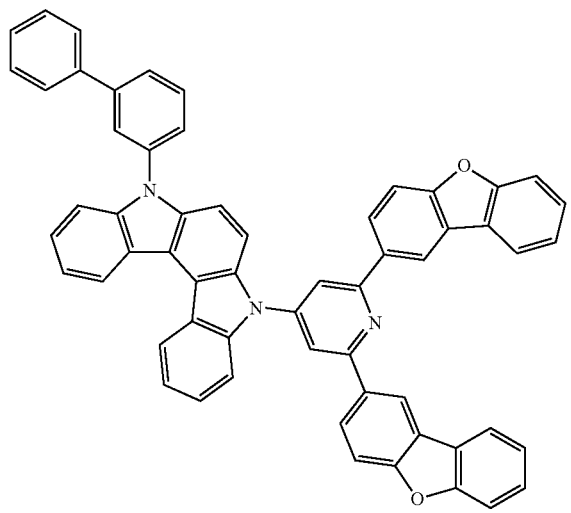
(E-9)
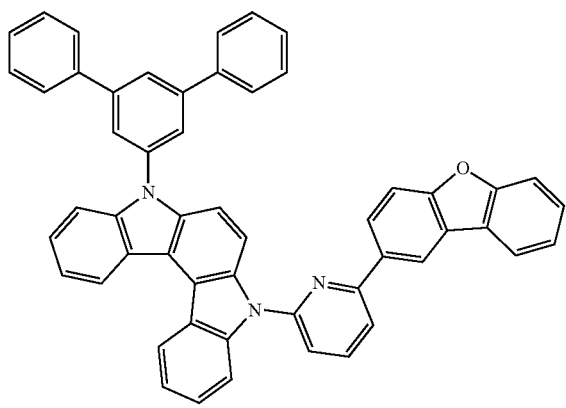
(E-10)
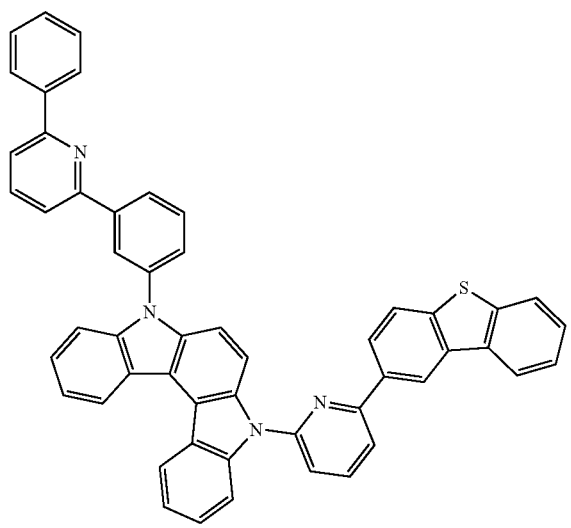

-continued
(E-11)
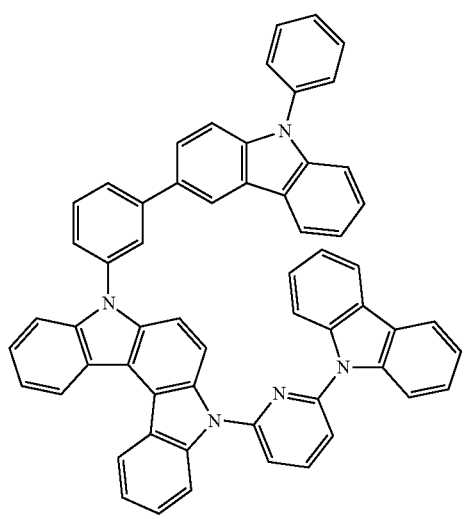
(E-12)
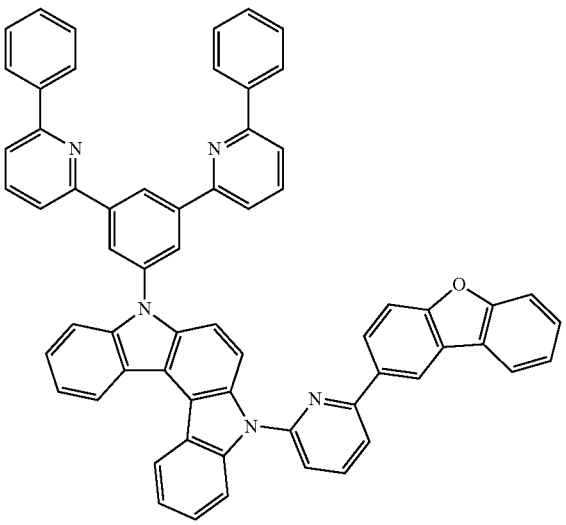
(E-13)
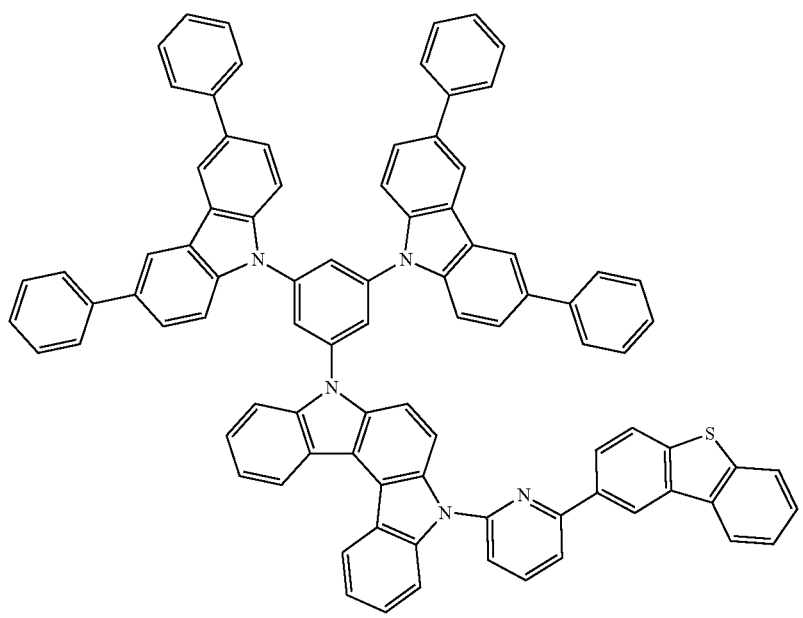

-continued
(E-14)
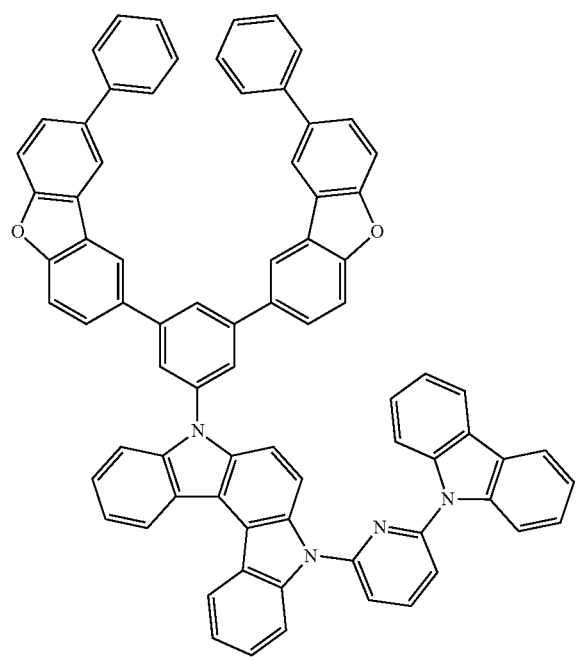
(E-15)
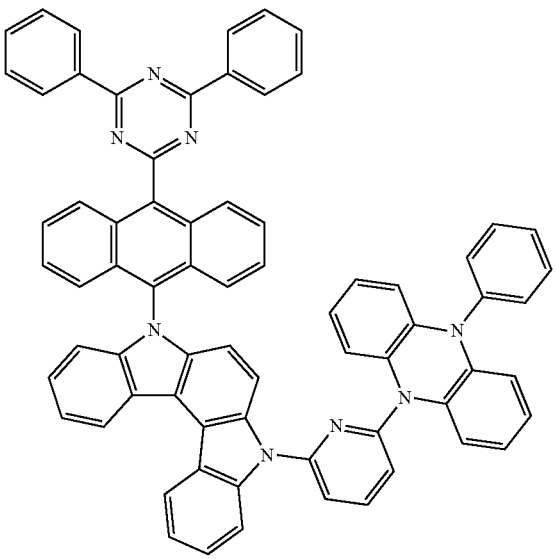
(E-16)
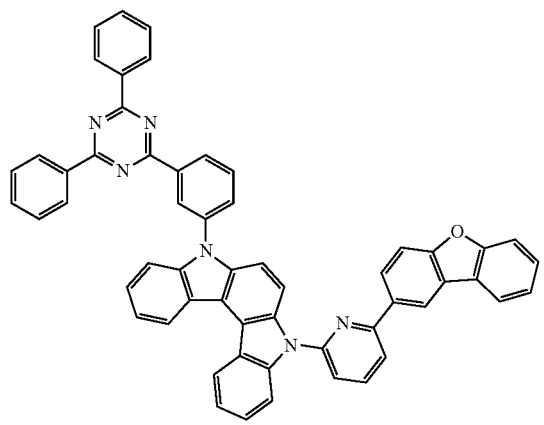
(E-17)
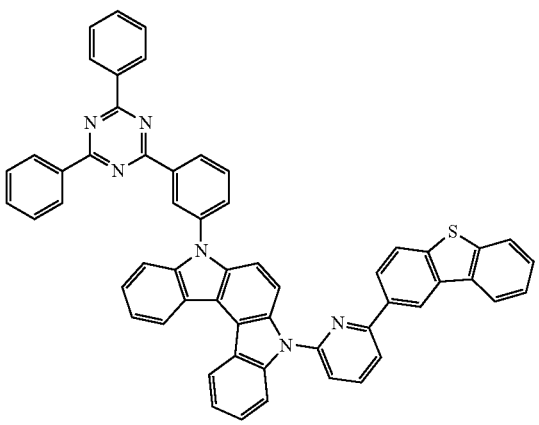

-continued
(E-18)
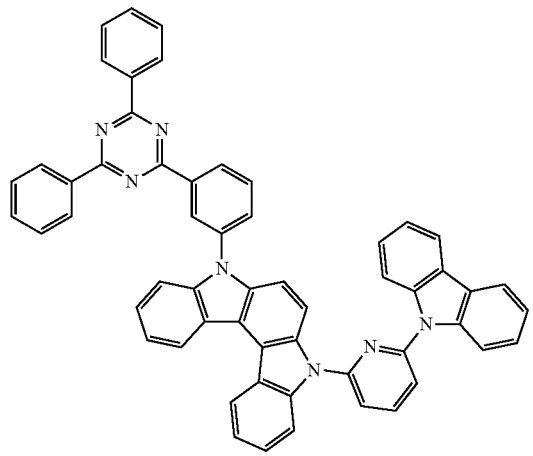
(E-19)
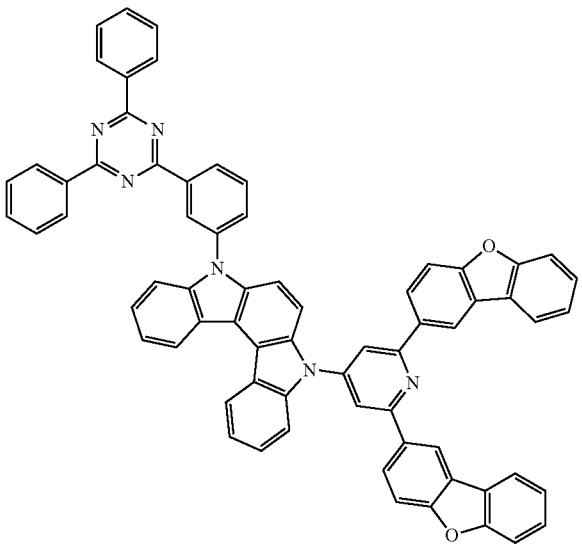
(E-20)
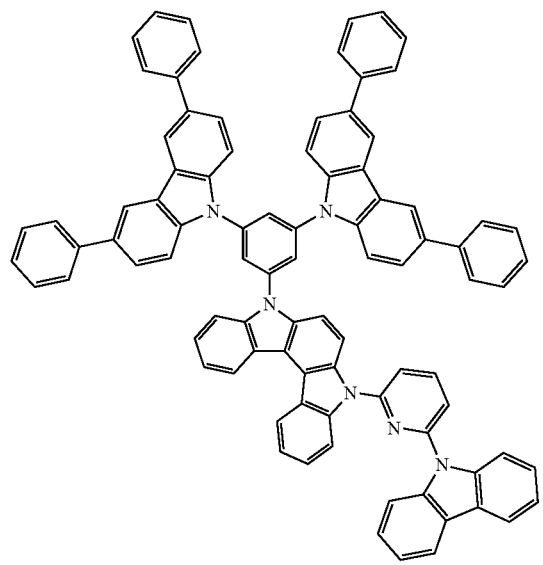
(E-21)
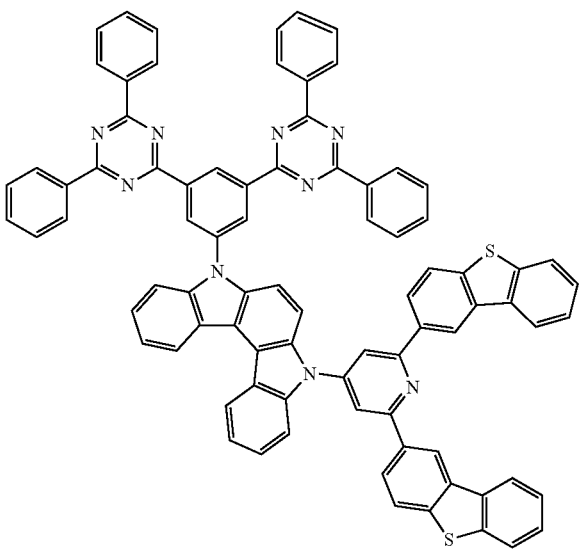
(E-22)
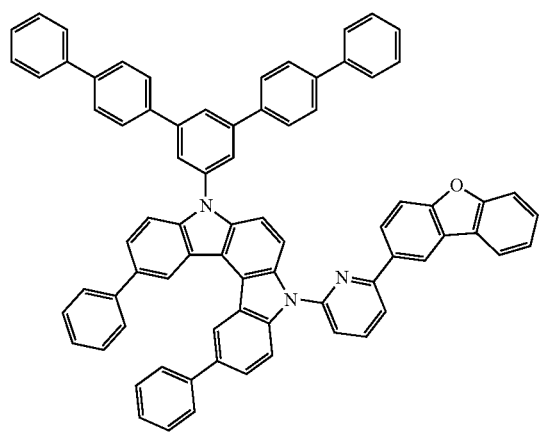
(E-23)
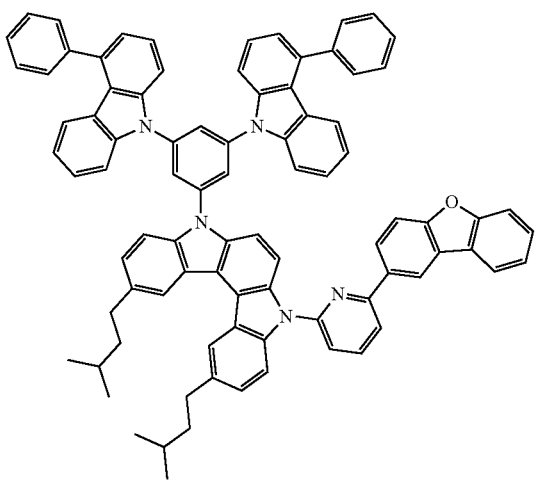

-continued
(E-24)
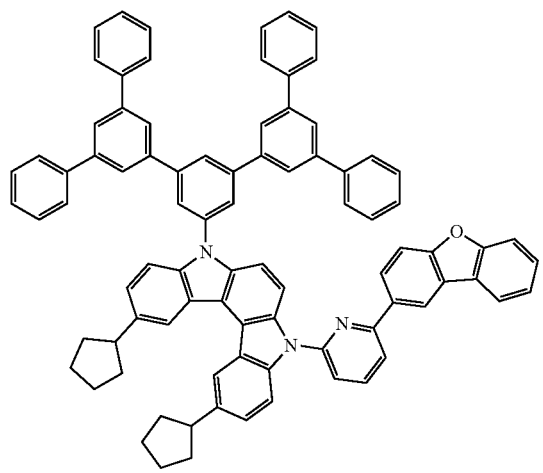
(E-25)
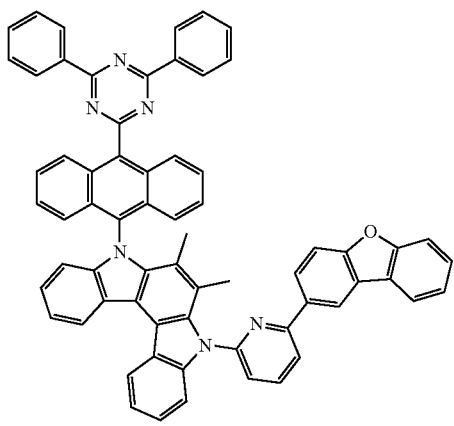
(E-26)
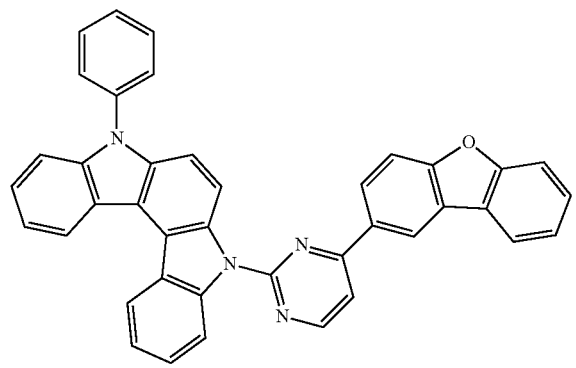
(E-27)
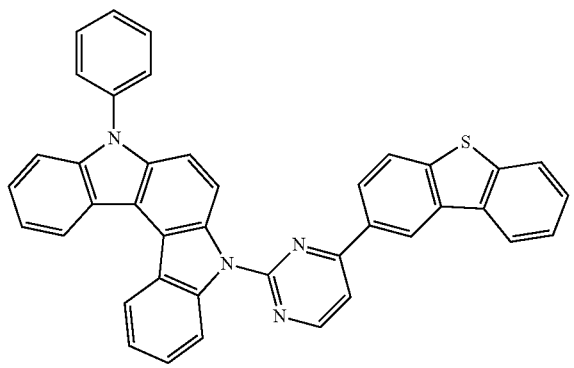
(E-28)
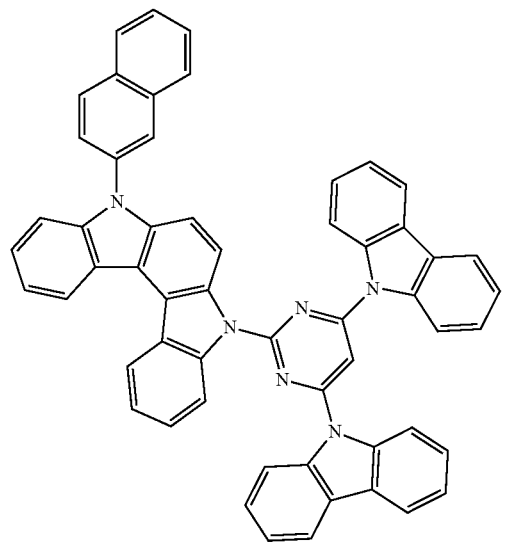
(E-29)
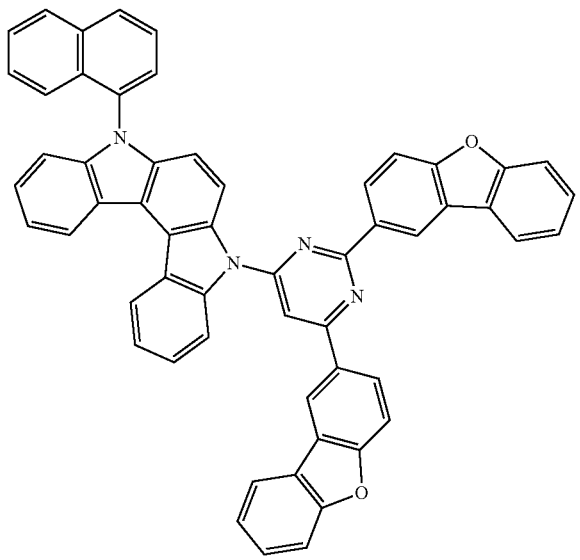

-continued
(E-30)
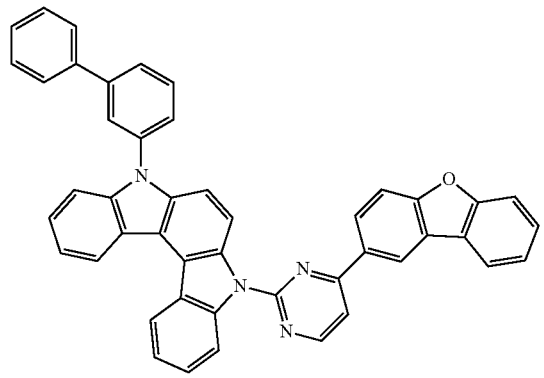
(E-31)
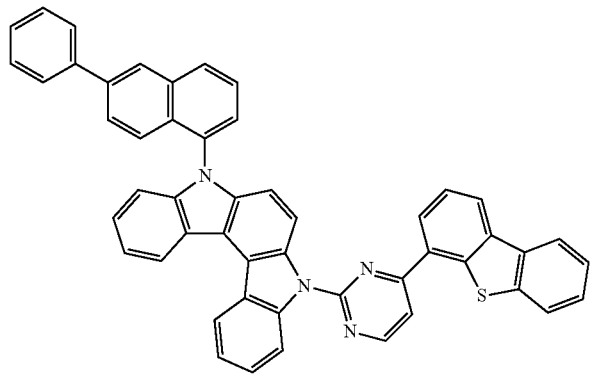
(E-32)
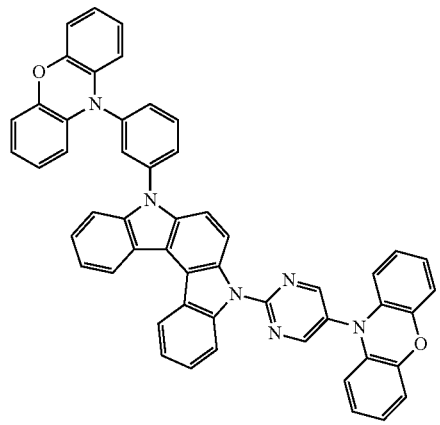
(E-33)
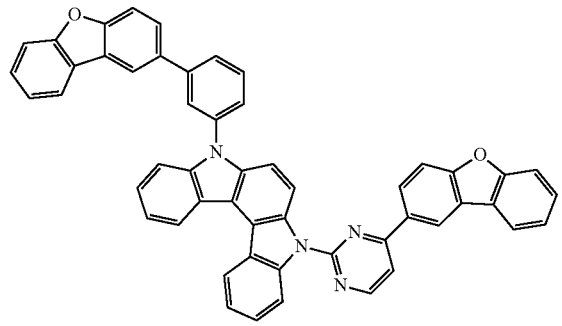
(E-34)
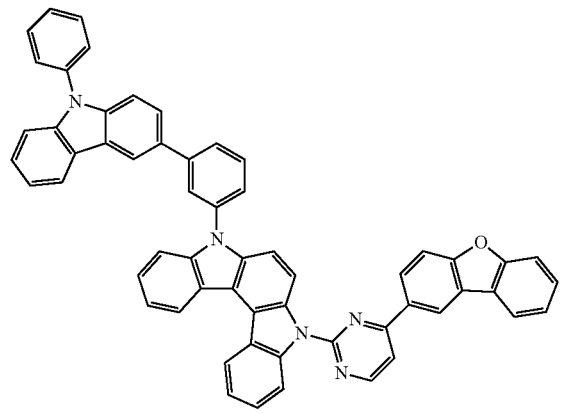
(E-35)
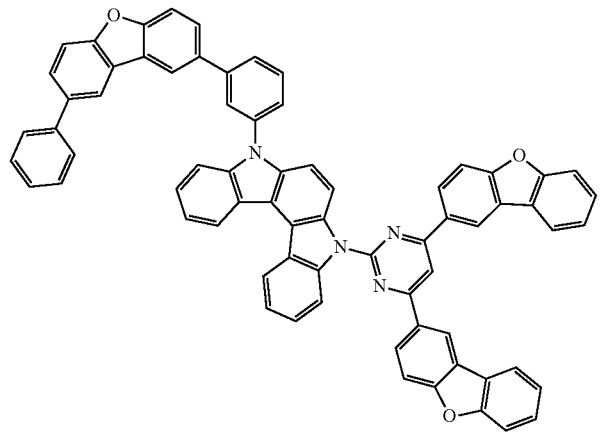

(E-36)
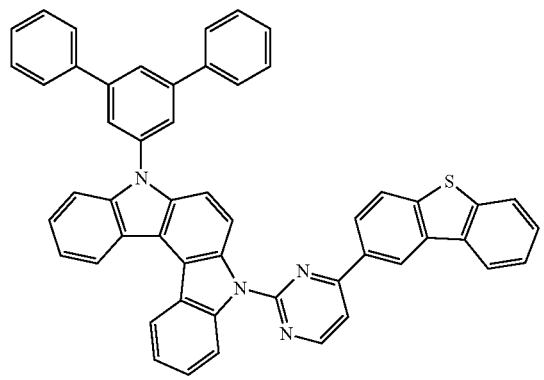
(E-37)
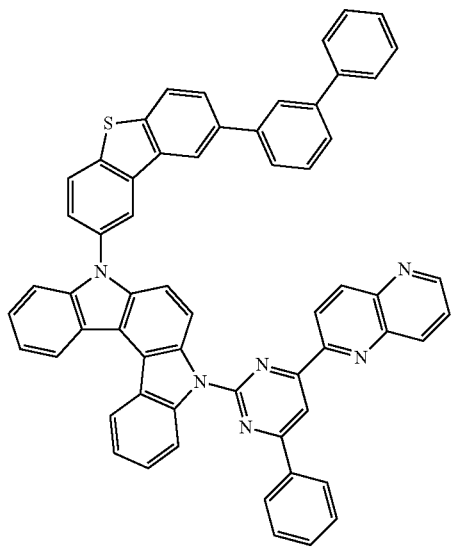
(E-38)
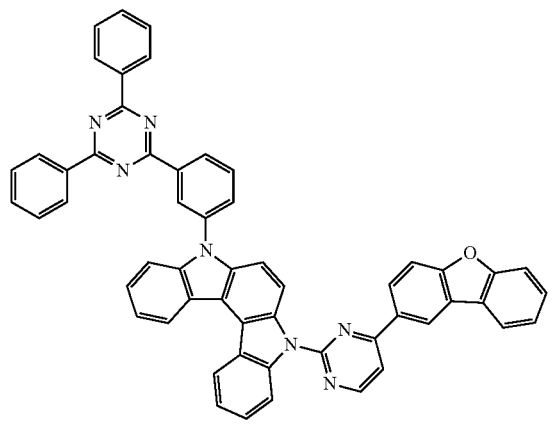
(E-39)
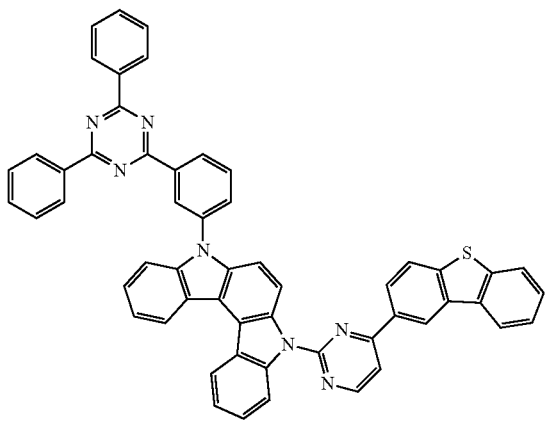
(E-40)
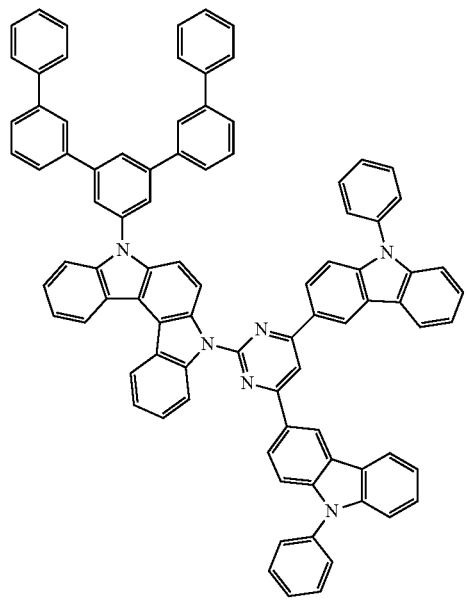
(E-41)
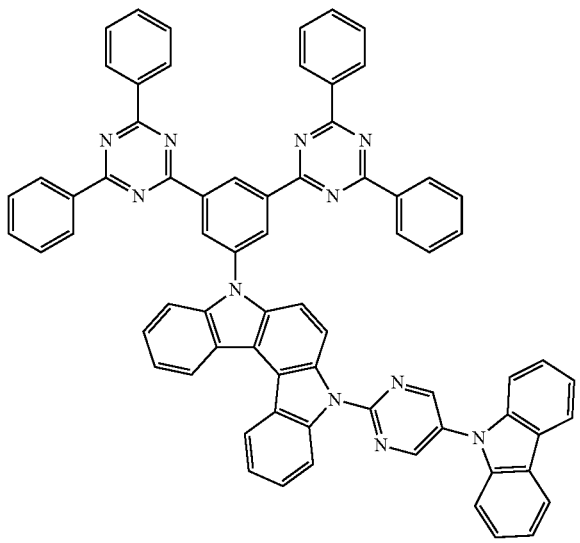

-continued
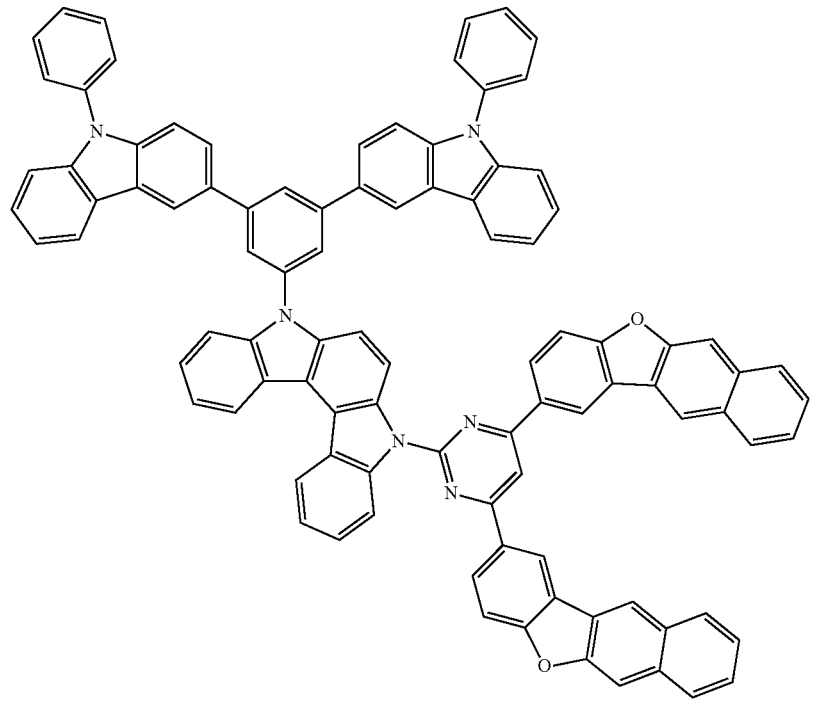
(E-42)
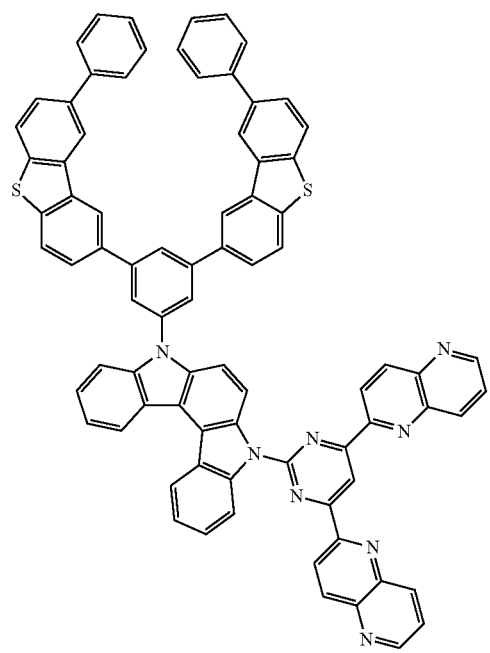
(E-43)
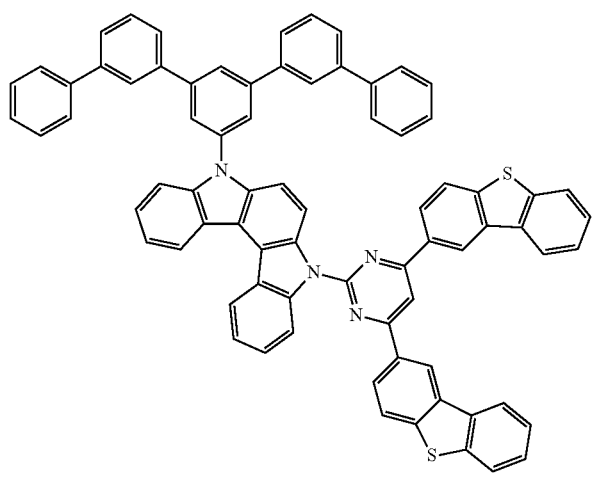
(E-44)

-continued
(E-45)
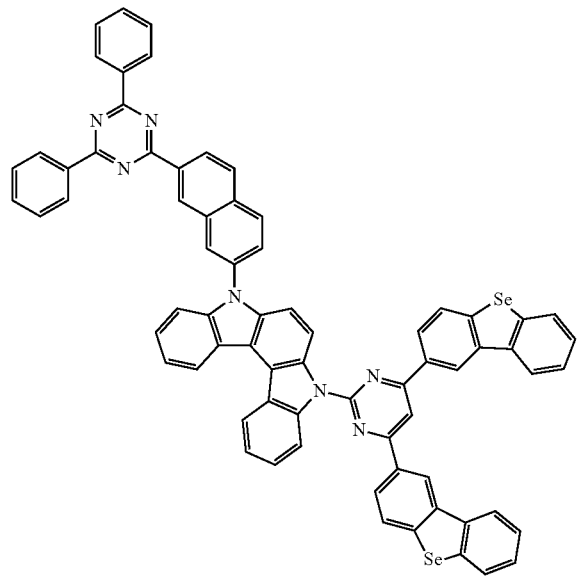
(E-46)
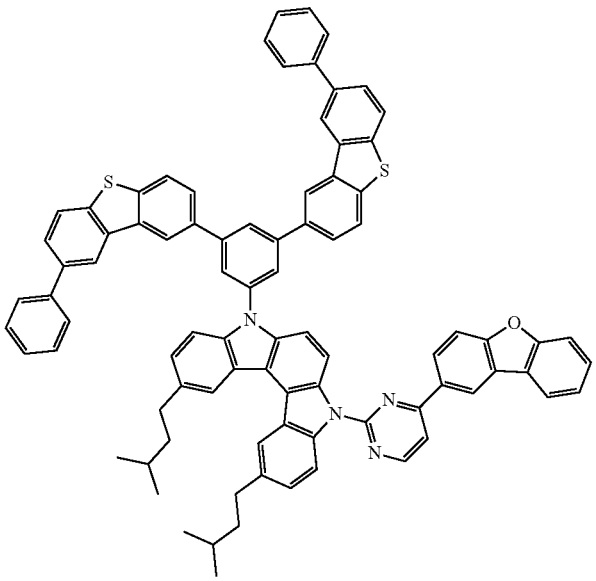
(E-47)
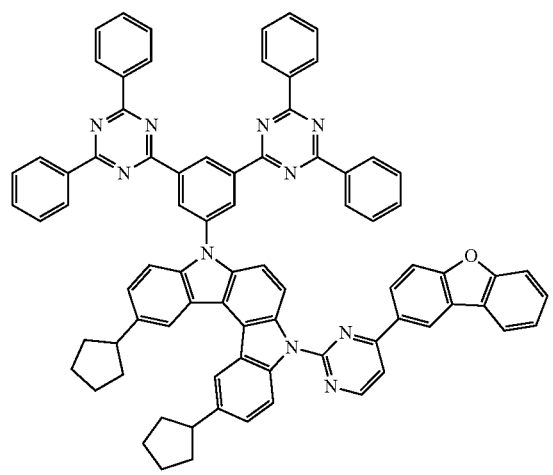
(E-48)
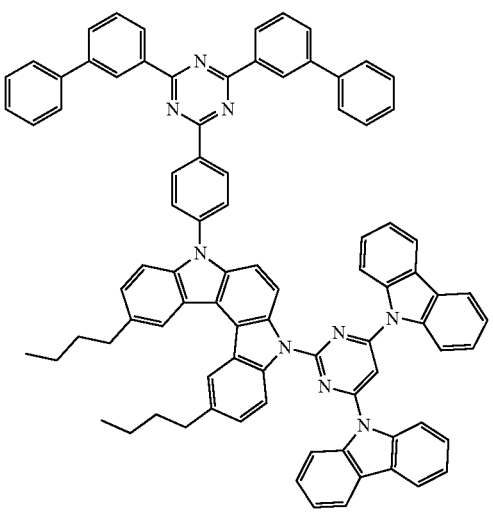
(E-49)
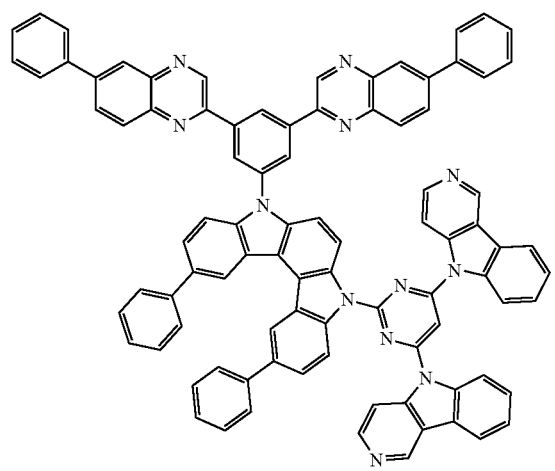
(E-50)
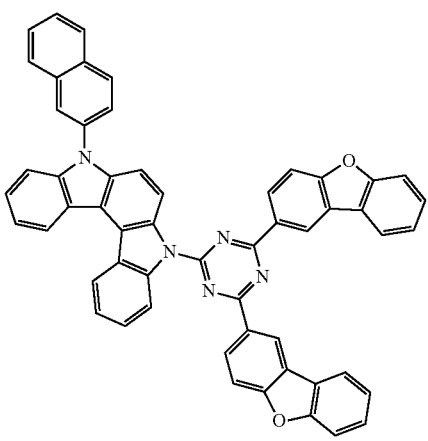

-continued
(E-51)
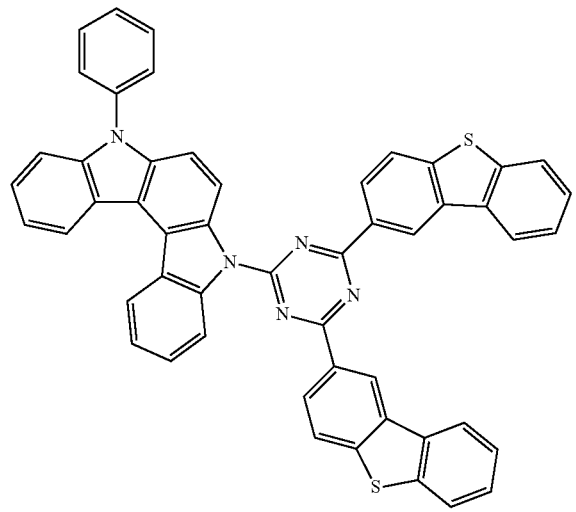
(E-52)
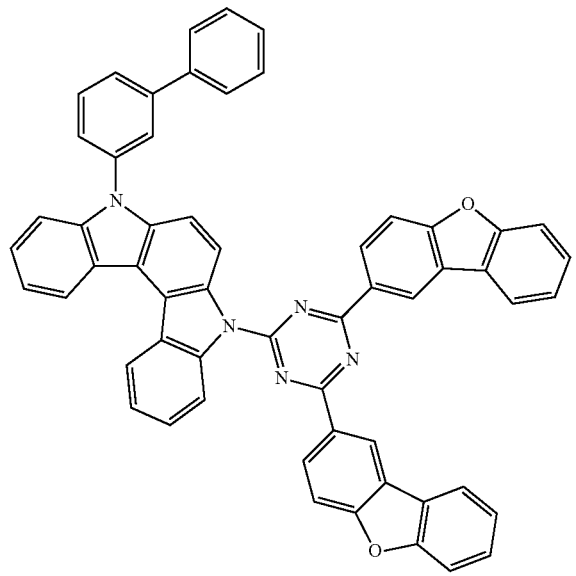
(E-53)
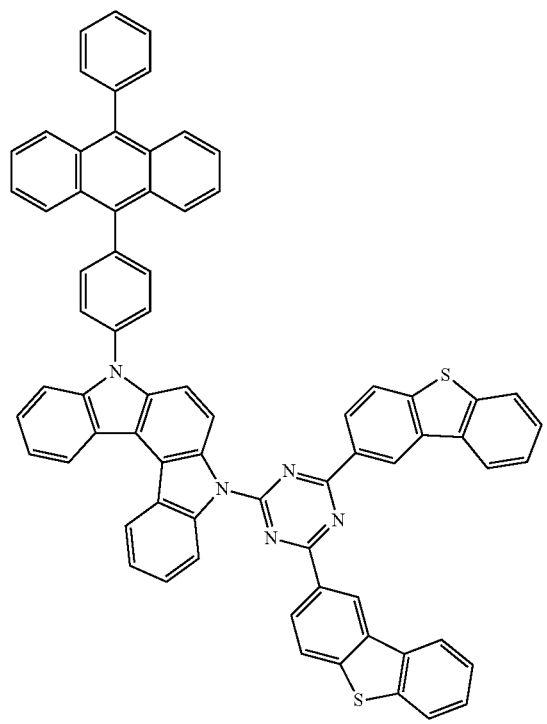
(E-54)
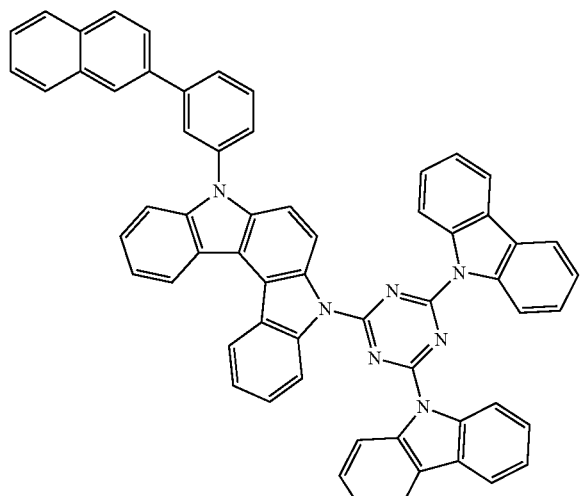

-continued
(E-55)
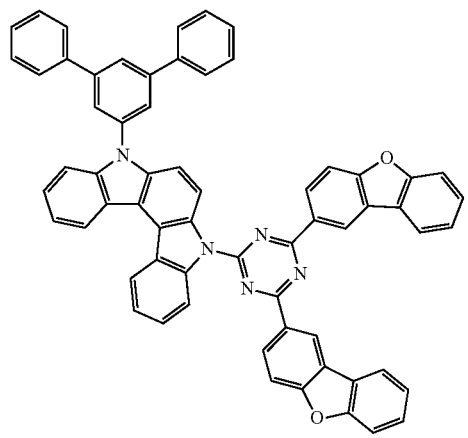
(E-56)
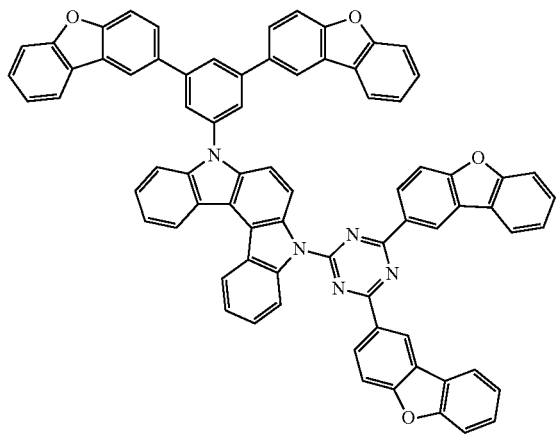
(E-57)
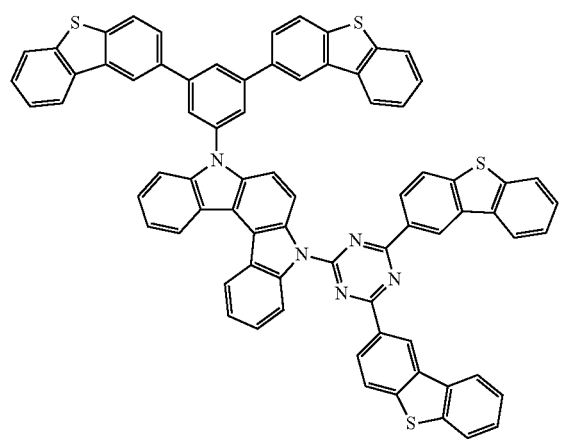
(E-58)
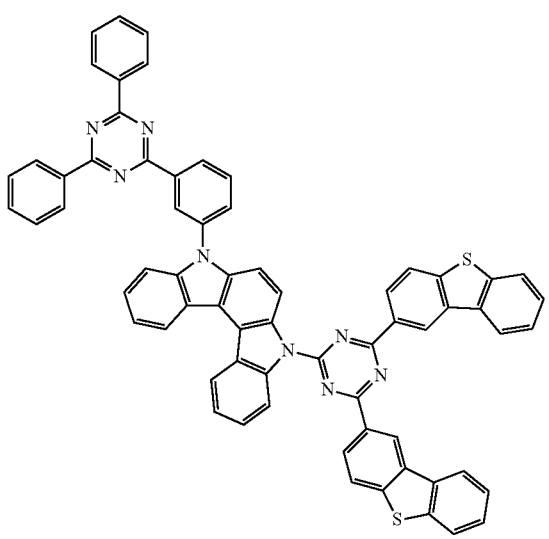
(E-59)
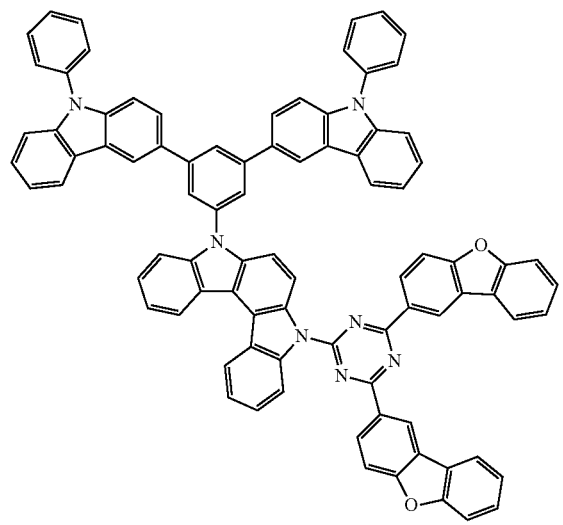
(E-60)
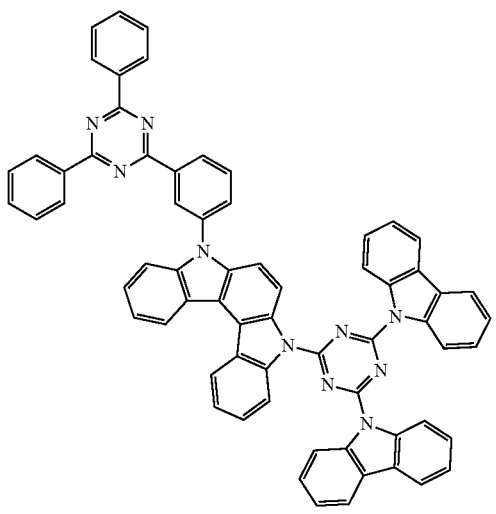

(E-61)
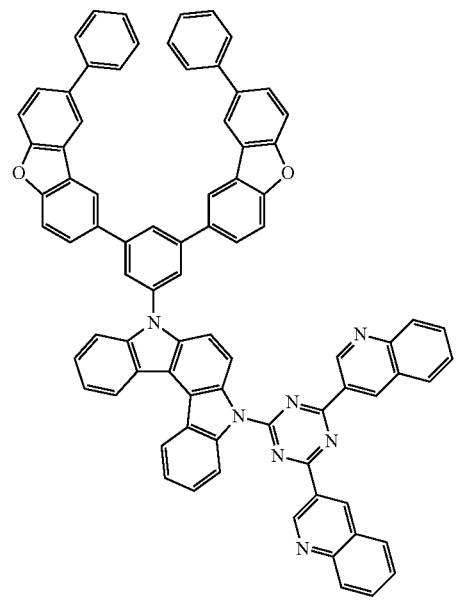
(E-62)
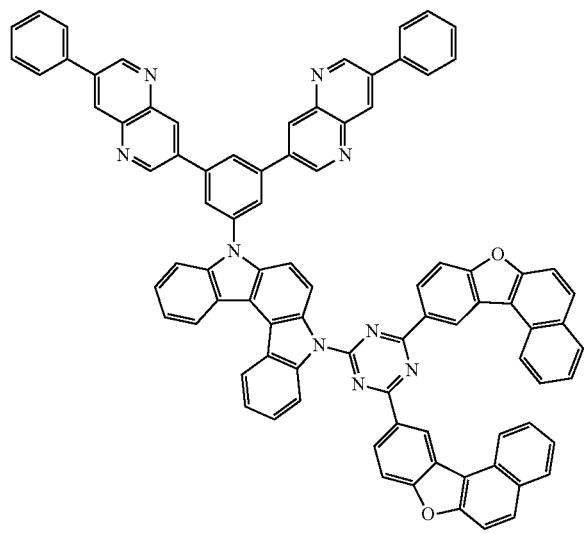
(E-63)
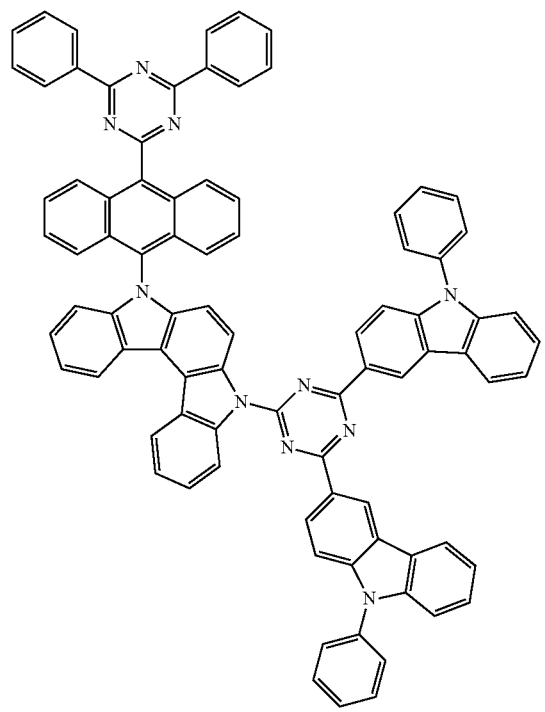
(E-64)
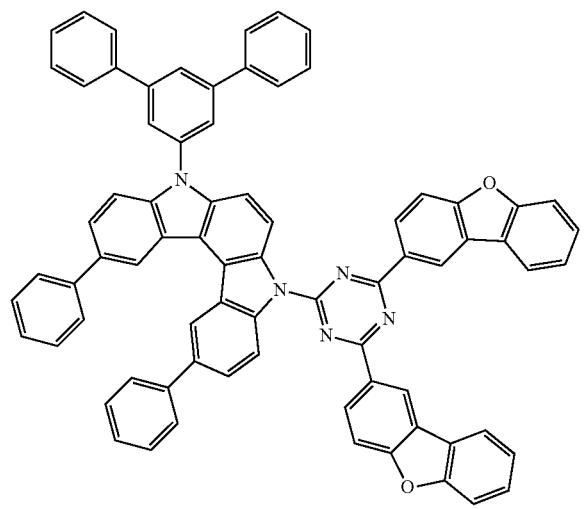

(E-65)
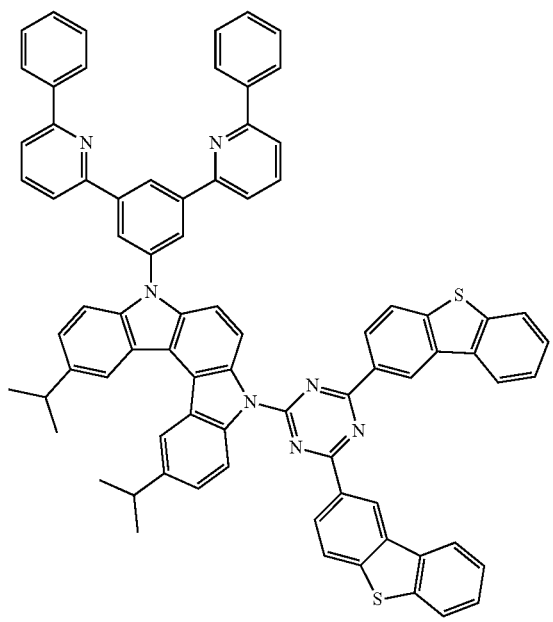
(E-66)
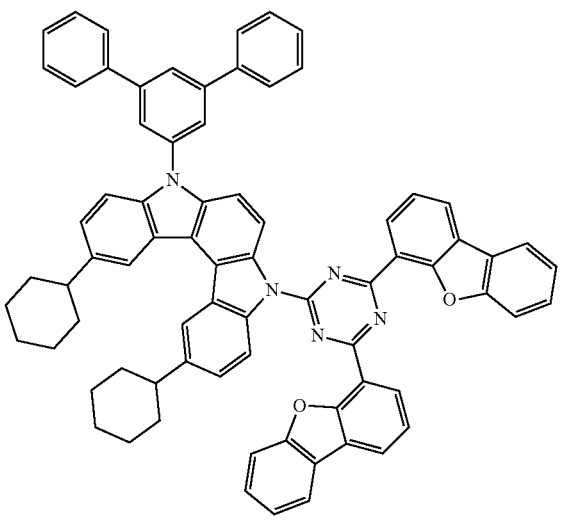
(F-1)
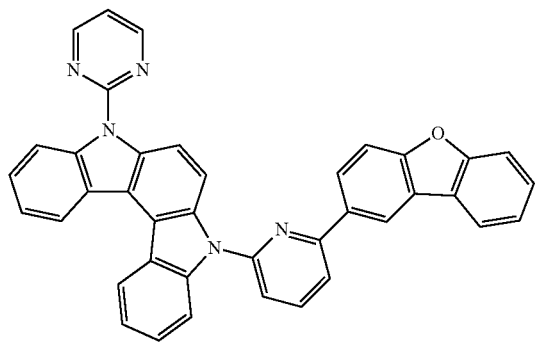
(F-2)
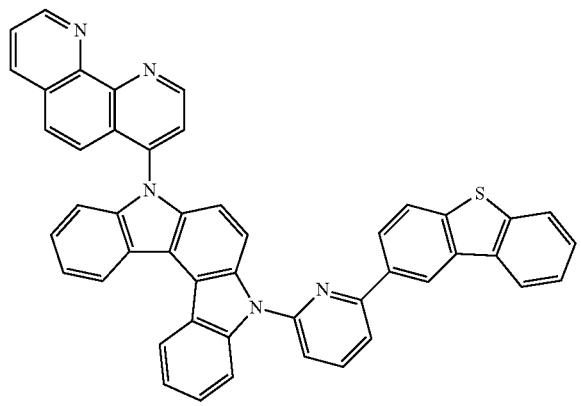
(F-3)
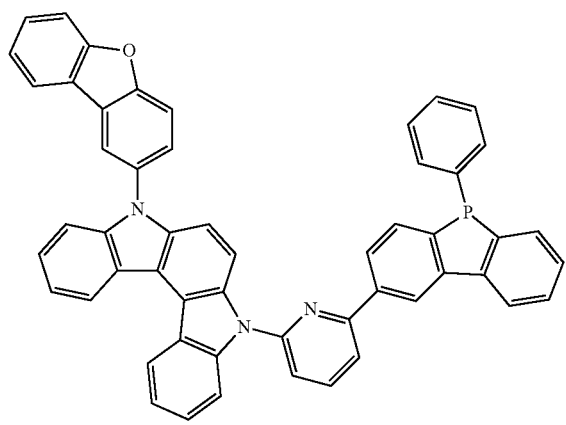
(F-4)
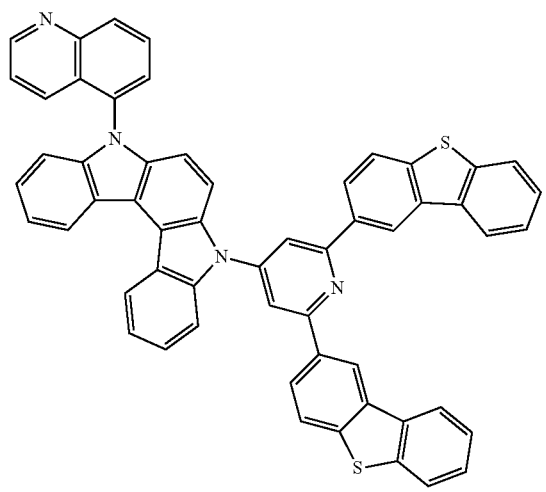

-continued
(F-5)
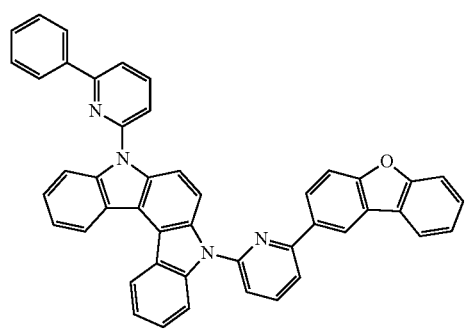
(F-6)
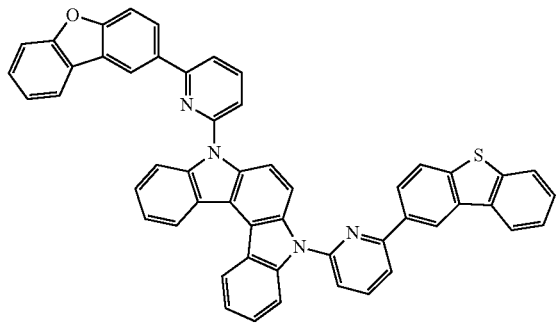
(F-7)
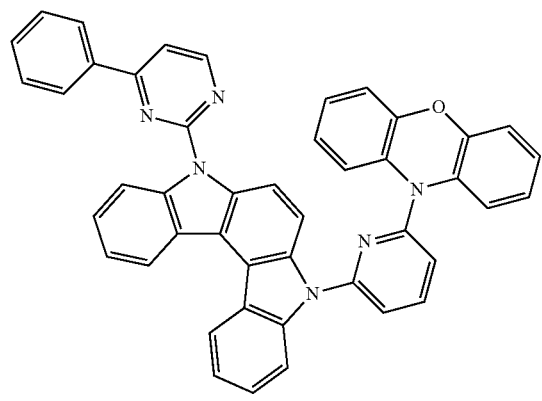
(F-8)
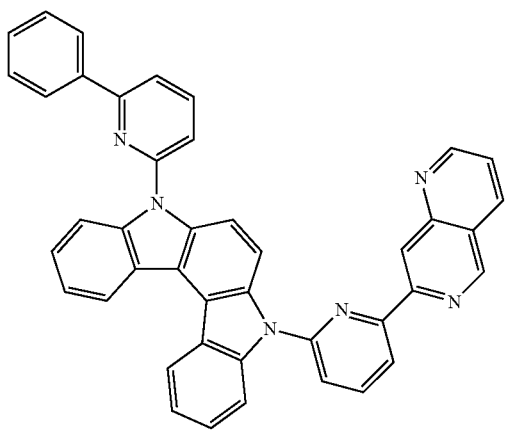
(F-9)
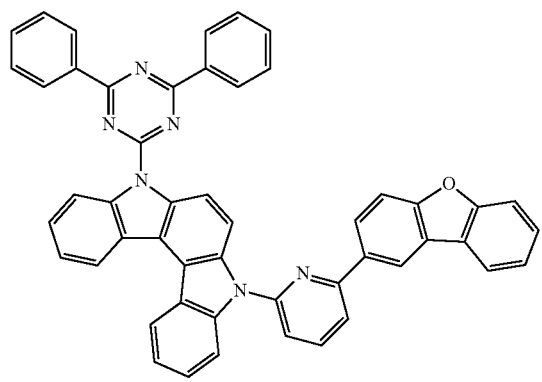
(F-10)
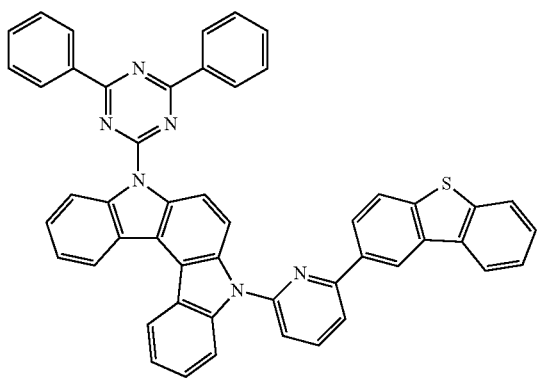

-continued
(F-11)
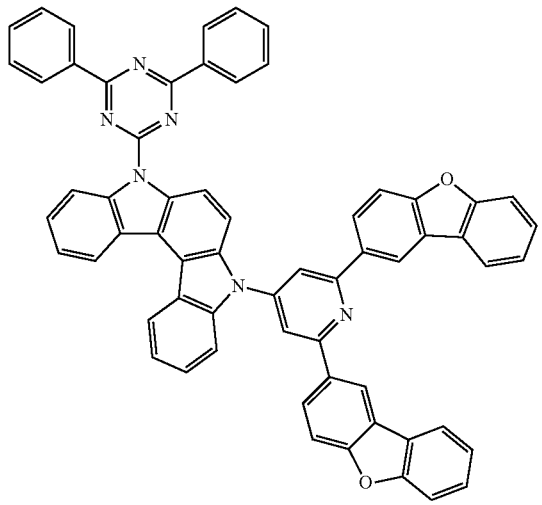
(F-12)
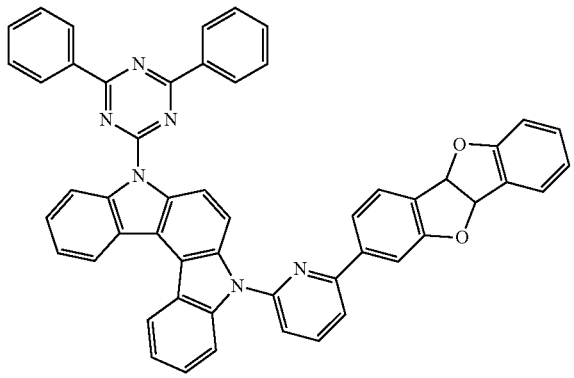
(F-13)
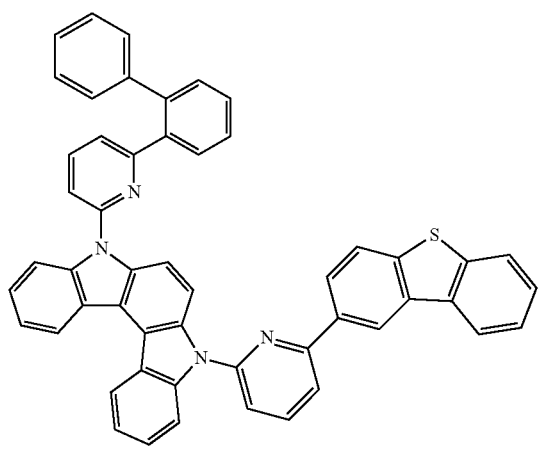
(F-14)
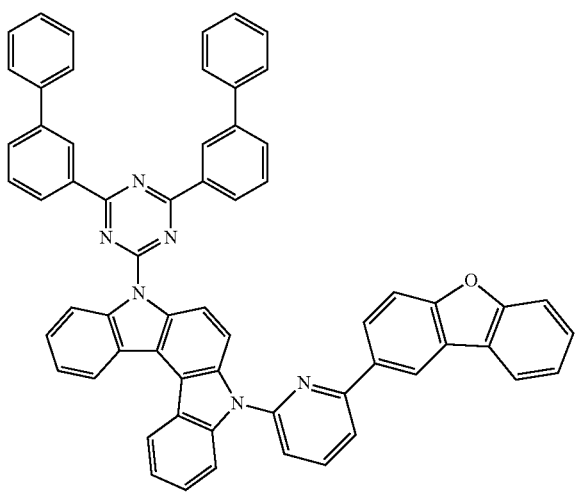
(F-15)
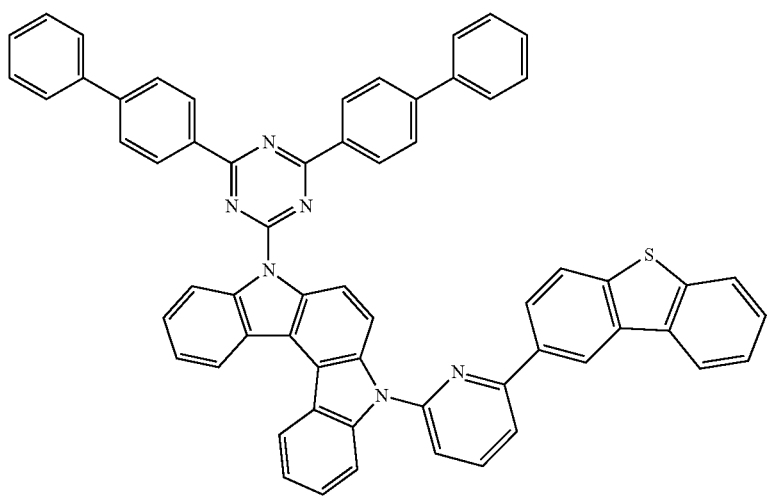

(F-16)
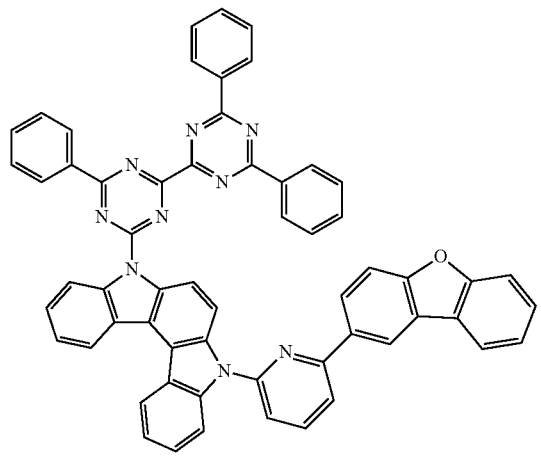
(F-17)
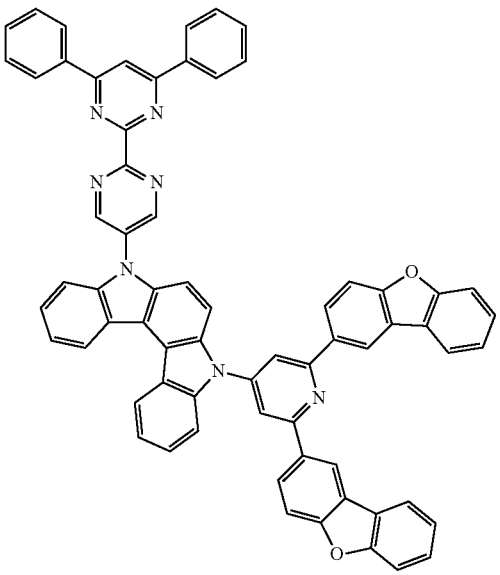
(F-18)
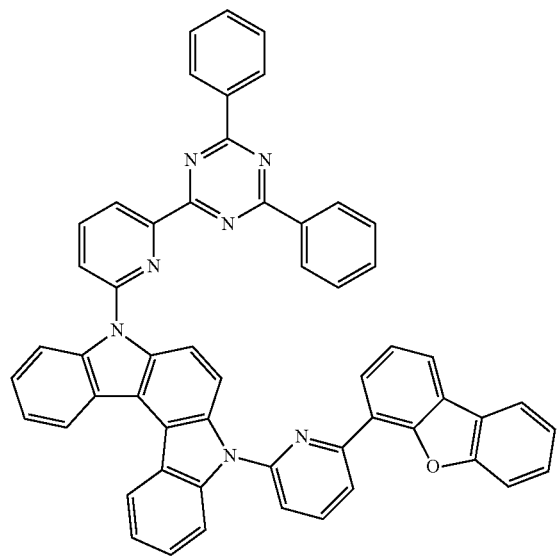

(F-19)
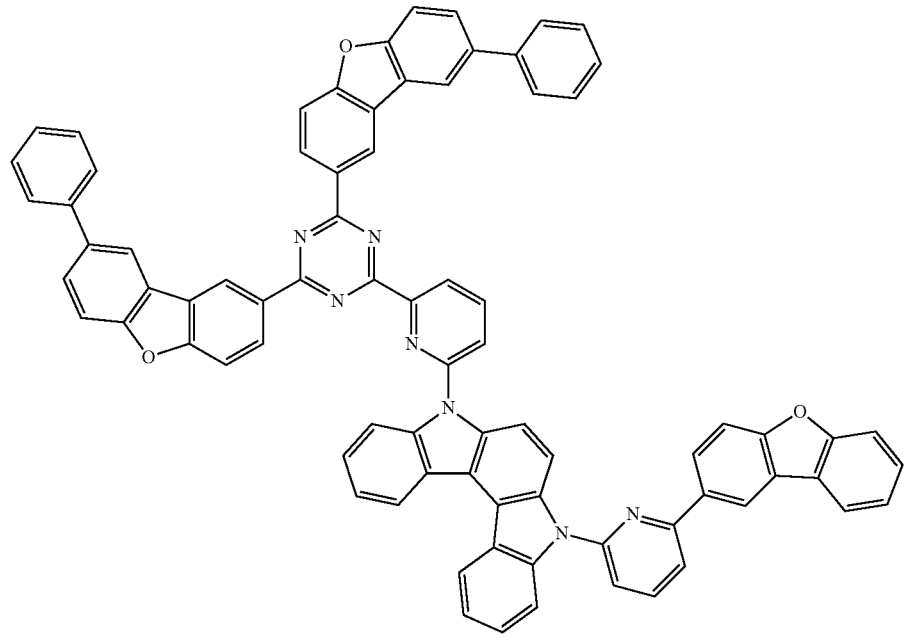
(F-20)
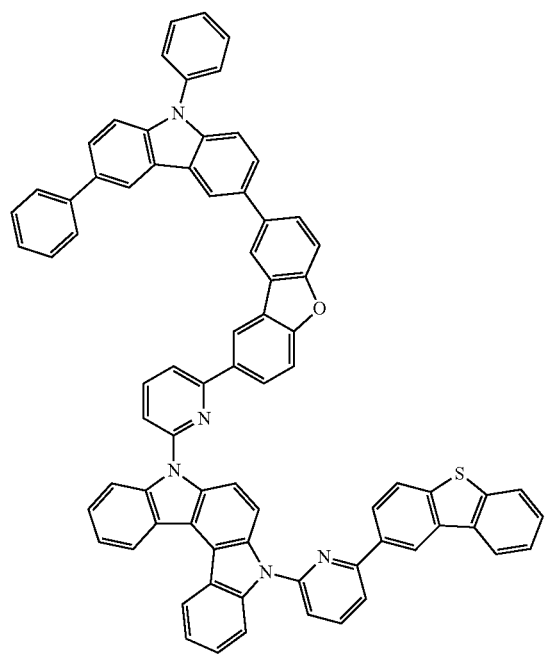
(F-21)
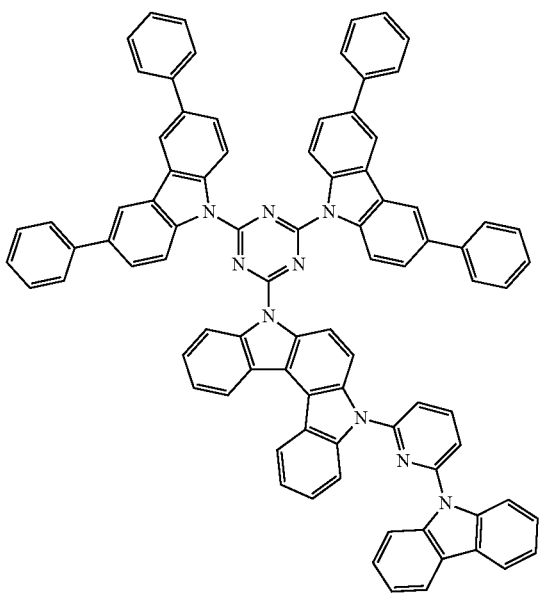

-continued
(F-22)
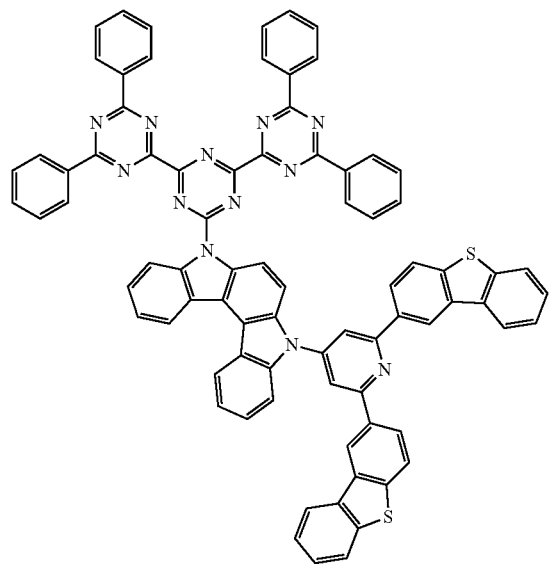
(F-23)
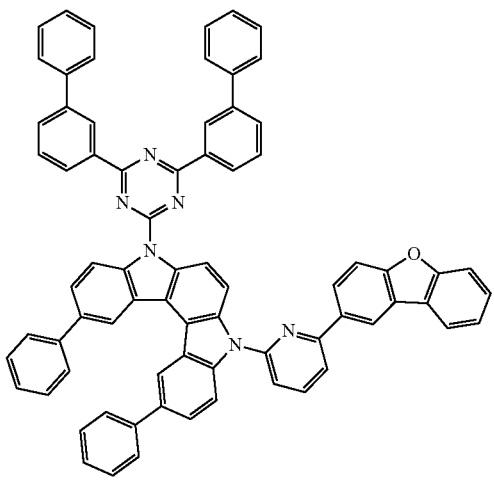
(F-24)
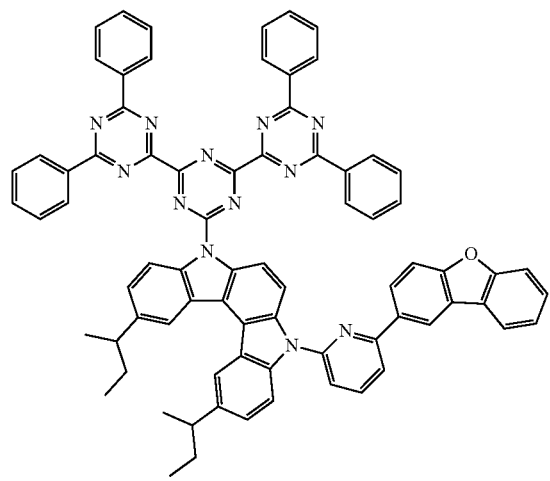
(F-25)
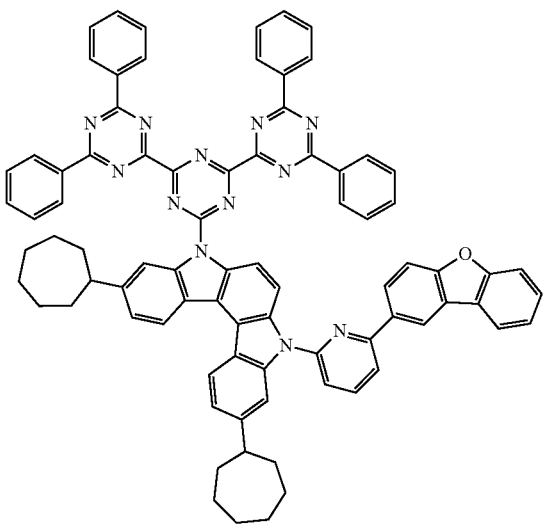
(F-26)
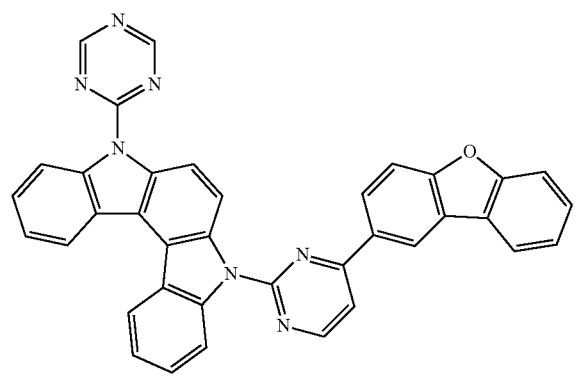
(F-27)
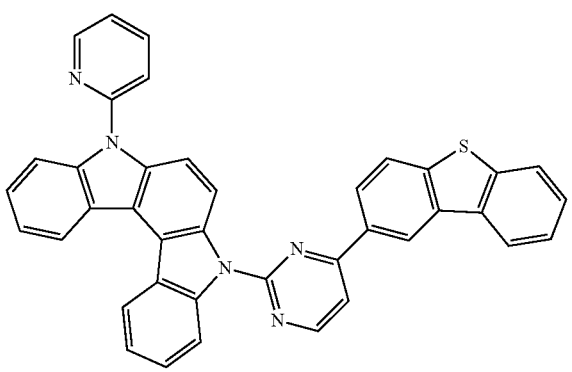

(F-28)
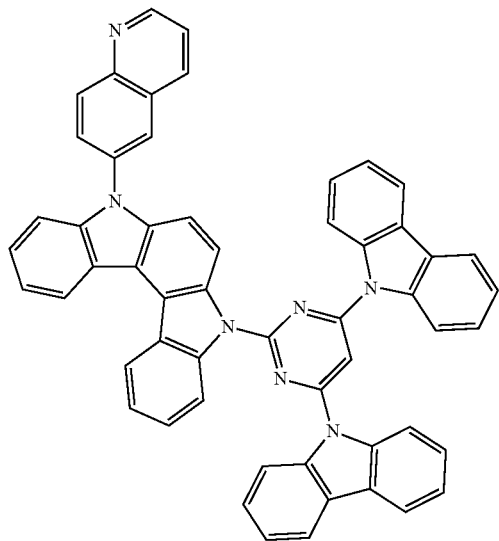
(F-29)
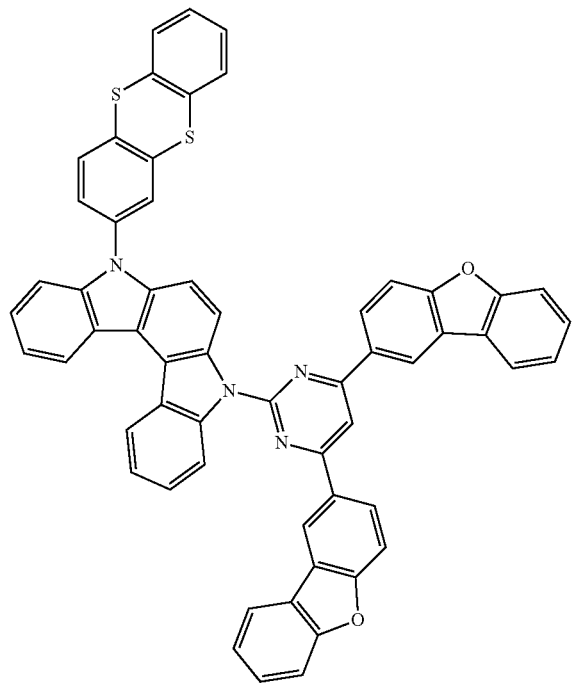
(F-30)
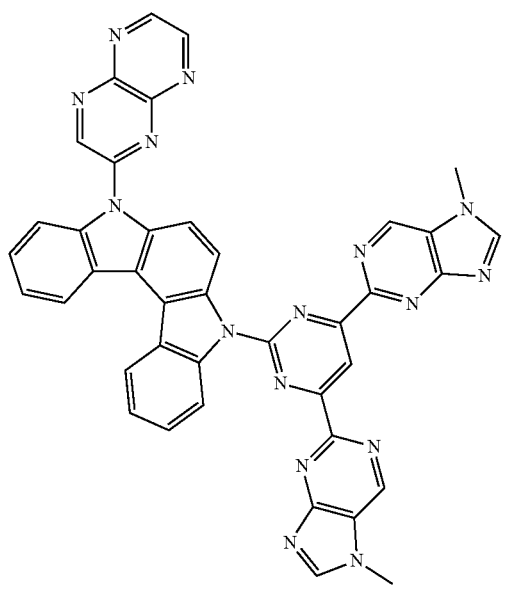
(F-31)
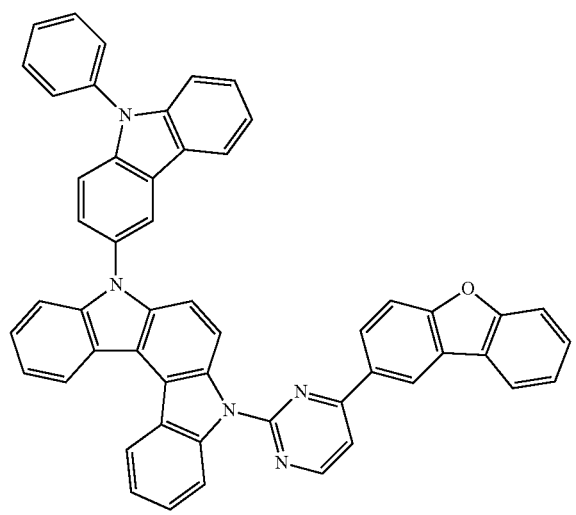

(F-32)
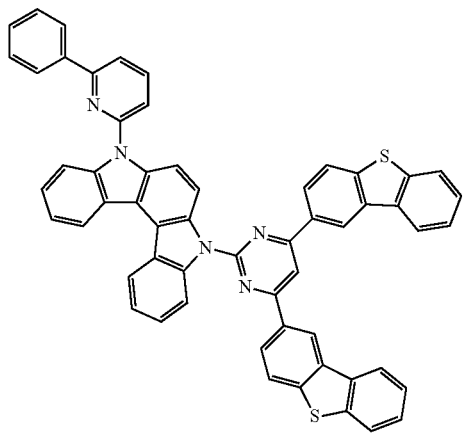
(F-33)
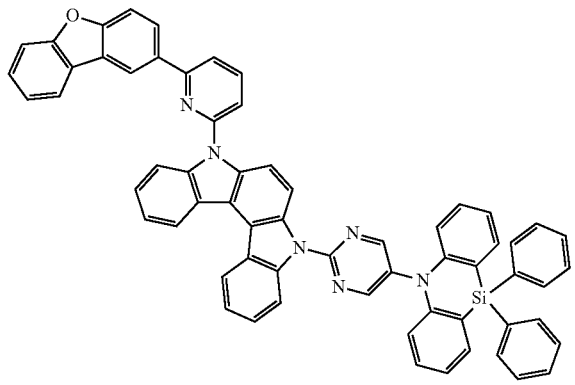
(F-34)
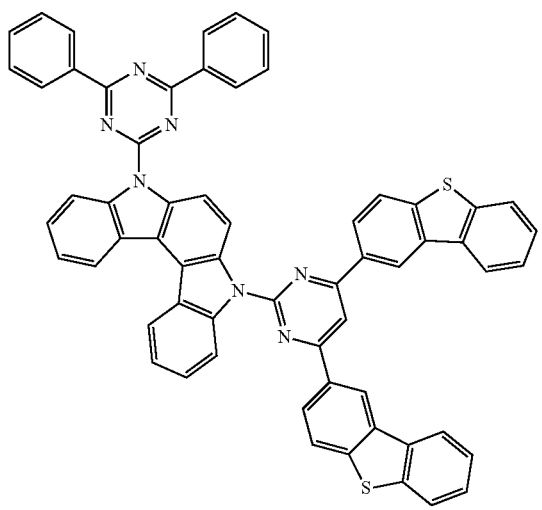
(F-35)
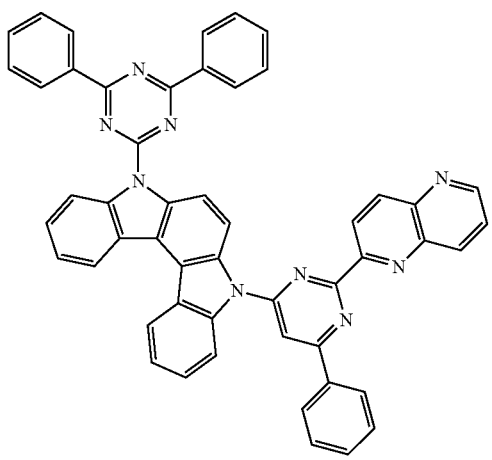
(F-36)
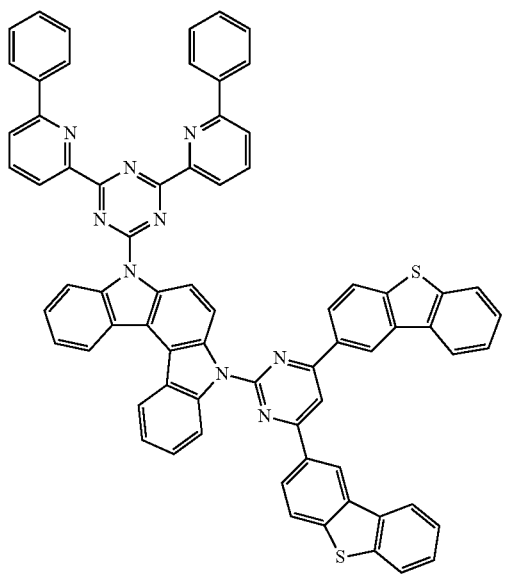
(F-37)
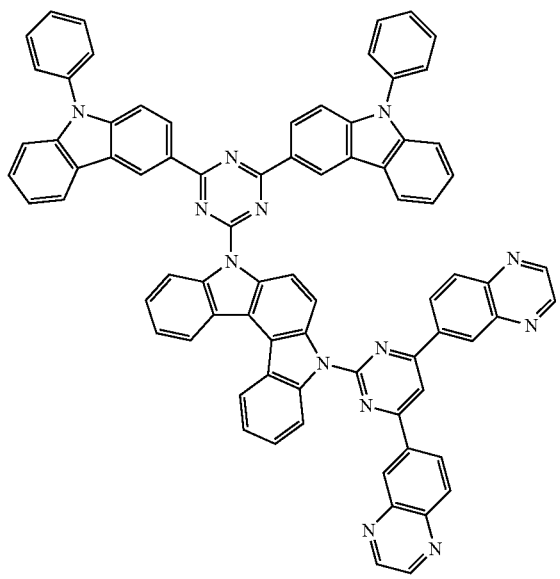

-continued
(F-38)
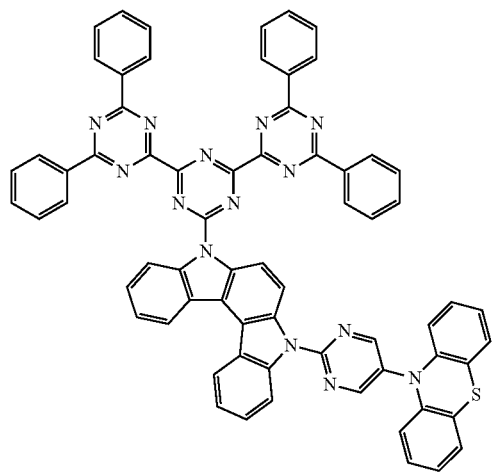
(F-39)
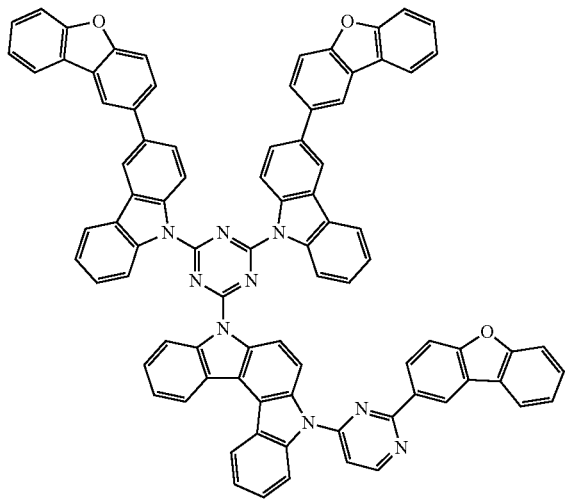
(F-40)
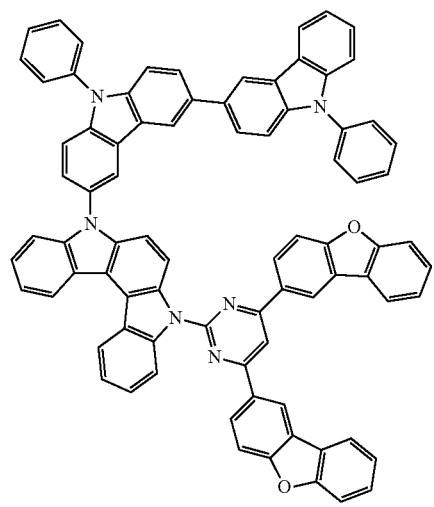
(F-41)
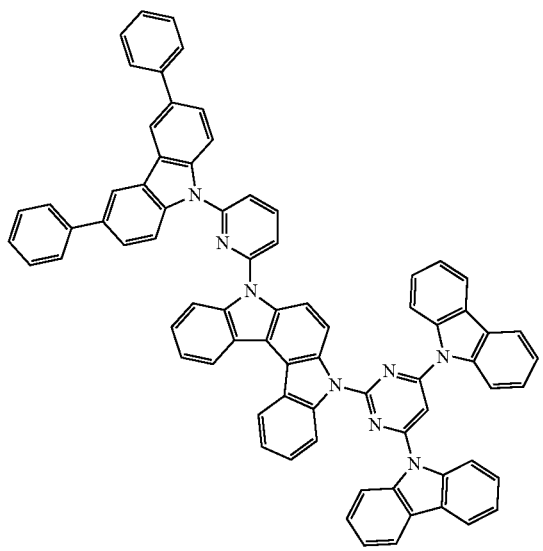
(F-42)
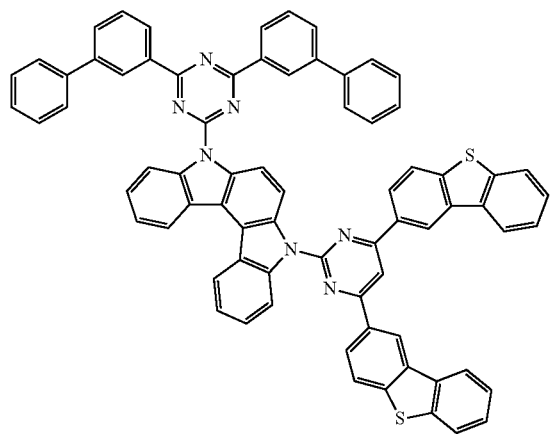
(F-43)
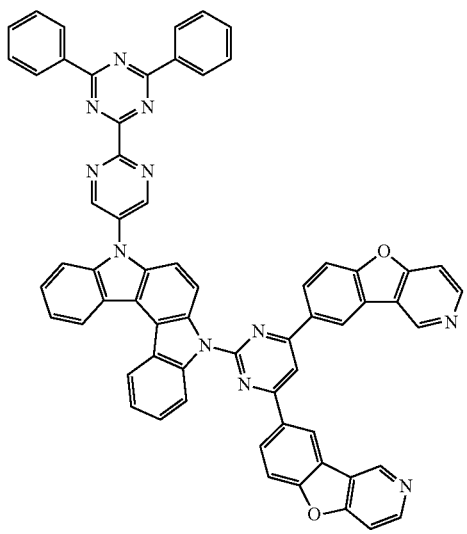

(F-44)
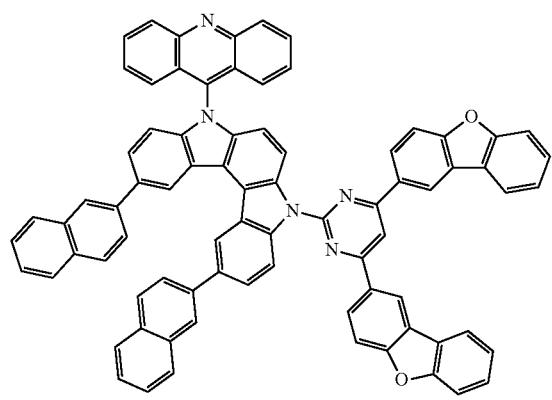
(F-45)
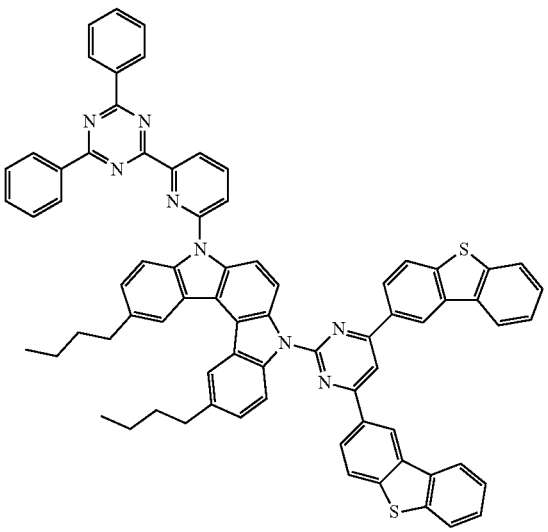
(F-46)
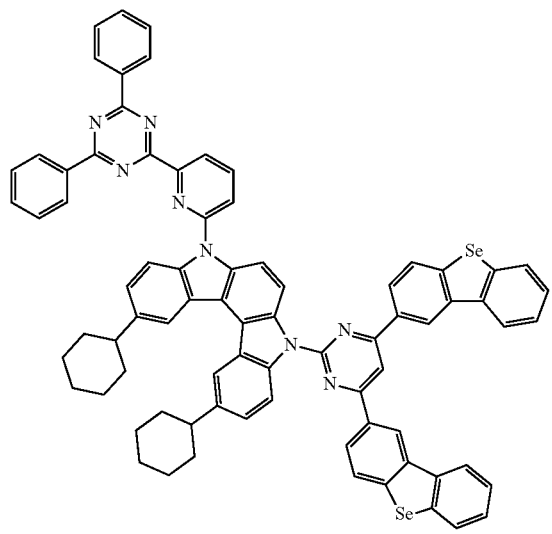
(F-47)
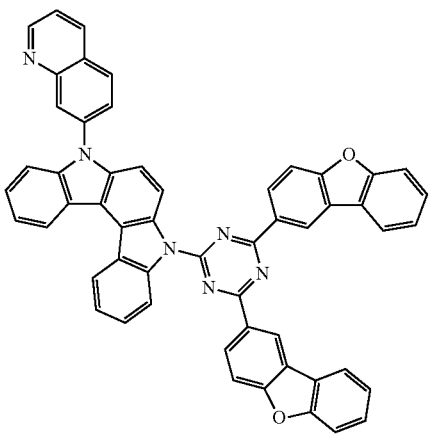

(F-48)
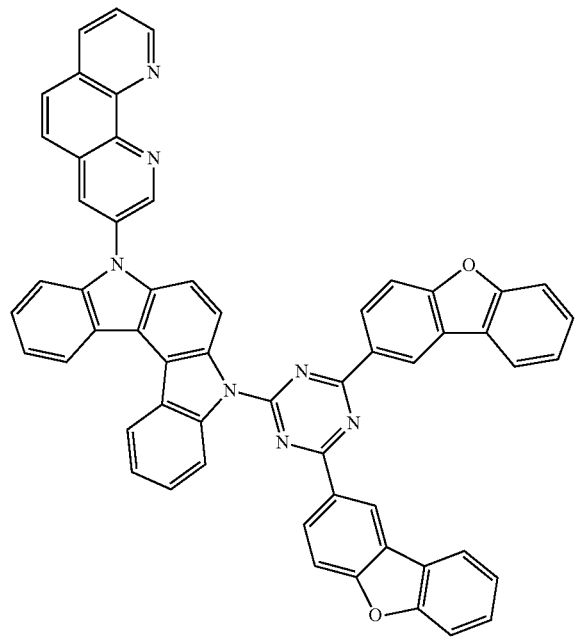
(F-49)
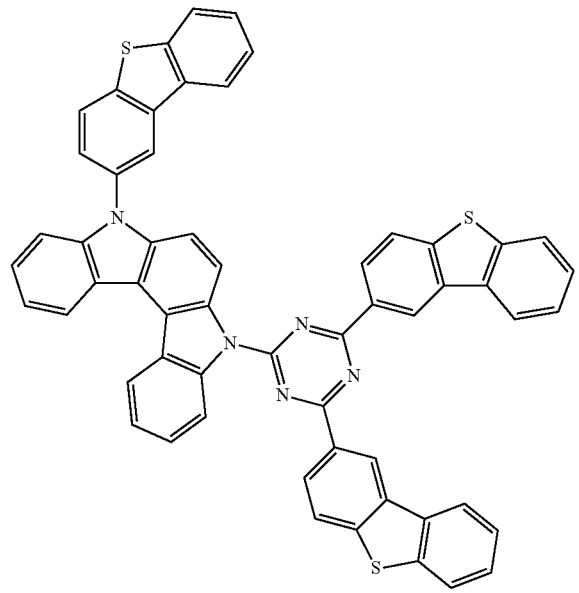
(F-50)
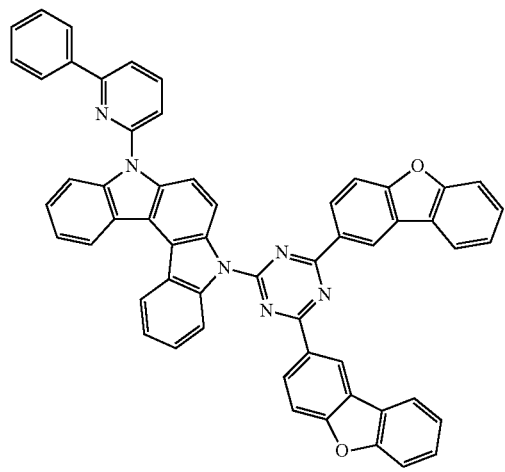
(F-51)
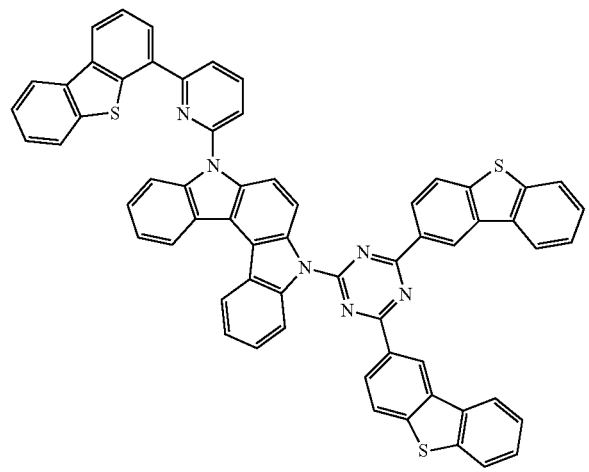

-continued
(F-52)
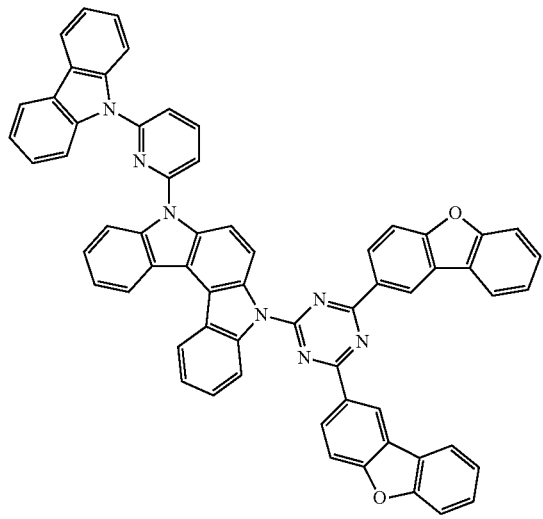
(F-53)
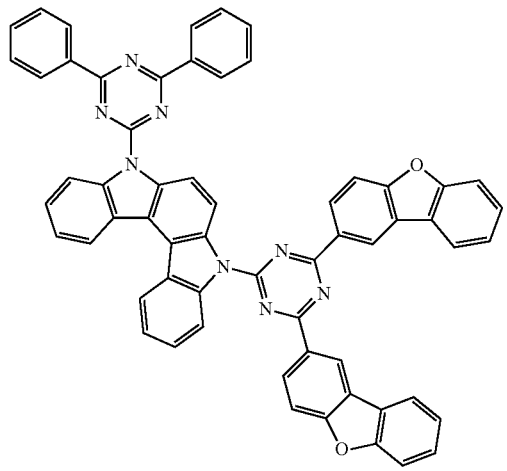
(F-54)
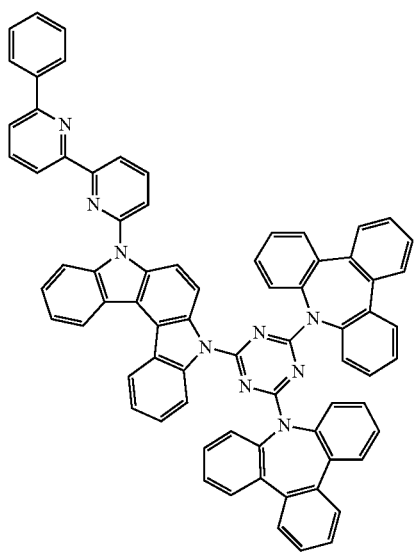
(F-55)
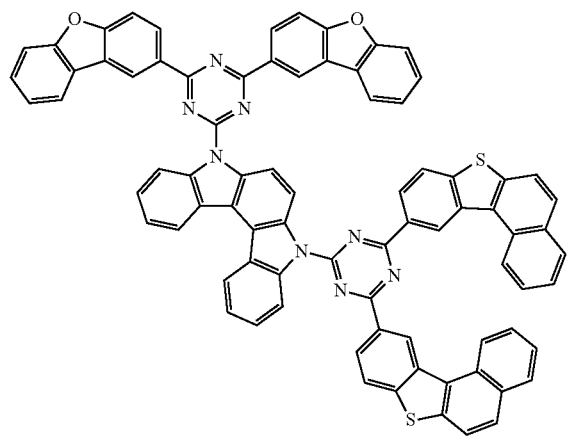
(F-56)
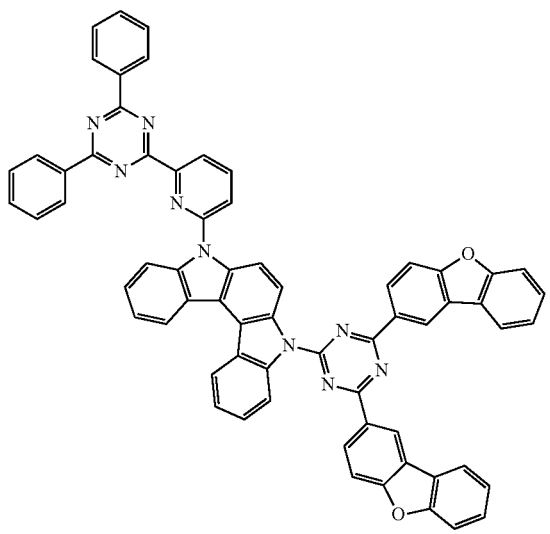
(F-57)
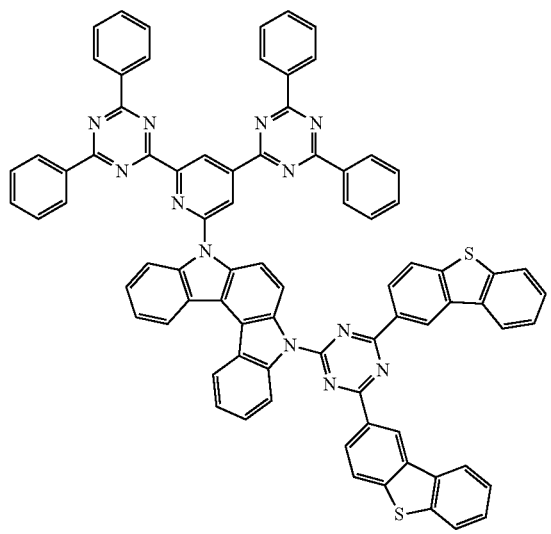

(F-58)
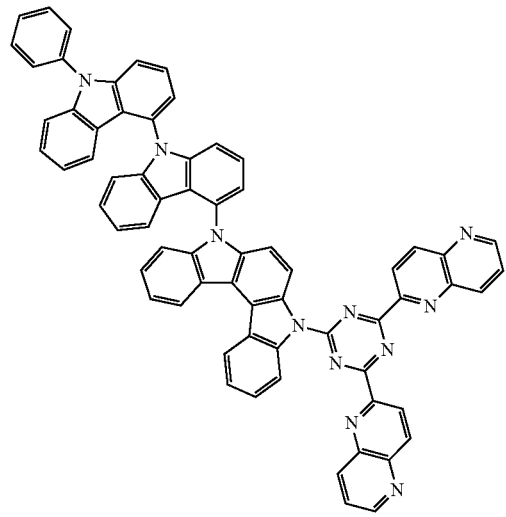
(F-59)
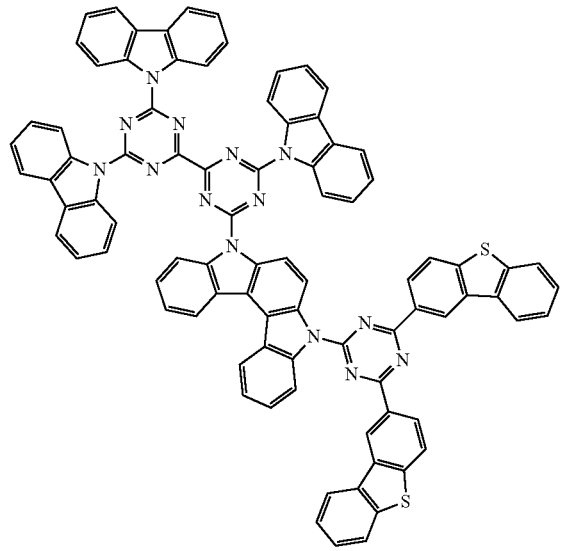
(F-60)
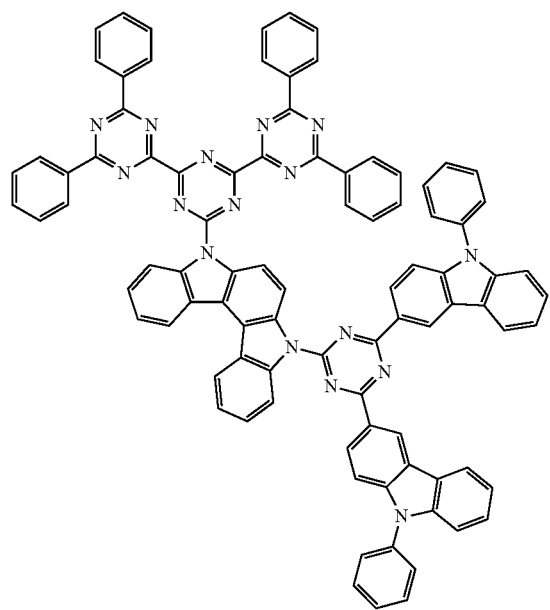
(F-61)
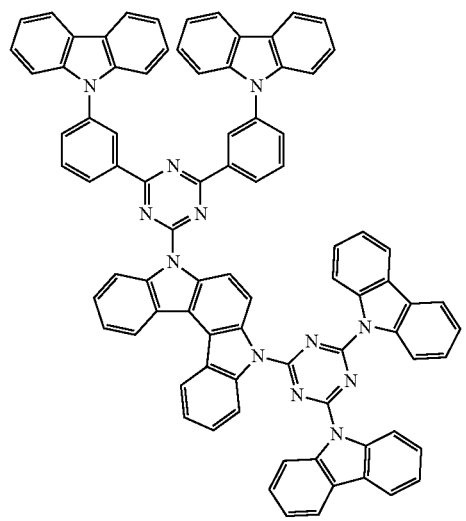

-continued
(F-62)
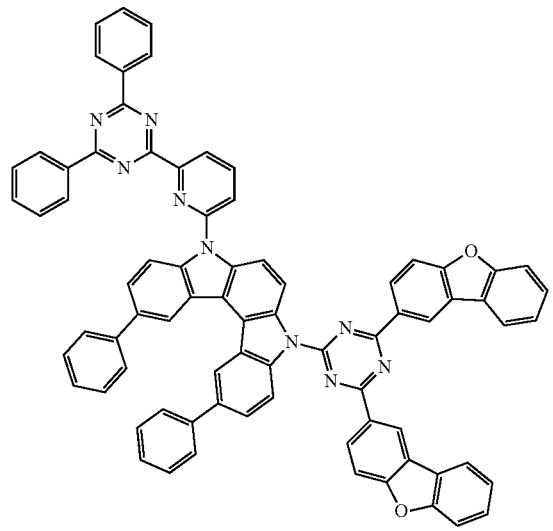
(F-63)
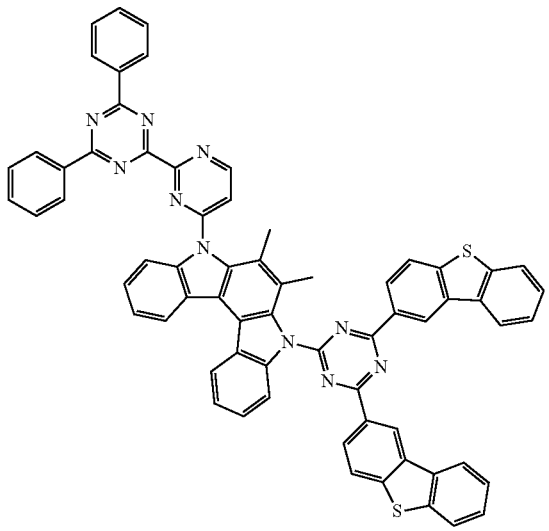
(F-64)
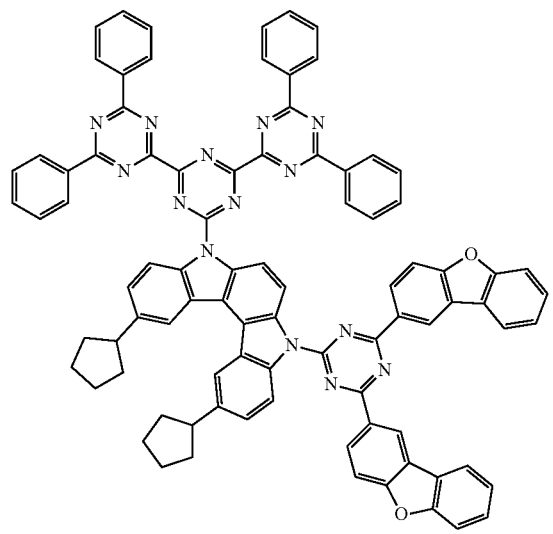
(G-1)
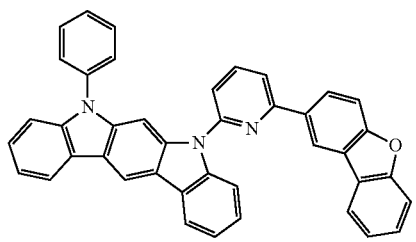
(G-2)
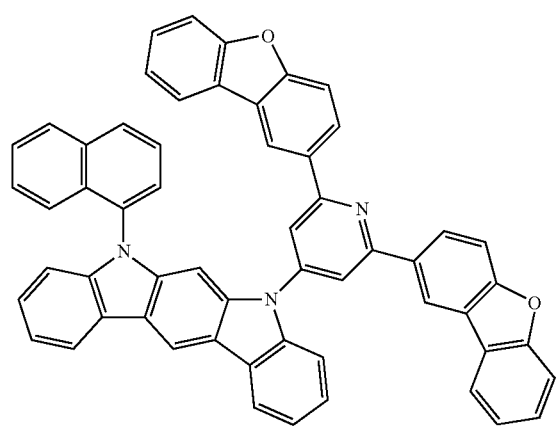
(G-3)
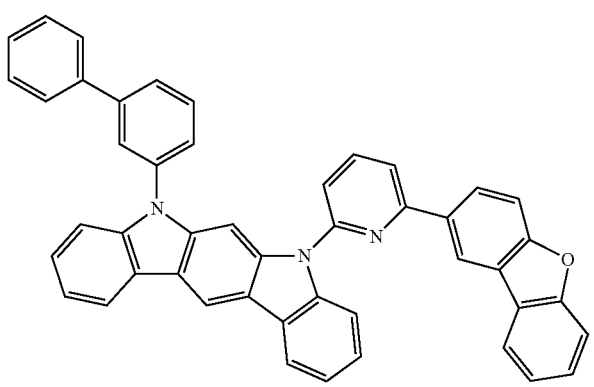

-continued
(G-4)
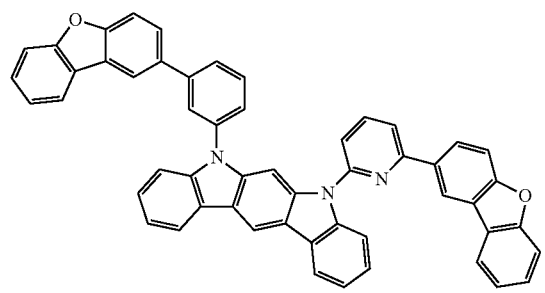
(G-5)
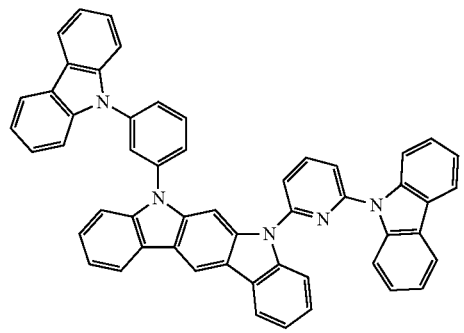
(G-6)
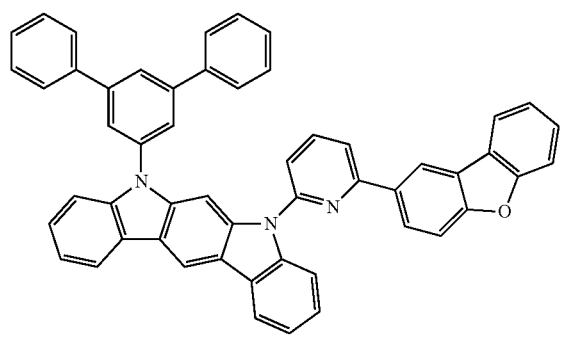
(G-7)
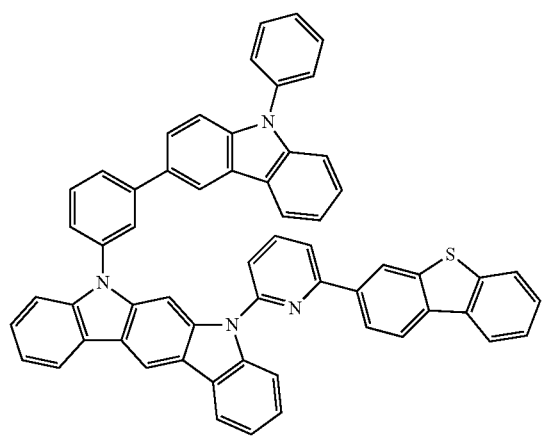
(G-8)
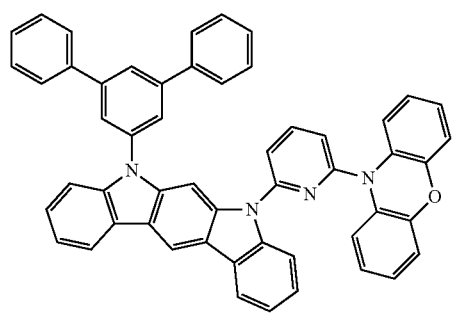
(G-9)
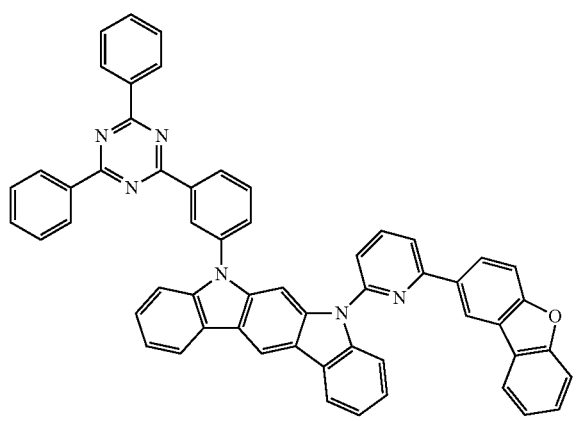

-continued
(G-10)
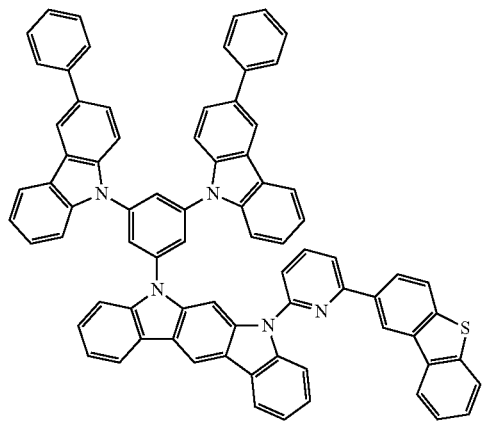
(G-11)
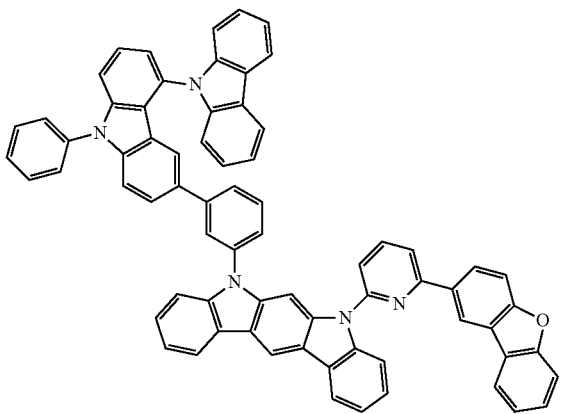
(G-12)
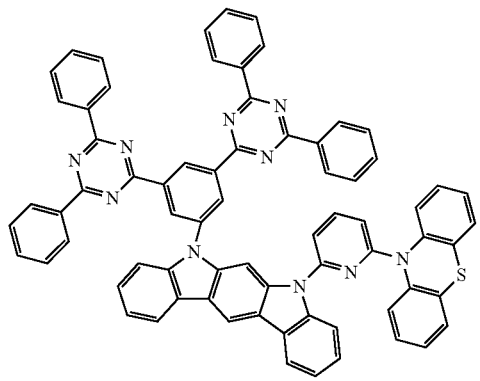
(G-13)
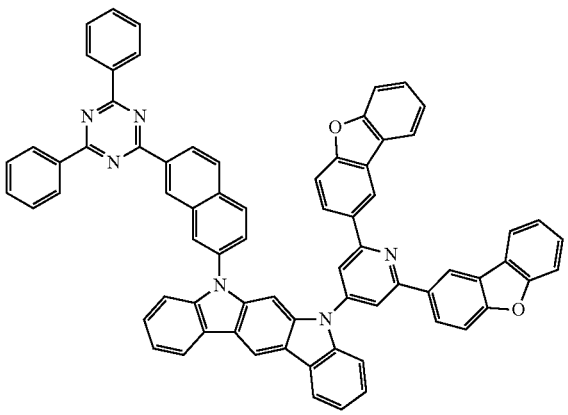
(G-14)
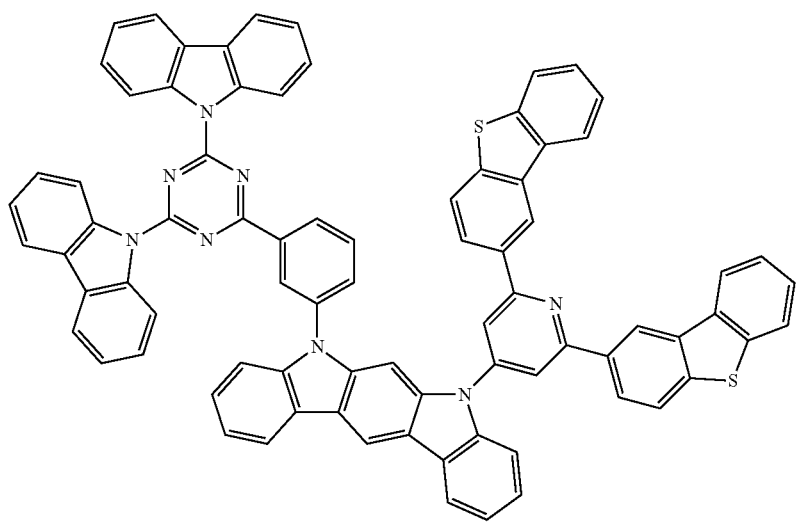

-continued
(G-15)
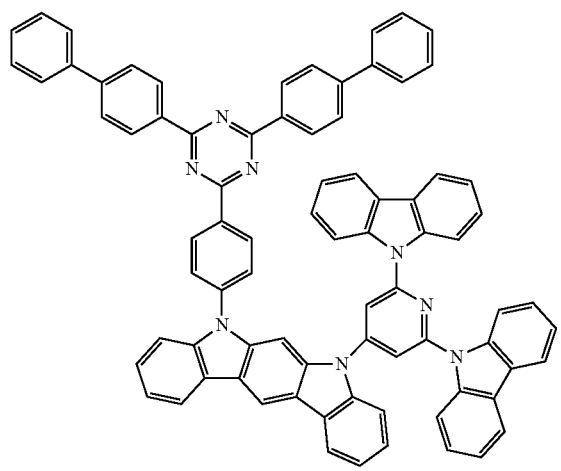
(G-16)
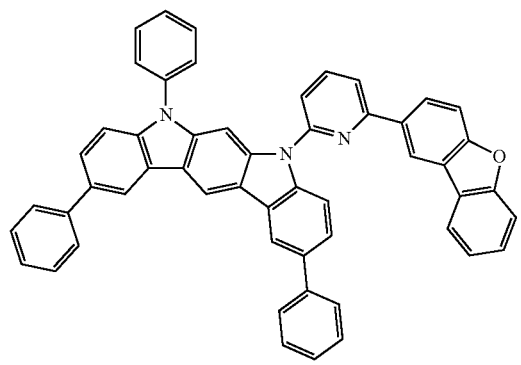
(G-17)
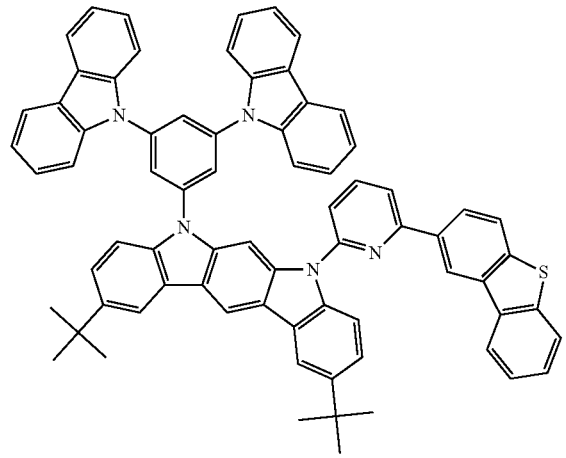
(G-18)
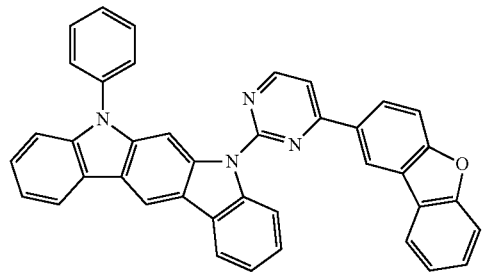
(G-19)
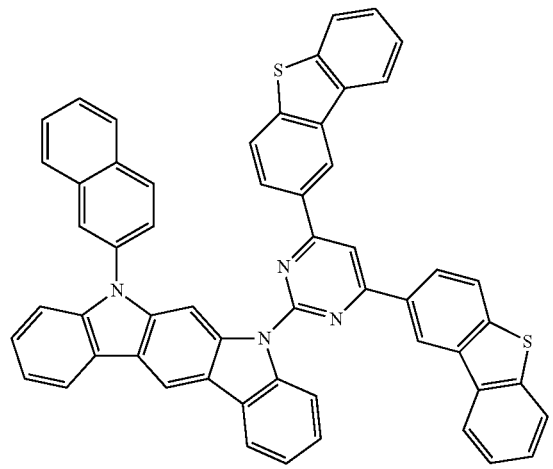
(G-20)
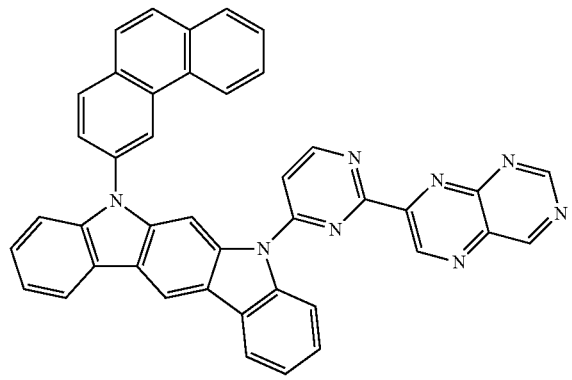

-continued
(G-21)
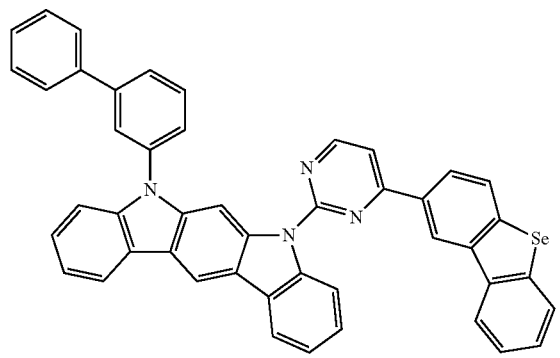
(G-22)
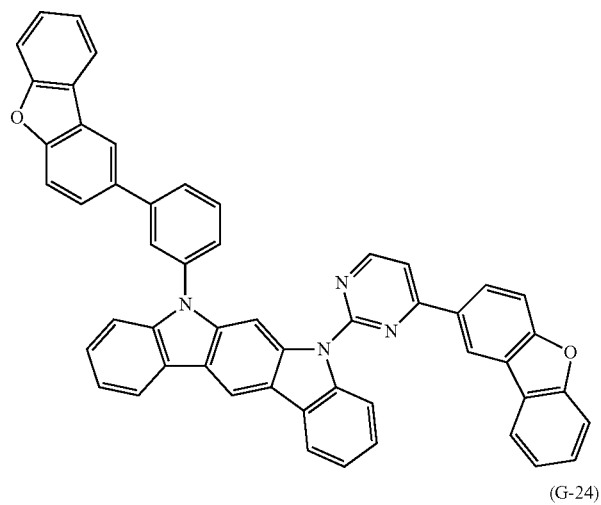
(G-23)
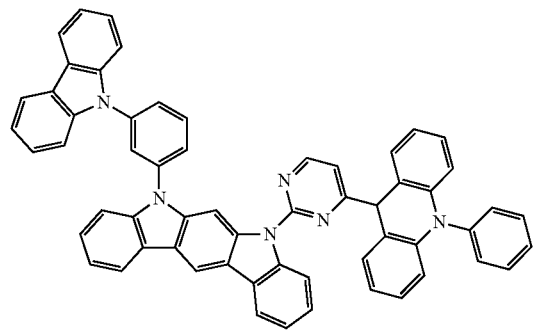
(G-24)
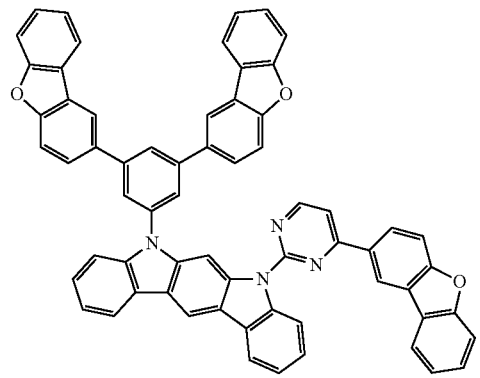
(G-25)
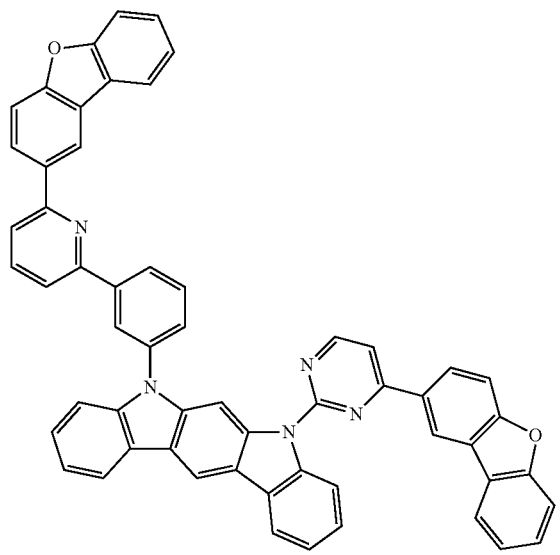
(G-26)
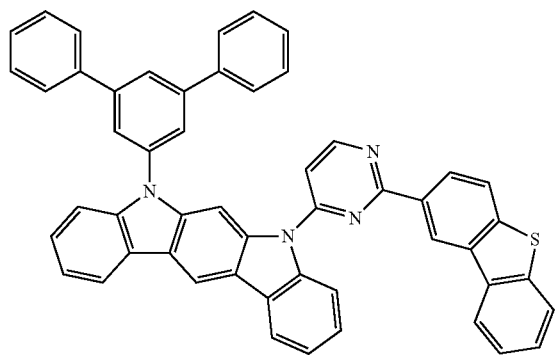

-continued
(G-27)
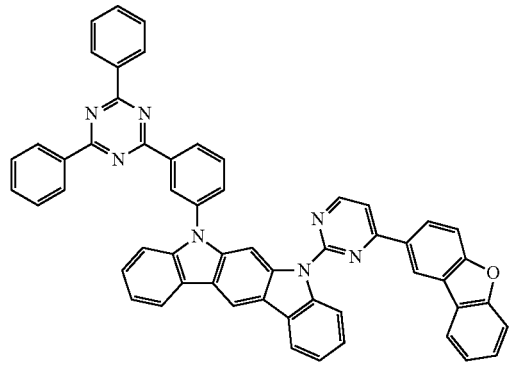
(G-28)
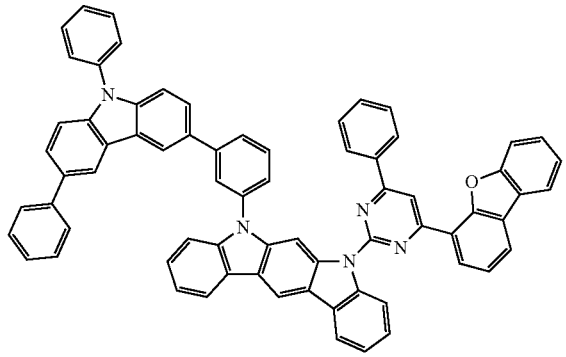
(G-29)
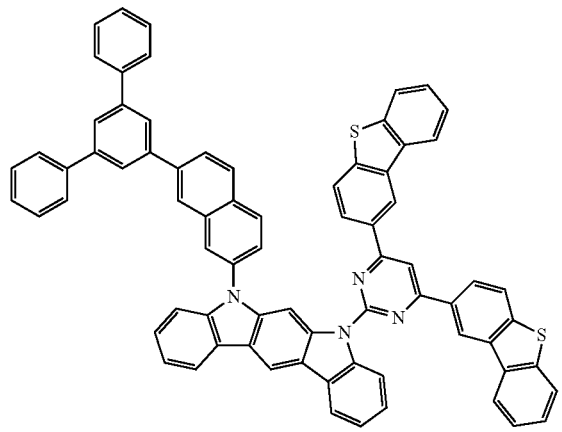
(G-30)
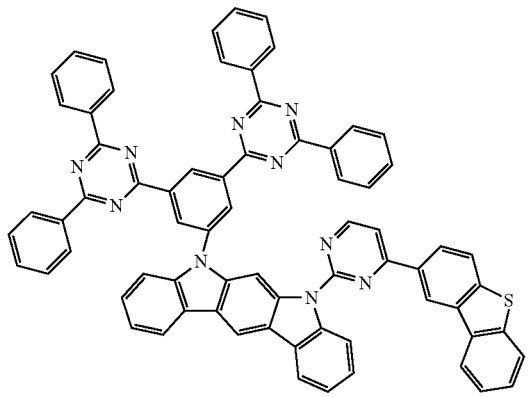
(G-31)
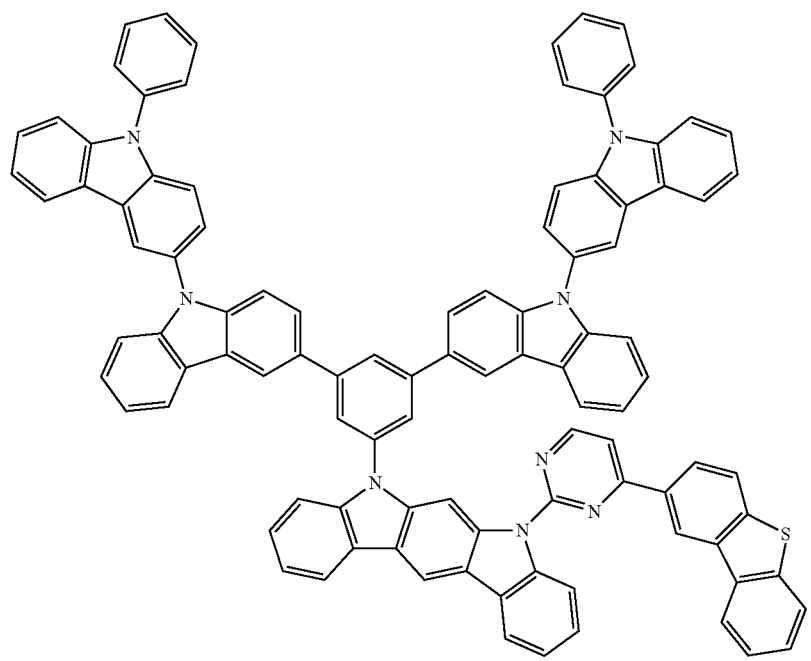

(G-32)
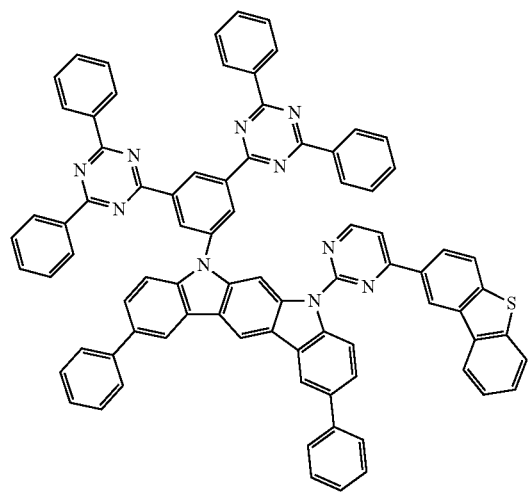
(G-33)
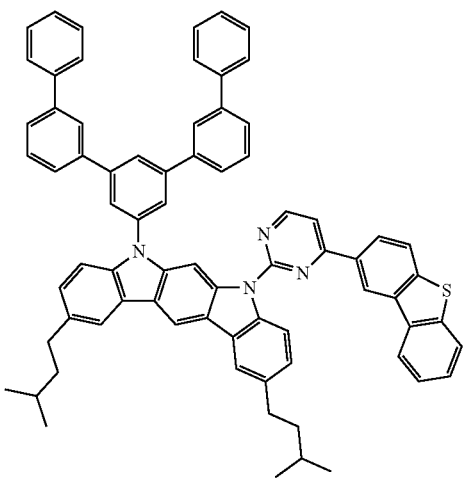
(G-34)
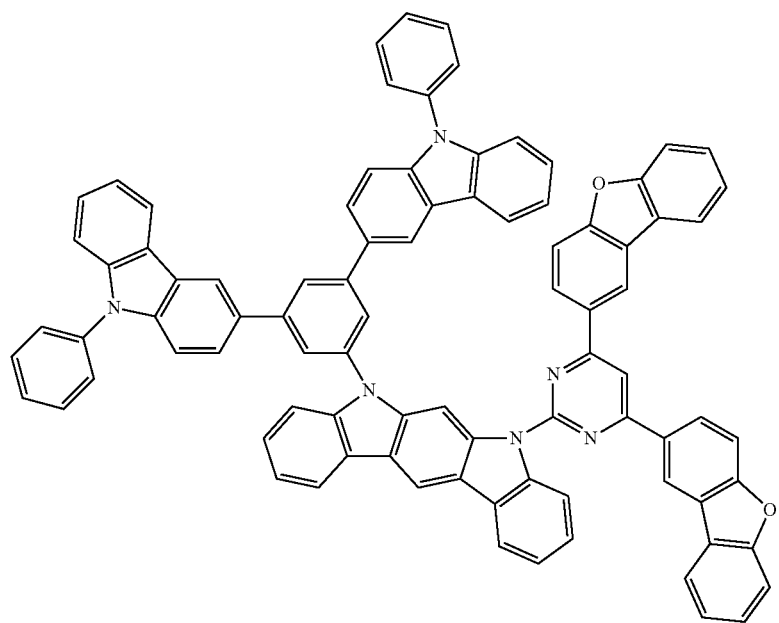

-continued
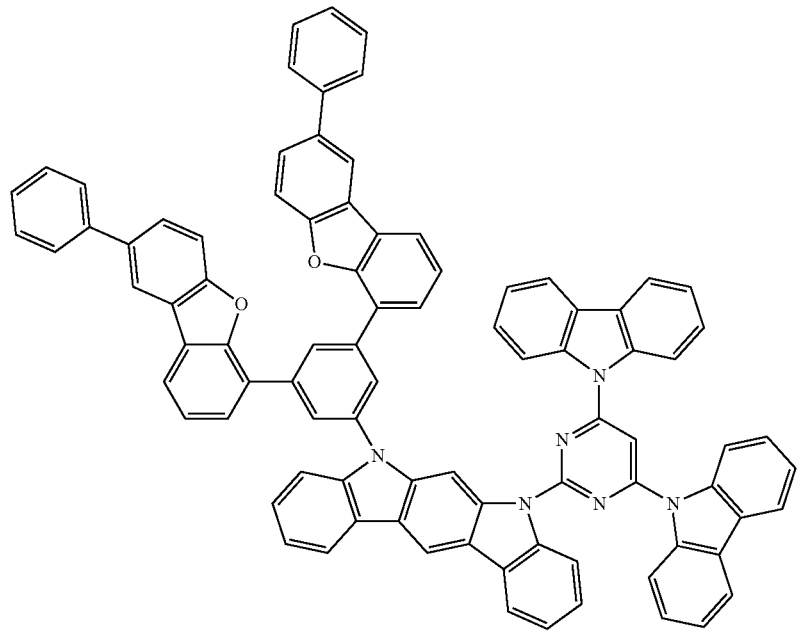
(G-35)
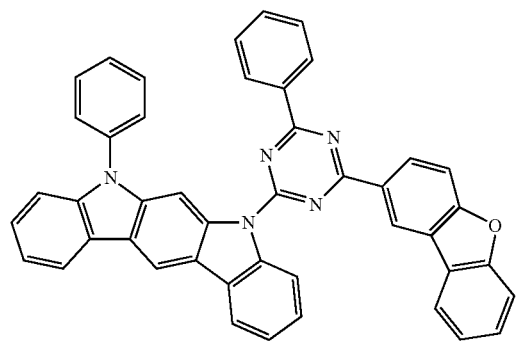
(G-36)
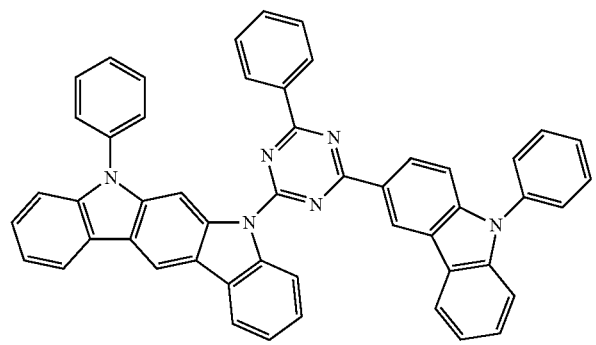
(G-37)
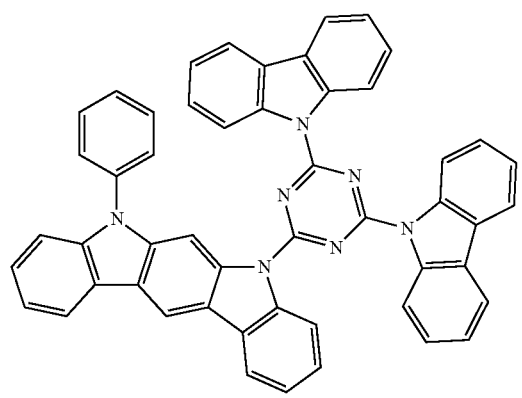
(G-38)
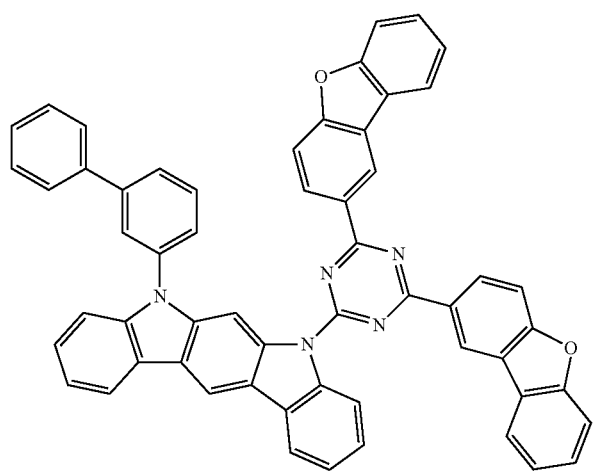
(G-39)

-continued
(G-40)
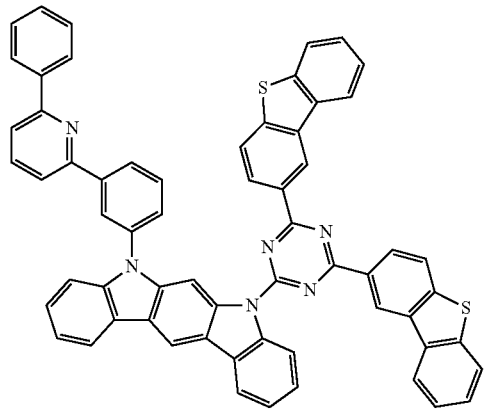
(G-41)
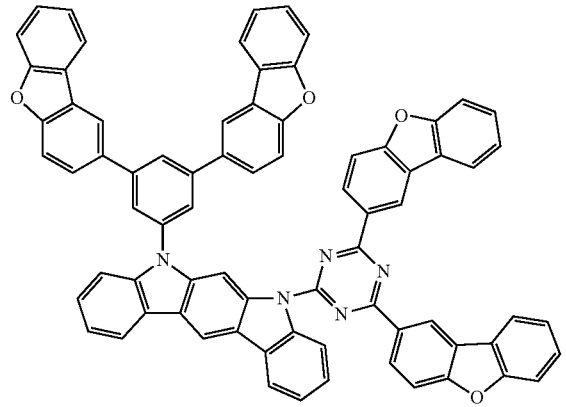
(G-42)
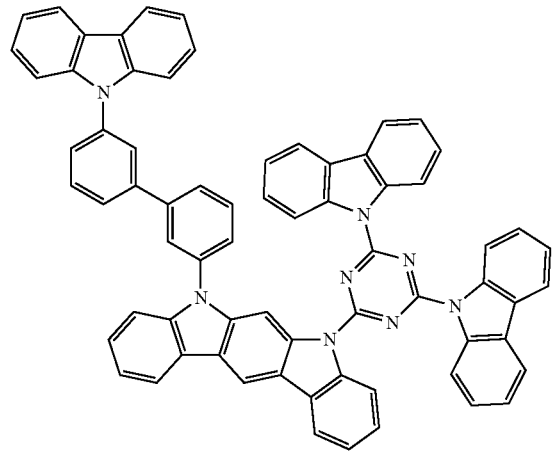
(G-43)
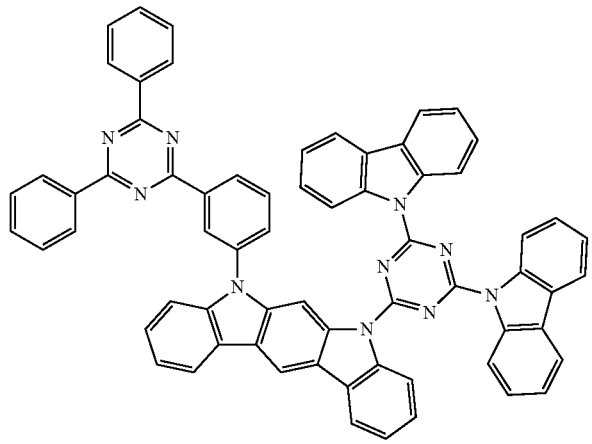
(G-44)
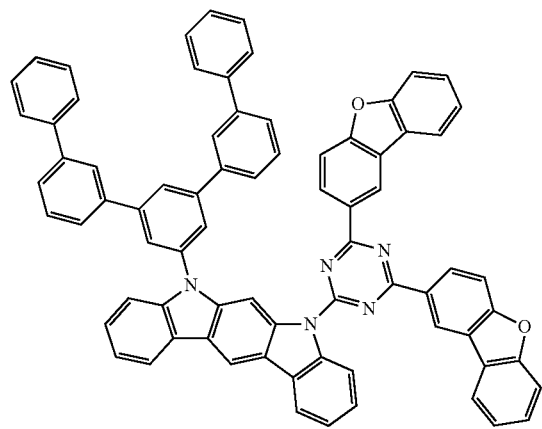
(G-45)
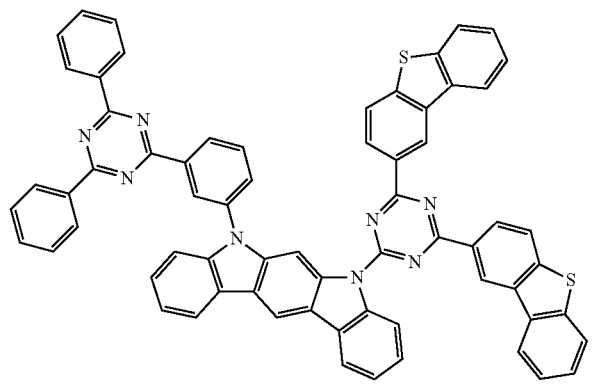

-continued
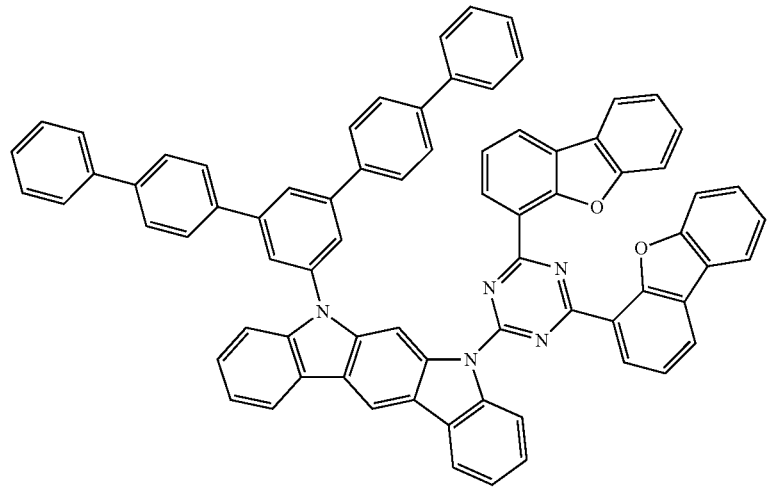
(G-46)
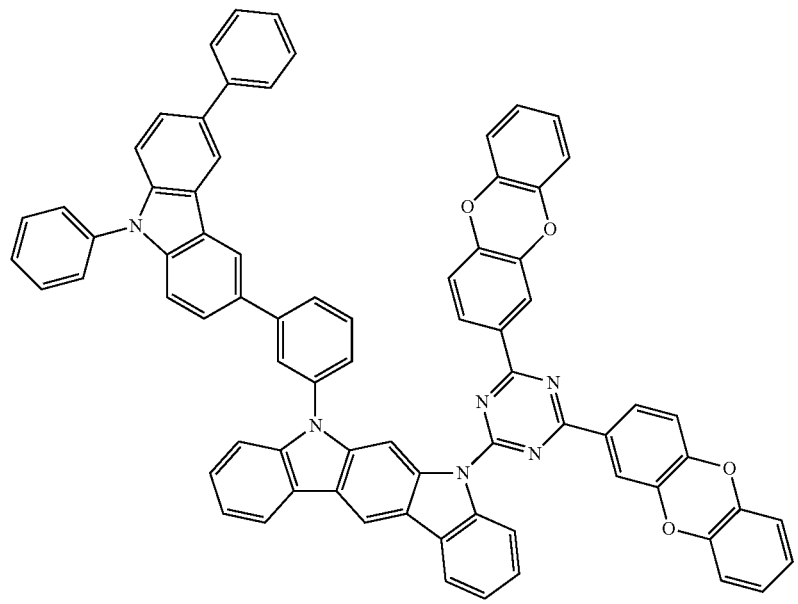
(G-47)

-continued
(G-48)
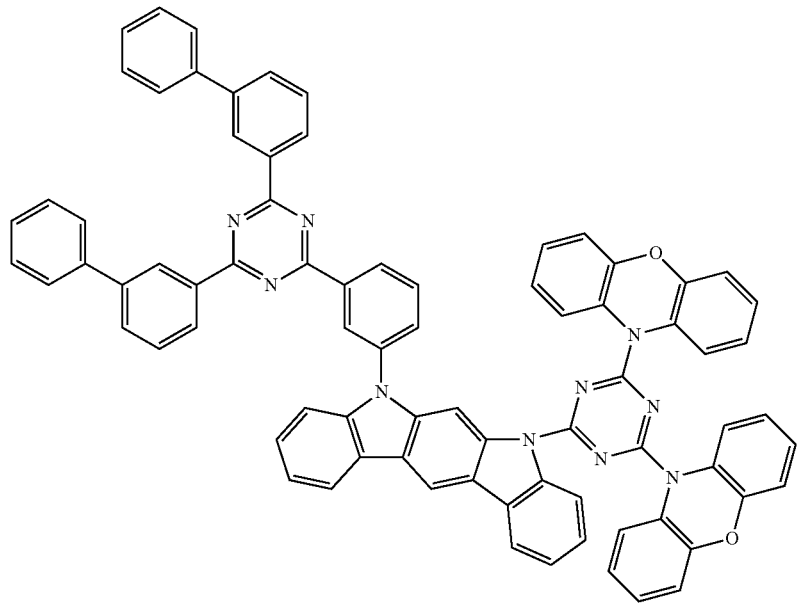
(G-49)
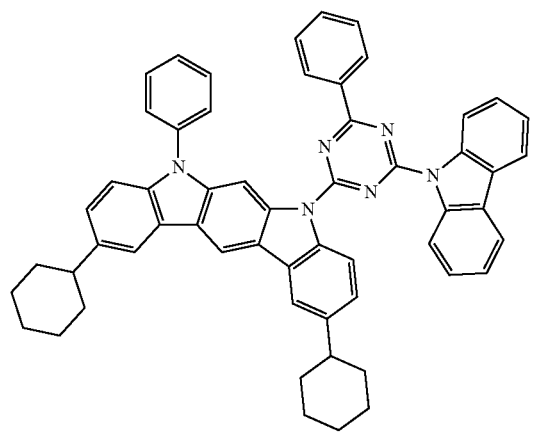
(G-50)
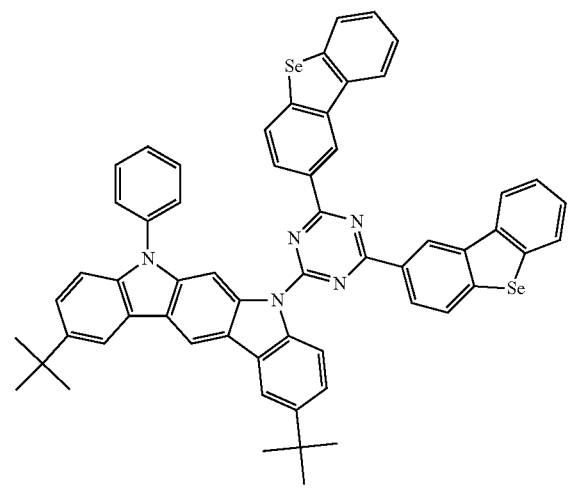
(H-1)
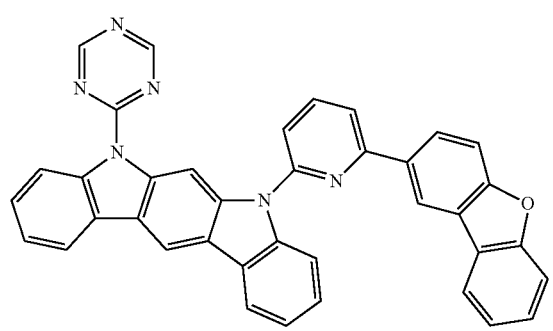
(H-2)
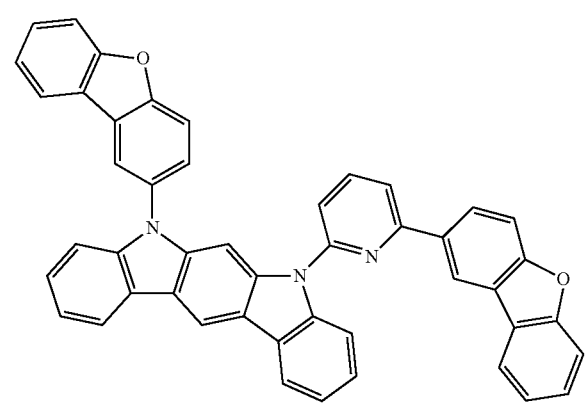

-continued
(H-3)
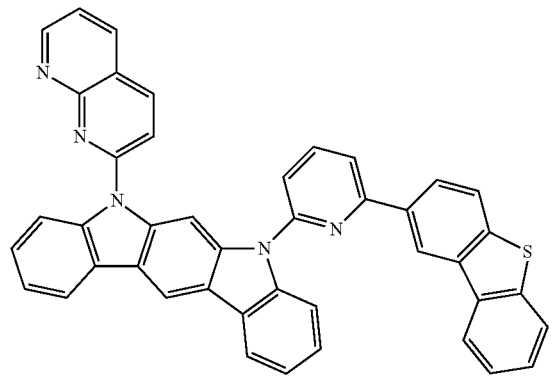
(H-4)
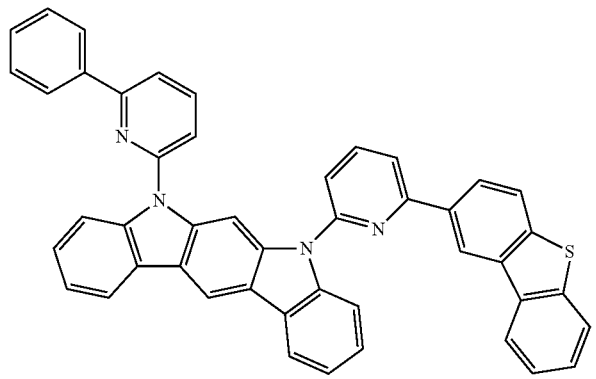
(H-5)
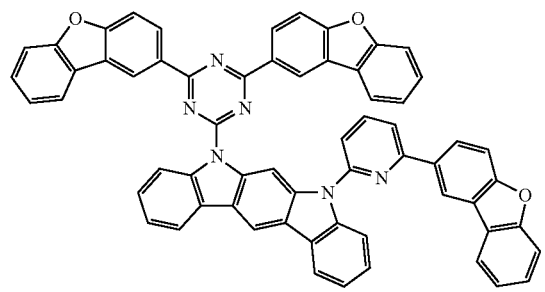
(H-6)
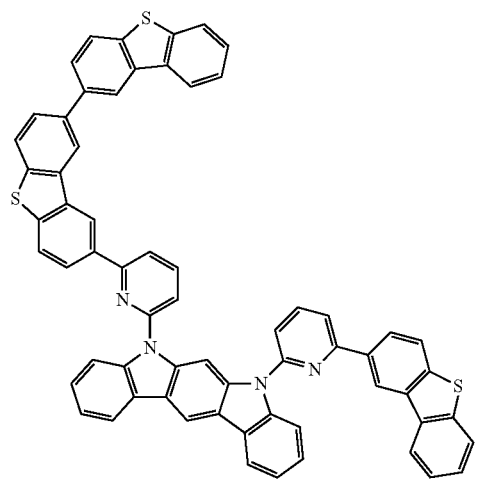
(H-7)
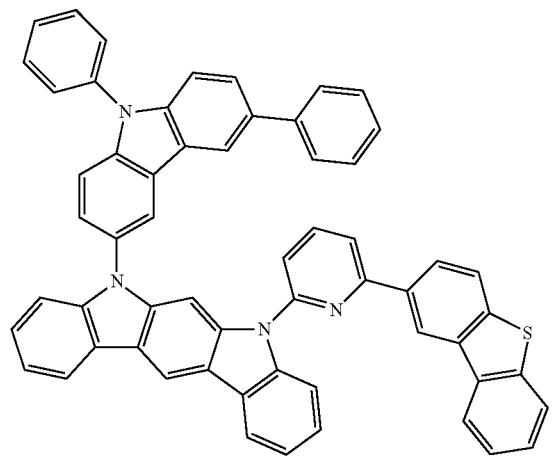
(H-8)
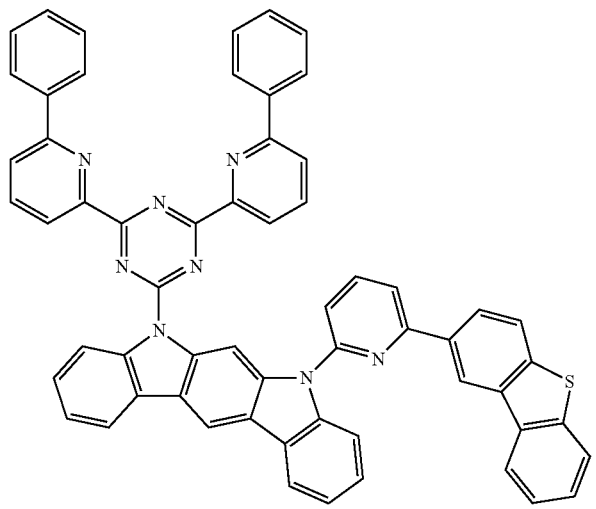

(H-9)
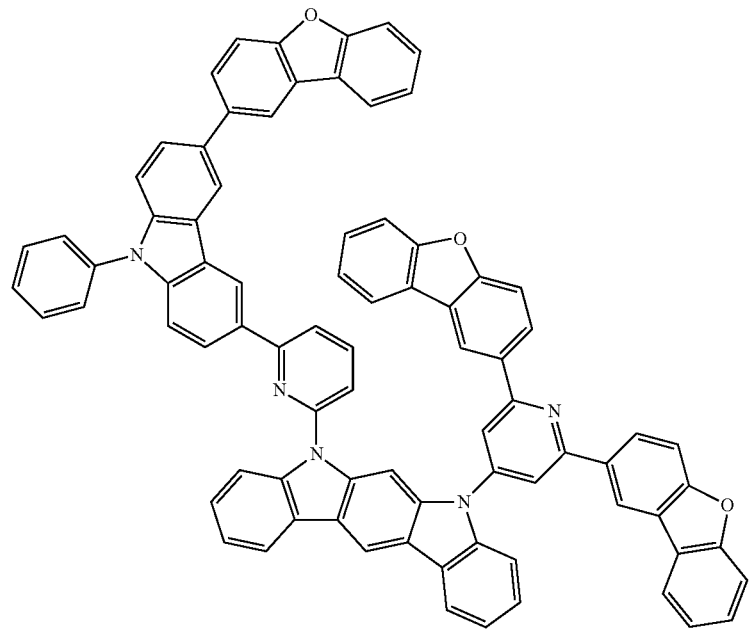
(H-10)
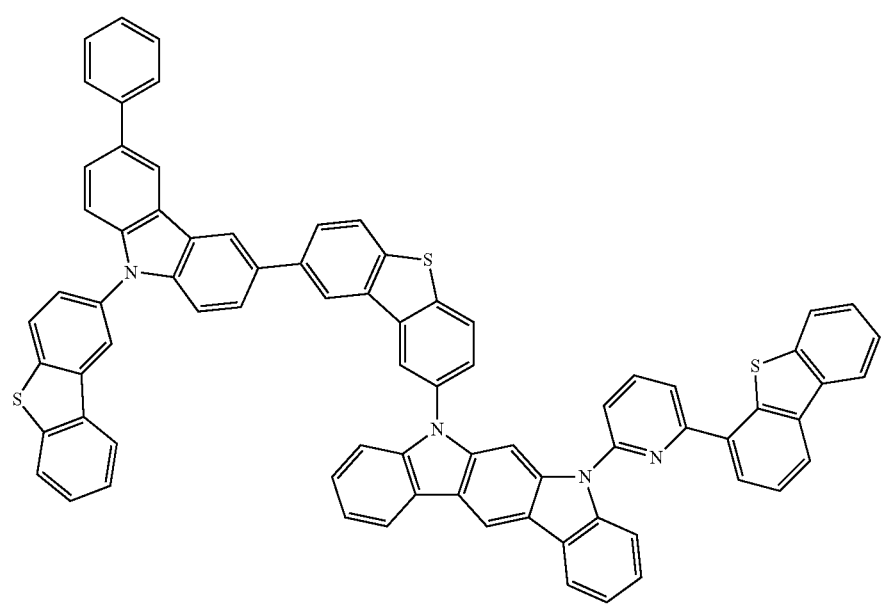

-continued
(H-11)
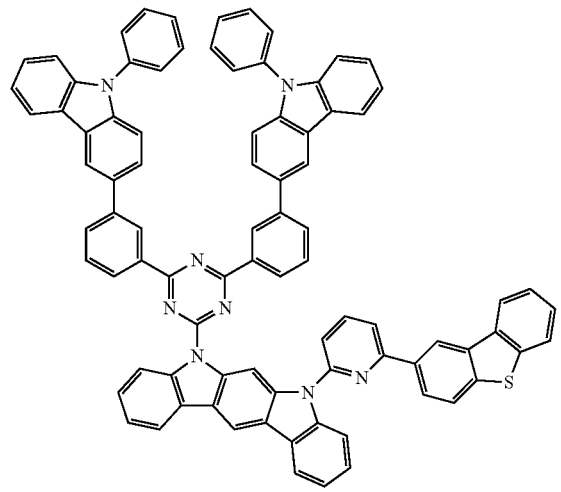
(H-12)
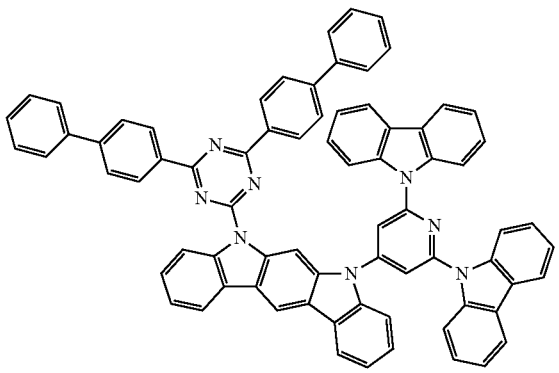
(H-13)
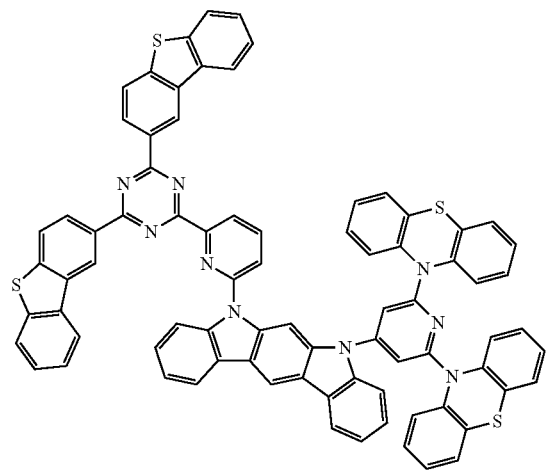
(H-14)
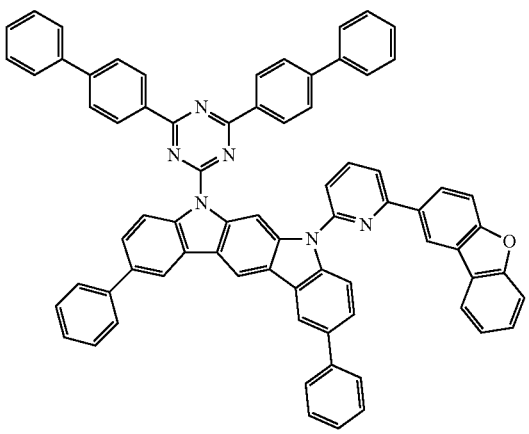
(H-15)
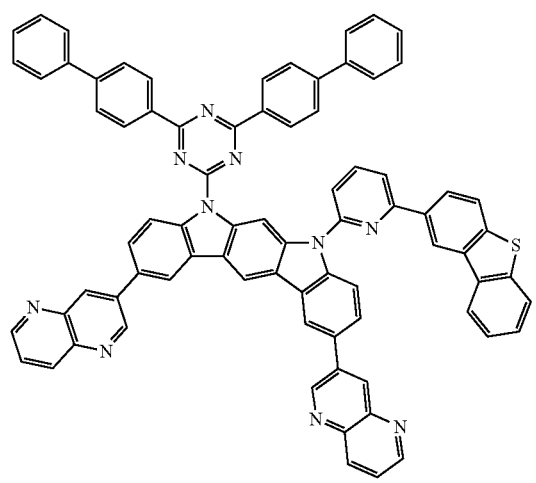
(H-16)
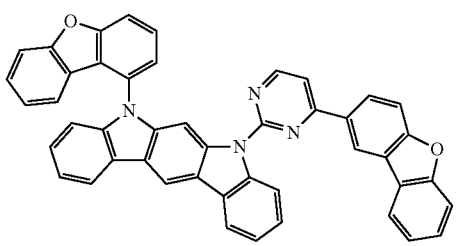

-continued
(H-17)
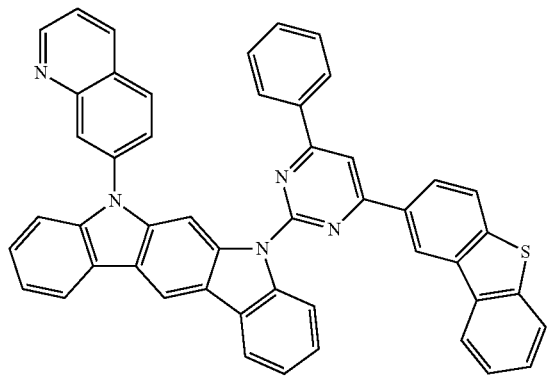
(H-18)
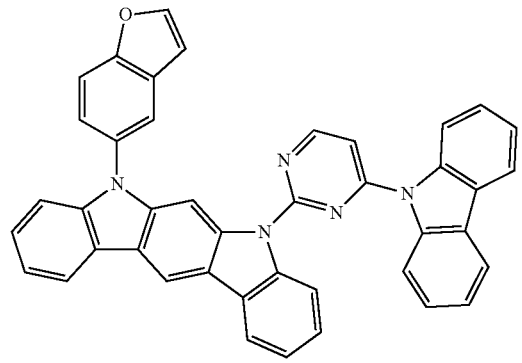
(H-19)
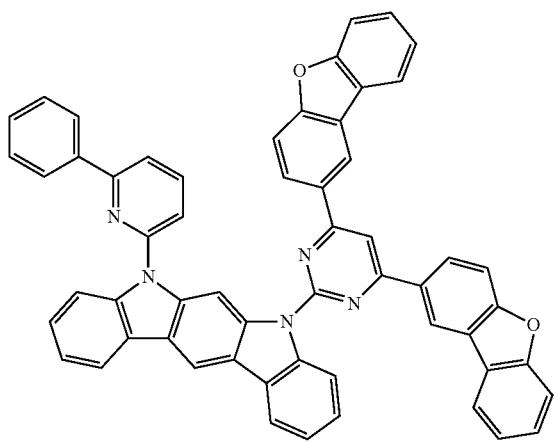
(H-20)
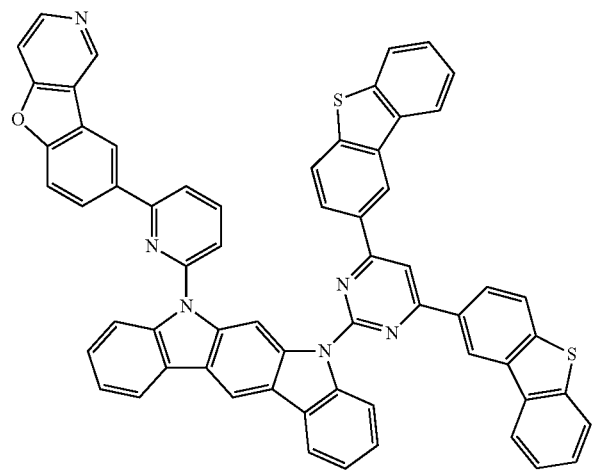
(H-21)
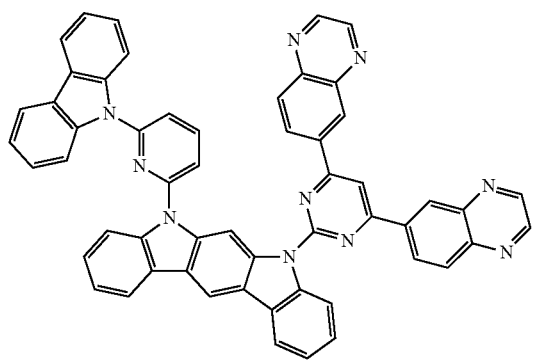
(H-22)
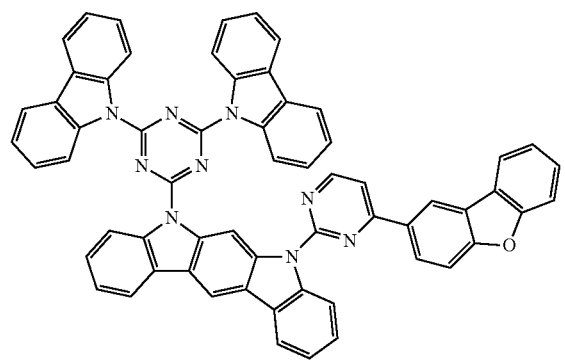

-continued
(H-23)
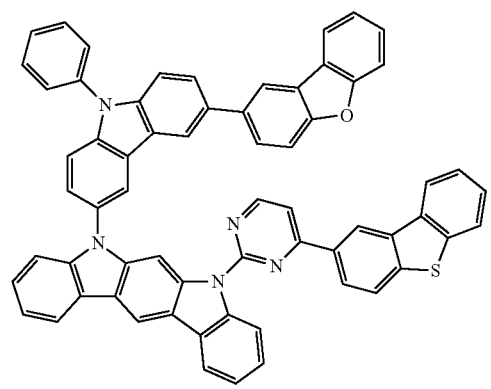
(H-24)
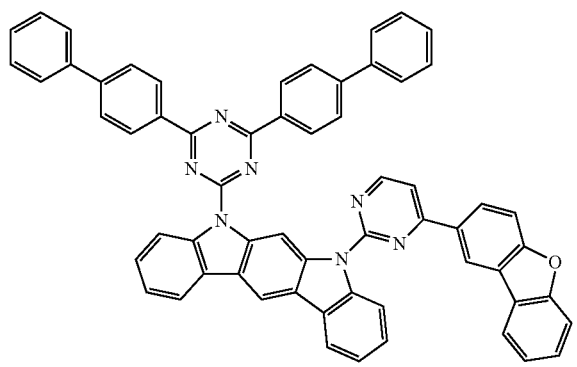
(H-25)
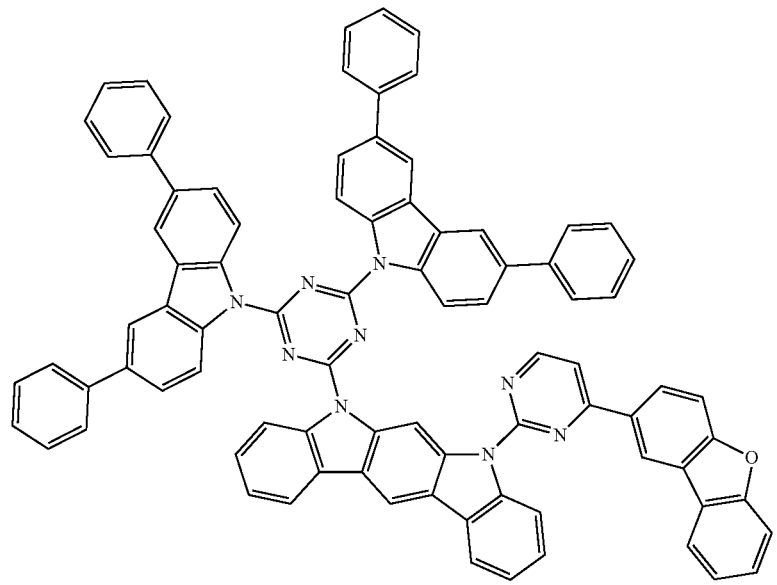
(H-26)
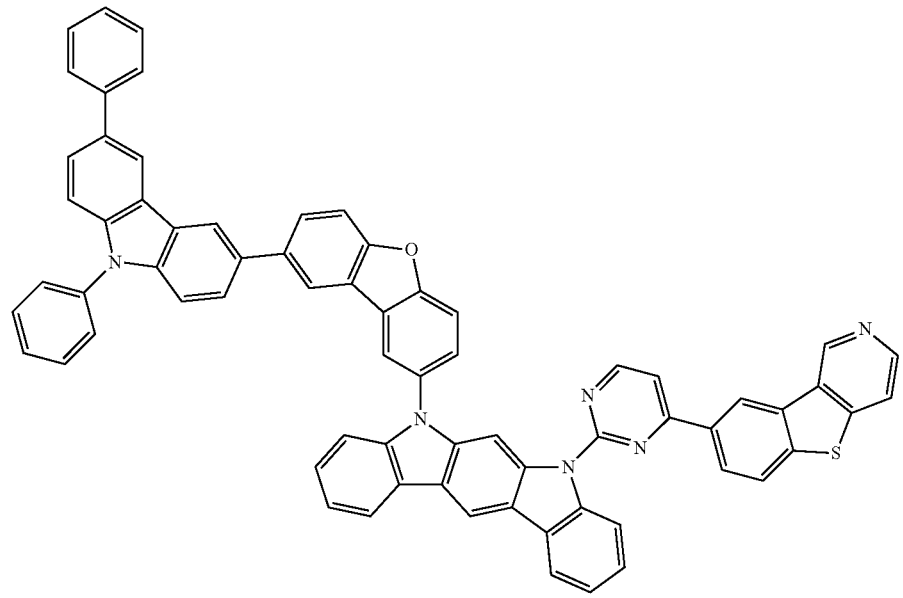

(H-27)
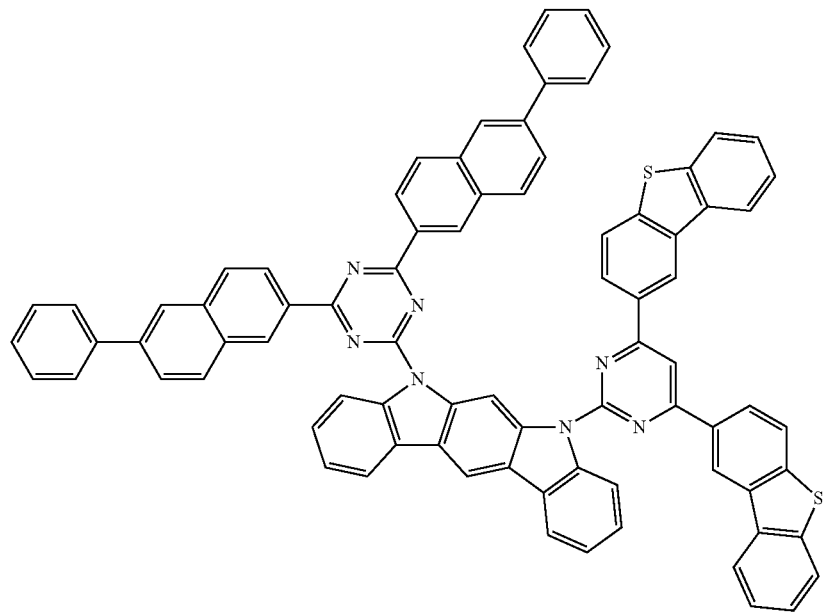
(H-28)
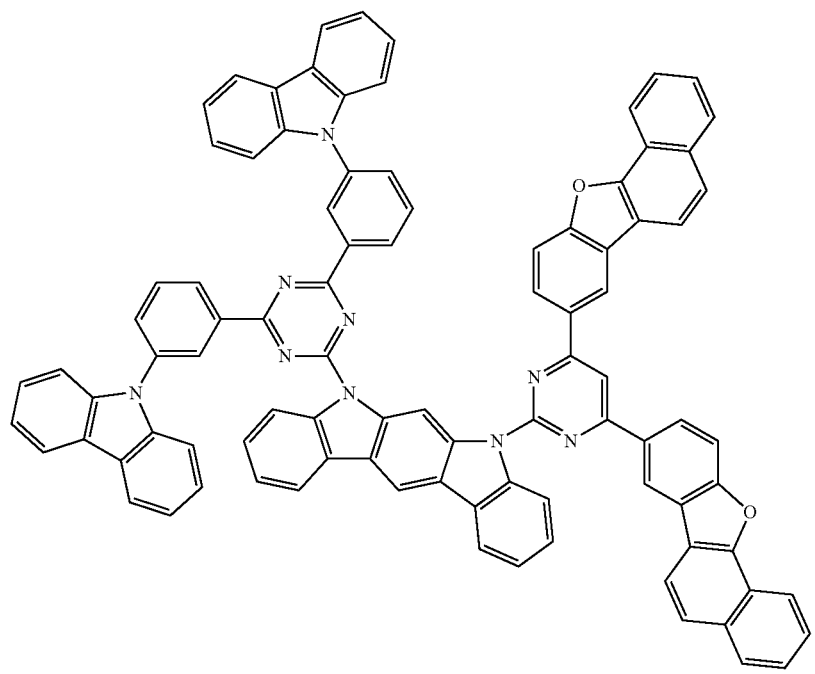

(H-29)
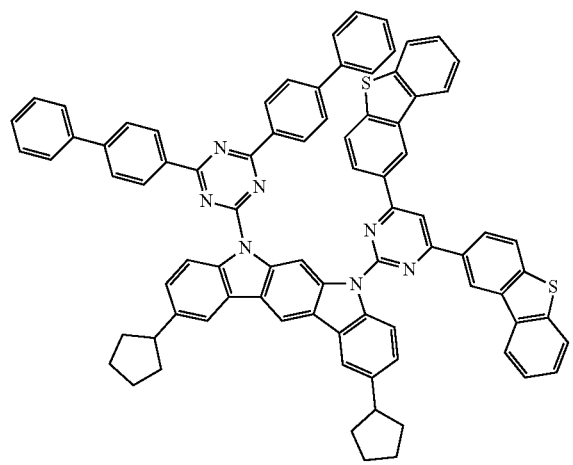
(H-30)
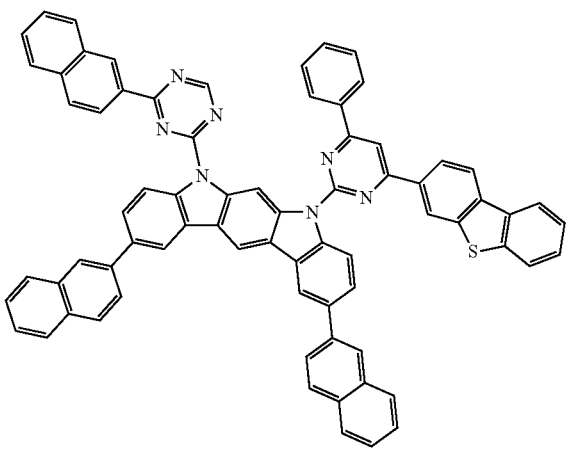
(H-31)
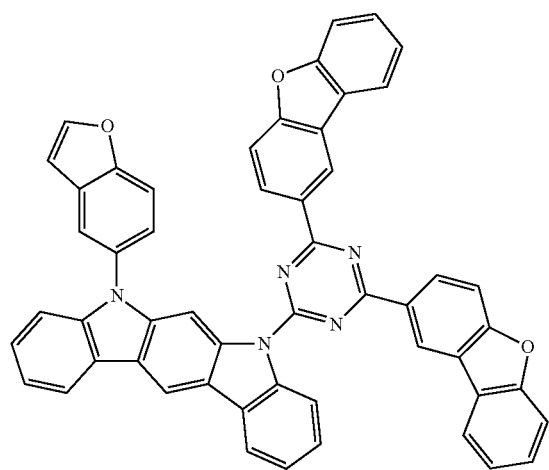
(H-32)
(H-33)
(H-34)
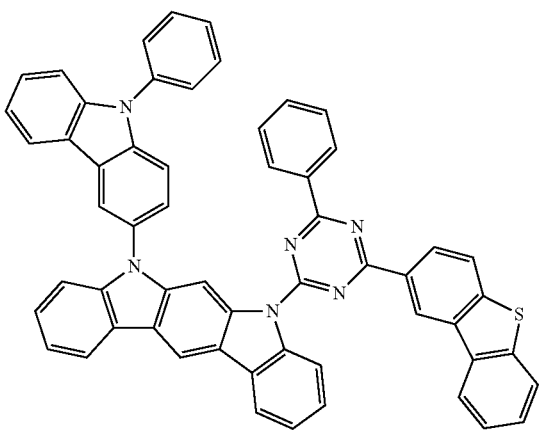

(H-35)
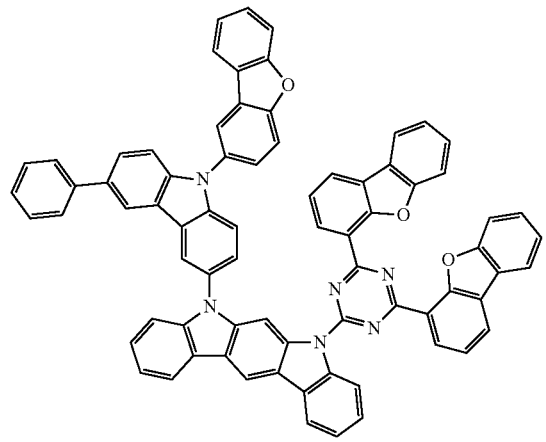
(H-36)
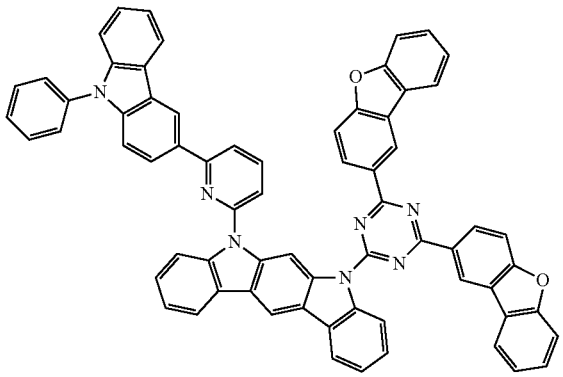
(H-37)
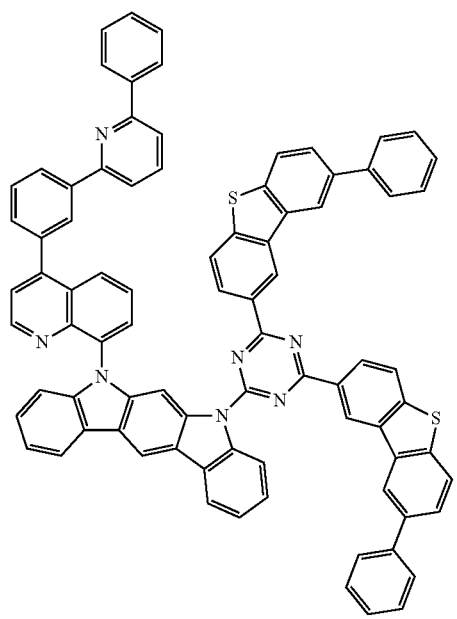
(H-38)
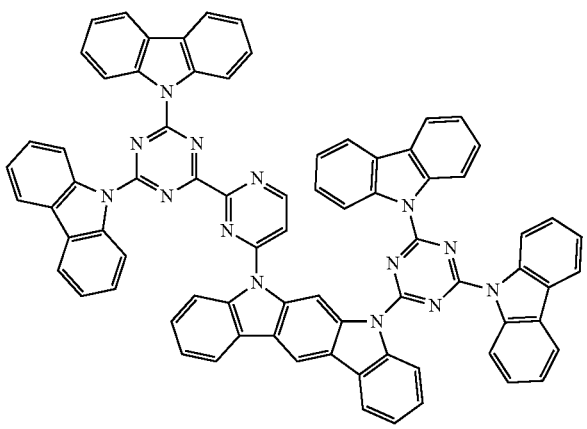
(H-39)
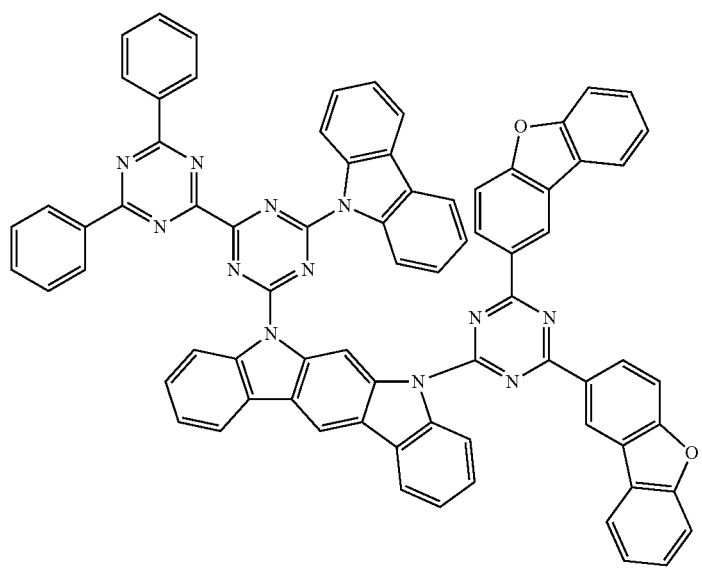

-continued
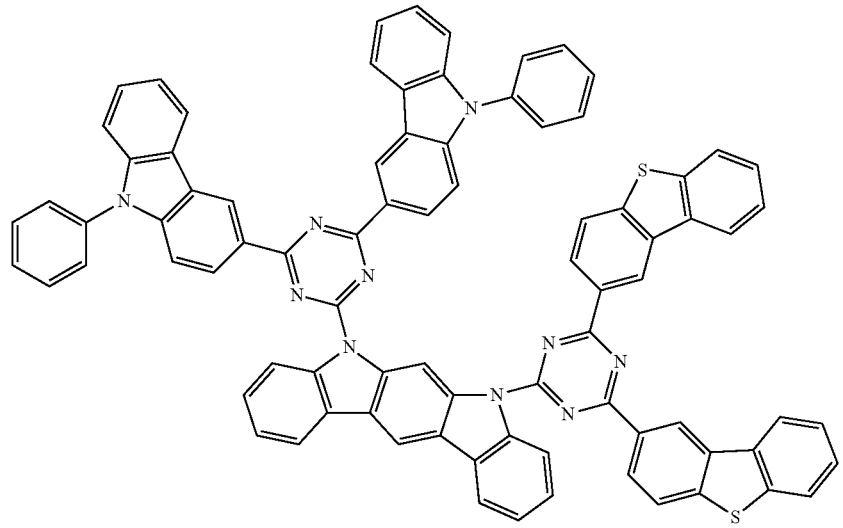
(H-40)
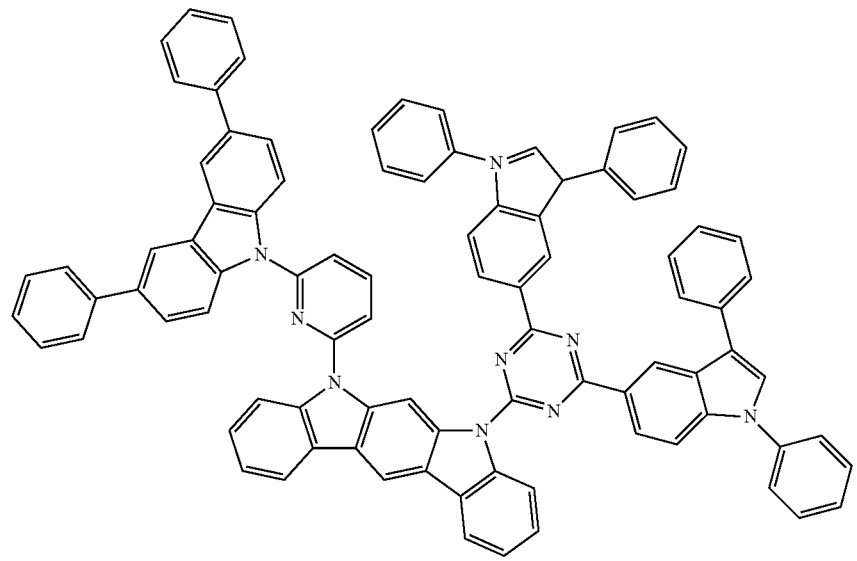
(H-41)
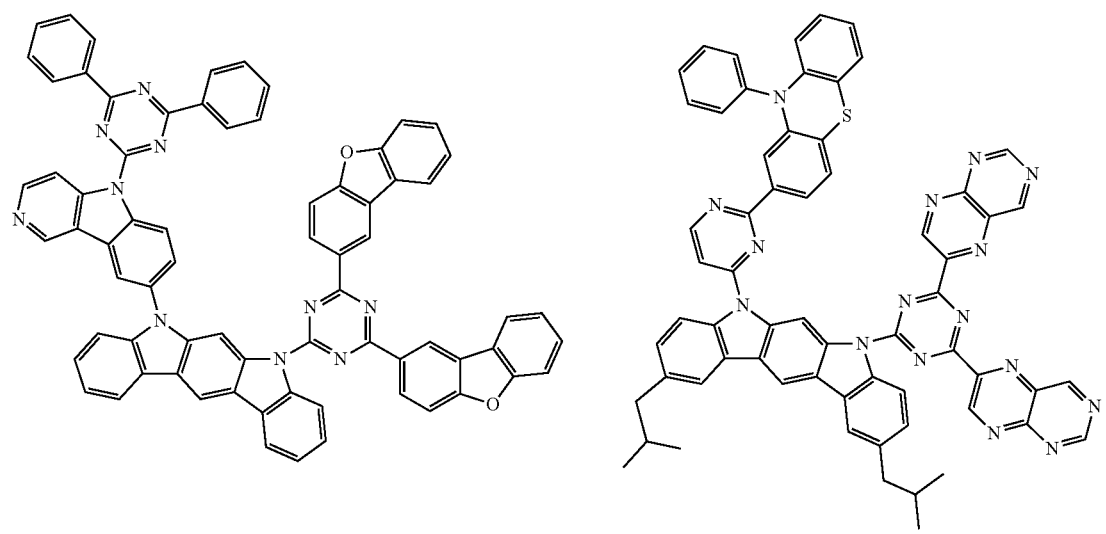
(H-42)
(H-43)

-continued
(H-44)
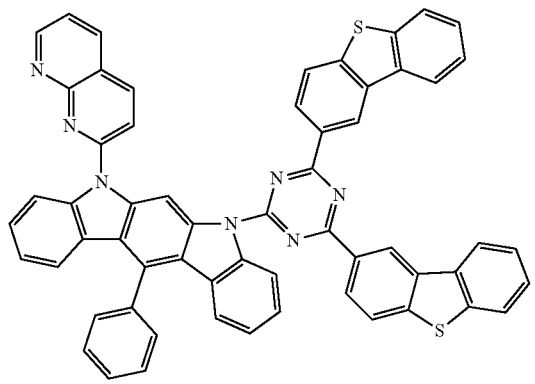
(J-1)
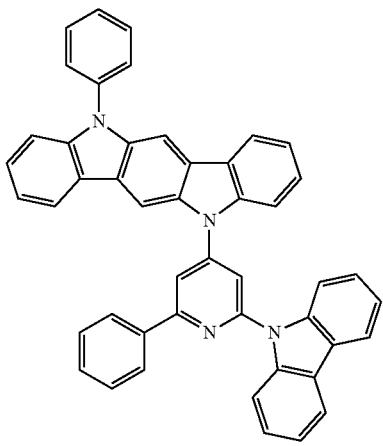
(J-2)
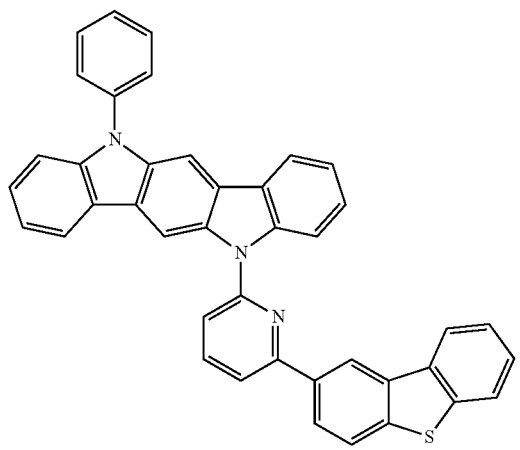
(J-3)
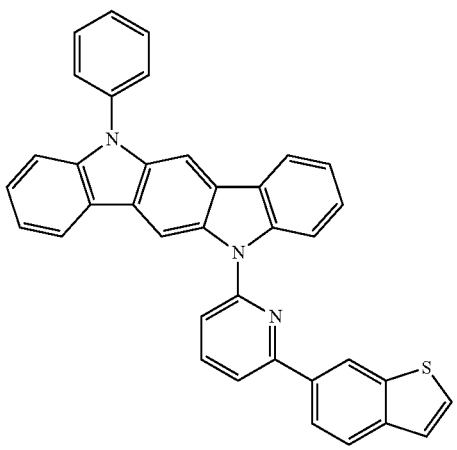
(J-4)
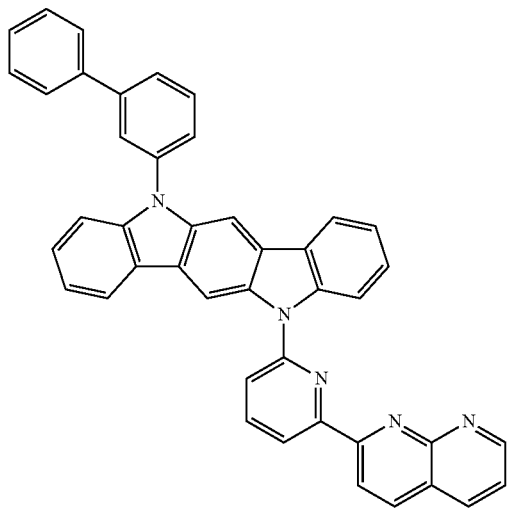
(J-5)
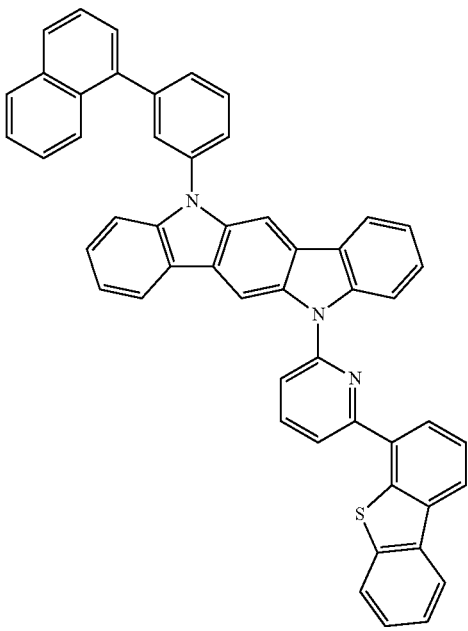

-continued
(J-6)
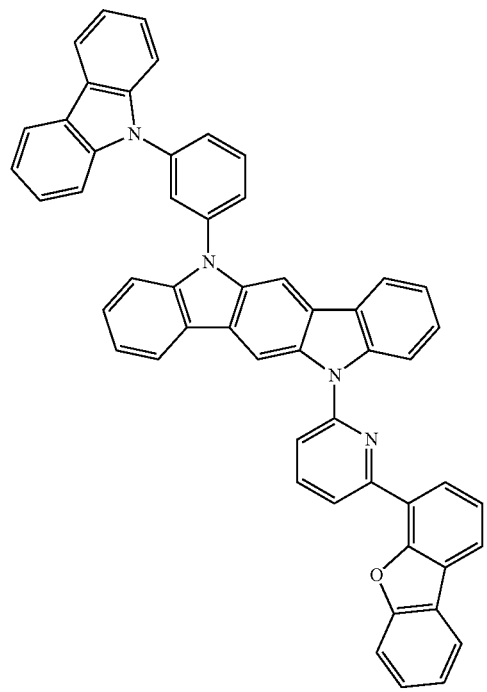
(J-7)
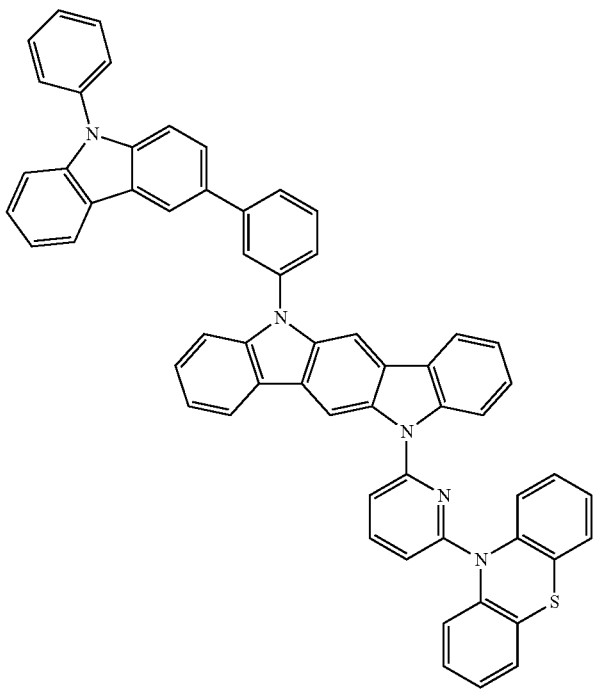
(J-8)
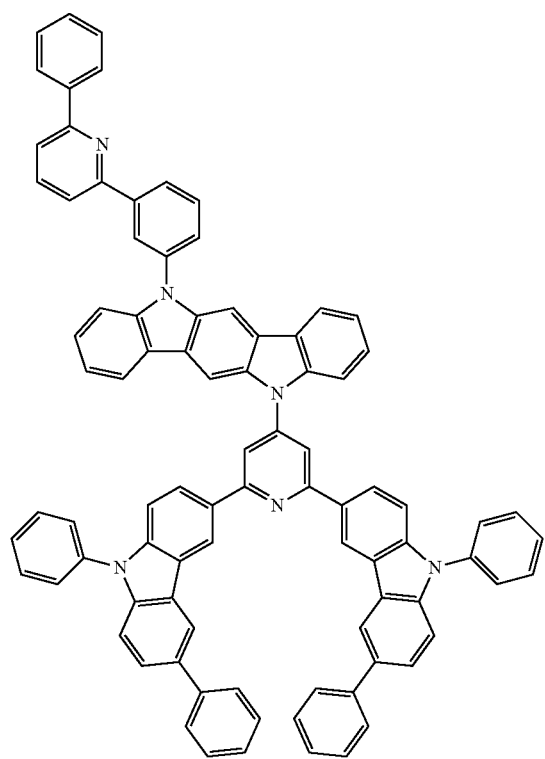
(J-9)
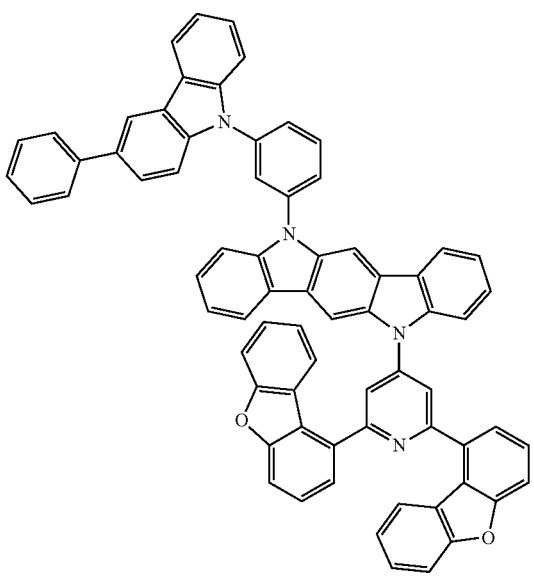

-continued
(J-10)
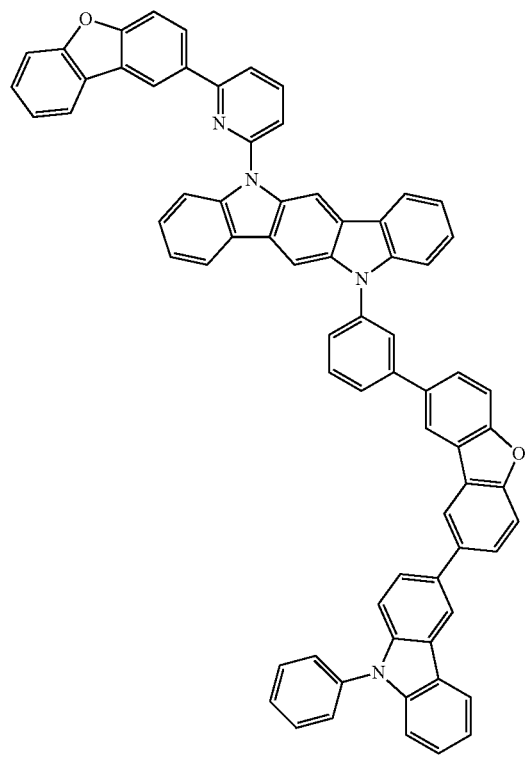
(J-11)
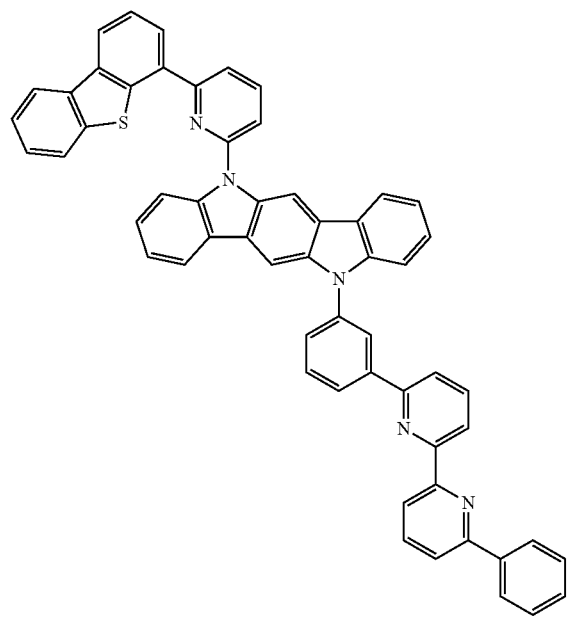
(J-12)
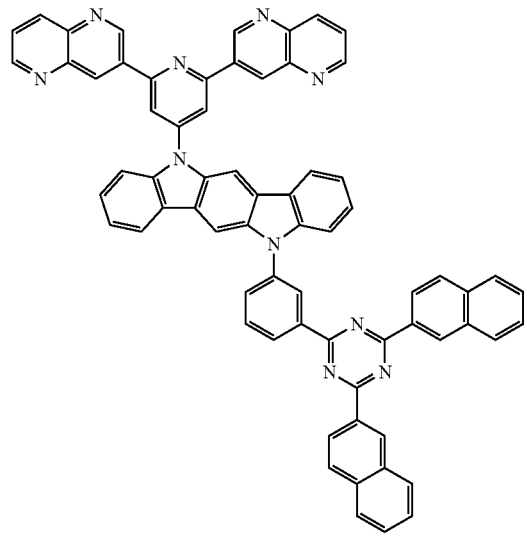
(J-13)
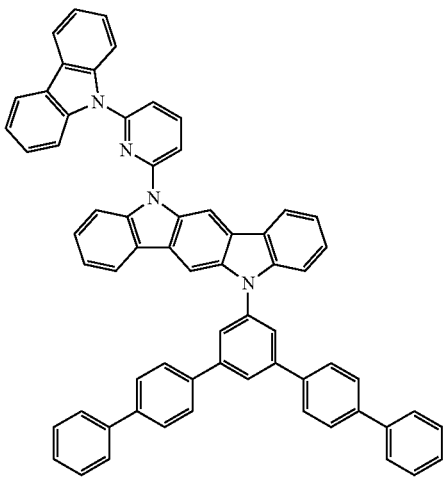

-continued
(J-14)
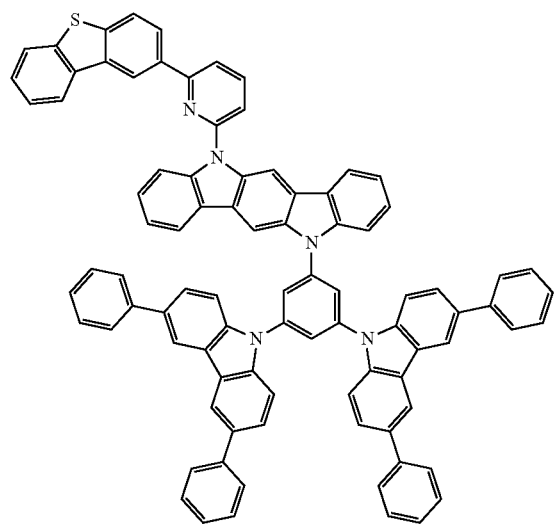
(J-15)
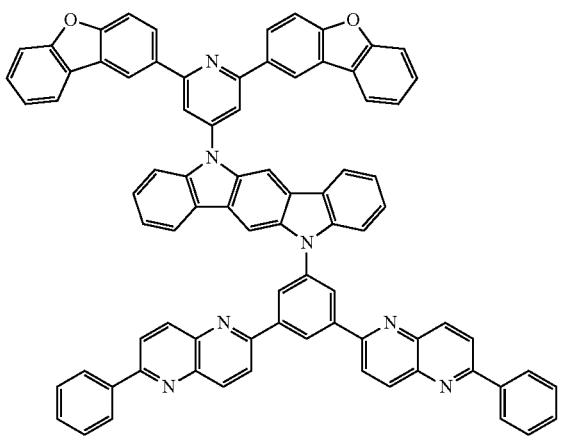
(J-16)
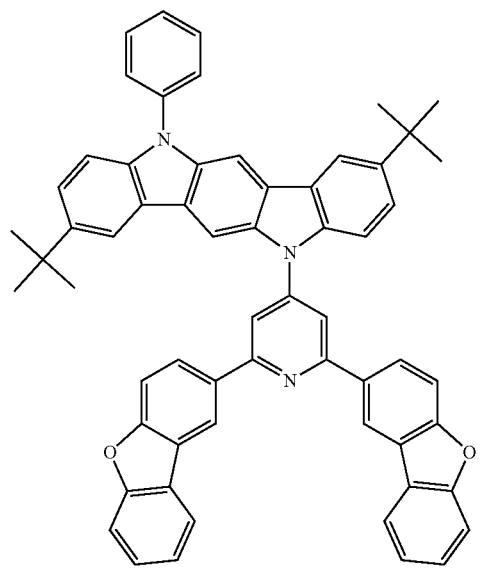
(J-17)
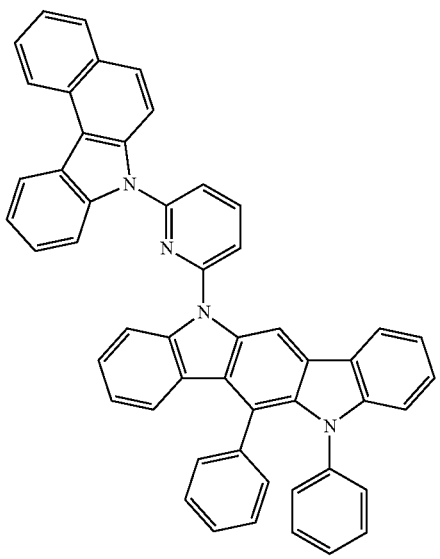
(J-18)
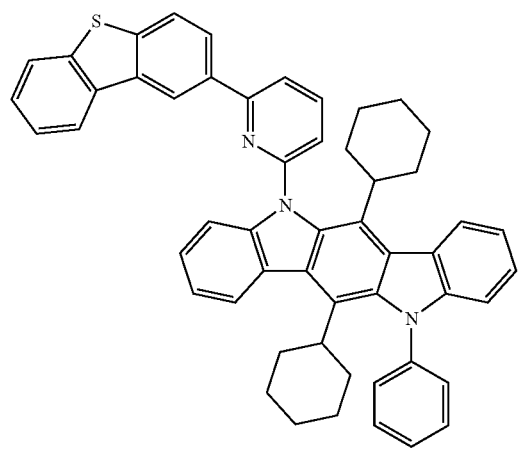
(J-19)
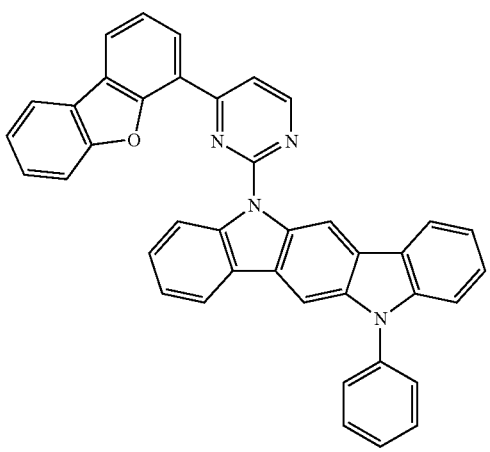

-continued
(J-20)
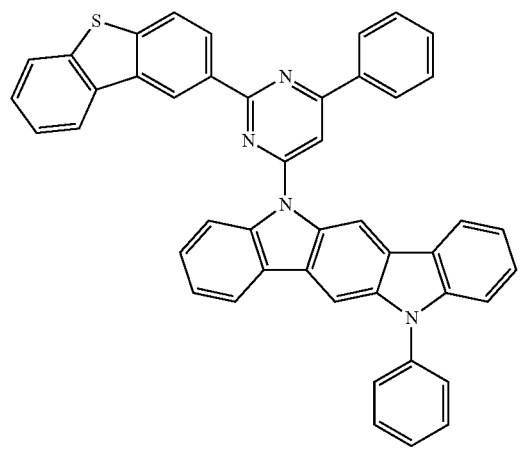
(J-21)
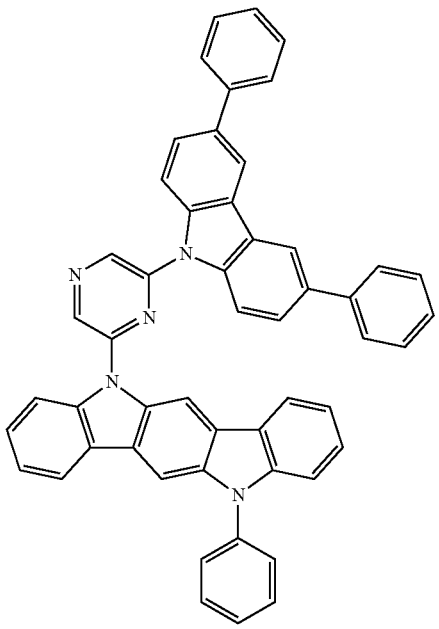
(J-22)
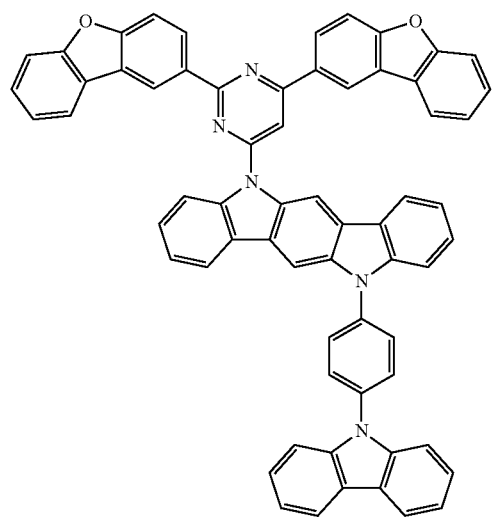
(J-23)
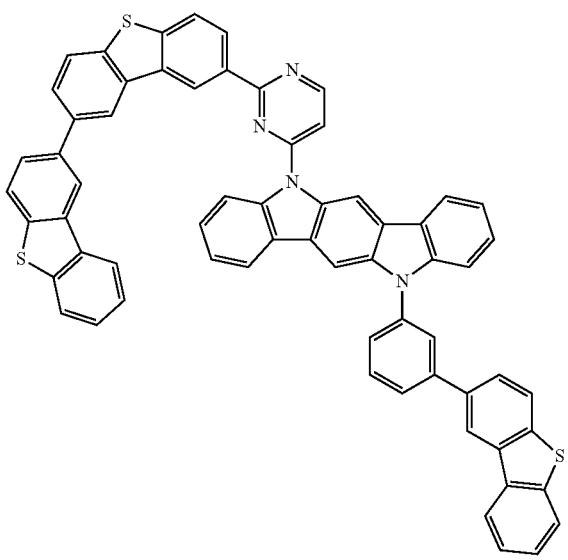

-continued
(J-24)
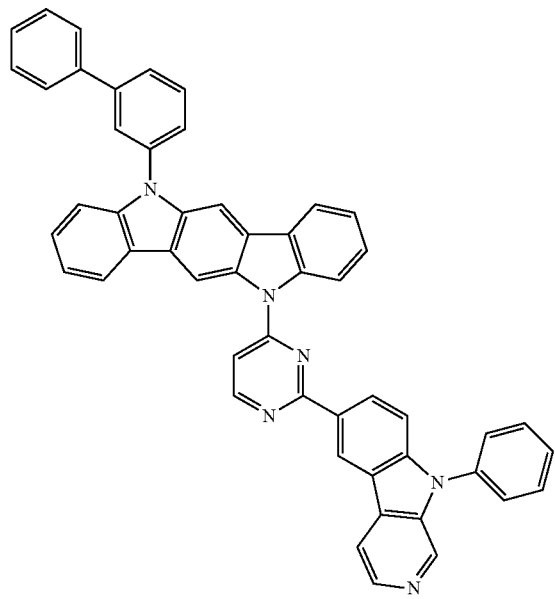
(J-25)
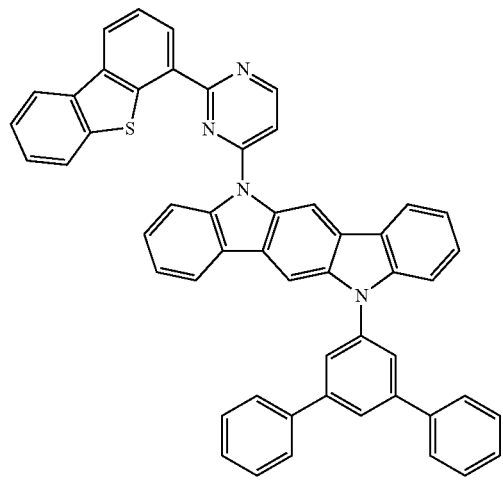
(J-26)
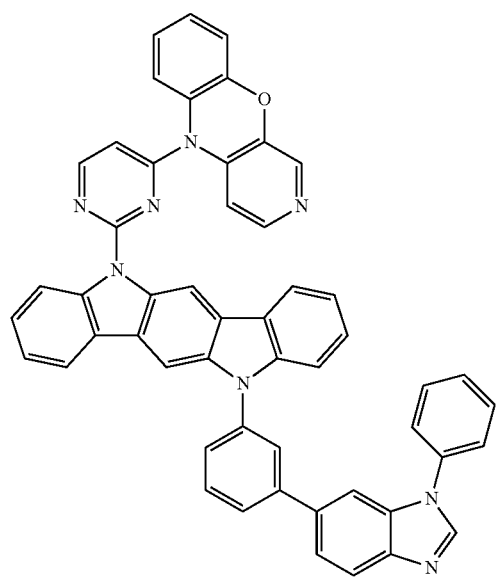
(J-27)
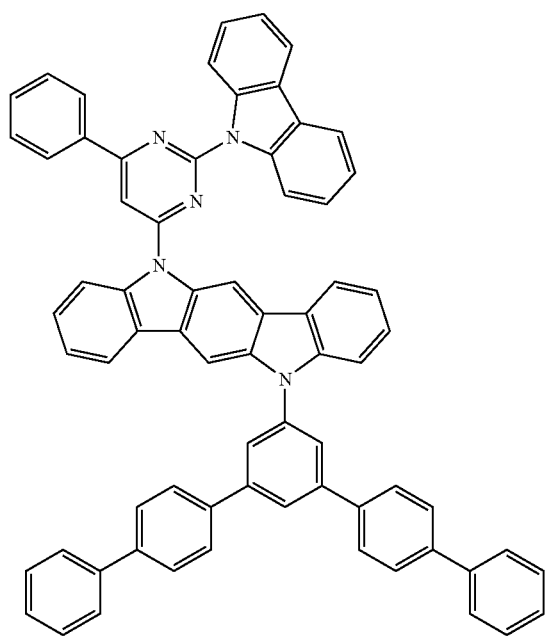

-continued
(J-28)
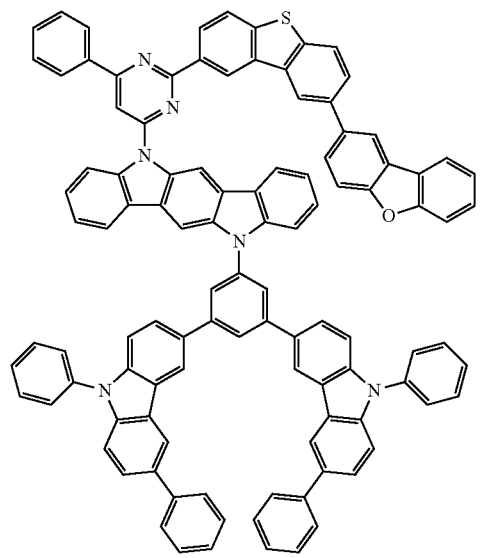
(J-29)
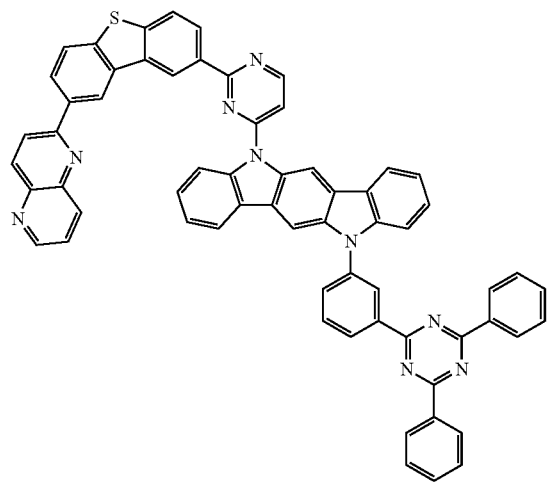
(J-30)
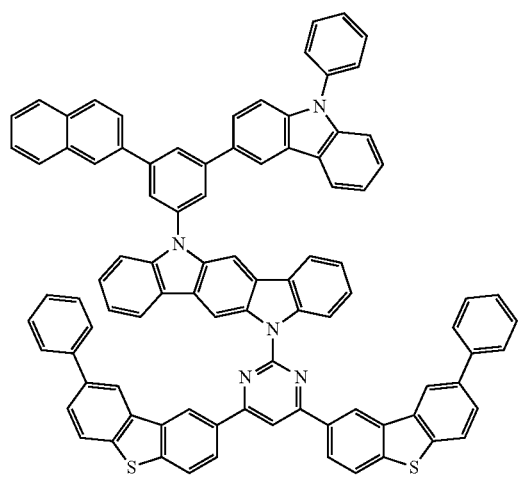
(J-31)
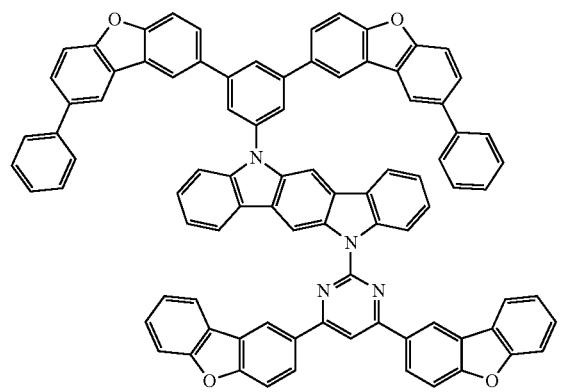
(J-32)
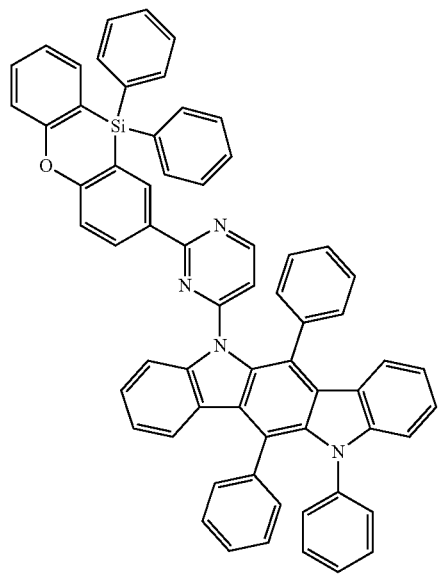
(J-33)
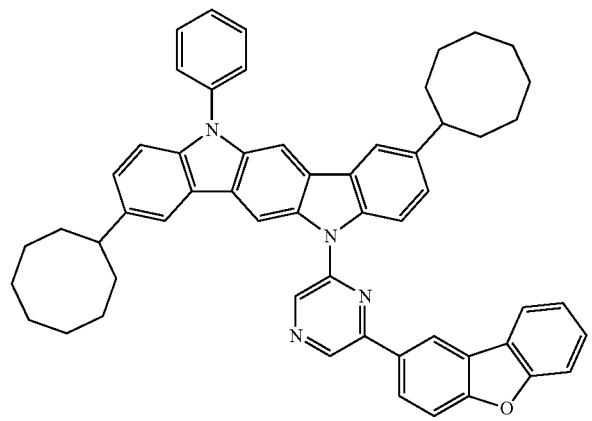

-continued
(J-34)
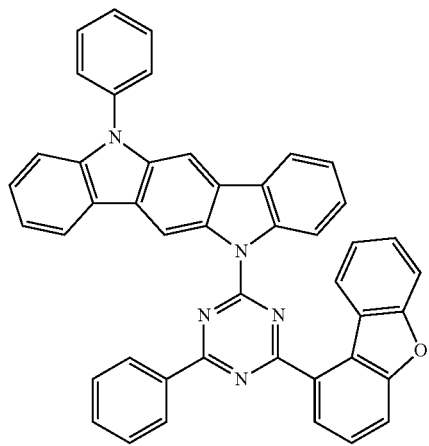
(J-35)
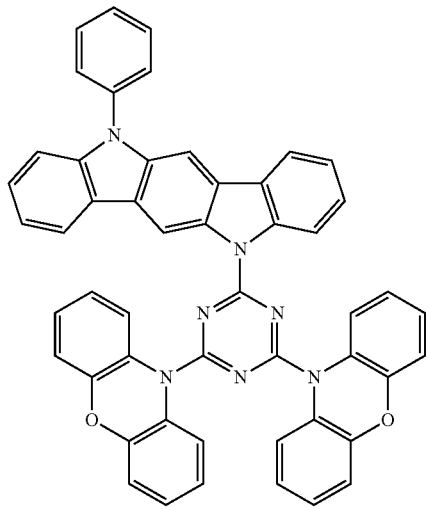
(J-36)
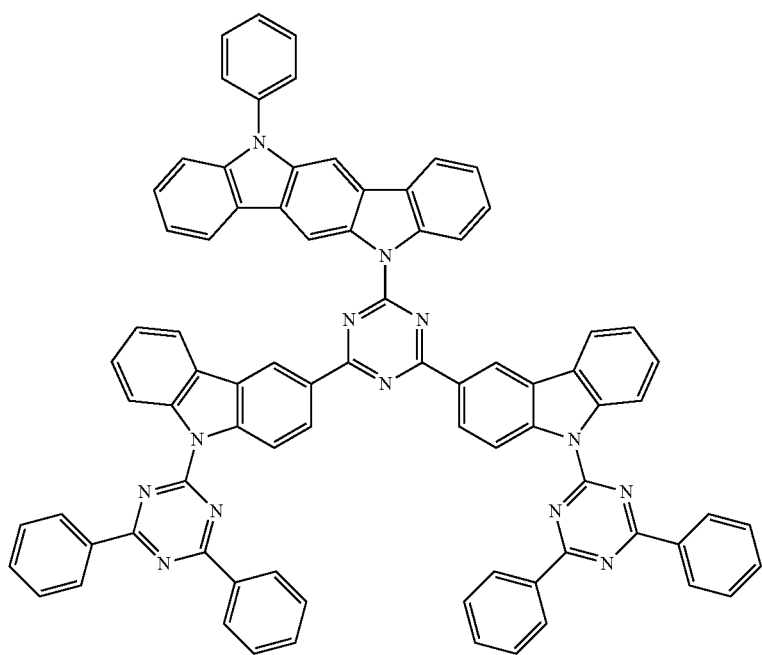

-continued
(J-37)
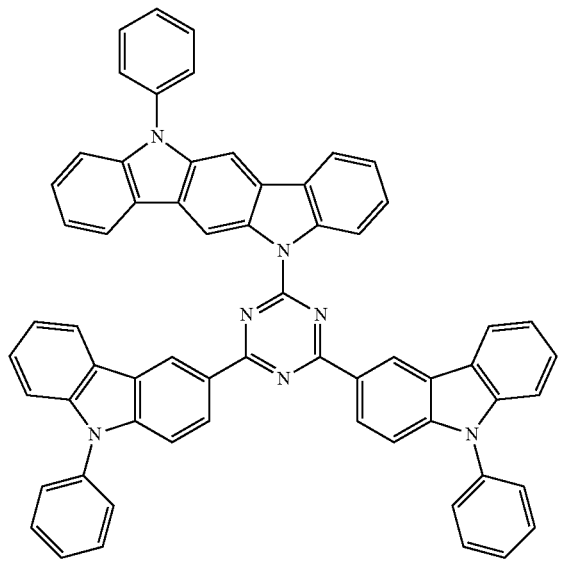
(J-38)
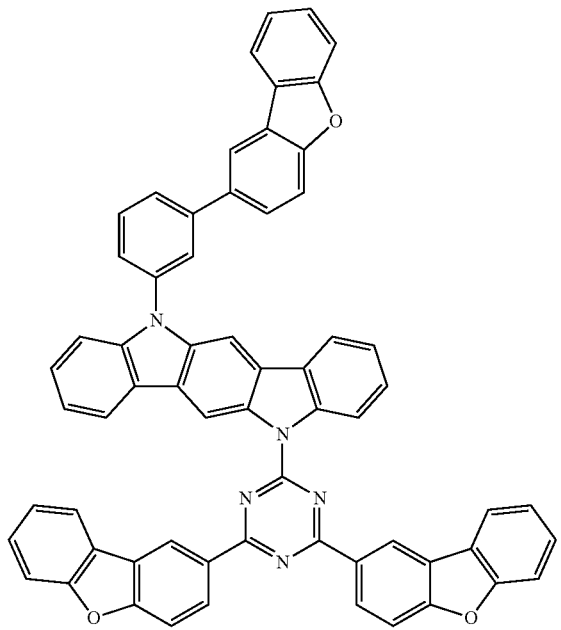
(J-39)
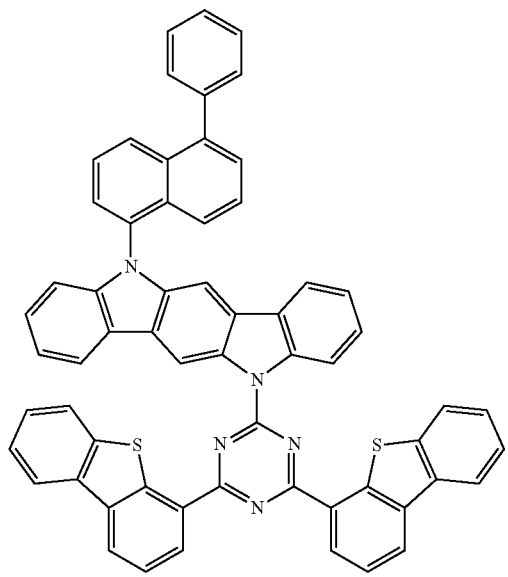
(J-40)
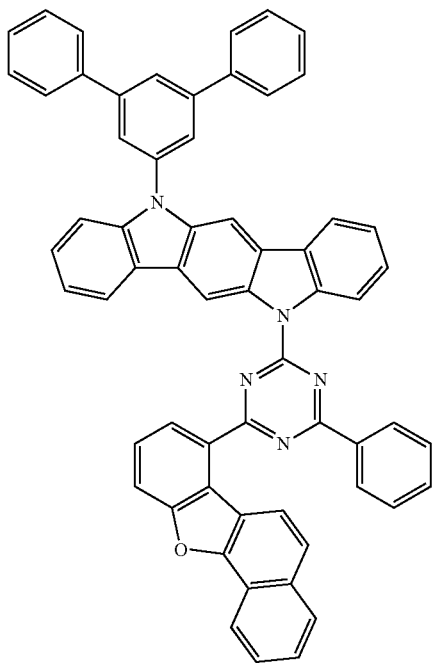

-continued
(J-41)
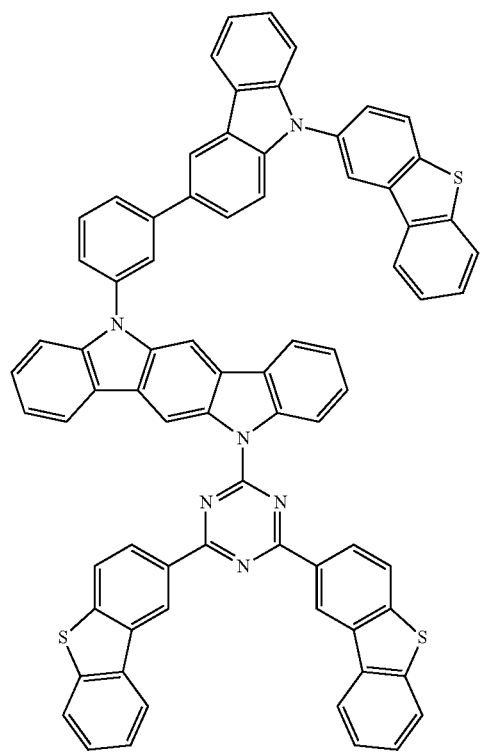
(J-42)
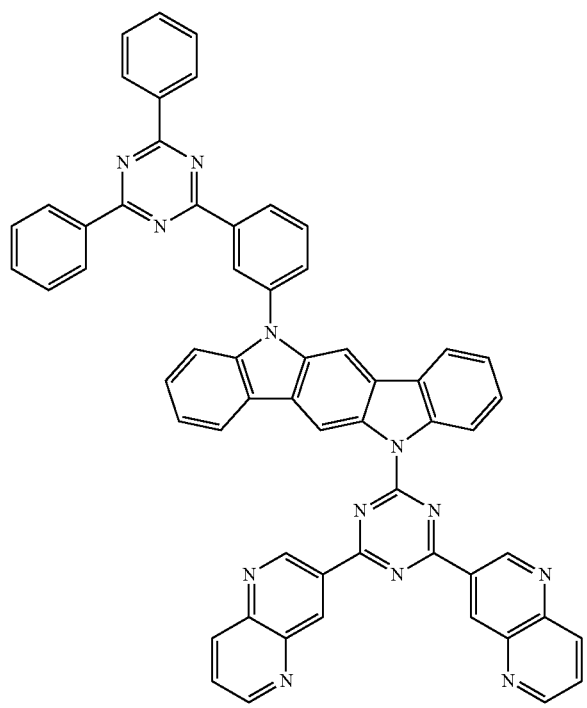
(J-43)
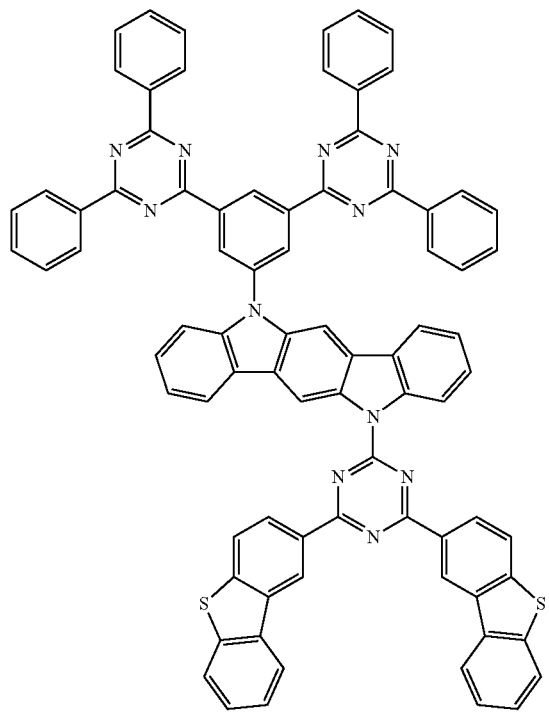
(J-44)
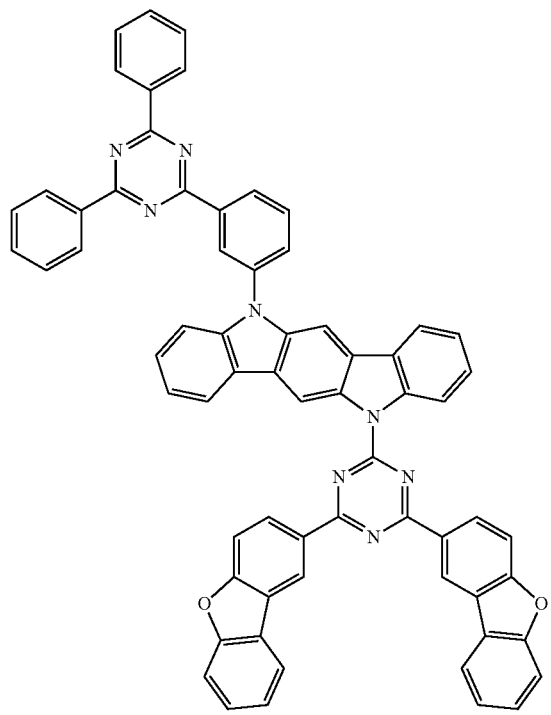

(J-45)
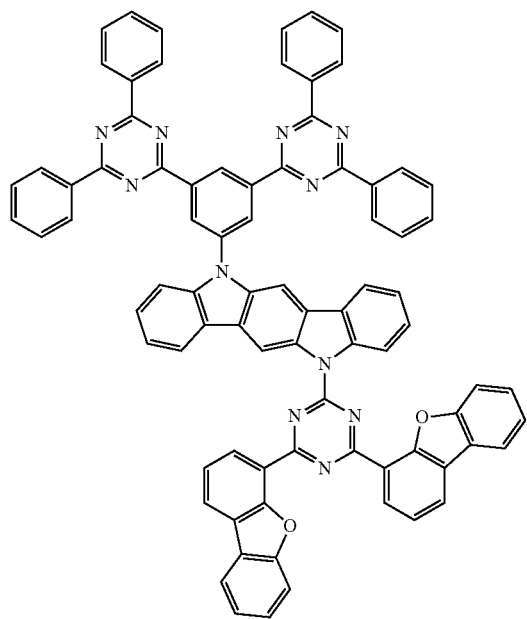
(J-46)
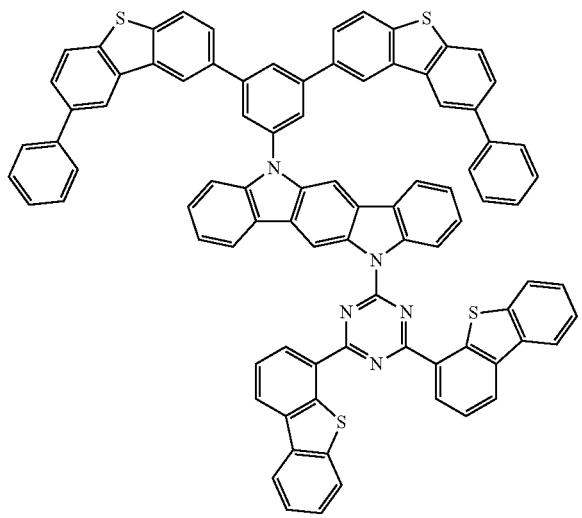
(J-47)
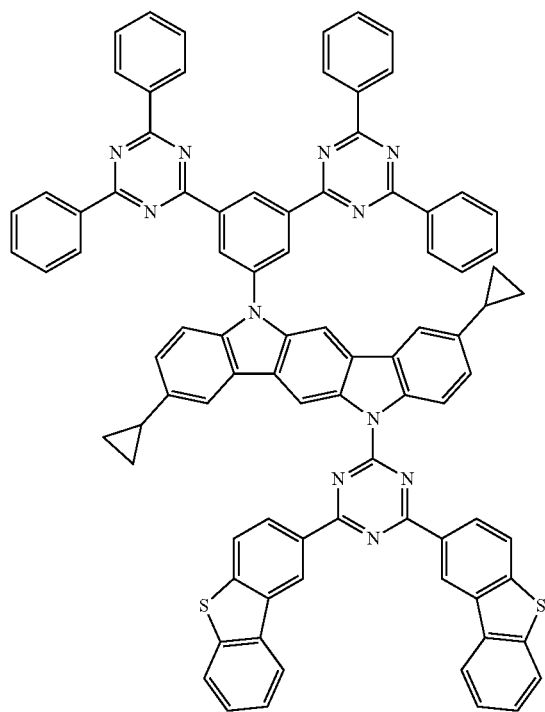
(J-48)
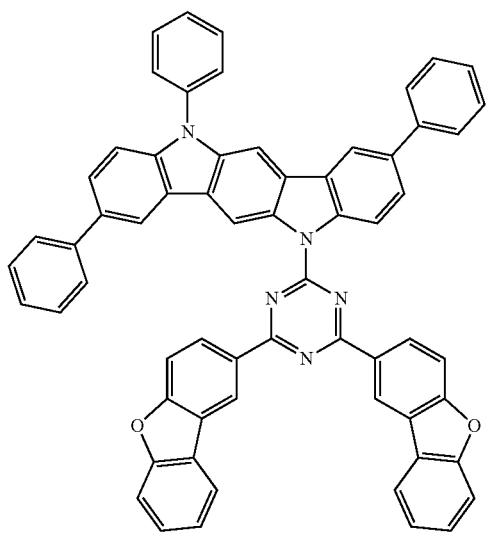

-continued
(K-1)
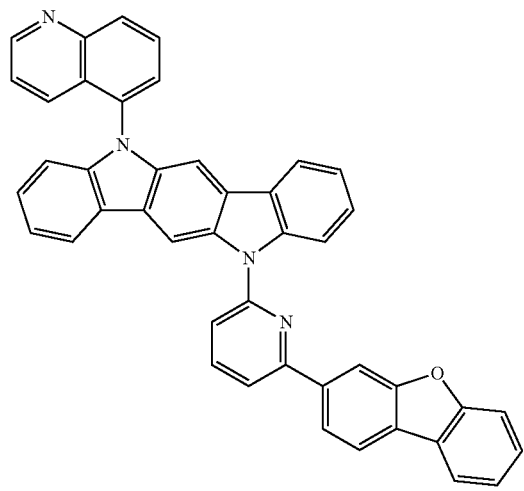
(K-2)
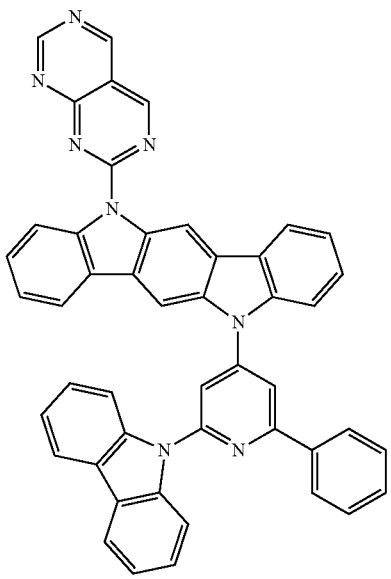
(K-3)
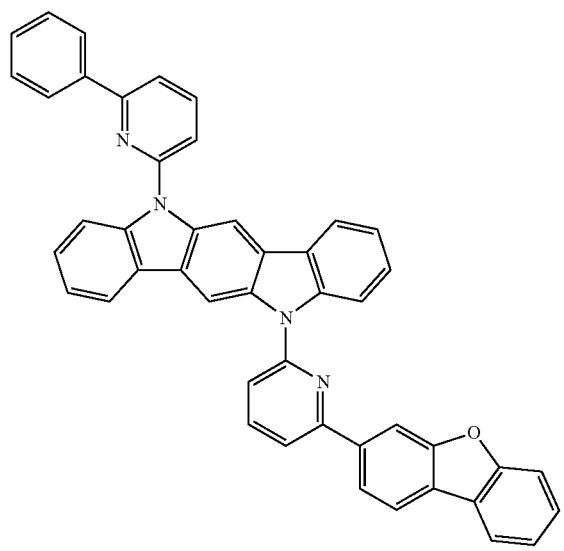
(K-4)
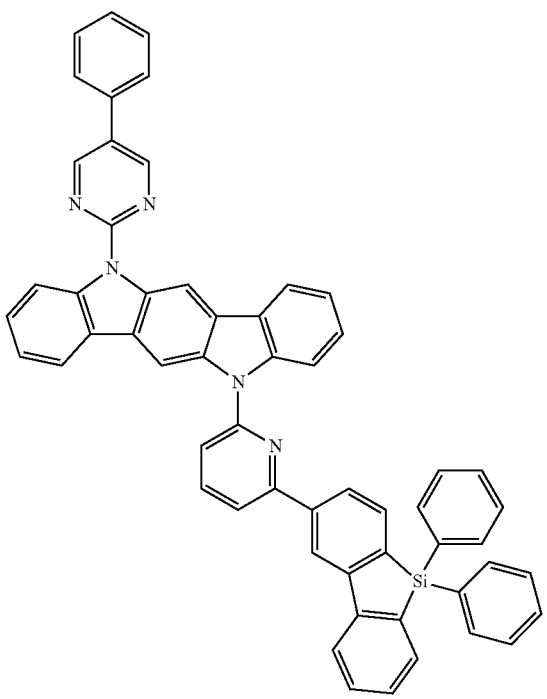

-continued
(K-5)
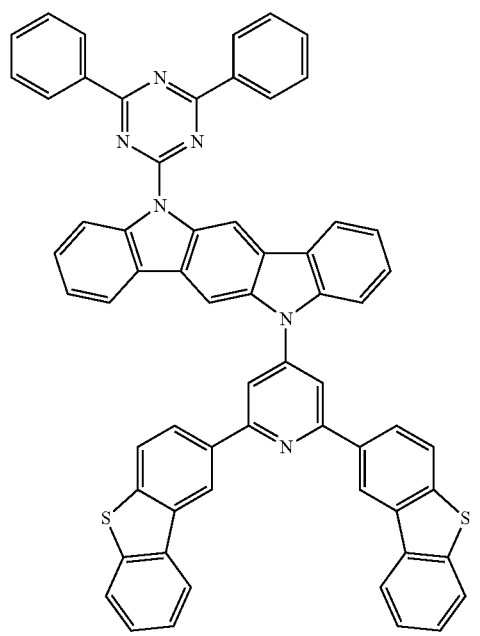
(K-6)
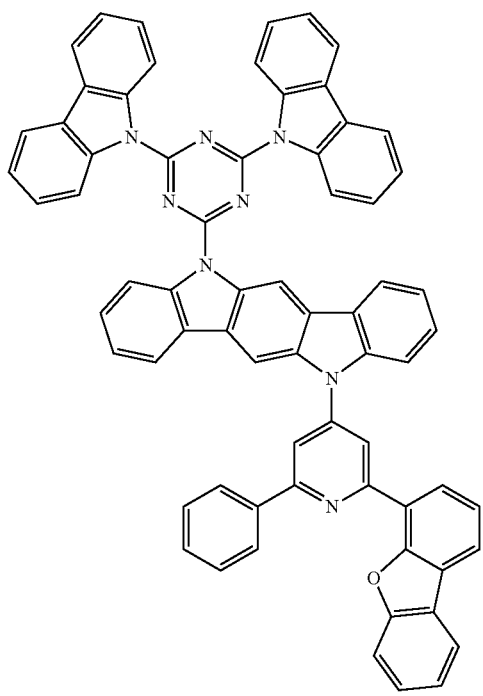
(K-7)
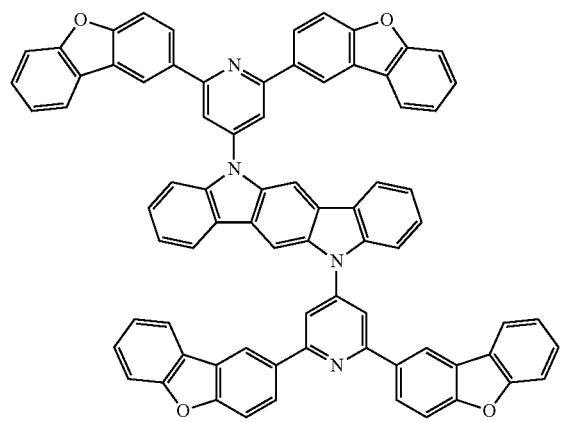
(K-8)
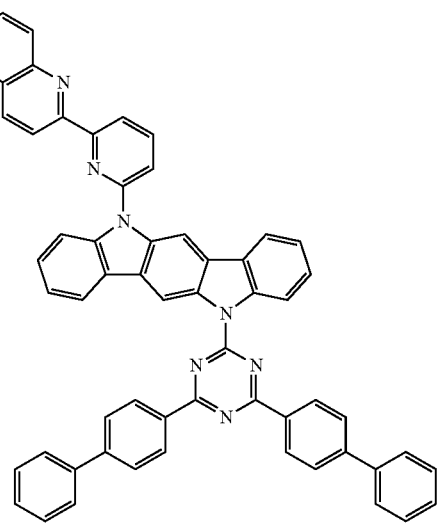

-continued
(K-9)
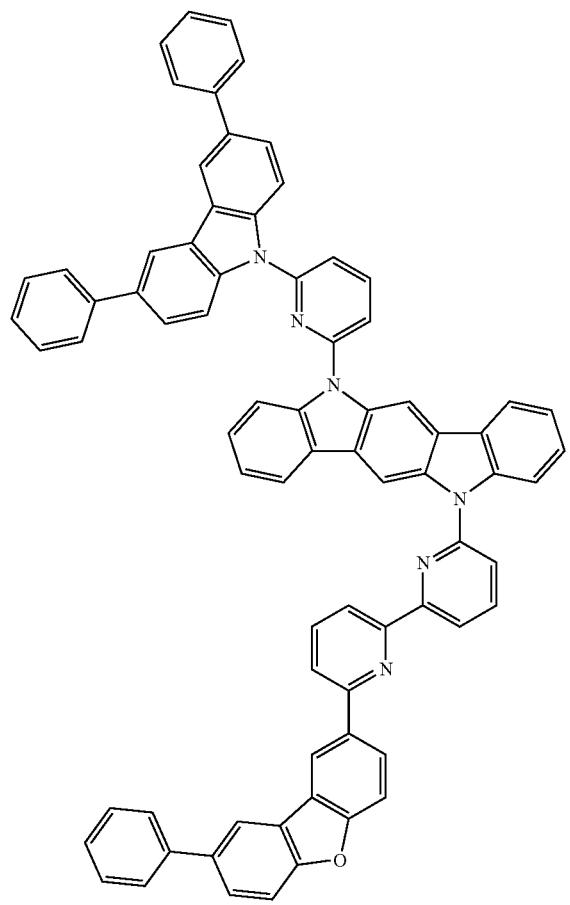
(K-10)
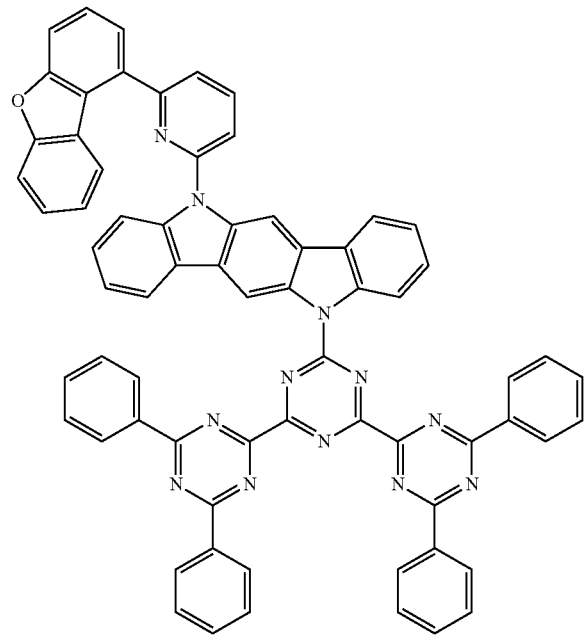
(K-11)
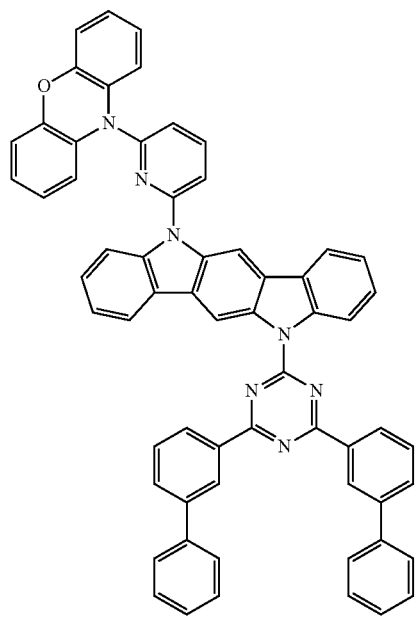
(K-12)
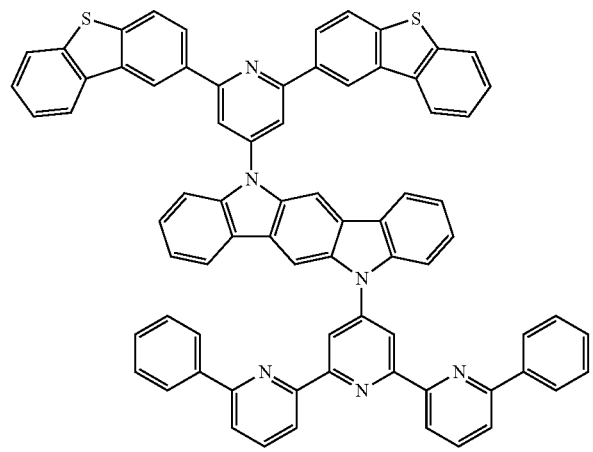

-continued
(K-13)
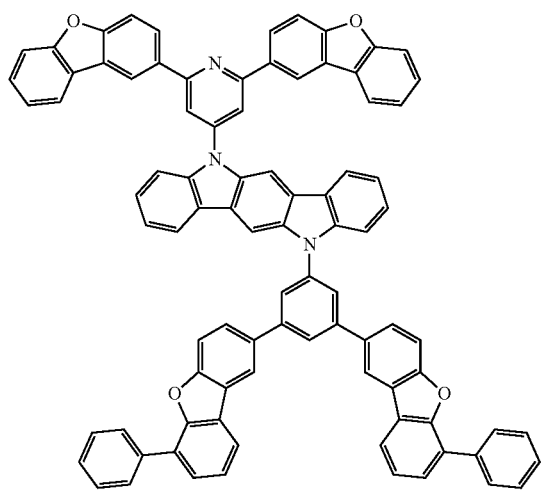
(K-14)
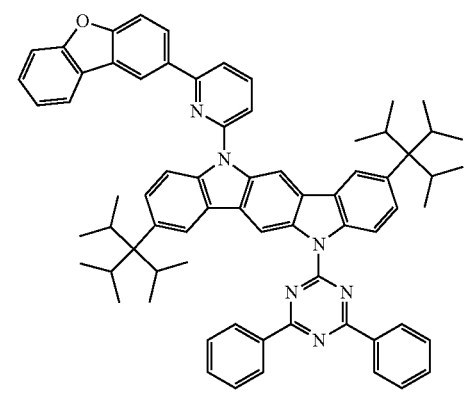
(K-15)
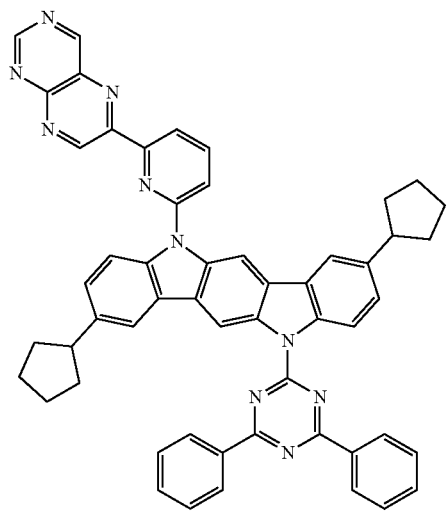
(K-16)
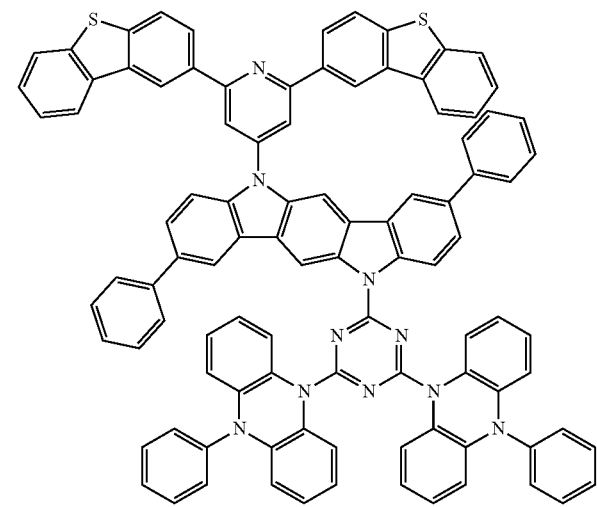
(K-17)
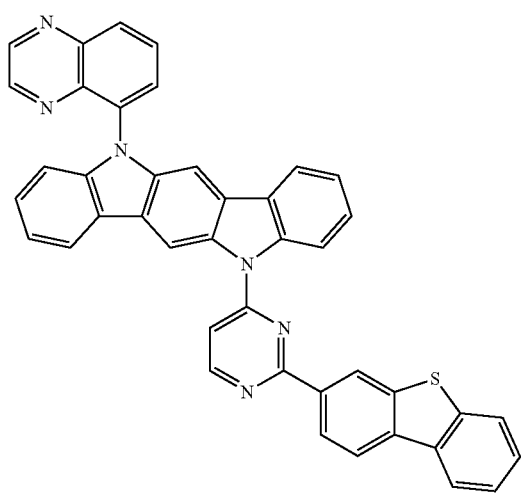
(K-18)
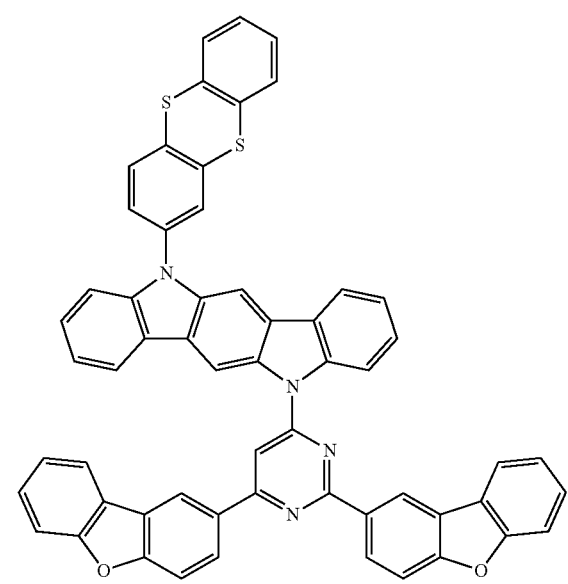

(K-19)
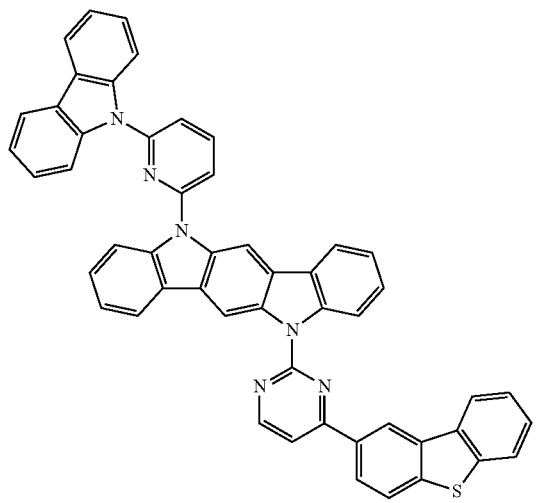
(K-20)
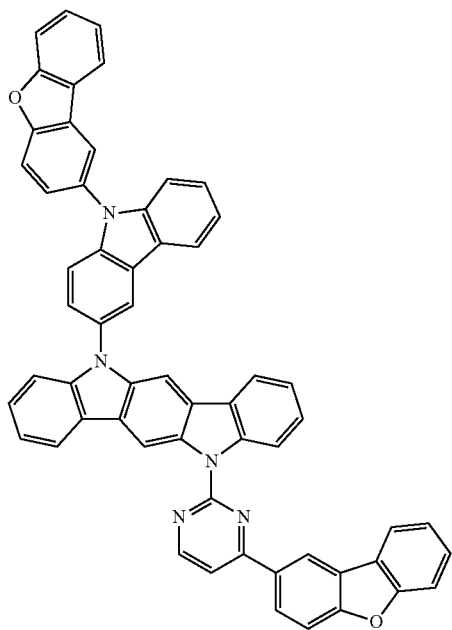
(K-21)
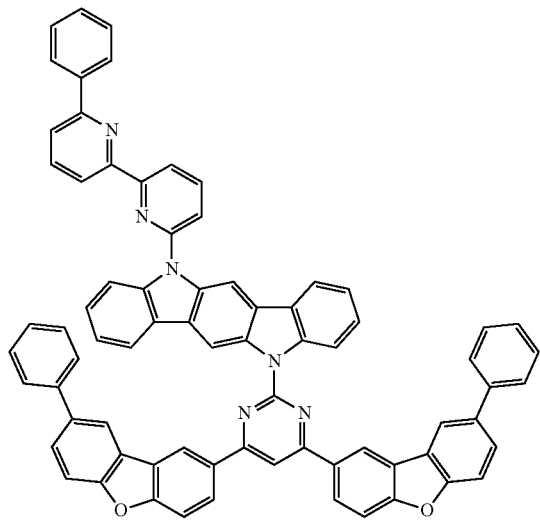
(K-22)
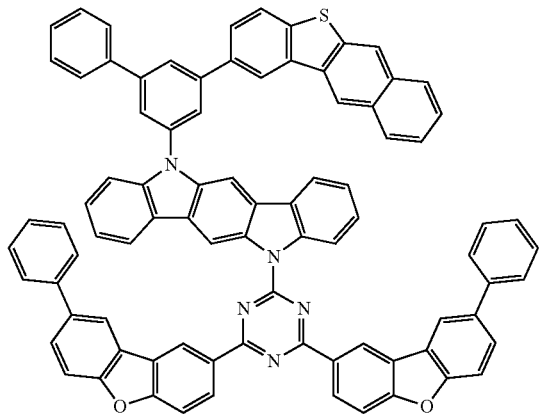

(K-23)
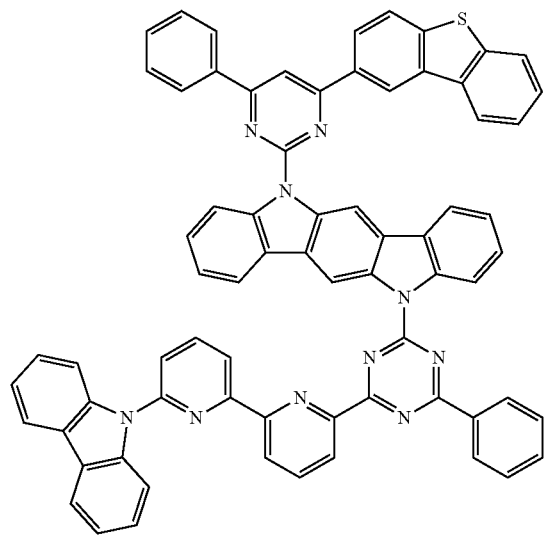
(K-24)
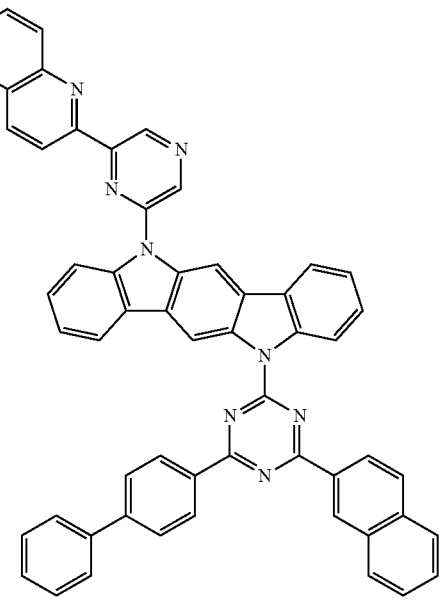
(K-25)
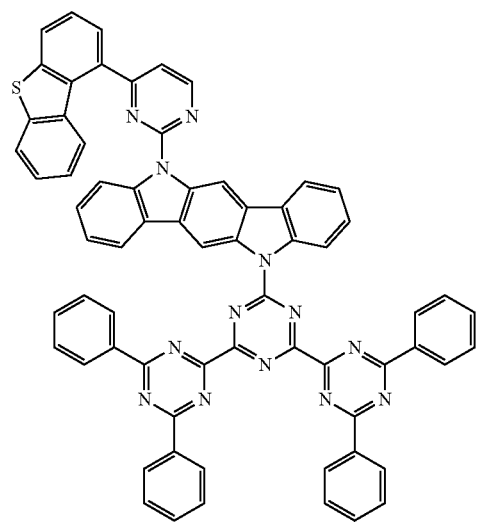
(K-26)
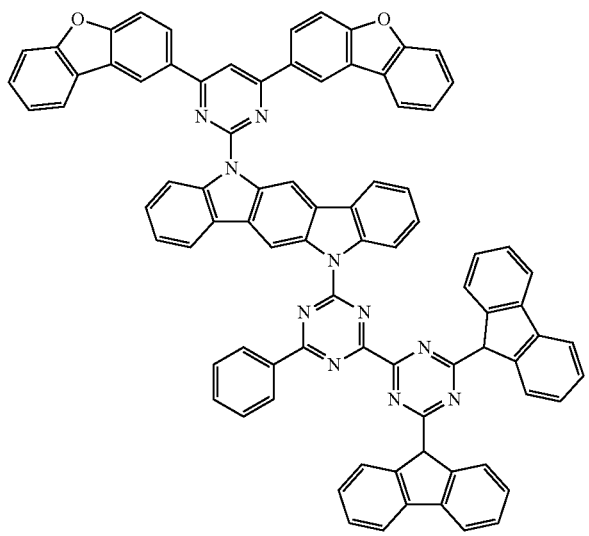

(K-27)
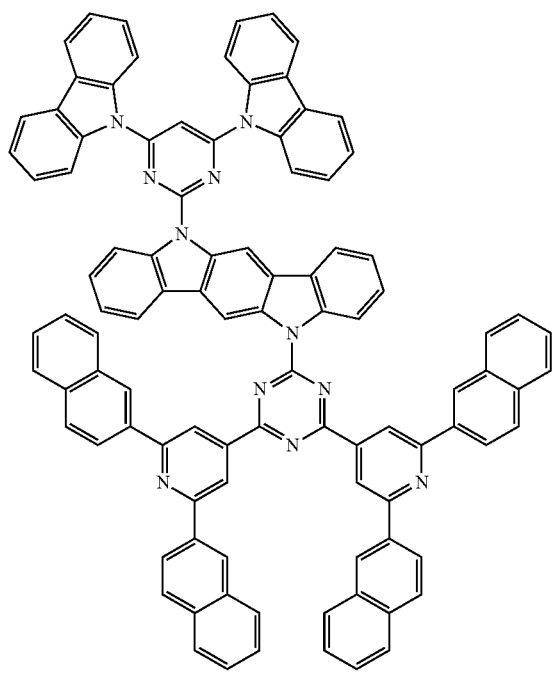
(K-28)
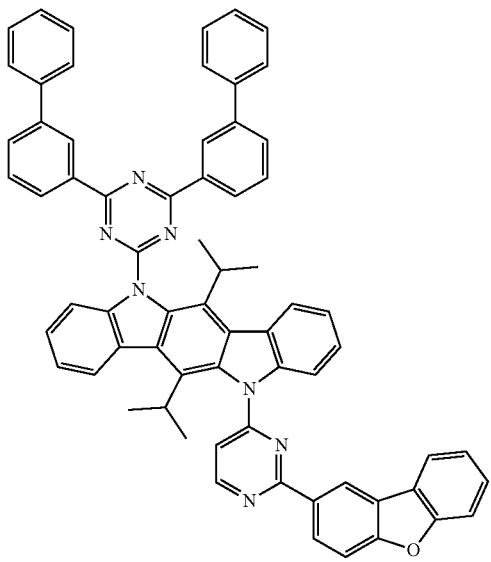
(K-29)
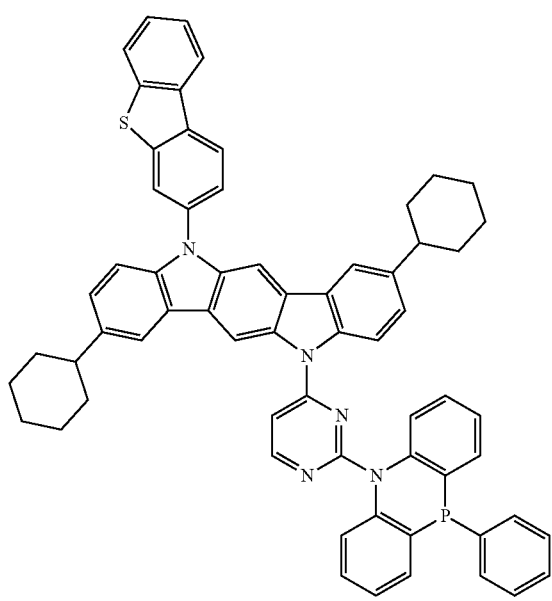

-continued
(K-30)
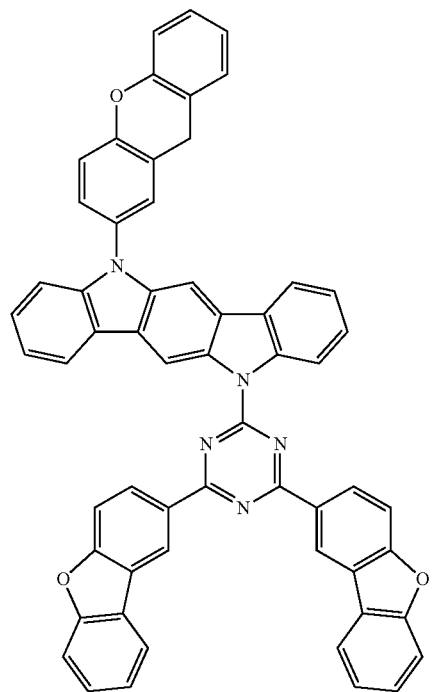
(K-31)
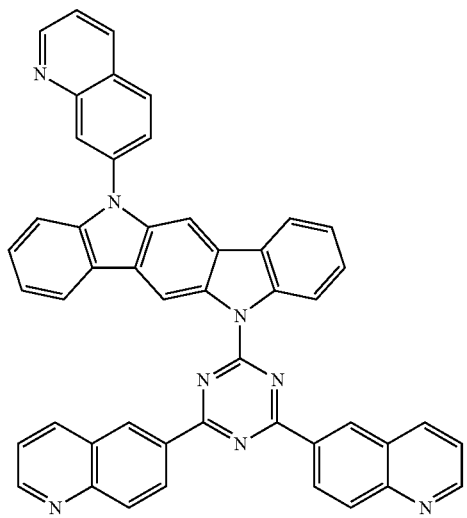
(K-32)
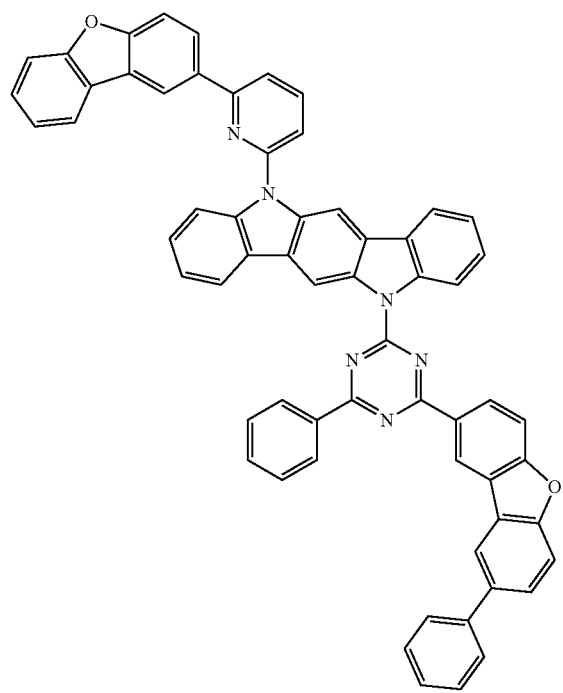
(K-33)
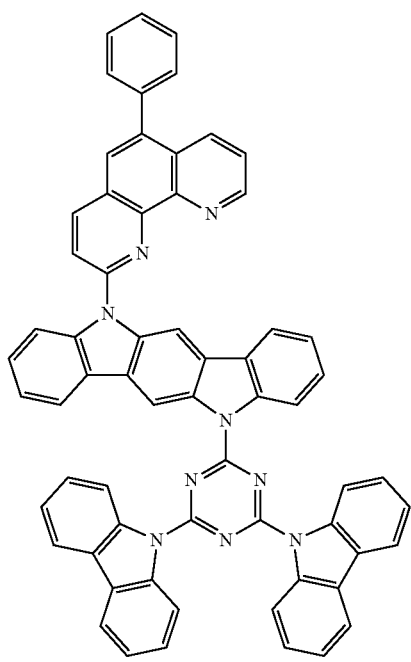

(K-34)
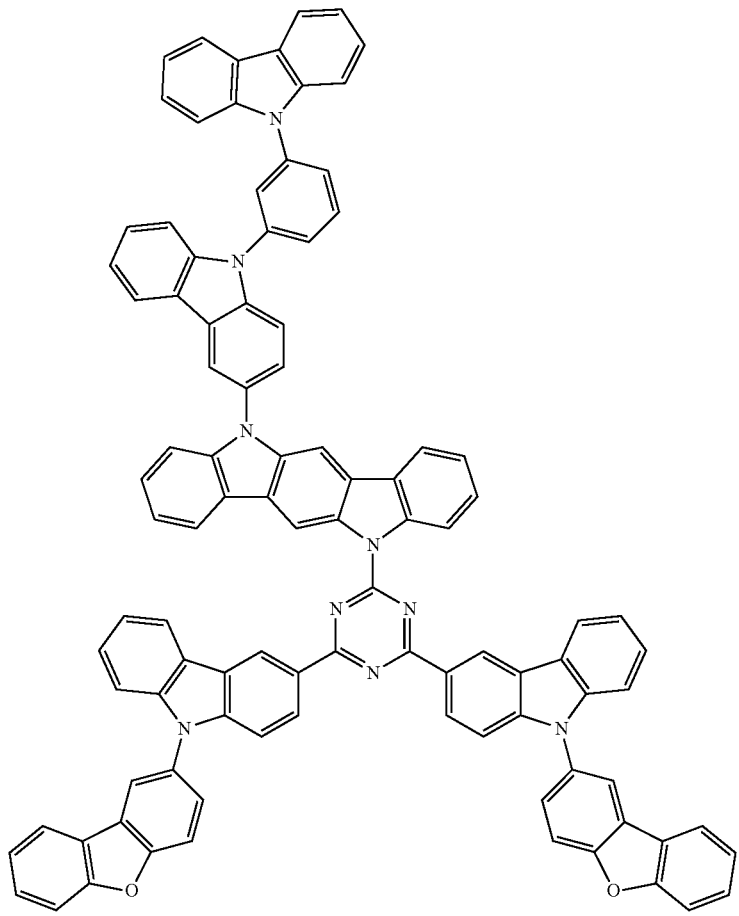
(K-35)
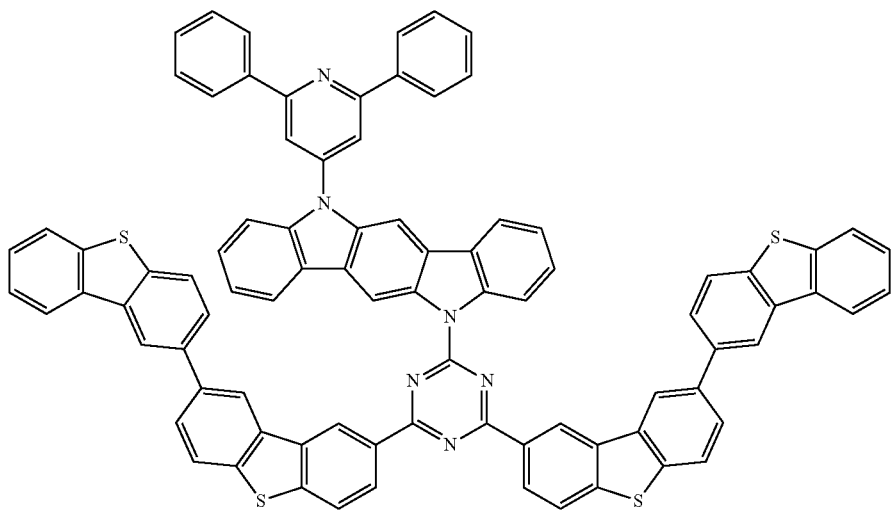

-continued
(K-36)
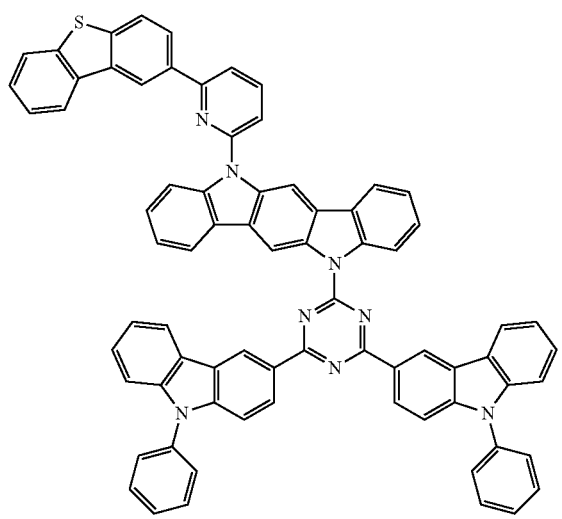
(K-37)
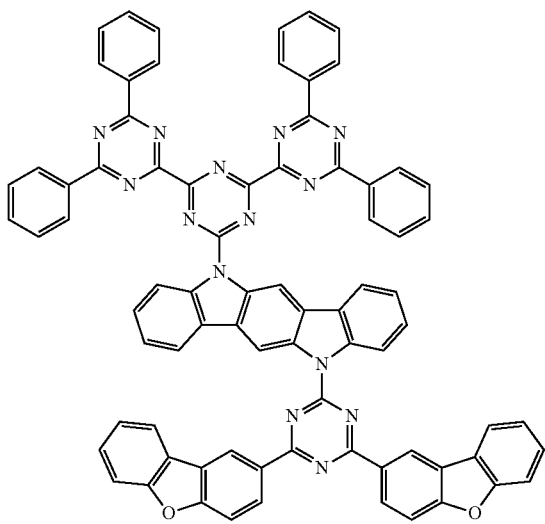
(K-38)
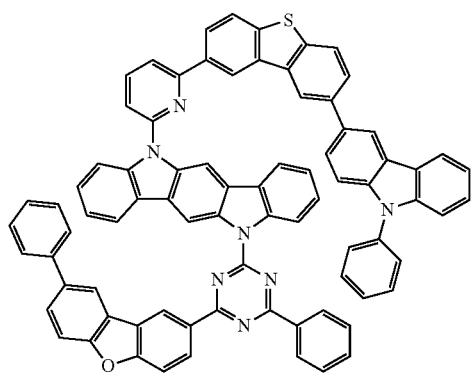
(K-39)
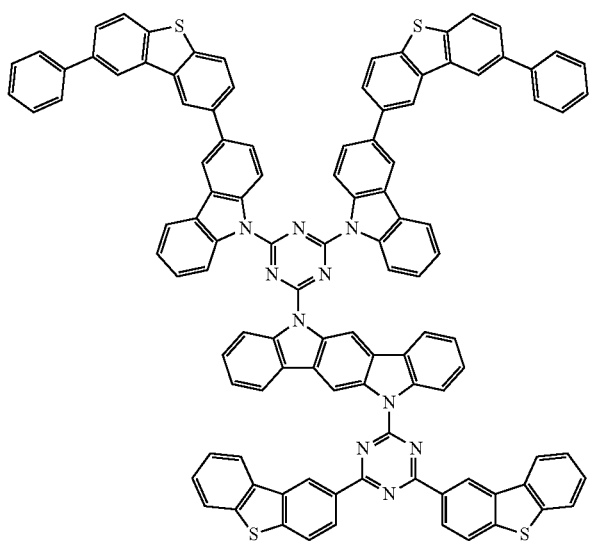

-continued
(K-40)
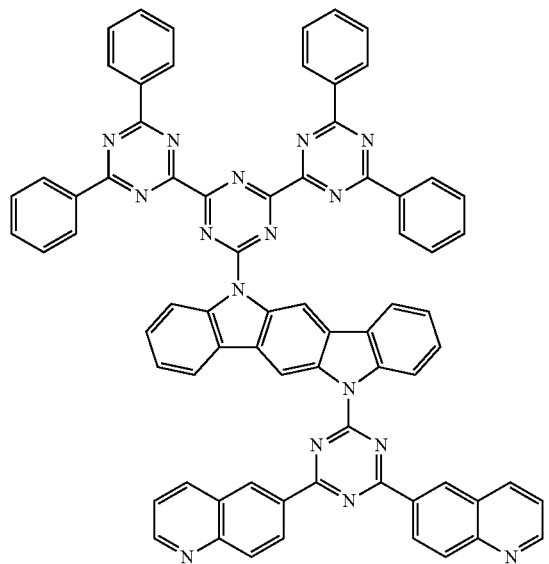
(K-41)
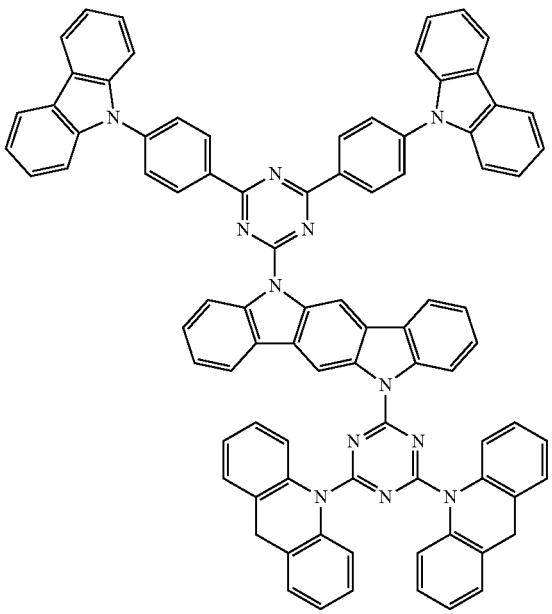
(K-42)
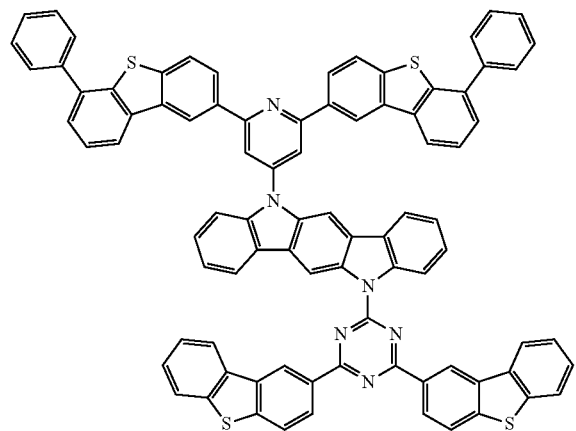
(K-43)
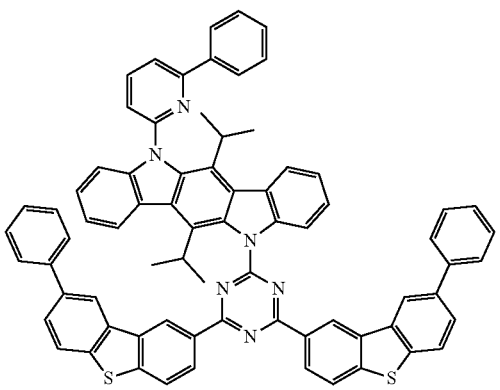
(K-44)
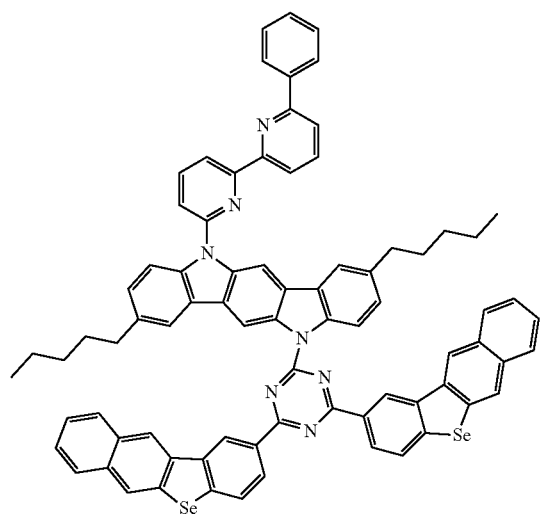
(K-45)
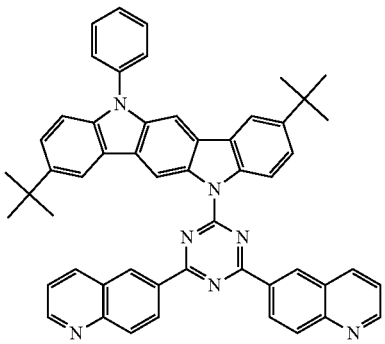

(K-46)

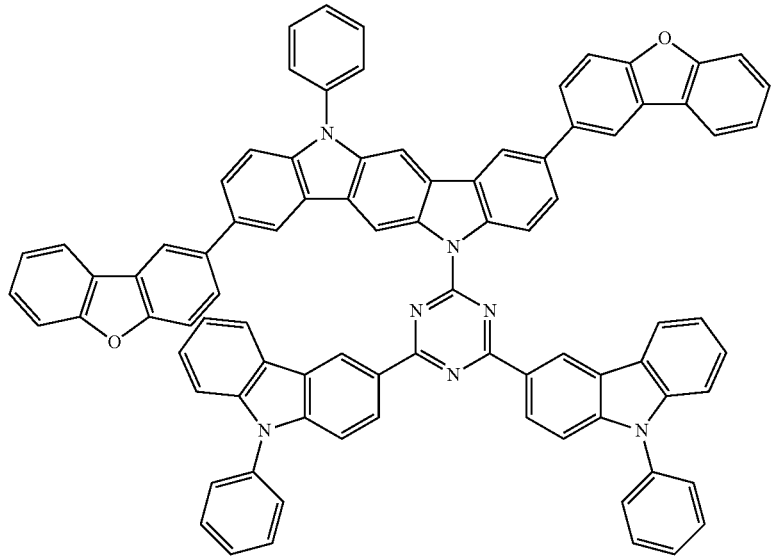

When the indolocarbazole compound represented by the general formula (1) is contained in at least one of a plurality of organic layers of an organic EL device formed by laminating an anode, the plurality of organic layers, and a cathode on a substrate, an excellent organic electroluminescent device is provided. A phosphorescent light-emitting layer, a hole-transporting layer, an electron-transporting layer, a hole-blocking layer, or an electron-blocking layer is suitable as the organic layer in which the indolocarbazole compound is contained. It is more preferred that the indolocarbazole compound be contained as a host material in a light-emitting layer containing a phosphorescent light-emitting dopant.

Next, the organic EL device of the present invention is described.

The organic EL device of the present invention has organic layers including at least one light-emitting layer between an anode and a cathode laminated on a substrate. In addition, at least one of the organic layers contains the indolocarbazole compound. The material for an organic electroluminescent device of the present invention is advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view illustrating a structure example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may have an exciton-blocking layer adjacent to the light-emitting layer, or may have an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention has the substrate, the anode, the light-emitting layer, and the cathode as its essential layers. The organic EL device of the present invention preferably has a hole-injecting/transporting layer and an electron-injecting/transporting layer in addition to the essential layers, and more preferably has a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure compared with FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated if necessary.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by using a method such as vapor deposition or sputtering and form a pattern having a desired shape thereon by photolithography. Alternatively, in the case of not requiring high pattern accuracy (about 100 µm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred $\Omega/\square$ or less. Further, the thickness of the resultant film is, depending on the material used, selected from usually the range of from 10 to 1,000 nm, preferably the range of from 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or sputtering. Further, the sheet resistance as the cathode is preferably several hundred $\Omega/\square$ or less, and the thickness of the resultant film is selected from usually the range of from 10 nm to 5 µm, preferably the range of from 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of from 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer is a phosphorescent light-emitting layer, and contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold. Specific examples thereof include, but not limited to, the compounds disclosed in the following patent publications.

For example, WO 2009/073245 A1, WO 2009/046266 A1, WO 2007/095118 A3, WO 2008/156879 A1, WO 2008/140657 A1, US 2008/261076 A1, JP 2008-542203 A, WO 2008/054584 A1, JP 2008-505925 A, JP 2007-522126 A, JP 2004-506305 A, JP 2006-513278 A, JP 2006-50596 A, WO 2006/046980 A1, WO 2005/113704 A3, US 2005/260449 A1, US 2005/2260448A1, US 2005/214576A1, WO 2005/076380 A3, US 2005/119485 A1, WO 2004/045001 A3, WO 2004/045000 A3, WO 2006/100888 A1, WO 2007/004380 A1, WO 2007/023659 A1, WO 2008/035664 A1, JP 2003-272861 A, JP 2004-111193 A, JP 2004-319438 A, JP 2007-2080 A, JP 2007-9009 A, JP 2007-227948 A, JP 2008-91906 A, JP 2008-311607 A, JP 2009-19121 A, JP 2009-46601 A, JP 2009-114369 A, JP 2003-253128 A, JP 2003-253129 A, JP 2003-253145 A, JP 2005-38847 A, JP 2005-82598 A, JP 2005-139185 A, JP 2005-187473 A, JP 2005-220136 A, JP 2006-63080 A, JP 2006-104201 A, JP 2006-111623 A, JP 2006-213720 A, JP 2006-290891 A, JP 2006-298899 A, JP 2006-298900 A, WO 2007/018067 A1, WO 2007/058080 A1, WO 2007/058104 A1, JP 2006-131561 A, JP 2008-239565 A, JP 2008-266163 A, JP 2009-57367 A, JP 2002-117978 A, JP 2003-123982 A, JP 2003-133074 A, JP 2006-93542 A, JP 2006-131524 A, JP 2006-261623 A, JP 2006-303383 A, JP 2006-303394 A, JP 2006-310479 A, JP 2007-88105 A, JP 2007-258550 A, JP 2007-324309 A, JP 2008-270737 A, JP 2009-96800 A, JP 2009-161524 A, WO 2008/050733 A1, JP 2003-73387 A, JP 2004-59433 A, JP 2004-155709 A, JP 2006-104132 A, JP 2008-37848 A, JP 2008-133212 A, JP 2009-57304 A, JP 2009-286716 A, JP 2010-83852 A, JP 2009-532546 A, JP 2009-536681 A, and JP 2009-542026 A.

Preferred examples of the phosphorescent light-emitting dopant include complexes such as Ir(ppy)3, complexes such as Ir(bt)2.acac3, and complexes such as PtOEt3, the complexes each having a noble metal element such as Ir as a central metal. Specific examples of those complexes are shown below, but the complexes are not limited to the compounds described below.

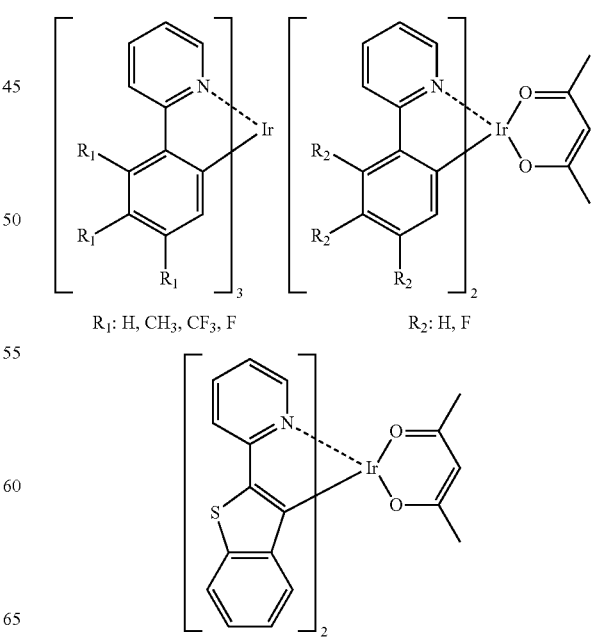

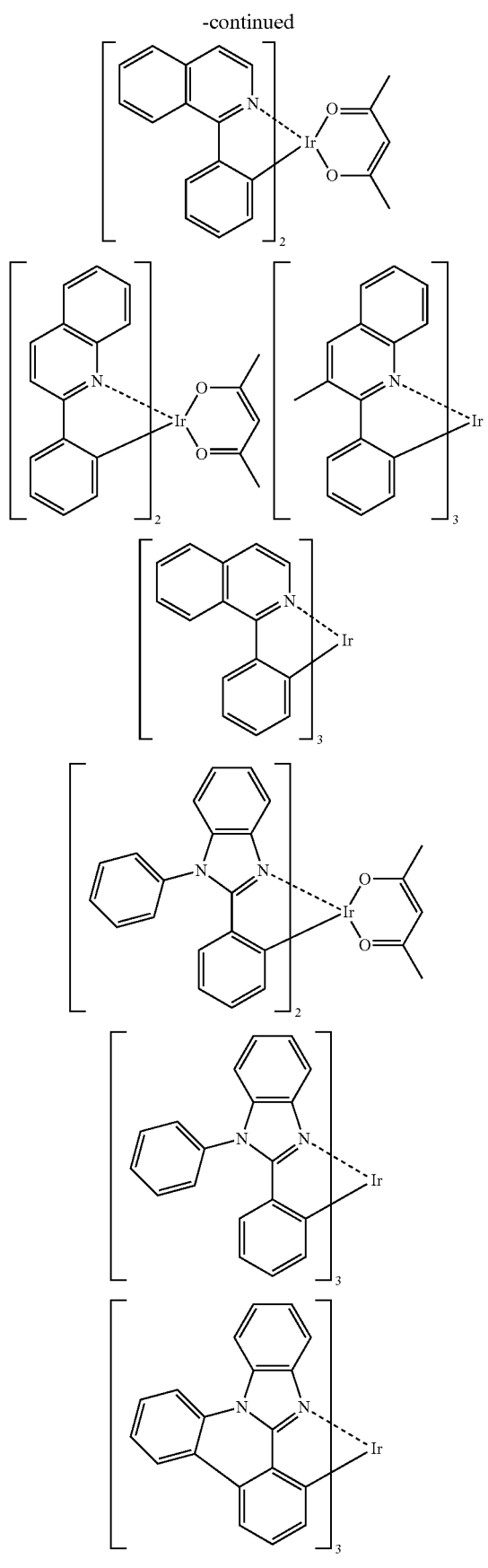

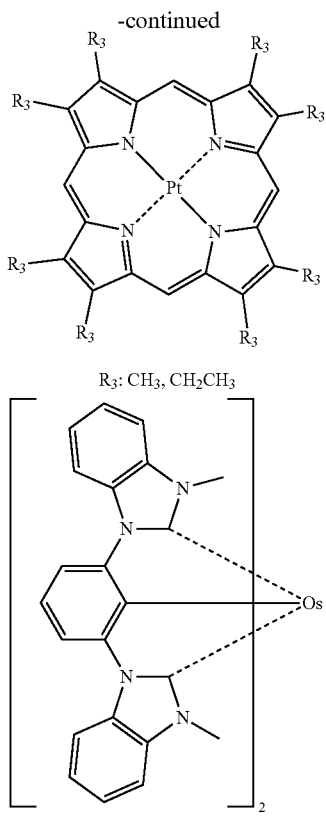

R3: CH3, CH2CH3

It is desirable that the content of the phosphorescent light-emitting dopant in the light-emitting layer be in the range of from 2 to 40 wt %, preferably from 5 to 30 wt %.

It is preferred to use, as a host material in the light-emitting layer, the indolocarbazole compound represented by the general formula (1). However, when the indolocarbazole compound is used in any of the organic layers other than the light-emitting layer, the material to be used in the light-emitting layer may be another host material other than the indolocarbazole compound, or the indolocarbazole compound and any other host material may be used in combination. Further, a plurality of kinds of known host materials may be used in combination.

It is preferred to use, as a usable known host compound, a compound that has a hole-transporting ability or an electron-transporting ability, is capable of preventing luminescence from having a longer wavelength, and has a high glass transition temperature.

Such other host materials are known because they are mentioned in many patent literatures and the like, and hence a suitable host material may be chosen from those in the patent literatures and the like. Specific examples of the host material include, but are not particularly limited to, an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly (N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer formed between an electrode and an organic layer for the purpose of lowering a driving voltage and improving light, emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use the indolocarbazole compound represented by the general formula (1) for the hole-blocking layer. However, when the indolocarbazole compound is used in any other organic layer, a known material for a hole-blocking layer may be used. Further, it is possible to use, as a material for the hole-blocking layer, any of the below-mentioned materials for the electron-transporting layer as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

Although the indolocarbazole compound represented by the general formula (1) according to the present invention can be used as a material for the electron-blocking layer, another material, i.e., any of the below-mentioned materials for the hole-transporting layer can be used as required. The thickness of the electron-blocking layer is preferably from 3 to 100 nm, more preferably from 5 to 30 nm.

—Exciton-Blocking Layer—

The exciton-blocking layer refers to a layer used for blocking excitons produced by the recombination of a hole and an electron in the light-emitting layer from diffusing into charge-transporting layers. Inserting this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

Although the indolocarbazole compound represented by the general formula (1) can be used as a material for the exciton-blocking layer, as other materials therefor, there are given, for example, 1,3-dicarbazolylbenzene (mCP) and bis(2-methyl-8-quinolinolato)-4-phenylphenolatoaluminum (III) (BAlq).

—Hole-Transporting Layer—

The hole-transporting layer is formed of a hole-transporting material having a function of transporting holes, and a single hole-transporting layer or a plurality of hole-transporting layers may be formed.

The hole-transporting material has hole-injecting property or hole-transporting property or has electron-blocking property, and any of an organic material and an inorganic material may be used as the hole-transporting material. Although it is preferred to use the indolocarbazole compound represented by the general formula (1) for the hole-transporting layer, any compound selected from conventionally known compounds may be used. Examples of the known hole-transporting material that may be used include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be formed.

An electron-transporting material (which also serves as a hole-blocking material in some cases) has only to have a function of transferring electrons injected from the cathode into the light-emitting layer. Although it is preferred to use the material represented by the general formula (1) according to the present invention for the electron-transporting layer, any compound selected from conventionally known compounds may be used. Examples thereof include a nitro-substituted fluorene derivative, a diphenylquinone derivative, a thiopyran dioxide derivative, a carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative that has a quinoxaline ring known as an electron withdrawing group. Further, it is also possible to use a polymer material in which any of those materials is introduced in a polymer chain or is used as a polymer main chain.

EXAMPLES

Hereinafter, the present invention is described in more detail by way of Examples. It should be appreciated that the present invention is not limited to Examples below and may be carried out in various forms as long as the various forms do not deviate from the gist of the present invention.

The routes described below were used to synthesize an indolocarbazole compound to be used as a material for a phosphorescent light-emitting device. It should be noted that the number of each compound corresponds to the number given to the exemplified compound.

Synthesis Example 1

Synthesis of (Compound A-81)

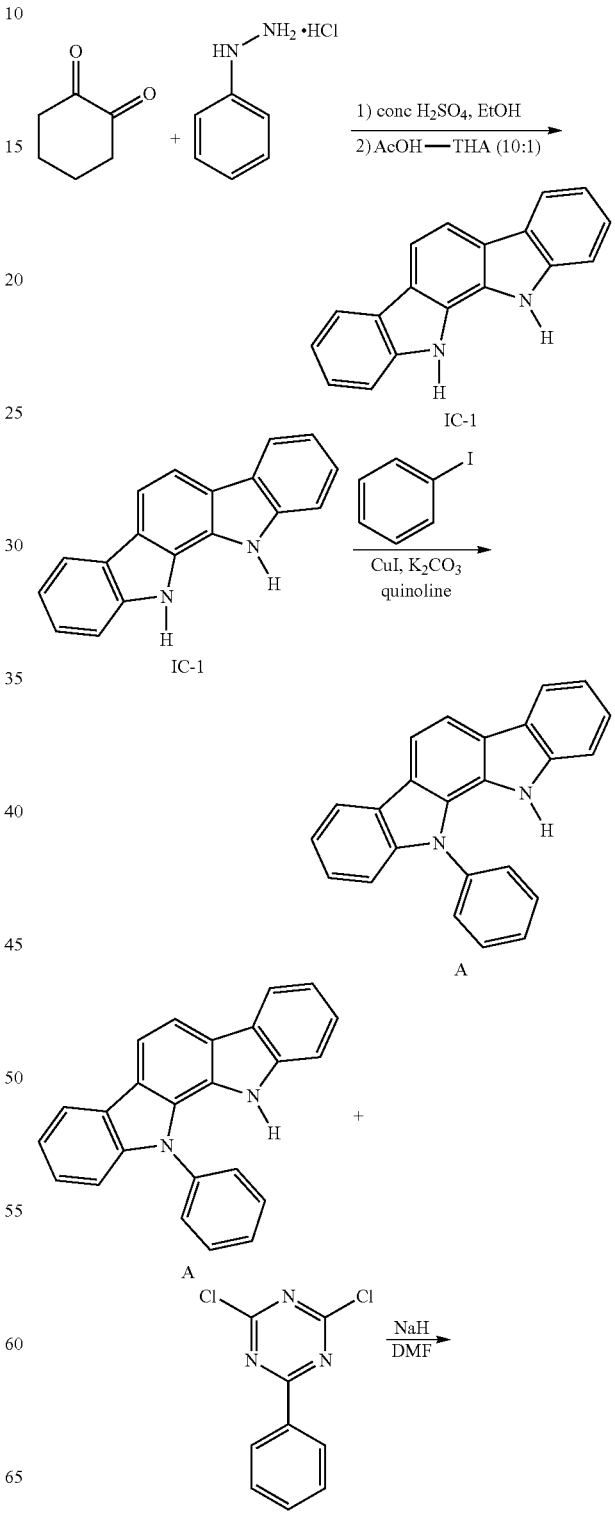

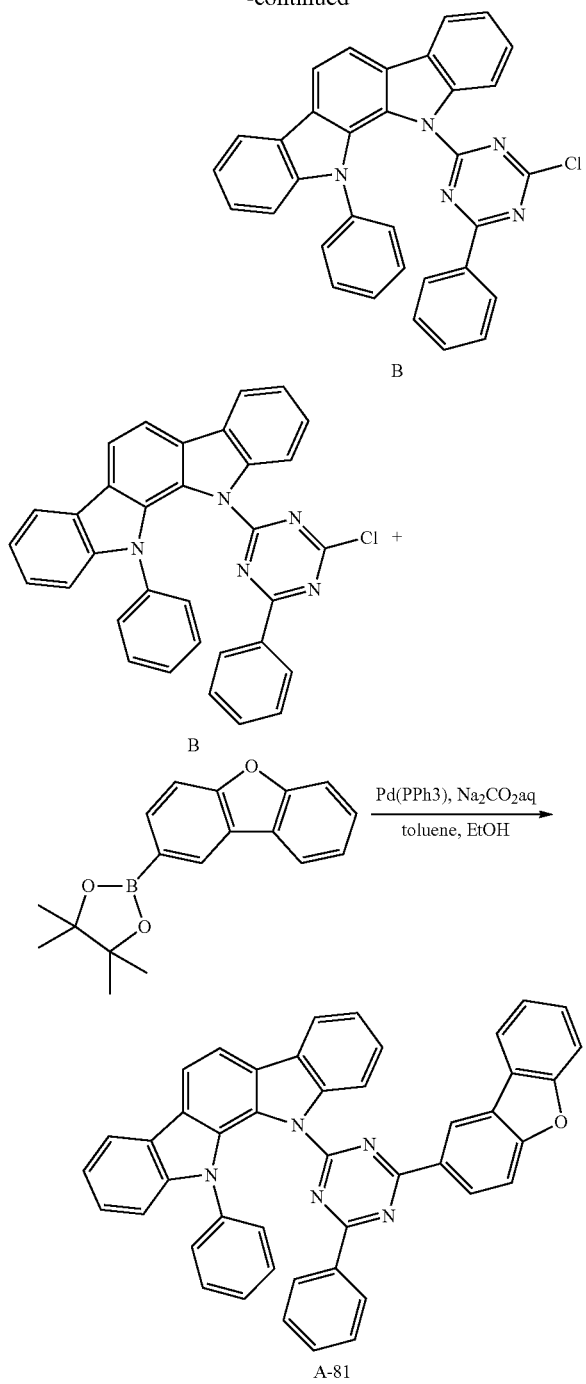

Under a nitrogen atmosphere, 3.0 g (0.031 mol) of concentrated sulfuric acid were dropped over 5 min while 33.3 g (0.30 mol) of 1,2-cyclohexanedione, 86.0 g (0.60 mol) of phenylhydrazine hydrochloride, and 1,000 ml of ethanol were stirred at room temperature. After that, the mixture was stirred for 4 hr while being heated at 65° C. After the reaction solution had been cooled to room temperature, the precipitated crystal was taken by filtration and washed with ethanol (2×500 ml) to provide 80.0 g of a purplish brown crystal. 72.0 g (0.28 mol) of the crystal, 72.0 g of trifluoroacetic acid, and 720.0 g of acetic acid were stirred for 15 hr while being heated at 100° C. After the reaction solution had been cooled to room temperature, the precipitated crystal was taken by filtration and washed with acetic acid (200 ml). The washed product was subjected to re-slurry purification to provide 30.0 g (0.12 mol, yield: 40%) of 11,12-dihydroindolo[2,3-a]carbazole (IC-1) as a white crystal.

Next, 26.0 g (0.10 mol) of the white powder obtained in the foregoing, 122.7 g (0.60 mol) of iodobenzene, 54.7 g (0.29 mol) of copper iodide, 66.7 g (0.48 mol) of potassium carbonate, and 800 ml of quinoline were loaded into a 1,000-ml three-necked flask purged with nitrogen and stirred. After that, the mixture was heated to 190° C. and stirred for 72 hr. Once the mixture was cooled to room temperature, and then 500 ml of water and 500 ml of dichloromethane were added to the mixture, followed by stirring. After that, the resultant yellow crystal was taken by filtration. The filtrate was transferred to a 2,000-ml separating funnel, and was fractionated into an organic layer and an aqueous layer. The organic layer was washed with 500 ml of water three times, and then the resultant organic layer was dried with magnesium sulfate. Once magnesium sulfate was separated by filtration and then the solvent was distilled off under reduced pressure. After that, the residue was purified by column chromatography to provide 13.7 g (0.041 mol, yield: 40.6%) of Intermediate A as a white solid.

Under a nitrogen atmosphere, 8.46 g (0.21 mol) of 60% sodium hydride and 150 ml of dry N,N-dimethylformamide were loaded and stirred. Next, a solution prepared by dissolving 50.0 g (0.15 mol) of Intermediate A in 150 ml of dry N,N-dimethylformamide was dropped to the mixture. After that, the mixture was continuously stirred for 1 hr. Next, the reaction solution was cooled to −40° C., a solution prepared by dissolving 37.4 g (0.17 mol) of 2,4-dichloro-6-phenyl-1,3,5-triazine in 200 ml of dry N,N-dimethylformamide was dropped to the reaction solution, and the mixture was continuously stirred at room temperature for 5 hr. Next, 1,000 ml of distilled water and 200 ml of methanol were charged into the flask, and the mixture was stirred at room temperature for 1 hr. After that, the precipitated yellow solid was taken by filtration. The yellow solid taken by filtration was dissolved in dichloromethane and washed with distilled water (100 ml×twice), followed by drying with anhydrous magnesium sulfate. After magnesium sulfate had been separated by filtration, the solvent was distilled off under reduced pressure. After that, the resultant solid was subjected to re-slurry purification with 600 ml of methanol and dried to provide 67.2 g (0.13 mol, yield: 61%) of Intermediate B.

Figure 2:
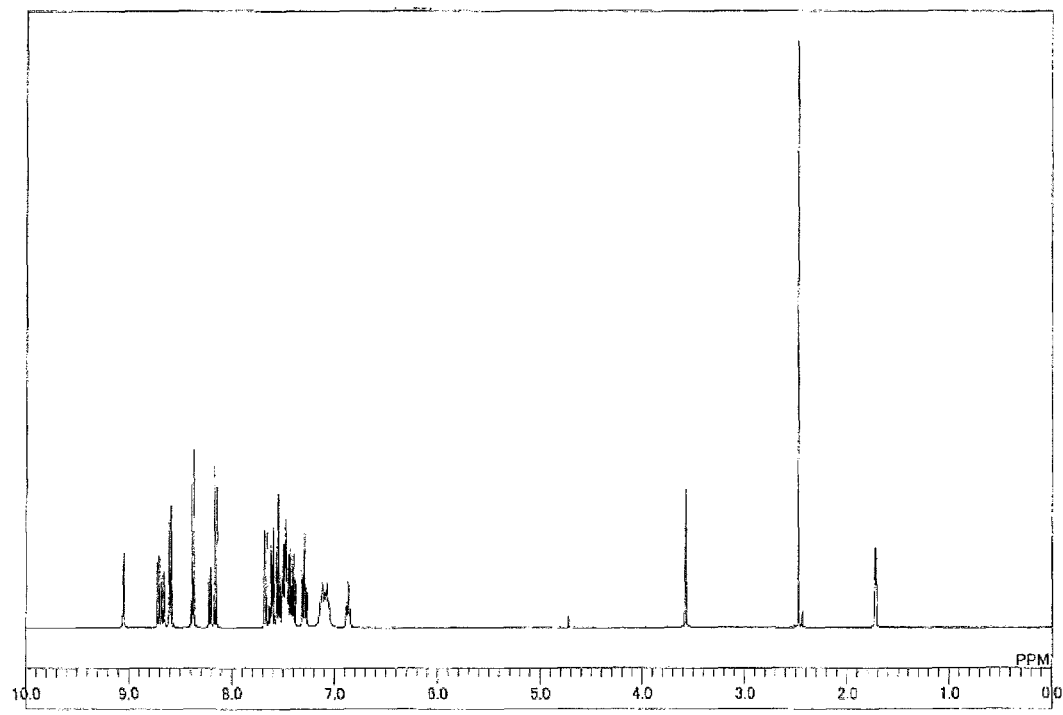
FIG. 2 shows the $^1$H-NMR chart of Indolocarbazole Compound (A-81).

Under a nitrogen atmosphere, 30.0 g (0.057 mol) of Intermediate B, 18.6 g (0.063 mol) of 2-(4,4,5,5-tetramethyl-1,3,2-dioxaborolan-2-yl)dibenzofuran, 0.73 g (0.00063 mol) of tetrakis(triphenylphosphine)palladium(0), 300 ml of toluene, and 150 ml of ethanol were loaded and stirred at room temperature. After that, a solution prepared by dissolving 53.4 g (0.50 mol) of sodium carbonate in 300 ml of distilled water was added to the mixture and the whole was refluxed for 14 hr. After the reaction solution had been cooled to room temperature, an organic layer was washed with distilled water (2×150 ml) and the organic layer was dried with anhydrous magnesium sulfate. After that, magnesium sulfate was separated by filtration and the solvent was distilled off under reduced pressure. The resultant solid was dissolved in tetrahydrofuran, activated carbon and Fuller's earth were added to the solution, and the mixture was stirred at room temperature for 1 hr. After the activated carbon and Fuller's earth had been separated by filtration, the solvent was distilled off under reduced pressure, and the resultant residue was subjected to silica gel column chromatography purification and re-slurry purification to provide 26.5 g (0.041 mol, yield: 71%) of Compound (A-81) as a white solid.
The APCI-TOFMS of the compound showed an [M+H]+ peak at an m/z of 654. FIG. 2 shows the results of its 1H-NMR measurement (measurement solvent: THF-d8).
Synthesis Example 2
Synthesis of (Compound C-90)
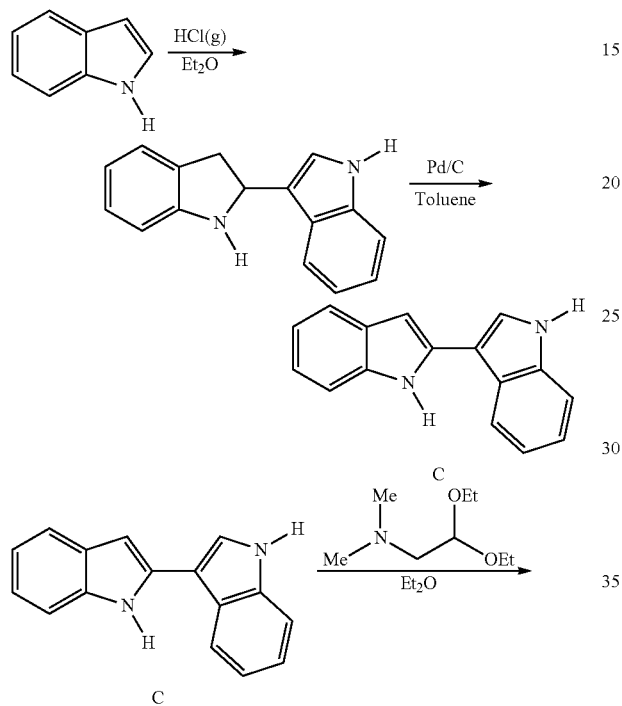
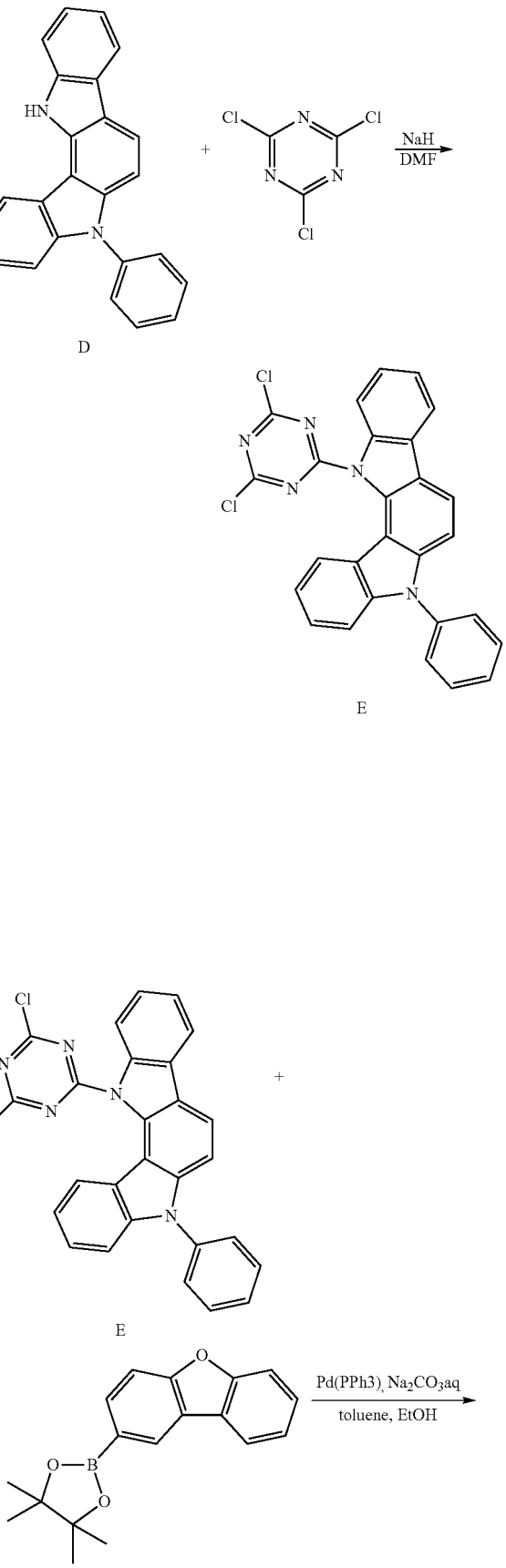

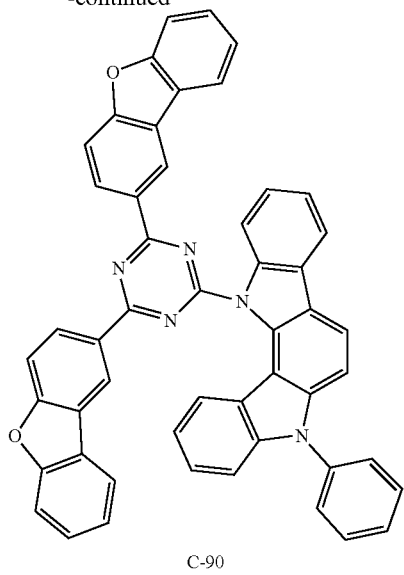

C-90

Under a nitrogen atmosphere, a hydrogen chloride gas generated by dropping 112.0 g (1.10 mol) of concentrated hydrochloric acid to 211.7 g (2.16 mol) of concentrated sulfuric acid over 1 hr was blown into a solution of 20.0 g (0.17 mol) of indole in 300 ml of dry diethyl ether while the solution was stirred at room temperature. After the reaction solution had been stirred at room temperature for 15 hr, 121.0 g of ethyl acetate and 303.2 g of a saturated aqueous solution of sodium hydrogen carbonate were added to the solution. After an aqueous layer had been extracted with ethyl acetate (2×100 ml), an organic layer was washed with a saturated aqueous solution of sodium hydrogen carbonate (100 ml) and distilled water (2×100 ml). After the organic layer had been dried with anhydrous magnesium sulfate, magnesium sulfate was separated by filtration and the solvent was distilled off under reduced pressure. The resultant residue was dissolved in 150 ml of toluene and 2.5 g of palladium/activated carbon were added to the solution. After that, the mixture was stirred for 3 hr while being refluxed under heat at 111° C. After the reaction solution had been cooled to room temperature, the palladium/activated carbon was separated by filtration and the solvent was distilled off under reduced pressure. The residue was purified by recrystallization to provide 14.7 g (0.063 mol, yield: 37%) of Intermediate C as a white crystal.

Under a nitrogen atmosphere, 14.1 g (0.061 mol) of Intermediate C, 11.4 g (0.071 mol) of N,N'-dimethylaminoacetaldehyde diethyl acetal, and 110.0 g of acetic acid were stirred for 8 hr while being refluxed under heat at 118° C. After the reaction solution had been cooled to room temperature, the precipitated crystal was taken by filtration and washed with acetic acid (30 ml). The resultant crystal was subjected to re-slurry purification to provide 10.4 g (0.041 mol, yield: 67%) of 5,12-dihydroindolo[3,2-a]carbazole (IC-5) as a white crystal.

Under a nitrogen atmosphere, 10.0 g (0.039 mol) of (IC-5), 39.8 g (0.20 mol) of iodobenzene, 6.2 g (0.098 mol) of copper, 8.1 g (0.059 mol) of potassium carbonate, and 200 ml of tetraglyme were loaded and stirred. After that, the mixture was heated to 190° C. and stirred for 24 hr. After the reaction solution had been cooled to room temperature, copper and inorganic matter were separated by filtration. 200 ml of distilled water were added to the filtrate, the mixture was stirred, and the precipitated crystal was separated by filtration. The crystal was dried under reduced pressure and then purified by column chromatography to provide 9.7 g (0.029 mol, yield: 75.0%) of Intermediate D as white powder.

Under a nitrogen atmosphere, 1.3 g (0.033 mol) of 60% sodium hydride and 50 ml of dry N,N-dimethylformamide were loaded and stirred. Next, a solution prepared by dissolving 10.0 g (0.030 mol) of Intermediate D in 100 ml of dry N,N-dimethylformamide was dropped to the mixture. After that, the mixture was continuously stirred for 30 min. Next, a solution prepared by dissolving 5.5 g (0.030 mol) of 2,4,6-trichloro-1,3,5-triazine in 50 ml of dry N,N-dimethylformamide was dropped to the mixture under −60° C., and the whole was stirred at −60° C. for 1 hr and then at room temperature for 1 hr. Next, 500 ml of distilled water were charged into the flask and the mixture was stirred at room temperature for 1 hr. After that, the precipitated solid was taken by filtration. The solid taken by filtration was dissolved in toluene and washed with distilled water (100 ml×twice), followed by drying with anhydrous magnesium sulfate. After magnesium sulfate had been separated by filtration, the solvent was distilled off under reduced pressure. After that, the resultant solid was purified by column chromatography to provide 10.0 g (0.010 mol, yield: 35%) of Intermediate E in a state of containing 50% of Intermediate D.

Under a nitrogen atmosphere, 5.0 g (0.010 mol) of Intermediate E, 7.35 g (0.025 mol) of 2-(4,4,5,5-tetramethyl-1,3,2-dioxaborolan-2-yl)dibenzofuran, 0.58 g (0.00050 mol) of tetrakis(triphenylphosphine)palladium(0), 100 ml of toluene, and 50 ml of ethanol were loaded and stirred at room temperature. After that, a solution prepared by dissolving 21.2 g (0.20 mol) of sodium carbonate in 100 ml of distilled water was added to the mixture and the whole was stirred at 90° C. for 3 hr. After the reaction solution had been cooled to room temperature, the resultant solid was subjected to silica gel column chromatography purification and re-slurry purification to provide 1.3 g (0.0017 mol, yield: 17%) of Compound (C-90) as a white solid.

Figure 3:
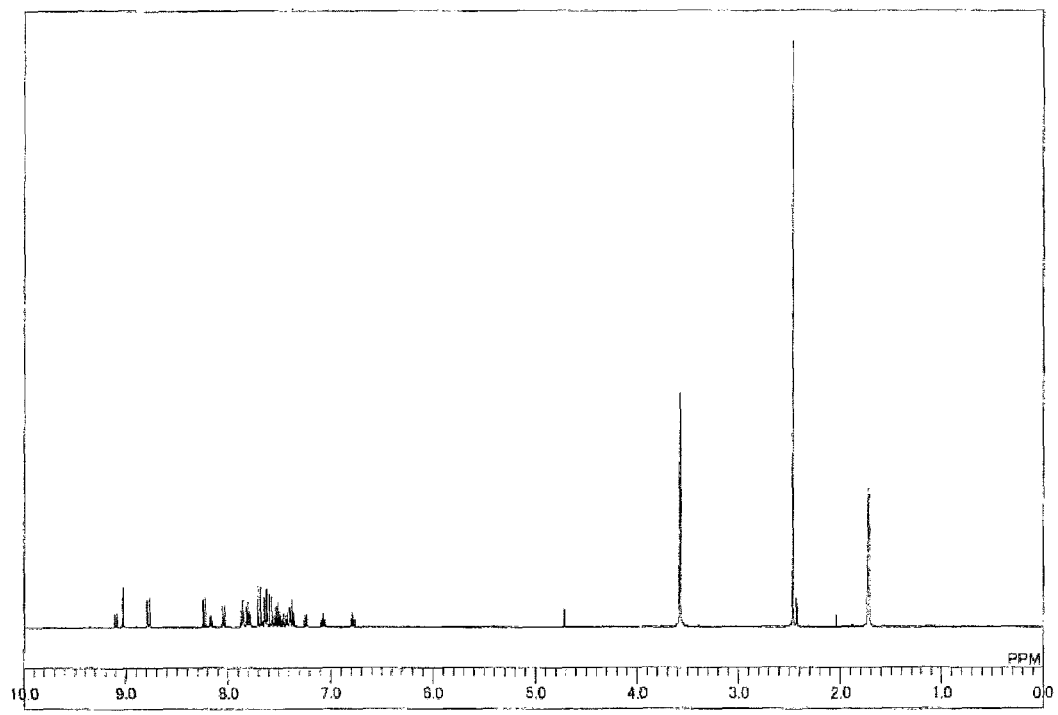
FIG. 3 shows the $^1$H-NMR chart of Indolocarbazole Compound (C-90).

The APCI-TOFMS of the compound showed an [M+H]+ peak at an m/z of 744. FIG. 3 shows the results of its 1H-NMR measurement (measurement solvent: THF-d8).

Example 1

Each thin film was laminated by a vacuum deposition method at a degree of vacuum of $4.0 \times 10^{-5}$ Pa on a glass substrate on which an anode formed of an ITO substrate having a thickness of 110 nm had been formed. First, copper phthalocyanine (CuPC) was formed into a layer having a thickness of 25 nm on the ITO. Next, 4,4'-bis[N-(1-naphthyl)-N-phenylamino]biphenyl (NPB) was formed into a layer having a thickness of 40 nm to serve as a hole-transporting layer. Next, Compound (A-81) as a host material and tris(2-phenylpyridine)iridium(III) (Ir(ppy)$_3$) as a phosphorescent light-emitting dopant were co-deposited from different deposition sources onto the hole-transporting layer to form a light-emitting layer having a thickness of 40 nm. The concentration of Ir(ppy)$_3$ in the light-emitting layer was 10.0 wt %. Next, tris(8-hydroxyquinolinato)aluminum (III) (Alq3) was formed into a layer having a thickness of 20 nm to serve as an electron-transporting layer. Further, lithium fluoride (LiF) was formed into a layer having a thickness of 1.0 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

An external power source was connected to the resultant organic EL device to apply a DC voltage to the device. As a result, it was confirmed that the device had such light-emitting characteristics as shown in Table 1. The columns "luminance", "voltage", and "luminous efficiency" in Table 1 show values at 20 mA/cm². It was found that the local maximum wavelength of the emission spectrum of the device was 520 nm and hence light emission from Ir(ppy)$_3$ was obtained.

Examples 2 to 17

Compounds A-24, B-17, B-46, C-40, C-113, D-92, E-64, F-15, G-8, H-11, H-38, J-37, K-35, K-37, and K-45 were synthesized in the same manner as in Synthesis Example 1 and Synthesis Example 2. Organic EL devices were each produced in the same manner as in Example 1 except that Compounds A-24, B-17, B-46, C-40, C-90, C-113, D-92, E-64, F-15, G-8, H-11, H-38, J-37, K-35, K-37, and K-45 were each used instead of Compound A-81 as the host material for the light-emitting layer of Example 1. It was found that the local maximum wavelength of the emission spectrum of each of the devices was 520 nm, and hence light emission from Ir(ppy)$_3$ was obtained. Table 1 shows the respective light-emitting characteristics.

Example 18 (Comparative)

An organic EL device was produced in the same manner as in Example 1 except that CBP was used as the host material for the light-emitting layer.

Example 19 (Comparative)

An organic EL device was produced in the same manner as in Example 1 except that the following compound Ho-1 was used as the host material for the light-emitting layer.

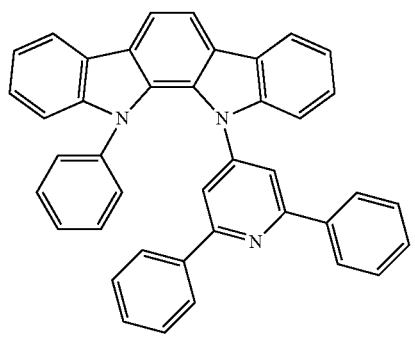

(Ho-1)

Example 20 (Comparative)

An organic EL device was produced in the same manner as in Example 1 except that the following compound Ho-2 was used as the host material for the light-emitting layer.

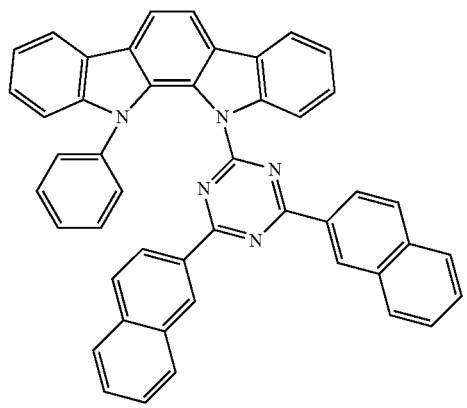

(Ho-2)

It was found that the local maximum wavelength of the emission spectrum of each of the organic EL devices produced in Examples 18 to 20 was 520 nm, and hence light emission from Ir(ppy)$_3$ was obtained. Table 1 shows a compound used as a host material and the total of $X_1$ to $X_4$ in the formula (1b) of the compound as an X number. Table 1 shows the respective light-emitting characteristics at 20 mA/cm². The X number is the total number of $X_1$ to $X_4$.

TABLE 1

| | Compound (X number) | Luminance (cd/m²) | Voltage (V) | Visual luminous efficiency (lm/W) |
|---|---|---|---|---|
| Ex. 1 | A-81 (1) | 5,680 | 6.7 | 13.3 |
| Ex. 2 | A-24 (4) | 5,880 | 6.5 | 14.2 |
| Ex. 3 | B-17 (5) | 5,850 | 6.7 | 13.7 |
| Ex. 4 | B-46 (5) | 5,835 | 6.5 | 14.1 |
| Ex. 5 | C-40 (5) | 5,870 | 6.4 | 14.4 |
| Ex. 6 | C-90 (1) | 5,830 | 6.9 | 13.3 |
| Ex. 7 | C-113 (4) | 5,860 | 6.5 | 14.2 |
| Ex. 8 | D-92 (7) | 5,870 | 6.6 | 14.0 |
| Ex. 9 | E-64 (3) | 5,760 | 6.9 | 13.1 |
| Ex. 10 | F-15 (5) | 5,845 | 6.5 | 14.1 |
| Ex. 11 | G-8 (3) | 5,580 | 7.0 | 12.5 |
| Ex. 12 | H-11 (7) | 5,790 | 6.4 | 14.2 |
| Ex. 13 | H-38 (4) | 5,800 | 6.5 | 14.0 |
| Ex. 14 | J-37 (1) | 5,675 | 6.8 | 13.1 |
| Ex. 15 | K-35 (3) | 5,720 | 6.8 | 13.2 |
| Ex. 16 | K-37 (7) | 5,865 | 6.5 | 14.2 |
| Ex. 17 | K-45 (1) | 5,590 | 6.8 | 12.9 |
| Ex. 18 | CBP | 4,860 | 9.3 | 8.2 |
| Ex. 19 | Ho-1 | 4,713 | 7.4 | 10.0 |
| Ex. 20 | Ho-2 | 3,980 | 5.9 | 10.6 |

It is found from Table 1 that the organic EL device using the indolocarbazole compound represented by the general formula (1) shows good light-emitting characteristics as compared with the case where CBP generally known as a phosphorescent host is used. It is also found that the device shows good light-emitting characteristics as compared with those in the case where any one of Ho-1 and Ho-2 as compounds each having a nitrogen-containing six-membered ring on the N of indolocarbazole and having a substituent that is not a fused heterocyclic group at an end of the ring is used. The superiority of the organic EL device using the indolocarbazole compound is apparent from the foregoing.

INDUSTRIAL APPLICABILITY

The indolocarbazole compound to be used in the organic electroluminescent device of the present invention has a nitrogen-containing six-membered ring group on one of the two Ns of its indolocarbazole skeleton, and has a fused heterocyclic group as a substituent on the nitrogen-containing six-membered ring. Probably because of the foregoing, the compound shows good hole- and electron-injecting/transporting characteristics, and has high durability while maintaining a high T1. In particular, when the fused heterocyclic group is a dibenzofuranyl group or a dibenzothiophenyl group, a LUMO orbital expands on the nitrogen-containing six-membered ring and the dibenzofuran ring or the dibenzothiophene ring, and hence the compound can be expected to show good electron-transporting property. Further, changing the kinds or number of aromatic rings as substituents on the other N enables the fine adjustment of the rates at which a hole and an electron transfer, and the control of the various energy values, i.e., IP, EA, and T1. In particular, when four or more, preferably five or more aromatic rings are linked, overlap between the molecules of the compound is improved by the expansion of a conjugated system and hence an improvement in electronic stability of each molecule can be expected. In addition, a material having a high mobility can be provided.

As can be seen from the foregoing, the organic EL device using the indolocarbazole compound can realize a carrier balance optimum for various dopants in its light-emitting layer. As a result, an organic EL device significantly improved in light-emitting characteristics can be provided. Further, the indolocarbazole compound can be improved in stability in each of active states, i.e., oxidation, reduction, and excitation, and at the same time, has a good amorphous characteristic. Accordingly, the compound can realize an organic EL device having a long driving lifetime and high durability.

The organic EL device according to the present invention has light-emitting characteristics, driving lifetime, and durability at practically satisfactory levels. Thus, the organic EL device has a large technical value in applications to flat panel displays (display devices for portable phones, in-vehicle display devices, display devices for OA computers, televisions, and the like), light sources utilizing characteristics of planar light emitters (light sources in lighting equipment and copying machines and backlight sources in liquid crystal displays and instruments), sign boards, sign lamps, and the like.

The invention claimed is:

1. An organic electroluminescent device, comprising an anode, a plurality of organic layers including a phosphorescent light-emitting layer, and a cathode laminated on a substrate, wherein at least one of the plurality of organic layers, which is selected from the group consisting of the phosphorescent light-emitting layer, a hole-transporting layer, an electron-transporting layer, and a hole-blocking layer, contains an indolocarbazole compound represented by the general formula (1):

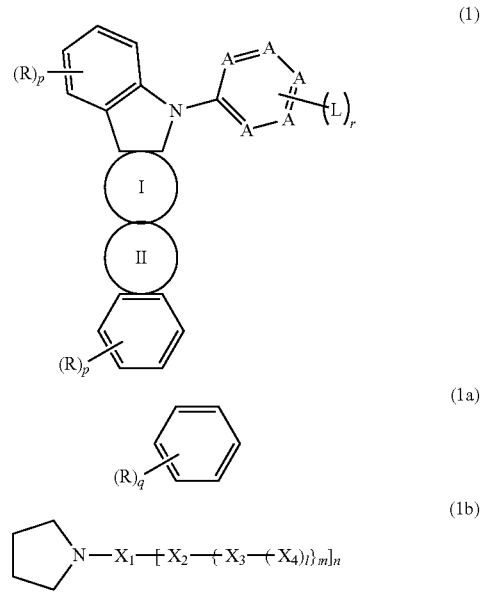

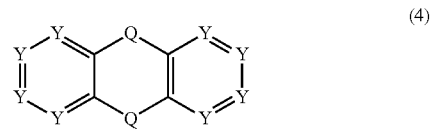

wherein,
a ring I represents an aromatic hydrocarbon ring represented by the formula (1a) to be fused to adjacent rings at arbitrary positions, and a ring II represents a heterocycle represented by the formula (1b) to be fused to adjacent rings at arbitrary positions;
As each represent C—R or N and at least one of As represents N; and
Ls each independently represent a substituted or unsubstituted aromatic hydrocarbon group having 6 to 18 carbon atoms, or a substituted or unsubstituted aromatic heterocyclic group having 3 to 17 carbon atoms, r represents an integer of 2 or 3, and at least one of Ls represents a monovalent aromatic heterocyclic group represented by the following formula (4);

$$\text{(4)}$$

wherein, Ys each independently represent methine, substituted methine, or nitrogen, and one of Ys represents a carbon atom providing a monovalent group, Qs each independently represent any one of a single bond, —S—, and —O—, and at least one of Ys and Qs represents a heteroatom;
in the general formula (1) and the formula (1a), Rs each independently represent an aliphatic hydrocarbon group having 1 to 10 carbon atoms, an aromatic hydrocarbon group having 6 to 18 carbon atoms, or an aromatic heterocyclic group having 3 to 17 carbon atoms, ps each independently represent an integer of from 0 to 4, and q represents an integer of from 0 to 2;
in the formula (1b), $X_1$ to $X_4$ each independently represent an aromatic hydrocarbon group having 6 to 18 carbon atoms or an aromatic heterocyclic group having 3 to 17 carbon atoms, l, m, and n each independently represent an integer of from 0 to 5, and when l, m, or n represents 2 or more, $X_2$s, $X_3$s, or $X_4$s may be identical to or different from each other, and a total number of $X_1$ to $X_4$ in the formula (1b) is from 4 to 7.

2. An organic electroluminescent device according to claim 1, wherein at least one of Ls in the general formula (1) represents a substituted or unsubstituted dibenzofuranyl or dibenzothiophenyl group.

3. An organic electroluminescent device according to claim 1, wherein the total number of $X_1$ to $X_4$ in the formula (1b) is from 5 to 7.

4. An organic electroluminescent device according to claim 1, wherein the organic layer containing the indolocarbazole compound represented by the general formula (1) comprises a light-emitting layer containing a phosphorescent light-emitting dopant.

5. An organic electroluminescent device according to claim 2, wherein the organic layer containing the indolocarbazole compound represented by the general formula (1) comprises a light-emitting layer containing a phosphorescent light-emitting dopant.

6. An organic electroluminescent device according to claim 3, wherein the organic layer containing the indolocarbazole compound represented by the general formula (1) comprises a light-emitting layer containing a phosphorescent light-emitting dopant.

7. An organic electroluminescent device according to claim 2, wherein the total number of $X_1$ to $X_4$ in the formula (1b) is from 5 to 7.

8. An organic electroluminescent device according to claim 1, wherein, in the formula (1b), the group of:

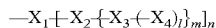

is a group produced by removing hydrogen from an aromatic ring selected from the group consisting of benzene, pentalene, indene, naphthalene, anthracene, phenanthrene, pyrrole, imidazole, pyrazole, thiazole, thiophene, pyridine, pyrazine, pyrimidine, pyridazine, triazine, isoindole, indazole, purine, benzimidazole, indolizine, chromene, benzoxazole, isobenzofuran, quinolizine, isoquinoline, imidazole, naphthyridine, phthalazine, quinazoline, quinoxaline, cinnoline, quinoline, pteridine, perimidine, phenanthroline, phenanthridine, acridine, phenazine, phenothiazine, phenoxazine, phenazasiline, dibenzodioxin, carboline, indole, indoloindole, carbazole, furan, benzofuran, isobenzofuran, benzothiazole, oxanthrene, dibenzofuran, thiophene, thioxanthene, thianthrene, phenoxathiin, thionaphthene, isothianaphthene, thiophthene, thiophanthrene, and dibenzothiophene.

9. An organic electroluminescent device according to claim 1, wherein, in the formula (1b), the group of:

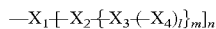

is selected from the group consisting of:

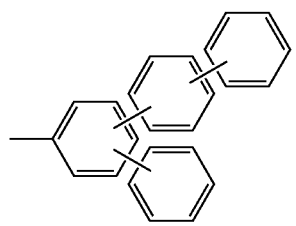

-continued

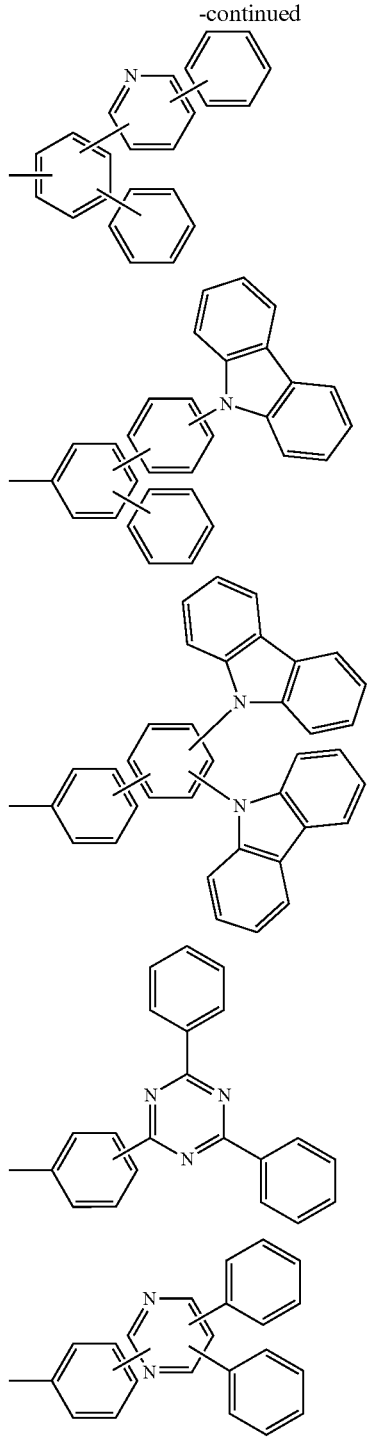

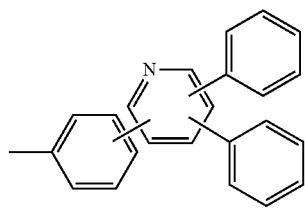

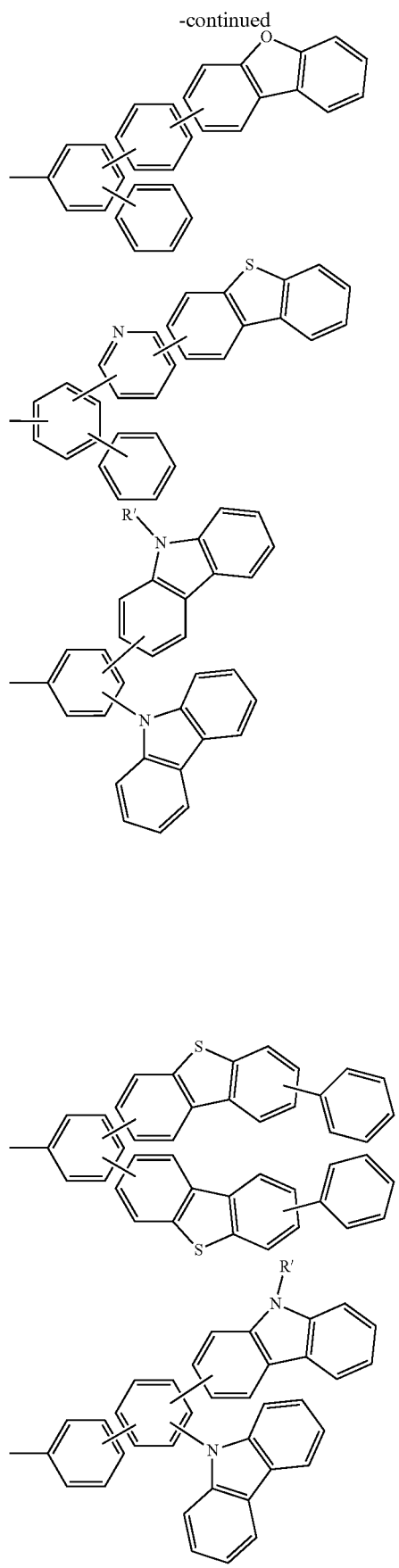

319
-continued
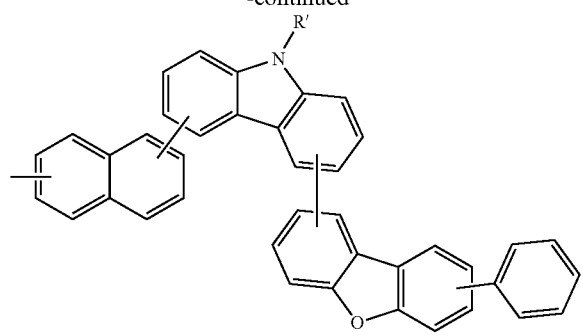
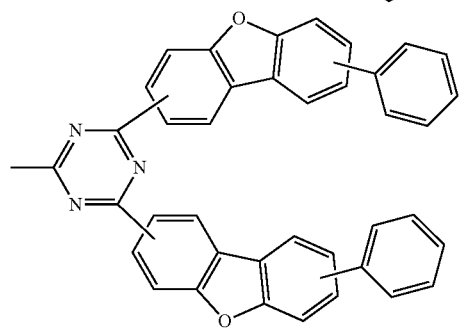
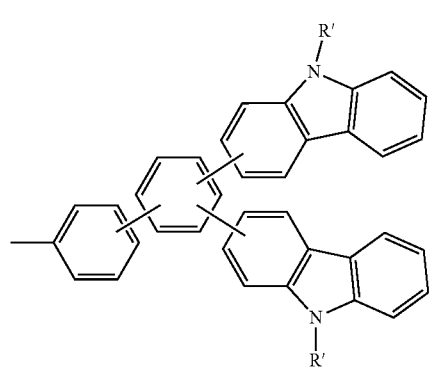
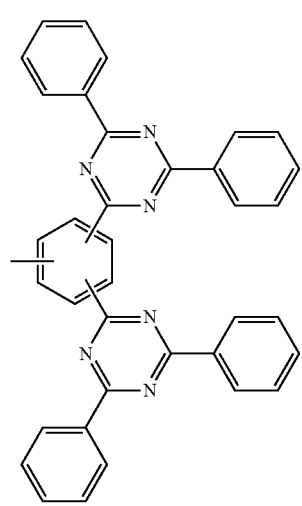
320
-continued
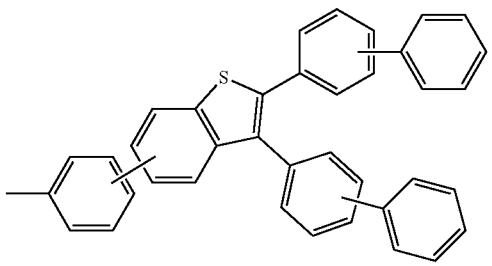
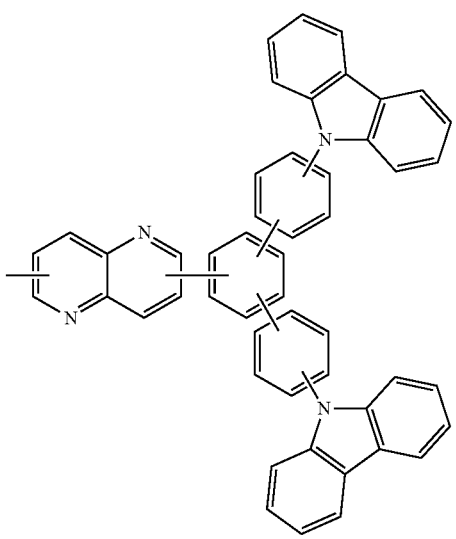
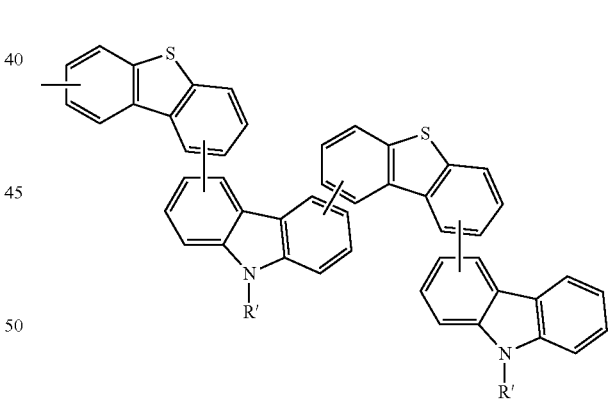
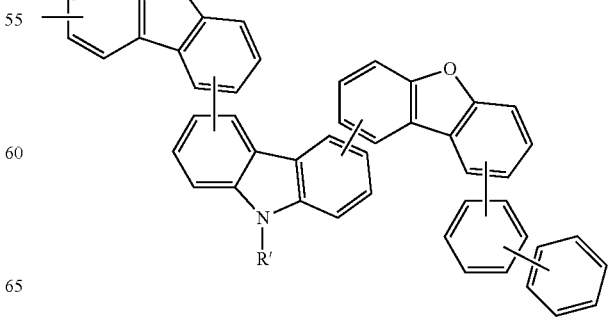

321
-continued
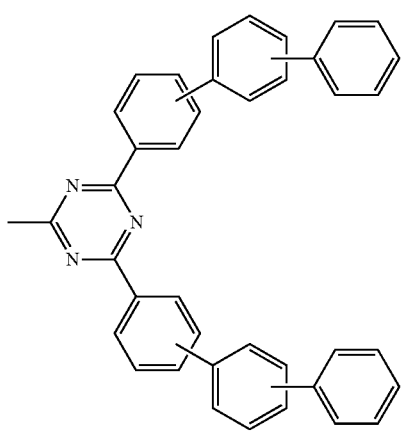
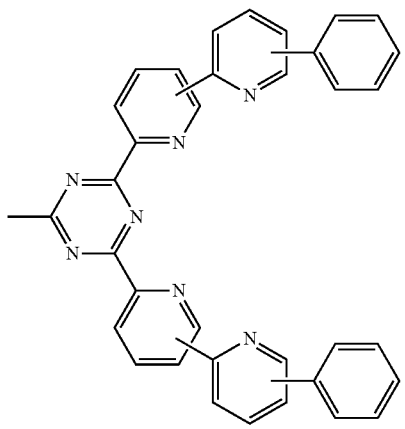
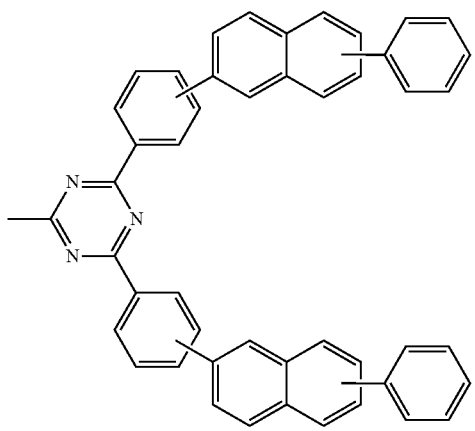
322
-continued
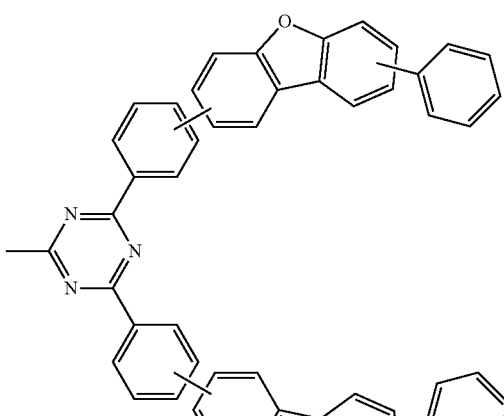
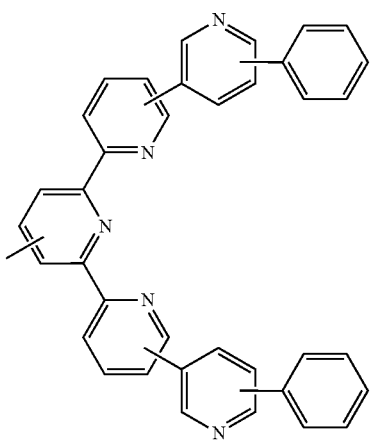
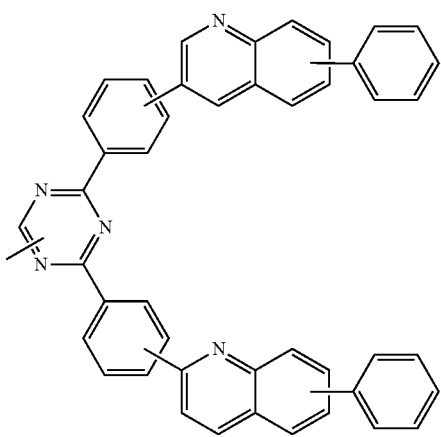

323
-continued
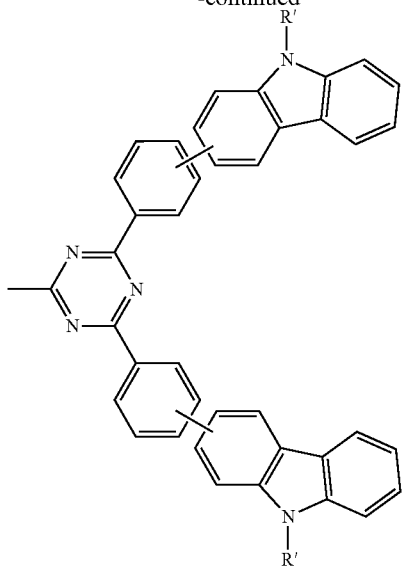
324
-continued
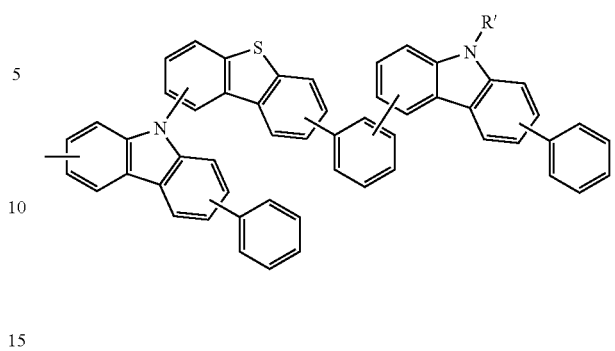
where R' represents an aromatic hydrocarbon group having 6 to 18 carbon atoms or an aromatic heterocyclic group having 3 to 17 carbon atoms.
* * * * *